(12) United States Patent
Peled et al.

(10) Patent No.: US 9,175,266 B2
(45) Date of Patent: Nov. 3, 2015

(54) ENHANCEMENT OF NATURAL KILLER (NK) CELL PROLIFERATION AND ACTIVITY

(71) Applicant: Gamida Cell Ltd., Jerusalem (IL)

(72) Inventors: Tony Peled, Mevaseret Zion (IL); Gabi M. Frei, Bet-Shemesh (IL)

(73) Assignee: Gamida Cell Ltd., Jerusalem (IL)

( * ) Notice: Subject to any disclaimer, the term of this patent is extended or adjusted under 35 U.S.C. 154(b) by 0 days.

(21) Appl. No.: 13/946,266

(22) Filed: Jul. 19, 2013

(65) Prior Publication Data

US 2014/0023626 A1 Jan. 23, 2014

Related U.S. Application Data

(60) Provisional application No. 61/674,426, filed on Jul. 23, 2012.

(51) Int. Cl.
| | | |
|---|---|---|
| A01N 63/00 | (2006.01) |
| C12N 5/0783 | (2010.01) |
| A61K 35/17 | (2015.01) |
| C12N 15/85 | (2006.01) |

(52) U.S. Cl.
CPC .............. *C12N 5/0646* (2013.01); *A61K 35/17* (2013.01); *C12N 15/85* (2013.01); *C12N 2501/2302* (2013.01); *C12N 2501/2315* (2013.01); *C12N 2501/60* (2013.01); *C12N 2501/999* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan, Jr. et al. |
| 3,715,345 A | 2/1973 | Smith |
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,863,008 A | 1/1975 | Grant |
| 3,867,517 A | 2/1975 | Ling |
| 3,876,623 A | 4/1975 | Jackson et al. |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,036,945 A | 7/1977 | Haber |
| 4,098,876 A | 7/1978 | Piasio et al. |
| 4,331,647 A | 5/1982 | Goldenberg |
| 4,469,863 A | 9/1984 | Ts'o et al. |
| 4,476,301 A | 10/1984 | Imbach et al. |
| 4,642,120 A | 2/1987 | Nevo et al. |
| 4,666,828 A | 5/1987 | Gusella |
| 4,683,202 A | 7/1987 | Mullis |
| 4,687,808 A | 8/1987 | Jarrett et al. |
| 4,801,531 A | 1/1989 | Frossard |
| 4,806,484 A | 2/1989 | Petrossian et al. |
| 4,816,567 A | 3/1989 | Cabilly et al. |
| 4,866,052 A | 9/1989 | Hider et al. |
| 4,868,116 A | 9/1989 | Morgan et al. |
| 4,879,219 A | 11/1989 | Wands et al. |
| 4,946,778 A | 8/1990 | Ladner et al. |
| 4,980,286 A | 12/1990 | Morgan et al. |
| 5,011,771 A | 4/1991 | Bellet et al. |
| 5,013,830 A | 5/1991 | Ohtsuka et al. |
| 5,023,243 A | 6/1991 | Tullis |
| 5,034,506 A | 7/1991 | Summerton et al. |
| 5,081,035 A | 1/1992 | Halberstadt et al. |
| 5,149,797 A | 9/1992 | Pederson et al. |
| 5,166,315 A | 11/1992 | Summerton et al. |
| 5,166,320 A | 11/1992 | Wu et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,220,007 A | 6/1993 | Pederson et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,272,057 A | 12/1993 | Smulson et al. |

(Continued)

FOREIGN PATENT DOCUMENTS

| | | | |
|---|---|---|---|
| AU | 759522 B2 | 4/2003 |
| AU | 770896 B2 | 3/2004 |

(Continued)

OTHER PUBLICATIONS

Diani-Moore et al., J. Biol. Chem., 285:38801-38810 (2010).*
Bachanova et al. "Allogeneic Natural Killer Cells for Refractory Lymphoma." *Cancer Immunol. Immunother.* 59(2010):1739-1744.
Beider et al. "Involvement of CXCR4 and IL-2 in the Homing and Retention of Human NK and NK T Cells to the Bone Marrow and Spleen of NOD/SCID Mice." *Blood.* 102.6(2003):1951-1958.
Berg et al. "Clinical-Grade ex vivo-Expanded Human Natural Killer Cells Up-Regulate Activating Receptors and Death Receptor Ligands and Have Enhanced Cytolytic Activity Against Tumor Cells." *Cythotherapy.* 11.3(2009):341-355.
Bernardini et al. "CCL3 and CXCL12 Regulate Trafficking of Mouse Bone Marrow NK Cell Subsets." *Blood.* 111.7(2008):3626-3634.
Caligiuri. "Human Natural Killer Cells." *Blood.* 112.3(2008):461-469.

(Continued)

*Primary Examiner* — Robert Mondesi
*Assistant Examiner* — Thomas J Visone
(74) *Attorney, Agent, or Firm* — Cooley LLP; Ivor R. Elrifi; Matthew Pavao

(57) ABSTRACT

Methods of ex-vivo culture of natural killer (NK) cells are provided and, more particularly, methods for enhancing propagation and/or functionality of NK cells by treating the cells with an aryl hydrocarbon antagonist in combination with cytokines driving NK cell proliferation. Also envisioned are compositions comprising cultured NK cells and therapeutic uses thereof.

15 Claims, 3 Drawing Sheets

(56) References Cited

U.S. PATENT DOCUMENTS

| | | |
|---|---|---|
| 5,276,019 A | 1/1994 | Cohen et al. |
| 5,278,302 A | 1/1994 | Caruthers et al. |
| 5,281,521 A | 1/1994 | Trojanowski et al. |
| 5,286,717 A | 2/1994 | Cohen et al. |
| 5,320,963 A | 6/1994 | Knaack et al. |
| 5,321,131 A | 6/1994 | Agrawal et al. |
| 5,342,781 A | 8/1994 | Su |
| 5,366,878 A | 11/1994 | Pederson et al. |
| 5,378,725 A | 1/1995 | Bonjouklian et al. |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,434,257 A | 7/1995 | Matteucci et al. |
| 5,437,994 A | 8/1995 | Emerson et al. |
| 5,453,496 A | 9/1995 | Caruthers et al. |
| 5,455,233 A | 10/1995 | Spielvogel et al. |
| 5,466,677 A | 11/1995 | Baxter et al. |
| 5,470,967 A | 11/1995 | Huie et al. |
| 5,476,925 A | 12/1995 | Letsinger et al. |
| 5,480,906 A | 1/1996 | Creemer et al. |
| 5,486,359 A | 1/1996 | Caplan et al. |
| 5,489,677 A | 2/1996 | Sanghvi et al. |
| 5,491,133 A | 2/1996 | Walder et al. |
| 5,504,103 A | 4/1996 | Bonjouklian et al. |
| 5,519,126 A | 5/1996 | Hecht |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,545,806 A | 8/1996 | Lonberg et al. |
| 5,545,807 A | 8/1996 | Surani et al. |
| 5,550,111 A | 8/1996 | Suhadolnik et al. |
| 5,561,225 A | 10/1996 | Maddry et al. |
| 5,563,253 A | 10/1996 | Agrawal et al. |
| 5,565,350 A | 10/1996 | Kmiec |
| 5,569,825 A | 10/1996 | Lonberg et al. |
| 5,571,799 A | 11/1996 | Tkachuk et al. |
| 5,587,361 A | 12/1996 | Cook et al. |
| 5,596,086 A | 1/1997 | Matteucci et al. |
| 5,602,240 A | 2/1997 | De Mesmaeker et al. |
| 5,608,046 A | 3/1997 | Cook et al. |
| 5,610,289 A | 3/1997 | Cook et al. |
| 5,612,211 A | 3/1997 | Wilson et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,625,126 A | 4/1997 | Lonberg et al. |
| 5,631,219 A | 5/1997 | Rosenthal et al. |
| 5,633,360 A | 5/1997 | Bischofberger et al. |
| 5,633,425 A | 5/1997 | Lonberg et al. |
| 5,652,355 A | 7/1997 | Metelev et al. |
| 5,652,356 A | 7/1997 | Agrawal |
| 5,654,186 A | 8/1997 | Cerami et al. |
| 5,661,016 A | 8/1997 | Lonberg et al. |
| 5,663,312 A | 9/1997 | Chaturvedula |
| 5,674,750 A | 10/1997 | Kraus et al. |
| 5,677,437 A | 10/1997 | Teng et al. |
| 5,677,439 A | 10/1997 | Weis et al. |
| 5,700,922 A | 12/1997 | Cook |
| 5,712,154 A | 1/1998 | Mullon et al. |
| 5,714,331 A | 2/1998 | Buchardt et al. |
| 5,716,411 A | 2/1998 | Orgill et al. |
| 5,716,616 A | 2/1998 | Prockop et al. |
| 5,719,262 A | 2/1998 | Buchardt et al. |
| 5,733,541 A | 3/1998 | Taichman et al. |
| 5,736,396 A | 4/1998 | Bruder et al. |
| 5,741,899 A | 4/1998 | Capon et al. |
| 5,770,378 A | 6/1998 | Hwang et al. |
| 5,770,580 A | 6/1998 | Ledley et al. |
| 5,776,699 A | 7/1998 | Klein et al. |
| 5,789,245 A | 8/1998 | Dubensky, Jr. et al. |
| 5,789,543 A | 8/1998 | Ingham et al. |
| 5,792,751 A | 8/1998 | Ledley et al. |
| 5,814,482 A | 9/1998 | Dubensky, Jr. et al. |
| 5,830,760 A | 11/1998 | Tsai et al. |
| 5,837,544 A | 11/1998 | Capon et al. |
| 5,843,723 A | 12/1998 | Dubensky, Jr. et al. |
| 5,844,079 A | 12/1998 | Ingham et al. |
| 5,851,832 A | 12/1998 | Weiss et al. |
| 5,851,984 A | 12/1998 | Matthews et al. |
| 5,877,207 A | 3/1999 | Klein et al. |
| 5,945,309 A | 8/1999 | Ni et al. |
| 5,945,337 A | 8/1999 | Brown |
| 5,952,345 A | 9/1999 | Klein et al. |
| 5,958,954 A | 9/1999 | Klein et al. |
| 5,990,329 A | 11/1999 | Klaus et al. |
| 6,008,204 A | 12/1999 | Klein et al. |
| 6,015,686 A | 1/2000 | Dubensky, Jr. et al. |
| 6,015,694 A | 1/2000 | Dubensky, Jr. et al. |
| 6,063,797 A | 5/2000 | Fesus et al. |
| 6,077,947 A | 6/2000 | Capon et al. |
| 6,090,810 A | 7/2000 | Klein et al. |
| 6,130,230 A | 10/2000 | Chambon et al. |
| 6,133,309 A | 10/2000 | Bollag et al. |
| 6,165,747 A | 12/2000 | Ingham et al. |
| 6,177,850 B1 | 1/2001 | Furutani et al. |
| 6,218,128 B1 | 4/2001 | Klein et al. |
| 6,228,848 B1 | 5/2001 | Klein et al. |
| 6,232,291 B1 | 5/2001 | Ni et al. |
| 6,255,112 B1 | 7/2001 | Thiede et al. |
| 6,261,786 B1 | 7/2001 | Marigo et al. |
| 6,270,964 B1 | 8/2001 | Michnick et al. |
| 6,271,363 B1 | 8/2001 | Ingham et al. |
| 6,284,540 B1 | 9/2001 | Milbrandt et al. |
| 6,294,330 B1 | 9/2001 | Michnick et al. |
| 6,303,374 B1 | 10/2001 | Zhang et al. |
| 6,306,575 B1 | 10/2001 | Thomas et al. |
| 6,326,174 B1 | 12/2001 | Joyce et al. |
| 6,326,198 B1 | 12/2001 | Emerson et al. |
| 6,329,169 B1 | 12/2001 | Ni et al. |
| 6,335,195 B1 | 1/2002 | Rodgers et al. |
| 6,338,942 B2 | 1/2002 | Kraus et al. |
| 6,342,219 B1 | 1/2002 | Thorpe et al. |
| 6,342,221 B1 | 1/2002 | Thorpe et al. |
| 6,342,372 B1 | 1/2002 | Dubensky, Jr. et al. |
| 6,342,581 B1 | 1/2002 | Rosen et al. |
| 6,372,210 B2 | 4/2002 | Brown |
| 6,372,473 B1 | 4/2002 | Moore et al. |
| 6,376,236 B1 | 4/2002 | Dubensky, Jr. et al. |
| 6,384,192 B1 | 5/2002 | Ingham et al. |
| 6,413,772 B1 | 7/2002 | Block |
| 6,413,773 B1 | 7/2002 | Ptasznik et al. |
| 6,642,019 B1 | 11/2003 | Anderson et al. |
| 6,645,489 B2 | 11/2003 | Pykett et al. |
| 6,680,166 B1 | 1/2004 | Mullon et al. |
| 6,887,704 B2 | 5/2005 | Peled et al. |
| 6,962,698 B1 | 11/2005 | Peled et al. |
| 7,169,605 B2 | 1/2007 | Peled et al. |
| 7,247,477 B2 | 7/2007 | Itskovitz-Eldor et al. |
| 7,344,881 B2 | 3/2008 | Peled et al. |
| 7,955,852 B2 | 6/2011 | Peled et al. |
| 8,080,417 B2 | 12/2011 | Peled et al. |
| 2001/0014475 A1 | 8/2001 | Frondoza et al. |
| 2002/0001826 A1 | 1/2002 | Wager et al. |
| 2002/0090603 A1 | 7/2002 | Lipton et al. |
| 2002/0114784 A1 | 8/2002 | Li et al. |
| 2002/0114789 A1 | 8/2002 | Peled et al. |
| 2002/0146678 A1 | 10/2002 | Benvenisty |
| 2002/0146816 A1 | 10/2002 | Vellinger et al. |
| 2002/0159981 A1 | 10/2002 | Peled et al. |
| 2002/0159984 A1 | 10/2002 | Brown |
| 2002/0182728 A1 | 12/2002 | Ramiya et al. |
| 2003/0002363 A1 | 1/2003 | Le et al. |
| 2003/0031665 A1 | 2/2003 | Dang et al. |
| 2003/0113913 A1 | 6/2003 | Purton et al. |
| 2003/0125410 A1 | 7/2003 | Keita et al. |
| 2003/0149074 A1 | 8/2003 | Melese et al. |
| 2003/0215445 A1 | 11/2003 | Serrero |
| 2003/0235563 A1 | 12/2003 | Strom et al. |
| 2003/0235909 A1 | 12/2003 | Hariri et al. |
| 2004/0076603 A1 | 4/2004 | Peled et al. |
| 2004/0247574 A1 | 12/2004 | Christopherson et al. |

(56) References Cited

U.S. PATENT DOCUMENTS

| | | |
|---|---|---|
| 2005/0008624 A1 | 1/2005 | Peled et al. |
| 2005/0031595 A1 | 2/2005 | Peled et al. |
| 2005/0054097 A1 | 3/2005 | Peled et al. |
| 2005/0054103 A1 | 3/2005 | Peled et al. |
| 2005/0069527 A1 | 3/2005 | Laughlin et al. |
| 2005/0084961 A1 | 4/2005 | Hedrick et al. |
| 2005/0095228 A1 | 5/2005 | Fraser et al. |
| 2005/0118150 A1 | 6/2005 | Peled et al. |
| 2005/0214262 A1 | 9/2005 | Peled et al. |
| 2005/0220774 A1 | 10/2005 | Peled et al. |
| 2005/0260748 A1 | 11/2005 | Chang et al. |
| 2006/0093605 A1 | 5/2006 | Campana et al. |
| 2006/0171932 A1 | 8/2006 | Hendricks et al. |
| 2006/0205071 A1 | 9/2006 | Hasson et al. |
| 2007/0077652 A1 | 4/2007 | Peled et al. |
| 2008/0279828 A1 | 11/2008 | Peled et al. |
| 2009/0257987 A1 | 10/2009 | Offen et al. |
| 2010/0015103 A1 | 1/2010 | Liu et al. |
| 2010/0021434 A1 | 1/2010 | Melamed et al. |
| 2010/0061963 A1 | 3/2010 | Peled |
| 2010/0183564 A1 | 7/2010 | Boitano et al. |
| 2012/0028354 A1 | 2/2012 | Lee et al. |
| 2014/0023623 A1 | 1/2014 | Peled et al. |
| 2015/0004146 A1 | 1/2015 | Peled et al. |
| 2015/0064273 A1 | 3/2015 | Peled et al. |

FOREIGN PATENT DOCUMENTS

| | | |
|---|---|---|
| EP | 0 331 464 A2 | 9/1989 |
| EP | 1 332 673 A1 | 8/2003 |
| EP | 1 332 676 A1 | 8/2003 |
| EP | 1424389 A1 | 6/2004 |
| JP | 2005528088 A | 9/2005 |
| KR | 20090065814 A | 6/2009 |
| WO | WO-8902468 A1 | 3/1989 |
| WO | WO-8905345 A1 | 6/1989 |
| WO | WO-8907136 A2 | 8/1989 |
| WO | WO-9207573 A1 | 5/1992 |
| WO | WO-9211355 A1 | 7/1992 |
| WO | WO-9309220 A1 | 5/1993 |
| WO | WO-9318132 A1 | 9/1993 |
| WO | WO-9418991 A1 | 9/1994 |
| WO | WO-9514078 A1 | 5/1995 |
| WO | WO-9521911 A1 | 8/1995 |
| WO | WO-9524464 A1 | 9/1995 |
| WO | WO-9601108 A1 | 1/1996 |
| WO | WO-9640876 A1 | 12/1996 |
| WO | WO-9704707 A1 | 2/1997 |
| WO | WO-9731647 A1 | 9/1997 |
| WO | WO-9733978 A1 | 9/1997 |
| WO | WO-9741209 A1 | 11/1997 |
| WO | WO-9741224 A1 | 11/1997 |
| WO | WO-9825634 A1 | 6/1998 |
| WO | WO-9907831 A1 | 2/1999 |
| WO | WO-9918885 A1 | 4/1999 |
| WO | WO-9940783 A1 | 8/1999 |
| WO | WO-9964566 A2 | 12/1999 |
| WO | WO-0018885 A1 | 4/2000 |
| WO | WO-0030635 A1 | 6/2000 |
| WO | WO-0046349 A1 | 8/2000 |
| WO | WO-0066712 A2 | 11/2000 |
| WO | WO-0073421 A2 | 12/2000 |
| WO | WO-02064755 A2 | 8/2002 |
| WO | WO-02080995 A1 | 10/2002 |
| WO | WO-02102299 A2 | 12/2002 |
| WO | WO-03004626 A1 | 1/2003 |
| WO | WO-03051419 A1 | 6/2003 |
| WO | WO-03062369 A2 | 7/2003 |
| WO | WO-03062404 A1 | 7/2003 |
| WO | WO-03072557 A1 | 9/2003 |
| WO | WO-03078567 A2 | 9/2003 |
| WO | WO-2004016731 A2 | 2/2004 |
| WO | WO-2004078917 A2 | 9/2004 |
| WO | WO-2005007073 A2 | 1/2005 |
| WO | WO-2005007799 A2 | 1/2005 |
| WO | WO-2005086845 A2 | 9/2005 |
| WO | WO-2006030442 A2 | 3/2006 |
| WO | WO-2006050270 A2 | 5/2006 |
| WO | WO-2007063545 A2 | 6/2007 |
| WO | WO-2008020815 A1 | 2/2008 |
| WO | WO-2008056368 A2 | 5/2008 |
| WO | WO-2011080740 A1 | 7/2011 |
| WO | WO-2011139357 A1 | 11/2011 |
| WO | WO-2013121426 A1 | 8/2013 |
| WO | WO-2013121427 A1 | 8/2013 |

OTHER PUBLICATIONS

Cho et al. "Expansion and Activation of Natural Killer Cells for Cancer Immunotherapy." *Korean J. Lab. Med.* 29.2(2009):89-96.

Decot et al. "Natural-Killer Cell Amplification for Adoptive Leukemia Relapse Immunotherapy: Comparison of Three Cytokines, IL-2, IL-15, or IL-7 and Impact on NKG2D, KIR2DL1, and KIR2DL2 Expression." *Exp. Hematol.* 38.5(2010):351-362.

Frias et al. "Generation of Functional Natural Killer and Dendritic Cells in a Human Stromal-Based Serum-Free Culture System Designed for Cord Blood Expansion." *Exp. Hematol.* 36(2008):61-68.

Harada et al. "A Wilms Tumor Cell Line, HFWT, Can Greatly Stimulate Proliferation of CD56+ Human Natural Killer Cells and Their Novel Precursors in Blood Mononuclear Cells." *Exp. Hematol.* 32(2004):614-621.

Humeau et al. "Successful Reconstitution of Human Hematopoiesis in the SCID-hu Mouse by Genetically Modified, Highly Enriched Progenitors Isolated from Fetal Liver." *Blood.* 90.9(1997):3496-3506.

Klingemann et al. "Ex vivo Expansion of Natural Killer Cells for Clinical Applications." *Cythotherapy.* 6.1(2004):15-22.

Koehl et al. "Ex vivo Expansion of Highly Purified NK Cells for Immunotherapy After Haploidentical Stem Cell Transplantation in Children." *Klin. Pädiatr.* 217(2005):345-350.

Markel et al. "Natural Killer Lysis Receptor (NKLR)/NKLR-Ligand Matching as a Novel Approach for Enhancing Anti-Tumor Activity of Allogeneic NK Cells." *PLoS ONE.* 4.5(2009):e5597.

Meyer-Monard et al. "Clinical-Grade Purification of Natural Killer Cells in Haploidentical Hematopoietic Stem Cell Transplantation." *Transfusion.* 49(2009):362-371.

Miller et al. "Role of Monocytes in the Expansion of Human Activated Natural Killer Cells." *Blood.* 80.9(1992):2221-2229.

Robertson et al. "Biology and Clinical Relevance of Human Natural Killer Cells." *Blood.* 76.12(1990):2421-2438.

Rosenberg. "Lymphokine-Activated Killer Cells: A New Approach to Immunotherapy of Cancer." *J. Natl. Cancer Inst.* 75.4(1985):595-603.

Schleinitz et al. "Natural Killer Cells in Human Autoimmune Diseases." *Immunology.* 131(2010):451-458.

Von Drygalski et al. "Murine Bone Marrow Cells Cultured Ex Vivo in the Presence of Multiple Cytokine Combinations Lose Radioprotective and Long-Term Engraftment Potential." *Stem Cells Dev.* 13(2004):101-111.

Yu et al. "CD94 Surface Density Identifies a Functional Intermediary Between the CD56bright and CD56dim Human NK-Cell Subsets." *Blood.* 115.2(2010):274-281.

Zucchini et al. "Natural Killer Cells in Immunodefense Against Infective Agents." *Exp. Rev. Anti Infect. Ther.* 6.6(2008):867-885.

"Chelation Therapy." *American Cancer Society.* Jun. 1, 2005. Web. Sep. 26, 2006. www.cancer.org/docroot/ETO/content/ETO_5_3X_Chelation_Therapy.asp?sitearea=ETO.

"Duraguard 100 (Part B-Hardener)." *ChemMasters Material Data Sheet.* (1999).

Acsadi et al. "Human Dystrophin Expression in MDX Mouse after Intramuscular Injection of DNA Constructs." *Nature.* 352.6338(1991):815-818.

Aiuti et al. "The Chemokine SDF-1 is a Chemoattractant for Human CD34+ Hematopoietic Progenitor Cells and Provides a New Mechanism to Explain the Mobilization of CD34+ Progenitors to Peripheral Blood." *J. Exp. Med.* 185.1(1997):111-120.

(56) References Cited

OTHER PUBLICATIONS

Alici et al. "Autologous Antitumor Activity by NK Cells Expanded from Myeloma Patients Using GMP-Compliant Components." *Blood.* 111.6(2008):3155-3162.
Alter. "Fetal Erythropoiesis in Stress Hematopoiesis." *Exp. Hematol.* 7.55(1979):200-209.
American Cyanamid Co Lederle Laboratories DIV. "6505-01-047-3872: Thiotepa Product Indentification Sheet." (1990).
Anderlini et al. "The Use of Mobilized Peripheral Blood Stem Cells from Normal Donors for Allografting." *Stem Cells.* 15(1997):9-17.
Aoki et al. "In Vivo Transfer Effciency of Antisense Oligonucleotides into the Myocardium Using HVJ-Liposome Method." *Biochem. Biophys. Res. Commun.* 231(1997):540-545.
Armentano et al. "Expression of Human Factor IX in Rabbit Hepatocytes by Retrovirus-Mediated Gene Transfer: Potential for Gene Therapy of Hemophilia B." *PNAS.* 87(1990):6141-6145.
Arriero et al. "Adult Skeletal Muscle Stem Cells Differentiate into Endothelial Lineage and Ameliorate Renal Dysfunction after Acute Ischemia." *Am. J. Physiol.* 287(2004):F621-F627.
Asahara et al. "Stem Cell Therapy and Gene Transfer for Regneration." *Gene Ther.* 7(2000):451-457.
Auger et al. "PDGF-Dependent Tyrosine Phosphorylation Stimulates Production of Novel Polyphosphoinositides in Intact Cells." *Cell.* 57(1989):167-175.
Avital et al. "Isolation, Characterization, and Transplantation of Bone Marrow-Derived Hepatocyte Stem Cells." *Biochem. Biophys. Res. Commun.* 288.1(2001):156-164.
Bae et al. "Copper Uptake and Intracellular Distribution During Retinoic Acid-Induced Differentiation of HL-60 Cells." *J. Nutr. Biochem.* 5(1994):457-461.
Bae et al. "Retinoic Acid-induced HL-60 Cell Differentiation is Augmented by Copper Supplementation." *J. Nutr.* 123.6(1993):997-1002.
Baggiolini. "Chemokines and Leukocyte Traffic." *Nature.* 392(1998):565-568.
Banasik et al. "Specific Inhibitors of Poly(ADP-Ribose) Synthetase and Mono(ADP-Ribosyl)transferase." *J. Biol. Chem.* 267.3(1992):1569-1575.
Banno et al. "Anemia and Neutropenia in Elderly Patients Caused by Copper Deficiency for Long-Term Eternal Nutrition." *Jap. J. Clin. Hematol.* 35(1994):1276-1280. (Japanese Original and English Abstract).
Baum et al. "Isolation of a Candidate Human Hematopoietc Stem-Cell Population." *PNAS.* 89(1992):2804-2808.
Belovari et al. "Differentiation of Rat Neural Tissue in a Serum-Free Embryo Culture Model Followed by in vivo Transplantation." *Croat. Med. J.* 42.6(2001):611-617. (English Abstract Only).
Berardi et al. "Individual CD34+CD38lowCD19-CD10—Progenitor Cells from Human Cord Blood Generate B Lymphocytes and Granulocytes." *Blood.* 89.10(1997):3554-3564.
Berkner. "Development of Adenovirus Vectors for the Expression of Heterologous Genes." *Bio Tech.* 6.7(1998):616-629.
Bernhard et al. "Generation of Immunostimulatory Dendritic Cells from Human CD34+ Hematopoietic Progenitor Cells of the Bone Marrow and Peripheral Blood." *Cancer Res.* 55(1995):1099-1104.
Bertagnolo et al. "Phophoinositide 3-Kinase Activity is Essential for All-*Trans*-Retinoic Acid-Induced Granulocyte Differentiation of HL-60 Cells." *Cancer Res.* 59(1999):542-546.
Bhat-Nakshatri et al. "Tumour Necrosis Factor and PI3-Kinase Control Oestrogen Receptor Alpha Protein Level and its Transrepression Function." *Brit. J. Cancer.* 90(2004):853-859.
Bhatia et al. "Purification of Primitive Human Hematopoietic Cells Capable of Repopulating Immune-Deficient Mice." *PNAS.* 94(1997):5320-5325.
Bi et al. "Effect of Lactoferrin on Proliferation and Differentiation of the Jurkat Human Lymphoblastic T Cell Line." *Arch. Immunol. Ther. Exp.* 45.4(1997):315-320.
Bieback et al. "Critical Parameters for the Isolation of Mesenchymal Stem Cell from Umbilical Cord Blood." *Stem Cells.* 22(2004):625-634.

Bird et al. "Single-Chain Antigen-Binding Proteins." *Science.* 242(1988):423-426.
Birkenkamp et al. "An Inhibitor of PI3-K Differentially Affects Proliferation and IL-6 Protein Secretion in Normal and Leukemic Myeloid Cells Depending on the Stage of Differentiation." *Exp. Hematol.* 28.11(2000):1239-1249.
Blau et al. "Fetal Hemoglobin in Acute and Chronic Stage of Erythroid Expansion." *Blood.* 8.1(1993):227-233.
Blyszczuk et al. "Embryonic Stem Cells Differentiate into Insulin-Producing Cells without Selection of Nestin-Expressing Cells." *Int. J. Dev. Biol.* 48(2004):1095-1104.
Boerner et al. "Production of Antigen-Specific Human Monoclonal Antibodies from in vitro-Primed Human Splenocytes." *J. Immunol.* 147.1(1991):86-95.
Bohmer et al. "Fetal Cell Isolation from Maternal Blood Cultures by Flow Cytometric Hemoglobin Profiles." *Fetal Diagn. Ther.* 17.2(2002):83-89.
Boitano et al. "Aryl Hydrocarbon Receptor Antagonists Promote the Expansion of Human Hematopoietic Stem Cells." *Science.* 329.5997(2010):1345-1348.
Bongers et al. "Kinetics of Dipeptyl Peptidase IV Proteolysis of Growth Hormone-Releasing Factor and Analogs." *Biochim. Biophs. Acta.* 1122(1992):147-153.
Bonora-Centelles et al. "Sequential Hepatogenic Transdifferentiation of Adipose Tissue-Derived Stem Cell: Relevance of Different Extracellular Signaling Molecules, Transcription Factors Involved, and Expression of New Key Marker Genes." *Cell Transplant.* 18.12(2009):1319-1340.
Borthwick et al. "A Comparison of Cupruretic Responses to Various Tetramines and D-penicillamine." *J. Lab. Clin. Med.* 95.4(1980):575-580.
Brandt et al. "Ex Vivo Expanstion of Autologous Bone Marrow CD34+ Cells with Porcine Microvascular Endothelial Cells Results in a Graft Capable of Rescuing Lethally Irradiated Baboons." *Blood.* 94.1(1999):106-113.
Brazelton et al. "From Marrow to Brain: Expression of Neuronal Phenotypes in Adult Mice." *Science.* 290.5497(2000):1775-1779.
Breitman et al. "Induction of Differentiation of the Human Promylocytic Leukemia Cell Line (HL-60) by Retinoic Acid." *PNAS.* 77.5(1980):2936-2940.
Briddell et al. "Purification of CD34+ Cells is Essential for Optimal Ex Vivo Expansion of Umbilical Cord Blood Cells." *J. Hematother.* 6(1997):145-150.
Brigham et al. "Rapid Communication: In vivo Transfection of Murine Lungs with a Functioning Prokaryotic Gene Using a Liposome Vehicle." *J. Med. Sci.* 298.4(1989):278-281.
Brott et al. "Flow Cytometric Characterization of Perfused Human Bone Marrow Cultures: Identification of the Major Cell Lineages and Correlation with the CFU-GM Assay." *Cytometry Part A.* 53A(2003):22-27.
Broxmeyer. "Regulation of Hematopoiesis by Chemokine Family Members." *Int. J. Hematol.* 74(2001):9-17.
Brugger et al. "Ex Vivo Expanstion of Enriched Peripheral Blood CD34+ Progenitor Cells by Stem Cell Factor, Interleukin-1β (IL-1β), IL-6, IL-3, Interferon-γ, and Erythropoietin." *Blood.* 81.10(1993):2579-2584.
Brugger et al. "Reconstitution of Hematopoiesis after High-Dose Chemotherapy by Autologous Progenitor Cells Generated Ex Vivo." *N. Eng. J. Med.* 333.5(1995):283-287.
Brugnera et al. "Cloning, Chromosomal Mapping and Characterization of the Human Metal-Regulatory Transcription Factor MTF-1." *Nucleic Acids Res.* 22.15(1994):3167-3173.
Bryder et al. "Hematopoietic Stem Cells: The Paradigmatic Tissue-Specific Stem Cell." *Am. J. Pathol.* 169.2(2006):338-346.
Burgada et al. "Synthesis of New Phosphonated Tripod Ligands as Putative New Therapeutic Agents in the Chelation Treatment of Metal Intoxications." *Eur. J. Org. Chem.* (2001):349-352.
Buskin et al. "Identification of a Myocyte Nuclear Factor that Binds to the Muscle-Specific Enhancer of the Mouse Muscle Creatine Kinase Gene." *Mol. Cell. Biol.* 9.6(1989):2627-2640.
Butt. "Introduction to Chemical Reactor Therapy." *Reaction Kinetics and Reactor Design.* Boca Raton, FL: CRC Press. (1980):184-241.

(56) References Cited

OTHER PUBLICATIONS

Cable et al. "Exposure of Primary Rat Hepatocytes in Long-Term DMSO Culture to Selected Transition Metals Induces Hepatocyte Proliferation and Formation of Duct-Like Structure." *Hepatol.* 26.6(1997):1444-1457.

Cakir-Kiefer et al. "Kinetic Competence of the cADP-Ribose-CD38 Complex as an Intermediate in the D38/NAD+ Glycohydrolase-Catalysed Reactions: Implication for CD38 Signalling." *Biochem. J.* 358(2001):399-406.

Caliaro et al. "Response of Four Human Ovarian Carcinoma Cell Lines to All-Trans Retinoic Acid: Relationship with Induction of Differentiation and Retinoic Acid Receptor Expression." *Int. J. Cancer.* 56.5(1994):743-748.

Canaple et al. "Improving Cell Encapsulation Through Size Control." *J. Biomater. Sci. Polym. Ed.* 13.7(2002):783-796.

Casal et al. "In utero Transplantation of Fetal Liver Cells in the Mucopolysaccharidosis Type VII Mouse Results in Low-Level Chimerism, but Overexpression of β-Glucuronidase can Delay Onset of Clinical Signs." *Gene Ther.* 97.6(2001):1625-1634.

Cepko. "Overview of the Retrovirus Transduction System." *Short Protocols in Molecular Biology.* Unit 9/10-9/14. (1984):9-41-9-57.

Chang et al. "Procedures for Microencapsulation of Enzymes, Cells and Genetically Engineered Microorganisms." *Mol. Biotechnol.* 17.3(2001):249-260.

Charrier et al. "Normal Human Bone Marrow CD34+CD133+ Cells Contain Primitive Cells Able to Produce Different Categories of Colony-Forming Unit Megacryocytes in vitro." *Exp. Hematol.* 30(2002):1051-1060.

Chen et al. "Differentiation of Rat Marrow Mesenchymal Stem Cells into Pancreatic Islet Beta-Cells." *World J. Gastroenterol.* 10.20(2004):3016-3020.

Chen et al. "Fibroblast Growth Factor (FGF) Signaling Through PI 3-Kinase and Akt/PKS is Required for Embryoid Body Differentiation." *Oncogene.* 19(2000):3750-3756.

Chen et al. "Therapeutic Benefit of Intravenous Administration of Bone Marrow Stromal Cells after Cerebral Ischemia in Rats." *Stroke.* 32.4(2001):1005-1011.

Chia et al. "Multi-Layered Microcapsules for Cell Encapsulation." *Biomaterials.* 23.2(2002):849-856.

Chisi et al. "Inhibitory Action of the Peptide AcSDKP on the Proliferative State of Hematopoietic Stem Cells in the Presence of Captopril but not Lisinopril." *Stem Cells.* 15.6(1997):455-460.

Chivu et al. "In Vitro Hepatic Differentiation of Human Bone Marrow Mesenchymal Stem Cells under Differential Exposure to Liver-Specific Factors." *Translational Res.* 154.3(2009):122-132.

Chowhudry et al. "Long-Term Improvement of Hypercholesterolemia after ex Vivo Gene Therapy in LDLR-Deficient Rabbits." *Science.* 254(1991):1802-1805.

Christopherson et al. "Cell Surface Peptidase CD26/Dipeptidylpeptidase IV Regulates CXCL12/Stromal Cell-Derived Factor-1?-Mediated Chemotaxis of Human Cord Blood CD34+ Progenitor Cells."*J. Immunol.* 169(2002):7000-7008.

Christopherson et al. "Modulation of Hematopoietic Stem Cell Homing and Engraftment by CD26." *Science.* 305(2004):1000-1003.

Cicuttini et al. "Support of Human Cord Blood Progeniotr Cells on Human Stromal Cell Lines Transformed by SV40 Larger T Antigen Under the Influence of an Inducible (Metallothionein) Promoter." *Blood.* 80.1(1992):102-112.

Cole et al. "The EBV-Hybridoma Technique and its Application to Human Lung Cancer." *Monoclonal Antibodies Cancer Ther.* (1985):77-96.

Collins et al. "Stirred Culture of Peripheral and Cord Blood Hematopoietic Cells Offers Advantages over Traditional Static Systems for Clinically Relevant Applications." *Biotechnol. Bioeng.* 59.5(1998):534-543.

Colter et al. "CD34+ Progenitor Cell Selection: Clinical Transplantation, Tumor Cell Purging, Gene Therapy, Ex Vivo Expansion, and Cord Blood Processing." *J. Hematol.* 5(1996):179184.

Corda et al. "Functional Aspects of Protein Mono-ADP-Ribosylation." *EMBO J.* 22.9(2003):1953-1958.

Côté et al. "Response to Histone Deacetylase Inhibition of Novel PML/RARα Mutants Detected in Retinoic Acid-Resistant APL Cells." *Blood.* 100.7(2002):2586-2596. (Abstract Only).

Coutinho et al. "Effects of Recombinant Human Granulocyte Colony-Stimulating Factor (CSF), Human Granulocyte Macrophage-CSF, and Gibbon Interleukin-3 on Hemaotpoiesis in Human Long-Term Bone Marrow Culture." *Blood.* 75.11(1990):2118-2129.

Cowan et al. "Bone Morphogenetic Protein 2 and Retinoic Acid Accelerate in Vivo Bone Formation, Osteoclast Recruitment, and Bone Turnover." *Tissue Eng.* 11.3-4(2005):645-658.

Cristiano et al. "Hepatic Gene Therapy: Adenovirus Enhancement of Receptor-Mediated Gene Delivery and Expression in Primary Hepatocytes." *PNAS.* 90(1993):2122-2126.

Curiel et al. "Adenovirus Enhancement of Transferrin-Polylysine-Medaited Gene Delivery." *PNAS.* 88(1991):8850-8854.

Czauderna et al. "Functional Studies of the PI(3)-Kinase Signalling Pathway Employing Synthetic and Expressed siRNA." *Nucleic Acids Res.* 31.2(2003):670-682.

Czyz et al. "Potential of Embryonic and Adult Stem Cell in vitro." *Biol. Chem.* 384(2003):1391-1409.

Dabeva et al. "Transcription Factor and Liver-Specific mRNA Expression in Facultative Epithelial Progenitor Cells of Liver and Pancreas." *Am. J. Pathol.* 147(1995):1633-1648. (Abstract Only).

Dahl et al. "Transformation of Hematopoietic Cells by the Ski Oncoprotein Involves Repression of Retinoic Acid Receptor Signaling." *PNAS.* 95.19(1998):11187-11192.

Dai et al. "Gene Therapy Via Primary Myoblasts: Long-Term Expression of Factor IX Protein Following Transplantation in vivo." *PNAS.* 89(1992):10892-10895.

Dalyot et al. "Adult and Neonatal Patterns of Human Globin Gene Expression are Recapitulated in Liquid Cultures." *Exp. Hematol.* 20(1992):1141-1145. (Abstract Only).

Danos et al. "Safe and Efficient Generation of Recombinant Retroviruses with Amphotropic and Ecotropic Host Ranges." *PNAS.* 85(1988):6460-6464.

Datta et al. "Ionizing Radiation Activates Transcription of the *EGR1* Gene via Carg Elements." *PNAS.* 89(1992):10149-10153.

De Bruyn et al. "Comparison of the Coexpression of CD33 and HLA-DR Antigens on CD34+ Purified Cells from Human Cord Blood Marrow." *Stem Cells.* 13(1995):281-288.

de la Cruz et al. "Do Protein Motifs Read the Histone Code?" *BioEssays.* 27.2(2005):164-175.

De Luca et al. "Retinoic Acid is a Potent Regulator of Growth Plate Chondrogenesis." *Endocrinol.* 141.1(2000):346-353. (Abstract Only).

De Ridder et al. "Hypoxic Tumor Cell Radiosensitization: Role of the iNOS/NO Pathway." *Bull. Cancer.* 95.3(2008):282-291.

De Wynter et al. "CD34+AC133+ Cells Isolated from Cord Blood are Highly Enriched in Long-Term Culture-Initiating Cells, NOD/SCID-Repopulating Cells and Dendritic Cell Progenitors." *Stem Cells.* 16(1998):387-396.

Defacque et al. "Expression of Retinoid X Receptor Alpha is Increased Upon Moncytic Cell Differentiation." *Biochem. Biophys. Res. Commun.* 220(1996):315-322.

Desai. "Microfabrication Technology for Pancreatic Cell Encapsulation." *Expert Opin. Biol. Ther.* 2.6(2002):633-646.

Dexter et al. "Conditions Controlling the Proliferation of Haemopoietic Stem Cells In Vitro." *J. Cell Physiol.* 91(1976):335-344.

DOD, Tetraethylene Pentamine DOD Hazardous Material Information; 6810-00F01771. (1991).

Donovan et al. "The End of the Beginning for Pluripotent Stem Cells." *Nature.* 414.6859(2001):92-97.

Dosil et al. "Mitogenic Signalling and Substrate Specificity of the Flk2/Flt3 Receptor Tyrosine Kinase in Fibroblasts and Interleuk in 3-Dependent Hematopoietic Cells." *Mol. Biol.* 13.1(1993):6572-6585. (Abstract Only).

Douer et al. "All-Trans-Retinoic Acid Effects the Growth, Differentiation and Apoptosis of Normal Human Myeloid Progenitors Derived from Purified CD34+ Bone Marrow Cells." *Leukemia.* 14.5(2000):874-881.

Drayson et al. "Cell Proliferation and CD11b Expression are Controlled Independently During HL60 Cell Differentiation Initiated by

(56) References Cited

OTHER PUBLICATIONS 1,25α-Dihydroxyvitamin D3 or All-*trans*-Retinoic Acid." *Exp. Cell Res.* 266.1(2001):126-134. (Abstract Only).
Dubois et al. "Treatment of Wilson's Disease with Triethylene Tetramine Hydrochloride (Trientine)." *J. Ped. Gastroenterol. Nutr.* 10.1(1990):77-81. (Abstract Only).
Duncan et al. "Repair of Mylein Disease: Strategies and Progress in Animal Models." *Mol. Med. Today.* 3.12(1997):554-561. (Abstract Only).
Ebner et al. "Distinct Roles for PI3K in Proliferation and Survival of Oligodendrocyte Progenitor Cells." *J. Neurosci. Res.* 62(2000):336-345.
Eglitis. "Gene Expression in Mice after High Efficiency Retroviral-Mediated Gene Transfer." *Science.* 230(1985):1395-1398.
Ehring et al. "Expansion of HPCs from Cord Blood in a Novel 3D Matrix." *Cytotherapy.* 5.6(2003):490-499.
Eipers et al. "Retroviral-Mediated Gene Transfer in Human Bone Marrow Cells Grown in Continuous Perfusion Culture Vessels." *Blood.* 86.10(1995):3754-3762.
Emerson et al. "Ex Vivo Expansion of Hematopoietic Precursors, Progenitors, and Stem Cells: The Next Generation of Cellular Therapeutics." *Blood.* 87.8(1996):3082-3088.
Englisch et al. "Chemically Modified Oligonucleotides as Probes and Inhibitors." *Angew. Chem.* 30.6(1991):613-629.
Farre et al. "FDF-4 Increases in vitro Expansion Rate of Human Adult Bone Marrow-Derived Mesenchymal Stem Cells." *Growth Factors.* 25.2(2007):71-76.
Fasouliotis et al. "Human Umbilical Cord Blood Banking and Transplantation: A Atet of the Art." *Eur. J. Obstet. Gynecol. Reprod. Biol.* 90.1(2000):13-25.
Feldman. "Israeli Start-Up Gamida-Cell to Receive Prize." *Globes Online.* Web. (2004).
Ferbeyre. "PML A Target of Translocations in APL is a Regulator of Cellular Senescence." *Leukemia.* 16(2002):1918-1926. (Abstract Only).
Ferrari et al. "Muscle Regeneration by Bone Marrow-Derived Myogenic Progenitors." *Science.* 279.5356(1998): 1528-1530.
Ferrari et al. "Erratum: Muscle Regeneration by Bone Marrow-Derived Myogenic Progenitors." *Science.* 281.5379(1998):923.
Ferrero et al. "The Metamorphosis of a Molecule: From Soluble Enzyme to the Leukocyte Receptor CD38." *J. Leukocyte Biol.* 65.2(1999):151-161.
Ferry et al. "Retroviral-Mediated Gene Transfer into Hepatocytes in vivo." *PNAS.* 88(1991):8377-8381.
Fibach et al. "Growth of Human Normal Erythroid Progenitors in Liquid Culture: A Comparison with Colony Growth in Semisolid Culture." *Int. J. Cell Cloing.* 9(1991):57-64. (Abstract Only).
Fibach et al. "Normal Differentiation of Myeloid Leukemic Cells Induced by a Protein Differentiation-Inducing Protein." *Nat. New Biol.* 237.78(1972):276-278.
Fibach et al. "Proliferation and Maturation of Human Erythroid Progenitors in Liquid Culture." *Blood.* 73.1(1989):100-103. (Abstract Only).
Fibach et al. "Retinoic Acid Antagonist Inhibits CD38 Antigen Expression on Human Hematopoietic Cells." *Blood.* 100.11(2002):172A. (Abstract #644).
Fibach et al. "The Two-Step Liquid Culture: A Novel Procedure for Studying Maturation of Human Normal and Pathological Erythroid Precursors." *Stem Cells.* 11.S1(1993):36-41. (Abstract Only).
Fietz et al. "Culturing Human Umbilical Cord Blood: A Compariso of Mononuclear Vs CD34+ Selected Cells." *Bone Marrow Transplant.* 23(1999):1109-1115.
Filvaroff et al. "Functional Evidence for an Extracellular Calcium Receptor Mechanism Triggering Tyrosine Kinase Activation Associated with Mouse Keratinocyte Differentiation." *J. Biol. Chem.* 369.34(1994):21735-21740.
Fingl et al. "General Principles." *Basis of THerapeutics.* New York: Macmillan Publishing Co., Inc. 5th ed. (1975):1-46.

Fisch et al. "Generation of Antigen-Presenting Cells for Soluble Protein Antigens ex vivo from Peripheral Blood CD34+ Hematopoietic Progenitor Cells in Cancer Patients." *Eur. J. Immunol.* 26(1996):595-600.
Fishwild et al. "High-Avidity Human IgGκ Monoclonal Antibodies from a Novel Strain of Minilocus Transgenic Mice." *Nat. Biotechnol.* 14(1996):845-851.
Flores et al. "Akt-Mediated Survival of Oligodendrocytes Induced by Neuregulins." *J. Neurosci.* 20.20(2000):7622-7630.
Flotte et al. "Expression of the Cystic Fibrosis Transmembrane Conductance Regulators from a Novel Adeno-Associated Virus Promoter." *J. Biol. Chem.* 268.5(1993):3781-3790.
Flotte et al. "Gene Expression from Adeno-Associated Virus Vectors in Airways Epithelial Cells." *Am. J. Resp. Cell Mol. Biol.* 7(1992):349-356.
Forraz et al. "AC133+ Umbilical Cord Blood Progenitors Demonstrate Rapid Self-Renewal and Low Apoptosis." *Br. J. Haematol.* 119.2(2002):516-524.
Fosmire. "Zinc Toxicity." *Am. J. Clin. Nutr.* 51.2(1990):225-227. (Abstract Only).
Freedman et al. "Generation of Human T Lymphocytes from Bone Marrow CD34+ Cells in vitro." *Nat. Med.* 2.1(1995):46-51.
Freshney, ed. "Culture of Specific Cell Types." *Culture of Animal Cells.* New York: John Wiley and Sons. Third Ed. (1994):309-311, 327-328.
Fry. "Phosphoinositide 3-Kinase Signalling in Breast Cancer: How Big a Role Might it Play?" *Breast Cancer Res.* 3.5(2001):304-312.
Fukuda. "Development of Regenerative Cardiomyoctes from Mesenchymal Stem Cells for Cardiovascular Tissue Engineering." *Artif. Organs.* 25.3(2001):187-193.
Gagnon et al. "Activation of Protein Kinase B and Induction of Adipogenesis by Insulin in 3T3-L1 Preadipocytes." *Diabetes.* 48(1999):691-698.
Gallacher et al. "Isolation and Characterization of Human CD34-Lin- and CD34+Lin-Hematopoietic Stem Cells Using Cell Surface Markers AC133 and CD7." *Blood.* 95.9(2000):2813-2820.
Gang et al. "Skeletal Myogenic Differentiation of Mesenchymal Stem Cells Isolated from Human Umbilical Cord Blood." *Stem Cells.* 22.4(2004):617-624.
Garmy-Susini et al. "Integrin α4β1-VCAM-1-Mediated Adhesion Between Endothelial and Mural Cells is Required for Blood Vessel Maturation." *J. Clin. Invest.* 115.6(2005):1542-1551.
Gloeckner et al. "New Miniaturization Hollow-Fiber Bioreactor for in Vivo Like Cell Culture, Cell Expansion, and Production of Cell-Derived Products." *Biotechnol. Prog.* 17(2001):828-831.
Gluckman et al. "Hematopoietic Reconstitution in a Patient with Fanconi's Anemia by Means of Umbilical-Cord Blood from an HLA-Identical Sibling." *New Eng. J. Med.* 321.17(1989):1174-1178.
Gossler et al. "Transgenesis by Means of Blasocyst-Derived Embryonic Stem Cell Lines." *PNAS.* 83(1986):9065-9069.
Gould-Fogerite et al. "Chimerasome-Mediated Transfer in vitro and in vivo." *Gene.* 84.2(1989):429-438. (Abstract Only).
Grande et al. "Physiological Levels of 1α, 25 Dihydroxyvitamin D3 Induce the Monocytic Commitment of CD34+ Hematopoietic Progenitors." *J. Leukoc. Biol.* 71.4(2002):641-651.
Grenda et al. "Mice Expressing a Neutrophil Elastase Mutation Derived from Patients with Severe Congenital Neutrophenia have Normal Granulopoiesis." *Blood.* 100.9(2002):3221-3228.
Gur et al. "Tolerance Induction by Megadose Hematopoietic Progenitor Cells: Expansion of Veto Cells by Short-Term Culture of Purified Human CD34+ Cells." *Blood.* 99.11(2002):4174-4181.
Haj-Ahmad et al. "Development of a Helper-Independent Human Adenovirus Vector and its Use in the Transfer of the Herpes Simplex Virus Thymidine Kinase Gene." *J. Virol.* 57.1(1986):267-274.
Hamilton. "Stem Cell Technology to Treat Leukemia Patients Show Promise." *Wall Street Journal Online.* (2003).
Hammond et al. "Suppression of in vitro Granulocytopoiesis by Captopril and Penicillamine." *Exp. Hematol.* 16(1988):674-680.
Handgretinger et al. "Biology and Plasticity of CD133+ Hematopoietic Stem Cells." *Ann. NY Acad. Sci.* 996(2003):141-151.
Hatayama et al. "Regulation of HSP70 Synthesis by Cupric Sulfate and Zinc Sulfate in Thermotolerant HeLa Cells." *J. Biochem.* 114.4(1993):592-597. (Abstract Only).

(56) References Cited

OTHER PUBLICATIONS

Haviernik et al. "Tissue Inhibitor of Matrix Metallaproteinase-1 Overexpression in M1 Myeloblasts Impairs IL-6-Induced Differentiation." *Oncogene.* 23.57(2204):9212-9219. (Abstract Only).

Hayashi et al. "Changes in the Balance of Phosphoinositide 3-Kinase/Protein Kianse B (Akt) and the Mitogen-Activated Protein Kinases (ERK/p38MAPK) Determine a Phenotype of Visceral and Vascular Smooth Muscle Cells." *J. Cell Biol.* 145.4(1999):727-740.

Haylock et al. "Ex Vivo Expansion and Maturation of Peripheral Blood CD34+ Cells Into the Myeloid Lineage." *Blood.* 80.5(1992):1405-1412.

Hermonat et al. "Use of Adeno-Associated Virus as a Mammalian DNA Cloning Vector: Transduction of Neomycin Resistance into Mammalian Tissue Culture Cells." *PNAS.* 81(1984):6466-6470.

Herz et al. "Adenovirus-Mediated Transfer of Low Density Lipoprotein Receptor Gene Acutely Accelerates Cholesterol Clearance in Normal Mice." *PNAS.* 90(1993):2812-2816.

Heslop et al. "Long-Term Restoration of Immunity Against Epstein-Barr Virus Infection by Adoptive Transfer of Gene-Modified Virus-Specific T Lymphocytes." *Nat. Med.* 2.5(1996):551-555.

Heuchel et al. "The Transcription Factor MTF-1 is Essential for Basal and Heavy Metal-Induced Metallotionein Gene Expression." *EMBO J.* 13.12(1994):2870-2875.

Hida et al. "Existence of Retinoic Acid-Receptor-Independent Retinoid X-Receptor-Dependent Pathway in Myeloid Cell Function." *Japan. J. Pharmacol.* 85.1(2001):60-69.

Higashi et al. "Autologous Bone-Marrow Mononuclear Cell Implantation Improves Endothelium-Dependent Vasodilation in Patients with Limb Ischemia." *Circulation.* 109(2004):1215-1218.

Hino et al. "A Long-Term Culture of Human Hepatocytes which Show a High Growth Potential and Express their Differential Phenotypes." *Biochem. Biophys. Res. Commun.* 256.1(1999):184-191. (Abstract Only).

Hirase et al. "Anemia and Neutropenia in a Case of Copper Deficiency: Role of Copper in Normal in Hematopoiesis." *Acta Haematol.* 87.4(1992):195-197.

Hirose et al. "Identification of a Transposon-Related RNA Down-Regulated by Retinoic Acid in Embryonic Carcinoma and Embryonic Stem Cells." *Exp. Cell Res.* 221.2(1995):294-300. (Abstract Only).

Hmama et al. "1α, 25-Dihydroxyvitamin D3-Induced Myeloid Cell Differentiation is Regulated by a Vitamin D Receptor-Phosphatidylinositol 3-Kinase Signaling Complex." *J. Exp. Med.* 190.11(1999):1583-1594.

Hoffman et al. "Zinc-Induced Copper Deficiency." *Gastroenterol.* 94.2(1988):508-512. (Abstract Only).

Hofmeister et al. "Ex vivo Expansion of Umbilical Cord Blood Stem Cells for Transplantation: Growing Knowledge from the Hematopoietic Niche." *Bone Marrow Transplant.* 39(2007):11-23.

Holleman. "Triethylene Tetramine." Chemical Hazard Iformation Profile Draft Report. (1990).

Hoogenboom et al. "By-Passing Immunisation: Human Antibodies from Synthetic Repertoires of Germline VH Gene Segments Rearranged in Vitro." *J. Mol. Biol.* 227(1992):381-388.

Hori et al. "Growth Inhibitors Promote Differentiation of Insulin-Producing Tissue from Embryonic Stem Cells." *PNAS.* 99.25(2002):16105-16110.

Hottinger et al. "The Copper Chelator D-Penicillamine Delays Onset of Disease a Extends Survival in a Transgenic Mouse Model of Familial Amyotrophic Lateral Sclerosis." *Eur. J. Neurosci.* 9.7(1997):1548-1551. (Abstract Only).

Howard et al. "Formation and Hydrolysis of Cyclic Acid ADP-Ribose Catalyzed by Lymphocyte Antigen CD38." *Science.* 262. 5136(1993):1056-1059.

Huang et al. "Differentiation of Human U937 Promonocytic Cells is Impaired by Moderate Copper-Deficiency." *Exp. Biol. Med.* 226. 3(2001):222-228.

Huber et al. "Retroviral-Mediated Gene Therapy for the Treatment of Hepatocellular Carcinoma: An Innovative Approach for Cancer Therapy." *PNAS.* 88(1991):8039-8043.

Hühn et al. "Molecular Analysis of CD26-Mediated Signal Transduction in T Cells." *Immunol. Lett.* 72(2000):127-132.

Hutvánger et al. "RNAi: Nature Abhors a Double-Strand." *Curr. Opin. Genet. Dev.* 12(2002):225-232.

Hwu et al. "Functional and Molecular Characterization fo Tumor-Infiltrating Lymphocytes Transduced with Tumor Necrosis Factor-α cDNA for the Gene Therapy of Cancer in Humans." *J. Immunol.* 150.9(1993):4104-4115.

Imai et al. "Selective Secretion of Chemoattractants for Haemapoietic Progenitor Cells by Bone Marrow Endothelial Cells: A Possible Role in Homing of Haemopoietic Progenitor Cells to Bone Marrow." *Brit. J. Haematol.* 106(1999):905-911.

Imitola et al. "Directed Migration of Neural Stem Cells to Sites of CNS Injury by the Stroman Cell-Derived Factor 1α/CXC Chemokine Receptor 4 Pathway." *PNAS.* 101.52(2004):18117-18122.

Inbar et al. "Localization of Antibody-Combining Sites Within the Variable Portions of Heavy and Light Chains." *PNAS.* 69.9(1972):2659-2662.

Itoh et al. "Inhibition of Urokinase Receptor (uPAR) Expression by RNA-Cleaving Catalytic DNA (DNAzyme) Containing Antisense uPAR." *Mol. Ther.* 5.5(2002):S134. (Abstract #409).

Jackson et al. "Regeneration of Ischemic Cardiac Muscle and Vascular Endothelium by Adult Stem Cells." *J. Clin. Invest.* 107. 11(2001):1395-1402.

Jelinek et al. "Novel Bioreactors for the ex vivo Cultivation of Hematopoietic Cells." *Eng. Life Sci.* 2.1(2002):15-18.

Jiang et al. "Phosphatidylinositol 3-Kinase Signaling Mediates Angiogenesis and Expression of Vascular Endothelial Growth Factor in Endothelial Cells." *PNAS.* 97.4(2000):1749-1753.

Johnson et al. "Synthesis and Biological Activity of High-Affinity Retinoic Acid Receptor Antagonists." *Bioorg. Med. Chem.* 7.7(1999):1321-1338.

Johnson et al. "The Cytokines IL-3 and GM-CSF Regulate the Transcriptional Activity of Retinoic Acid Receptors in Different in vitro Models of Myeloid Differentiation." *Blood.* 99.3(2002):746-753.

Jones et al. "Replacing the Complementarity-Determining Regions on a Human Antibody with Those from a Mouse." *Nature.* 321(1986):522-525.

Kahn et al. "Overexpression of CXCR4 on Human CD34+ Progenitors Increases their Proliferation, Migration, and NOD/SCID Repopulation." *Blood.* 103.8(2004):2942-2949.

Kähne et al. "Dipeptidyl Peptidase IV: A Cell Surface Peptidase Involved in Regulating T Cell Growth (Review)." *Int. J. Mol. Med.* 4(1999):3-15.

Kang et al. "Retinoic Acid and its Receptors Repress the Expression and Transactivation Functions of Nur77: A Possible Mechanism for the Inhibition of Apoptosis by Retinoic Acid." *Exp. Cell Res.* 256(2000):545-554.

Kassis et al. "Isolation of Mesenchymal Stem Cells from G-CSF-Mobilized Human Peripheral Blood Using Fibrin Microbeads." *Bone Marrow Transplant.* 37.10(2006):967-976.

Kastner et al. "Positive and Negative Regulation of Granulopoiesis by Endogenous RARalpha."*Blood.* 97.5(2001):1314-1320. (Abstract Only).

Kaufman et al. "Translational Efficiency of Polycistronic mRNAs and Their Utilization to Express Heterologous Genes in Mammalian Cells." *EMBO J.* 6.1(1987):187-193.

Kawa et al. "Stem Cell Factor and/or Endothelin-3 Dependent Immortal Melanoblast and Melanocyte Populations Derived from Mouse Neural Crest Cells." *Pigment Cell Res.* 13.58(2000):73-80.

Kay et al. "Hepatic Gene Therapy: Persistent Expression of Human α1-Antitrypsin in Mice after Direct Gene Delivery In Vivo." *Hum. Gene Ther.* 3(1992):641-647.

Keith et al. "Multicomponent Therapeutics for Networked Systems." *Nat. Rev. Drug Disc.* 4(2005):1-8.

Kern et al. "Comparative Analysis of Mesenchymal Stem Cells from Bone Marrow, Umbilial Cord Blood, or Adipose Tissue." *Stem Cells.* 24(2006):1294-1301.

Khachigian. "DNAzymes: Cutting a Path to a New Class of Therapeutics." *Curr. Opin. Mot Ther.* 4.2(2002):119-121.

Kim. "Differentiation and Identification of the Two Catalytic Metal Binding Sites in Bovine Lens Leucine Aminopeptidase by X-Ray Crystallography." *PNAS.* 90.11(1993):5006-5010.

(56) References Cited

OTHER PUBLICATIONS

Kishimoto et al. "Molecular Mechanism of Human CD38 Gene Expression by Retinoic Acid." *J. Biol. Chem.* 273.25(1998):15429-15434.

Kitanaka et al. "CD38 Ligation in Human B Cell Progenitors Triggers Tyrosine Phophorylation of CD19 and Association of CD19 with Lyn and Phosphatidylinositol 3-Kinase." *J. Immunol.* 159.1(1997):184-192. (Abstract Only).

Kizaki et al. "Regulation of Manganese Superoxide Dismutase and Other Antioxidant Genes in Normal and Leukemic Hematopoietic Cells and Their Relationship to Cytotoxicity by Tumor Necrosis Factor." *Blood.* 82.4(1993):1142-1150.

Kobari et al. "CD133+ Cell Selection is an Alternative to CD34+ Cell Selection for Ex Vivo Expansion of Hematopoietic Stem Cells." *J. Hematother. Stem Cell Res.* 10.2(2001):273-281.

Kocher et al. "Neovascularization of Ischemic Myocardium by Human Bone-Marrow-Derived Angioblasts Prevents Cardiomyocyte Apoptosis, Reduces Remodeling and Improves Cardiac Function." *Nat. Med.* 7.4(2001):430-436.

Köhler et al. "Defining Optimum Conditions for the Ex Vivo Expansion of Human Umbilical Cord Blood Cells Influences of Progenitor Enrichment, Interference with Feeder Layers, Early-Acting Cytokines and Agitation of Culture Vessels." *Stem Cells.* 17.1(1999):19-24.

Kohroki et al. "Induction of Differentiation and Apoptosis by Dithizone in Human Myeloid Leukemia Cell Lines." *Leuk. Res.* 22.5(1998):405-412.

Koizumi et al. "Large Scale Purification of Human Blood CD34+ Cells from Cryopreserved Peripheral Blood Stem Cells, Using a Nylon-Fiber Syringe System and Immunomagnetic Microspheres." *Bone Marrow Transplant.* 26(2000):787-793.

Koller et al. "Large-Scale Expansion of Human Stem and Progenitor Cells from Bone Marrow Mononuclear Cells in Continuous Perfusion Cultures." *Blood.* 82.2(1993):378-384.

Krause et al. "Multi-Organ, Multi-Lineage Engraftment by a Single Bone Marrow-Derived Stem Cell." *Cell.* 105.3(2001):369-377. (Abstract Only).

Kronenwett et al. "Oligodeoxyribonucleotide Uptake in Primary Human Hematopoietic Cells is Enhanced by Cationic Lipids and Depends on the Hematopoietic Cell Subset." *Blood.* 91.3(1998):852-862.

Ku et al. "Committing Embryonic Stem Cells to Early Endocrine Pancreas In Vitro." *Stem Cells.* 22(2004):1205-1217.

Kumagai et al. "Ligation of CD38 Suppresses Human B Lymphopoiesis." *J. Exp. Med.* 181.3(1995):1101-1110.

Labrecque et al. "Impaired Granulocytic Differentiation in Vitro in Hematopoietic Cells Lacking Retinoic Acid Receptors α1 and γ." *Blood.* 92.2(1998):607-615.

Lagasse et al. "Purified Hematopoietic Stem Cells can Differentiate into Hepatocytes in vivo." *Nat. Med.* 6.11(2000):1229-1234.

Lam et al. "Preclinical ex vivo Expansion of Cord Blood Hematopoietic Stem and Progenitor Cells: Duration of Culture; the Media, Serum Supplements, and Growth Factors Used; and Engraftment in NOD/SCID Mice." *Transfusion.* 41.12(2001):1567-1576.

Lambeir et al. "Kinetic Investigation of Chemokine Truncation by CD26/DipeptidylPeptidase IV Reveals a Striking Selectivity within the Chemokine Family." *J. Biol. Chem.* 276.32(2001):29839-29845.

Lange et al. "Biological and Clinical Advances in Stem Cell Expansion." *Leukemia.* 10(1996):943-945.

Lapidot et al. "Cytokine Stimulation of Multilineage Hematopoiesis from Immature Human Cells Engrafte in SCID Mice." *Science.* 255(1992):1137-1141. (Abstract Only).

Larrick et al. "PCR Amplification of Antibody Genes." *Methods: A Companion to Methods in Enzymology.* 2.2(1991):106-110.

Lassila et al. "Role for Lys-His-Gly-NH2 in Avian and Murine B Cell Development." *Cell. Immunol.* 122.2(1989):319-328.

Lau et al. "A Peptide Molecule Mimicking the Copper (II) Transport Site of Human Serum Albumin." *J. Biol. Chem.* 249.18(1974):5878-5884.

Lavigne et al. "Enhanced Antisense Inhibition of Human Immunodeficiency Virus Type 1 in Cell Cultures by DLS Delivery System." *Biochem. Biophys. Res. Commun.* 237(1997):566-571.

Lawlor et al. "Coordinate Control of Muscle Cell Survival by Distinct Insulin-Like Growth Factor Activated Signaling Pathways." *J. Cell Biol.* 151.6(2000):1131-1140.

Lebkowski et al. "Rapid Isolation and Serum-Free Expansion of Human CD34+ Cells." *Blood Cells.* 20(1994):404-410.

Lee et al. "Clonal Expansion of Adult Rat Hepatic Stem Cell Line by Suppression of Asymmetric Cell Kinetics (SACK)." *Biotechnol. Bioeng.* 83.7(2003):760-771.

Lee et al. "Effect of Vitamin D Analog, EB1089, on Hematopoietic Stem Cells from Normal and Myeloid Leukemic Blasts." *Leukemia.* 10(1996):1751-1757.

Lee et al. "Repair of Ischemic Heart Disease with Novel Bone Marrow-Derived Multipotent Stem Cells." *Cell Cycle.* 4.7(2005):861-864.

Lemarchand et al. "Adenovirus-Mediated Transfr of a Recombinant Human α1-Antitrypsin cDNA to Human Endothelial Cells." *PNAS.* 89(1992):6482-6486.

Leslie et al. "An Activating Mutation in the Kit Receptor Abolishes the Stroma Requirement for Growth of ELM Erythropoietin." *Blood.* 92.12(1998):4798-4807.

Lewandowski et al. "Phosphatidylinositol 3-Kinases are Involved in the All-Trans Retinoic Acid-Induced Upregulation of CD38 Antigen on Human Haematopoietic Cells." *Brit. J. Hematol.* 118.2(2002):535-544.

Li et al. "Activation of Phosphatidylinostiol-3 Kinase (PI-3K) and Extracellular Regulated Kinases (Erk1/2) is Involved in Muscarinic Receptor-Mediated DNA Synthesis in Neural Progenitor Cells." *J. Neurosci.* 21.5(2001):1569-1579.

Li et al. "Cell Life Verus Cell Longevity: The Mysteries Surrounding the NAD+ Precursor Nicotinamide." *Curr. Med. Chem.* 13.8(2206):883-895.

Lianguzova et al. "PI3-Kinase Inhibitors LY294002 and Wortmannin have Different Effects on Proliferation of Murine Embryonic Stem Cells." *Tsitologiia.* 48.7(2006):560-568. (Abstact Only).

Lonberg et al. "Antigen-Specific Human Antibodies from Mice Comprising Four Distinct Genetic Modifications." *Nature.* 368(1994):856-859.

Lonberg et al. "Human Antibodies from Transgenic Mice." *Int. Rev. Immunol.* 13.1(1995):65-93.

Lovejoy et al. "Novel "Hybrid" Iron Chelators Derived from Aroylhydrazones and Thiosemicarbazones Demonstrate Selective Antiproliferative Activity Against Tumor Cells." *Blood.* 100.2(2002):666-676.

Lu et al. "A Novel Cell Encapsulation Method Using Photosensitive Poly(allylamine α-Cyanocinnamylideneacetate)." *J. Microencapsul.* 17.2(2000):245-251.

Lu et al. "Cell Encapsulation with Alginate and α-Phenoxycinnamylidene-Acetylated Poly(Allylamine)." *Biotechnol. Bioeng.* 70.5(2000):479-483.

Lu et al. "Intravenous Administration of Human Umbilical Cord Blood Reduces Neurological Deficit in the Rat after Traumatic Brain Injury." *Cell Transplant.* 11.3(2002):275-281. (Abstract Only).

Luft. "Making Sense Out of Antisense Oligodeoxynucleotide Delivery: Getting There is Half the Fun." *J. Mol. Med.* 76(1998):75-76.

Lupi et al. "Endogenous ADP-Ribosylation of the G Protein β Subunit Prevents the Inhibition of Type 1 Adenylyl Cyclase." *J. Biol. Chem.* 275.13(2000):9418-9424.

Lutton et al. "Zinc Porphyrins: Potent Inhibitors of Hematopoiesis in Animal and Human Bone Marrow." *PNAS.* 94(1997):1432-1436.

Ma et al. "Inhibition of Phosphatidylinositol 3-Kinase Causes Apoptosis in Retinoic Acid Differentiated HL-60 Leukemia Cells." *Cell Cycle.* 3.1(2004):67-70.

Mader et al. "A Steroid-Inducible Promoter for the Controlled Overexpression of Cloned Genes in Eukaryotic Cells." *PNAS.* 90(1993):5603-5607.

Madlambayana et al. "Controlling Culture Dynamics for the Expansion of Hematopoietic Stem Cells." *J. Hematother. Stem Cell Res.* 10.4(2001):481-492. (Abstract Only).

(56) References Cited

OTHER PUBLICATIONS

Maitra et al. "Human Mesenchymal Stem Cells Support Unrelated Donor Hematopoietic Stem Cells and Suppress T-Cell Activation." *Bone Marrow Transplant.* 33.6(2004):597-604.
Manome et al. "Coinduction of C-Jun Gene Expression and Internucleosomal DNA Fragmentation by Ionizing Radiation." *Biochem.* 32(1993):10607-10613.
Mar et al. "A Conserved CATTCCT Motif is Required for Skeletal Muscle-Specific Activity of the Cardiac Troponin T Gene Promoter." *PNAS.* 85(1988):6404-6408.
Marcinkowska. "Does the Universal 'Signal Transduction Pathway of Differentiation' Exist? Comparison of Different Cell Differentiation Experimental Models with Differentiation of HL-60 Cells in Response to 1,25-dihydroxyvitamin D3." *Postepy Hig Med Dosw.* 53.2(1999):305-313. (Abstract Only).
Marks et al. "By-Passing Immunization: Building High Affinity Human Antibodies by Chain Shuffling." *Biotechnol.* 10(1992):779-783.
Marks et al. "By-Passing Immunization: Human Antibodies from V-Gene Libraries Displayed on Phage." *J. Mol. Biol.* 222(1991):581-597.
Martelli et al. "Transplants Across Human Leukocyte Antigen Barriers." *Sem. Hematol.* 39.1(2002):48-56.
Matuoka et al. "A Positive Role of Phosphatidylinositol 3-Kinase in Aging Phenotype Expression in Cultured Human Diploid Fibroblasts." *Arch. Gerontol. Geriatr.* 36(2003):203-219.
Matzner et al. "Bone Marrow Stem Cell Gene Therapy of Arylsulfatase A-Deficient Mice, Using an Arylsulfatase a Mutant that is Hypersecreted from Retrovirally Transduced Donor-Type Cells." *Hum. Gene Ther.* 12(2001):1021-1033.
McGrath et al. "Embryonic Expression and Function of the Chemokine SDF-1 and its Receptor, CSCR4." *Dev. Biol.* 213(1999):442-456.
McLaughlin et al. "Adeno-Associated Virus General Transduction Vectors: Analysis of Proviral Structures." *J. Virol.* 62.6(1988):1963-1973.
McNiece et al. "Action of Interleukin-3, G-CSF on Highly Enriched Human Hematopoetic Progenitor Cells: Synergistic Interaction of GM-CSF Plus G-CSF." *Blood.* 74(1989):110-114.
McNiece et al. "CD34+ Cell Selection from Frozen Cord Blood Products Using the Isolex 300i and CliniMACS CD34 Selection Devices." *J. Hematother.* 7(1998):457-461.
McNiece et al. "Ex vivo Expansion of Cord Blood Mononuclear Cells on Mesenchymal Stem Cells." *Cytotherapy.* 6.4(2004):311-317.
Mehta et al. "Human CD38, a Cell-Surface Protein with Multiple Functions." *FASEB J.* 10.12(1996):1408-1417.
Mehta et al. "Involvement of Retinioic Acid Receptor-Alpha-Mediated Signaling Pathway in Induction of CD38 Cell-Surface Antigen." *Blood.* 89.10(1997):3607-3614. (Abstract Only).
Mehta et al. "Retinoid-Mediated Signaling Pathways in CD38 Antigen Expression in Myeloid Leukemia Cells." *Leukemia and Lymphoma.* 32.5-6(1999):441-449.
Meissner et al. "Development of a Fixed Bed Bioreactor for the Expansion of Human Hematopoietic Progenitor Cells." *Cytotechnol.* 30(1999):227-234.
Mezey et al. "Turning Blood into Brain: Cells Beating Neuronal Antigens Generated in Vivo from Bone Marrow." *Science.* 290. 5497(2000):1779-1782.
Migliaccio et al. "Long-Term Generation of Colony-Forming Cells in Liquid Culture of CD34+ Cord Blood Cells in the Presence of Recombinant Human Stem Cell Factor." *Blood.* 79(1992):2620-2627.
Miller et al. "Expansion in vitro of Adult Murine Hemapoietic Stem Cells with Transplantable Lympho-Myeloid Reconstituting Ability." *PNAS.* 94(1997):13648-13653.
Miller. "Progress Toward Human Gene Therapy." *Blood.* 76.2(1990):271-278.
Mills et al. "Regulation of Retinoid-Induced Differentiation in Embryonal Carcinoma PCC4 Aza 1 R Cells: Effects of Retinoid-Receptor Selective Ligands." *Cell Growth Differ.* 7.3(1996):327-337. (Abstract Only).
Miraglia et al. "A Novel Five-Transmembrane Hematopoietic Stem Cell Antigen: Isolation, Characterization,a and Molecular Cloning." *Blood.* 90.12(1997):5013-5021.
Mood et al. "Contribution of JNK, Mek, Mos and PI-3K Signaling to GVBD in Xenopus Oocytes." *Cell Signal.* 16.5(2004):631-642. (Abstract Only).
Moore et al. "Ex Vivo Expansion of Cord Blood-Derived Stem Cells and Progenitors." *Blood Cells.* 20(1994):468-481.
Morier-Teissier et al. "Synthesis and Anti-Tumor Properties of an Anthraquinone Bisubstituted by the Copper Chelating Peptide Gly-Gly-L-His." *J. Med. Chem.* 36(1993):2084-2090. (Abstract Only).
Morimoto et al. "EDTA Induces Differentiation and Suppresses Proliferation of Promyelotic Leukemia Cell Line HL-60: Possible Participation of Zinc." *Biochem. Int* 28.2(1992):313-321.
Morita et al. "Heterogeneity and Hierarchy within Most Primitive Hematopoietic Stem Cell Compartment." *J. Exp. Med.* 207. 6(2010):1173-1182.
Morosetti et al. "Infrequent Alterations of the RARα Gene in Acute Myelogenous Leukemias, Retinoic Acid-Resistant Acute Promyelocytic Leukemias, Myelodysplastic Syndromes, and Cell Lines." *Blood.* 87.10(1996):4399-4403.
Morrison et al. "Identification of a Lineage of Multipotent Hemaotpoietic Progenitors." *Development.* 124(1997):1929-1939.
Morrison et al. "The Long-Term Repopulating Subset of Hematopoietic Stem Cell is Deterministic and Isolatable by Phenotype." *Immunity.* 1(1994):661-673. (Abstract Only).
Morrison. "Success in Specification." *Nature.* 368.6474(1994):812-813.
Mueller et al. "Heterozygous PU.1 Mutations are Associated with Acute Myeloid Leukemia." *Blood.* 100.3(2002):998-1007.
Muench et al. "Interactions Among Colony-Stimulating Factors, IL-1β, IL-6, and Kit-Ligand in the Regulation of Primitive Murine Hematopoietic Cells." *Exp. Hematol.* 20(1992):339-349.
Mulloy et al. "Maintaining the Self-Renewal and Differentiation Potential of Human CD34+ Hematopoietic Cells Using a Single Genetic Element." *Blood.*102.13(2003):4369-4376.
Munshi et al. "Evidence for a Casual Role of CD38 Expression in Granulocytic Differentiation of Human HL-60 Cells." *J. Biol. Chem.* 277.51(2002):49453-49458.
Muramatsu et al. "Reversible Integration of the Dominant Negative Retinoid Receptor Gene for ex vivo Expansion of Hematopoietic Stem/Progenitor Cells." *Biochem. Biophys. Res. Commun.* 285.4(2001):891-896. (Abstract Only).
Murray et al. "Modulation of Murine Lymphocyte and Macrophage Proliferation by Parental Zinc." *Clin. Exp. Immunol.* 53.3(1983):744-749.
Murray et al. "Thrombopoietin, Flt3, and Kit Ligands Together Suppress Apoptosis of Human Mobilized CD34+ Cells and Recruit Primitive CD34+Thy-1+ Cells into Rapid Division." *Exp. Hematol.* 27(1999):1019-1028.
Murry et al. "Haematopoeitic Stem Cells do not Transdifferentiate into Cardiac Myocytes in Myocardial Infarcts." *Nature.* 428(2004):664-668.
Muzyczka. "Use of Adeno-Associated Virus as a General Transduction Vector for Mammalian Cells." *Curr. Topics Microbiol. Immunol.* 158(1992):97-129.
Nagaya et al. "Intravenous Administration of Mesenchymal Stem Cells Improves Cardiac Functions in Rats with Acute Myocardial Infarction through Angiogenesis and Myogenesis." *Am. J. Physiol.* 287(2004):H2670-H2676.
Narita et al. "Cardiomyocyte Differentiation by GATA-4-Deficient Embryonic Stem Cells." *Development.* 122.19(1996):3755-3764.
Neuberger. "Generating High-Avidity Human Mabs in Mice." *Nat. Biotechnol.* 14(1996):826.
Nguyen et al. "The Search for Endogenous Activators of the Aryl Hydrocarbon Receptor." *Chem. Res. Toxicol.* 21.1(2008):102-116.
Nicolau et al. "Liposomes as Carriers for in Vivo Gene Transfer and Expression." *Meth. Enzymol.* 149(1987):157-176.

(56) References Cited

OTHER PUBLICATIONS

Ohishi et al. "Delta-1 Enchances Marrow and Thymus Repopulating Ability of Human CD34+CD38—Cord Blood Cells." *J. Clin. Invest.* 110.8(2002):1165-1174.
Okazaki et al. "Characteristics and Partial Purification of a Novel Cytosolic, Magnesium-Independent, Neutral Sphingomyelinase Activated in the Early Signal Transduction of 1α,25-Dihydroxyvitamin D3-Induced HL-60 Cell Differentiation." *J. Biol. Chem.* 269(1994):4070-4077.
Okuno et al. "Differential Regulation of the Human and Murine CD34 Genes in Hematopoietic Stem Cells." *PNAS.* 99.9(2002):6246-6251.
Olivares et al. "Copper as an Essential Nutrient." *Am. J. Clin. Nutr.* 63(1996):791S-796S. (Abstract Only).
Olson et al. "Tissue-Specific Homing and Expansion of Donor NK Cells in Allogeneic Bone Marrow Transplantation." *J. Immunol.* 183.5(2009):3219-3228.
Orlic et al. "Bone Marrow Cells Regenerate Infarcted Myocardium." *Nature.* 410(2001):701-705.
Orlic et al. "Exogenous Hematopoietic Stem Cells can Regenerate Infarcted Myocardium." *Circulation.* 102(2000):2672.
Orlic et al. "Mobilized Bone Marrow Cells Repair the Infarcted Heart, Improving Function and Survival." *PNAS.* 98.18(2001):10344-10349.
Orlic et al. "Transplanted Adult Bone Marrow Cells Repair Myocardial Infarcts in Mice." *Ann. N.Y. Acad. Sci.* 938(2001):221-230. (Abstract Only).
Osawa et al. "Long-Term Lymphohematopoietic Reconstitution by a Single CD34+-Low Hematopoietic Stem Cell." *Science.* 273.5272(1996):242-245.
Ostrakhovitch et al. "Copper Ions Strongly Activate the Phosphinositide-3-Kinase/Akt Pathway Independent of the Generation of Reactive Oxygen Species." *Arch. Biochem. Biophys.* 397.2(2002):232-239.
Pack et al. "Improved Bivalent Miniantibodies with Identical Avidity as Whole Antibodies, Produced by High Cell Density Fermentation of Escherichia coli." *Biotechnol.* 11(1993);1271-1277.
Paling et al. "Regulation of Embryonic Stem Cell Self-Renewal by Phosphoinositide 3-Kinase-Dependent Signaling." *J. Biol. Chem.* 279.46(2004):48063-48070.
Palmiter. "Regulation of Metallothionein Genes by Heavy Metals Appears to be Mediated by a Zinc-Sensitive Inhibitor that Interacts with a Constitutively Active Transcription Factor, MTF-1." *PNAS.* 91.4(1994):1219-1223.
Park et al. "Phostastidylinositol 3-Kinase Regulates PMA-Induced Differentiation and Superoxide Production in HL-60 Cells." *Immunopharmacol. Immunotoxicol.* 2402(2002):211-226. (Abstract Only).
Pearce et al. "Interaction of the Aryl Hydrocarbon Receptor Ligand 6-Methyl-1,3,8-Trichlorodibenzofuran with Estrogen Receptor α." *Cancer Res.* 64.8(2004):2889-2897.
Pei et al. "Bioreactors Mediate the Effectiveness of Tissue Engineering Scaffolds." *FASB J.* 16(2002):1691-1694.
Peled et al. "Cellular Copper Content Modulates Differentiation and Self-Renewal in Cultures of Cord Blood-Derived D34+ Cells." *Brit. J. Haematol.* 116.3(2002):655-661.
Peled et al. "Chelatable Cellular Copper Modulates Differentiation and Self-Renewal of Cord Blood-Derived Hematopoietic Progenitor Cells." *Exp. Hematol.* 33(2005):1092-1100.
Peled et al. "Copper Chelators Enable Long Term CFU and CD34+ Cells Expansion in Cultures Initiated with the Entire Mononuclear Cell (MNC) Fraction." *Blood.* 100.11(2002):148b. (Abstract #4076).
Peled et al. "Copper Chelators Sustain Long Term Expansion of Cord-Blood CD34+ Cultures Initiated with IL-3 and G-CSF: Late Acting, Differentiation-Inducing Cytokines." *Blood.* 96.1(2000):773a. (Abstract #3343).
Peled et al. "Dependence of Human Stem Cell Engraftment and Repopulation of NOD/SCID Mice on CXCR4." *Science.* 283(1999):845-848.
Peled et al. "Identification of a Serum-Derived Differentiation-Inducing Activity as the Copper-Binding Protein Ceruloplasmin." *Blood.* 10.A1(1998):618A-619A. (Abstract #2551).
Peled et al. "Linear Polyamine Copper Chelator Tetraethylenepentamine Augments Long-Term ex vivo Expansion of Cord Blood-Derived CD34+ Cells and Increases their Engraftment Potential in NOD/SCID Mice." *Exp. Hematol.* 32(2004):547-555.
Peled et al. "Nicotinamide Modulates Ex-Vivo Expansion of Cord Blood Derived CD34+ Cells Cultures with Cytokines and Promotes their Homing and Engraftment in SCID Mice." *Blood.* 108.11(2006):218A. (Abstract #725).
Peled et al. "Regulation of Long-Term Expansion of Hemopoietic Stem/Progenitor Cells (HPC) by Intracellular Copper Content." *Blood.* 96.11(2000):776a-777a. (Abstract #3359).
Pera. "Human Pluripotent Stem Cells: A Progress Report." *Curr. Opin. Genet. Dev.* 11(2001):595-599.
Percival et al. "Copper is Required to Maintaine Cu/Zn-Superoxide Dismutase Activity During HL-60 Cell Differentiation." *Proc. Soc. Exp. Biol. Med.* 203(1993):78-83.
Percival et al. "HL-60 Cells can be Made Copper Deficient by Incubating with Tetraethylenepentamine 1,2,3." *J. Nutr.* 122.12(1992):2424-2429.
Percival. "Copper and Immunity." *Am. J. Clin. Nutr.* 67.S5(1998):1064S-1068S.
Percival. "Neutropenia Caused by Copper Deficiency: Possible Mechanism of Action." *Nutr. Rev.* 53.3(1995):59-66.
Perrotti et al. "Overexpression of the Zinc Finger Protein MZF1 Inhibits Hematopoietic Development from Embryonic Stem Cells: Correlation with Negative Regulation of CD34 and C-MYB Promoter Activity." *Mol. Cell. Biol.* 15.11(1995):6075-6087.
Peters et al. "Long Term ex vivo Expansion of Human Fetal Liver Primitive Haematopoietic Progenitor Cells in Stroma-Free Cultures." *Brit. J. Haematol.* 119(2002):792-802.
Petersen et al. "Bone Marrow as a Potential Source of Hepatic Oval Cells." *Science.* 284.5417(1999):1168-1170.
Petersen et al. "Hepatic Oval Cells Express the Hematopoietic Stem Cell Marker Thy-1 in the Rat." *Heptaol.* 27.2(1998):433-445.
Petti et al. "Complete Remission Through Blast Cell Differentiation in *PLZF/RAR*α-Positive Acute Promyelocytic Leukemia: in vitro and in vivo Studies." *Blood.* 100.3(2002):1065-1067.
Petzer et al. "Differential Cytokine Effects on Primitive (CD34+CDe38-) Human Hematopoietic Cells: Novel Responses to Flt3-Ligand and Thrombopoietin." *J. Exp. Med.* 183(1996):2551-2558.
Petzer et al. "Self-Renewal of Primitive Human Hematopoietic Cells (Long-Term-Culture-Initiating Cells) in vitro and Their Expansion in Defined Medium." *PNAS.* 93(1996):1470-1474.
Piacibello et al. "Extensive Amplification and Self-Renewal of Human Primitive Hematopoetic Stem Cells from Cord Blood." *Blood.* 89.8(1997):2644-2653.
Pickart et al. "Growth Modulating Plasma Tripeptide may Function by Facilitating Copper Uptake into Cells." *Nature.* 288.18(1980):715-717. (Abstract Only).
Pittenger et al. "Mesenchymal Stem Cells and Their Potential as Cardiac Therapeutics." *Circ. Res.* 95.1(2004):9-20.
Podesta et al. "Cyclic ADP-Ribose Generation by CD38 Improves Human Hematopoietic Stem Cell Engraftment into NOD/SCID Mice." *FASEB J.* 17(2003):310-312.
Podesta et al. "Extracellular Cyclic ADP-Ribose Increases Intracellular Free Calcium Concentration and Stimulates Proliferation of Human Hematopoietic Progenitors." *FASEB J.* 14.5(2000):680-690.
Porter et al. "Graft-Versus-Leukemia Effect of Allogeneic Bone Marrow Transplantation and Donor Mononuclear Cell Infusions." *Cancer Treat. Res.* 77(1997):57-85. (Abstract Only).
Porter. "The Hydrolysis of Rabbit γ-Globulin and Antibodies with Crystalline Papain." *Biochem. J.* 73(1959):119-126.
Presta. "Antibody Engineering." *Curr. Opin. Struct. Biol.* 2(1992):593-596.
Prockop et al. "Isolation and Characterization of Rapidly Self-Renewing Stem Cells from Cultures of Human Marrow Stromal Cells." *Cytother.* 3.5(2001):393-396.

(56) References Cited

OTHER PUBLICATIONS

Protti et al. "Particulate Naturally Processed Peptides Prime a Cytyotoxic Response Against Human Melanoma in Vitro." *Cancer Res.* 56(1996):1210-1213.
Psaltis et al. "Enrichment for STRO-1 Expression Enhances the Cardiovascular Paracrine Activity of Human Bone Marrow-Derived Mesenchymal Cell Populations." *J. Cell. Physiol.* 223(2010):530-540.
Puccetti et al. "AML-Associated Translocation Products Block Vitamin D3-Induced Differentiation by Sequestering the Vitamin D3 Receptor." *Cancer Res.* 62(2002):7050-7058.
Punzel et al. "The Type of Stromal Feeder Used in Limiting Dilution Assays Influences Frequency and Maintainence Assessment of Human Long-Term Culture Initiating Cells." *Leukemia.* 13(1999):92-97.
Purdy et al. "Large Volume Ex Vivo Expansion of CD34-Positive Hematopoietic Progenitor Cells for Transplantation." *J. Hematother.* 4(1995):515-525.
Purton et al. "All-Trans Retinoic Acid Delays the Differentiation of Primitive Hematopoietic Precursors (lin-c-*kit*+Sca-1+) While Enhancing the Terminal Maturation of Committed Granulocyte/Monocyte Progenitors." *Blood.* 94.2(1999):483-495.
Purton et al. "All-Trans Retinoic Acid Enhances the Long-Term Repopulating Activity of Cultured Hematopoietic Stem Cells." *Blood.* 95.2(2000):470-477. (Abstract Only).
Purton et al. "All-Trans Retinoic Acid Facilitates Oncoretrovirus-Mediated Transduction of Hematopoietic Repopulating Stem Cells." *J. Hamatother. Stem Cell Res.* 10.8(2001):815-825. (Abstract Only).
Quantin et al. "Adenovirus as an Expression Vector in Muscle Cells in vivo." *PNAS.* 89(1992):2581-2584.
Rajur et al. "Covalent Protein-Oligonucleotide Conjugates for Efficient Delivery of Antisense Molecules." *Bioconj. Chem.* 8.6(1997):935-940.
Ramsfjell et al. "Distinct Requirements for Optimal Growth and in vitro Expansion of Human CD34+CD38- Bone Marrow Long-Term Culture-Initiating Cells (LTC-IC), Extended LTC-IC, and Murine in vivo Long-Term Reconstituting Stem Cells." *Blood.* 94.12(1999):4093-4102.
Rankin et al. "Quantitative Studies of Inhibitors of ADP-Ribosylation In Vitro and In Vivo." *J. Biol. Chem.* 264.8(1989):4312-4317.
Ratajczak et al. "Effect of Basic (FGF-2) and Acidic (FGF-1) Fibroblast Growth Factors on Early Haemopoietic Cell Development." *Brit. J. Hematol.* 93(1996):772-782.
Ratajczak et al. "Hunt for Pluripotent Stem Cell—Regenerate Medicine Search for Almighty Cell." *J. Autoimmun.* 30(2008):151-162.
Reeves et al. "High Zinc Concentrations in Culture Media Affect Copper Uptake and Transport in Differentiated Human Colon Adenocarcinoma Cells." *J. Nutr.* 126.6(1996):1701-1712. (Abstract Only).
Reid et al. "Interations of Tumor Necrosis Factor with Granulocyte-Macrophade Colony-Stimulating Factor and Other Cytokines in the Regulation of Dendritic Cell Growth in vitro from Early Bipotent CD34+ Progenitors in Human Bone Marrow." *J. Immunol.* 149.8(1992):2681-2688. (Abstract Only).
Ren et al. "Inflammatory Cytokine-Induced Intercellular Adhesion Molecule-1 and Vascular Cell Adhesion Molecule-1 in Mesenchymal Stem Cells are Critical for Immunosuppression." *J. Immunol.* 184.5(2010):2321-2328.
Reya. "Regulation of Hematopoietic Stem Cell Self-Renewal." *Rec. Prog. Hormone Res.* 58(2003):283-295.
Reyes et al. "Origin of Endothelial Progenitors in Human Postnatal Bone Marrow." *J. Clin. Invest.* 109(2002):337-346.
Riechmann et al. "Reshaping Human Antibodies for Therapy." *Nature.* 332(1988):323-327.
Roach et al. "Methods for the Isolation and Maintenance of Murine Embryonic Stem Cells." *Meth. Mol. Biol.* 185(2002):1-16.
Roberts. "Mesenchymal Stem Cells." *Vox Sanguinis.* 87.S2(2004):S38-S41.
Robinson et al. "Ex vivo Expansion of Umbilical Cord Blood." *Cytotherapy.* 7.3(2005):243-250.
Robinson et al. "Superior ex vivo Cord Blood Expansion Following Co-Culture with Bone Marrow-Derived Mesenchymal Stem Cells." *Bone Marrow Transplant.* 37(2006):359-366.
Rosenberg et al. "Prospective Randomized Trial of High-Dose Interleukin-2 Alone or in Conjunction with Lymphokine-Activated Killer Cells for the Treatment of Patients with Advanced Cancer." *J. Nat. Cancer Instit.* 85.8(1993):622-632.
Rosenfeld et al. "Adenovirus-Mediated Transfer of a Recombinant α1-Antitrypsin Gene to the Lung Epithelium in Vivo." *Science.* 252(1991):431-434.
Rosenfeld et al. "In Vivo Transfer of the Human Cystic Fibrosis Transmembrane Conductance Regulator Gene to the Airway Epithelium." *Cell.* 68(1992):143-155.
Ross et al. "Chelometric Indicator Titrations with the Solid-State Cupric Ion-Selective Electrode." *Anal. Chem.* 41.13(1969):1900-1902.
Rowley et al. "Isolation of CD34+ Cells from Blood Stem Cell Components Using the Baxter Isolex System." *Bone Marrow Transplant.* 21(1998):1253-1262.
Rubinstein et al. "Processing and Cryopreservation of Placental/Umbilical Cord Blood for Unrelated Bone Marrow Reconstitution." *PNAS.* 92(1995):10119-10122.
Rusten et al. "The RAR-RXR as Well as the RXR-RXR Pathway is Involved Signaling Growth Inhibition of Human CD34+ Erythroid Progenitor Cells." *Blood.* 87.5(1996):1728-1736. (Abstract Only).
Ryu et al. "Adenosine Triphosphate Induces Proliferation of Human Neural Stem Cells: Role of Calcium and p70 Ribosomal Protein S6 Kinase." *J. Neurosci. Res.* 72(2003):352-362.
Sambanis. "Encapsulated Islets in Diabetes Treatment." *Diabetes Technol. Ther.* 5.4(2003):665-668.
Sammons et al. "Mechanisms Mediating the Inhibitory Effect of All-Trans Retinoic Acid on Primitive Hematopoietic Stem Cells in Human Long-Term Bone Marrow Culture." *Stem Cells.* 18.3(2000):214-219.
Samulski et al. "Helper-Free Stocks of Recombinant Adeno-Associated Viruses: Normal Integration does not Require Viral Gene Expression." *J. Virol.* 63.9(1989):3822-3828.
Sandstrom et al. "Effects of CD34+ Cell Selection and Perfustion on Ex Vivo Expansion of Peripheral Blood Mononuclear Cells." *Blood.* 86.3(1995):958-970.
Santoro et al. "A General Purpose RNA-Cleaving DNA Enzyme." *PNAS.* 9(1997):4262-4266.
Sato et al. "In Vitro Expansion of Human Peripheral Blood CD34+ Cells." *Blood.* 82.12(1993):3600-3609.
Saulnier et al. "An Efficient Method for the Synthesis of Guanidino Prodrugs." *Bioorg. Med. Chem. Lett.* 4.16(1994):1985-1990.
Sauve et al. "Mechanism-Based Inhibitors of CD38: A Mammalian Cyclic ADP-Ribose Synthetase." *Biochem.* 41.26(2002):8455-8463.
Savouret et al. "The Aryl Hydrocarbon Receptor and its Xenobiotic Ligands: A Fundamental Trigger for Cardiovascular Diseases." *Nutr. Metab. Cardiovasc. Dis.* 13.2(2003):104-113.
Schaeffer et al. "Enzyme Inhibitors. 25." *J. Med. Chem.* 15.5(1972):456-458.
Schechter et al. "Sickle Cell Disease." *The Molecular Basis of Blood Diseases.* Stamatoyannopoulos et al., eds. Philadelphia: W.B. Saunders. (1987):179-218.
Schmetzer et al. "Effect of GM-CSF, 1,25-Dihydroxycholecalciferol (Vit. D) and All-Trans-Retinocin Acid (ATRA) on the Proliferation and Differentiation of MDS-Bone Marrow (BM)-Cells In Vitro." *Hematol.* 2(1997):11-19.
Schwartz et al. "In Vitro Myelopoiesis Stimulated by Rapid Medium Exchange and Supplementation with Hematopoietic Growth Factors." *Blood.* 78.12(1991):3155-3161.
Seed. "An LFA-3 cDNA Encodes a Phospholipid-Linked Membrane Protein Homologous to its Receptor CD2." *Nature.* 329(1987):840-842.
Seeliger et al. "Human Fat-Derived Stem Cells: From Mesoderm to Hepatocyte-Like Differentiation." *Langenbecks Arch. Surg.* 394(2009):958-959. (Abstract #132).
Segev et al. "Differentiation of Human Embryonic Stem Cells into Insulin-Producing Clusters." *Stem Cells.* 22.3(2004):265-274.

(56) References Cited

OTHER PUBLICATIONS

Sekhar et al. "Retroviral Transduction of CD34-Enriched Hematopoietic Progenitor Cells under Serum-Free Conditions." *Hum. Gene Ther.* 7(1996):33-38.
Selden. "Optimization of Transfection." *Short Prot. Mol. Biol.* (1984):262-263.
Selden. "Transfection Using DEAE-Dextran." *Short Prot. Mol. Biol.* (1984):9.9-9.11.
Sergeant et al. "Iron and Copper Requirements for Proliferation and Differentiation of a Human Promyelocytic Leukemia Cell Line (HL-60)." *J. Cell. Physiol.* 163.3(1995):477-485.
Shimakura et al. "Murine Stromal Cell Line HESS-5 Maintains Reconstituting Ability of Ex Vivo-Generated Hematopoietic Stem Cells from Human Bone Marrow and Cytokine-Mobilized Peripheral Blood." *Stem Cells.* 18(2000):183-189.
Shimizu et al. "Treatment and Management of Wilson's Disease." *Ped. Int* 41.4(1999):419-422. (Abstract Only).
Shioda et al. "Anti-HIV-1 and Chemotactic Activities of Human Stromal Cell-Derived Factor 1α (SDF-1α) and SDF-1β are Abolished by CD26/dipeptidyl Peptidase IV_Mediated Cleavage." *PNAS.* 95(1998):6331-6336.
Sieff et al. "Changes in Cell Surface Antigen Expression During Hemopoietic Differentiation." *Blood.* 60.3(1982):703-713.
Siena et al. "Massive ex vivo Generation of Functional Dendritic Cells from Mobilized CD34+ Blood Progenitors for Anticancer Therapy." *Exp. Hematol.* 23(1995):1463-1471.
Sigurdsson et al. "Copper Chelation Delays the Onset of Prion Disease." *J. Biol. Chem.* 278.47(2003):46199-46202.
Silvenoinen et al. "CD38 Signal Transduction in Human B Cell Precursors Rapid Induction of Tyrosine Phosphorylation, Activation of Syk Tyrosine Kinase and Phosphorylation of Phospholipase C-gamma and Phosphatidylinositol 3-Kinase." *J. Immunol.* 156.1(1996):100-107. (Abstract Only).
Simmons et al. "Identification of Stromal Cell Precursors in Human Bone Marrow by a Novel Monoclonal Antibody, STRO-1." *Blood.* 78.1(1991):55-62.
Simon et al. "Copper Deficiency and Sideroblastic Anemia Associated with Zinc Ingestion." *Am. J. Hematol.* 28(1988):181-183.
Slavin et al. "Donor Lymphocyte Infusion: The Use of Alloreactive and Tumor-Reactive Lymphocytes for Immunotherapy of Malignant and Nonmalignant Diseases in Conjunction with Allogeneic Stem Cell Transplantation." *J. Hematother. Stem Cell Res.* 11(2002):265-276.
Slavin et al. "Treatment of Leukemia by Alloreactive Lymphocytes and Nonmyeloablative Stem Cell Transplantation." *J. Clin. Immunol.* 22.2(2002):64-69.
Smith. "Embryo-Derived Stem Cells: Of Mice and Men." *Ann. Rev. Cell Dev. Biol.* 17(2001):435-462.
Smith. "The World According to PARP." *Trends Biochem. Sci.* 26.3(2001):174-179.
Spencer et al. "Controlling Signal Transduction with Synthetic Ligands." *Science.* 262(1993):1019-1024.
Sprangrude et al. "Purification and Characterization of Mouse Hematopoietic Stem Cells." *Science.* 241.4861(1988):58-62.
Struyf et al. "Natural Truncation of RANTES Abolishes Signaling Through the CC Chemokine Receptor CCR1 and CCR3, Impairs its Chemotactic Potency and Generates a CC Chemokine Inhibitor." *Eur. J. Immunol.* 28(1998):1262-1271.
Suda et al. "A Study of Trientine Therapy in Wilson's Disease with Neurology Symptoms." *No To Hattatsu.* 25.5(1993):429-434. (English Abstract Only).
Sylvester et al. "Stem Cells: Review and Update." *Arch. Surg.* 139(2004):93-99.
Szilvassy et al. "Differential Homing and Engraftment Properties of Hematopoietic Progenitor Cells from Murine Bone Marrow Mobilized Peripheral Blood Cells and Fetal Liver." *Blood.* 98.7(2001):2108-2115.
Takeshita et al. "Selective Stimulation by Ceramide of the Expression of the β Isoform of Retinoic Acid and Retinoid X Receptors in Osteoblastic Cells." *J. Biol. Chem.* 275.41(2000):32220-32226.
Tashiro-Itoh et al. "Metallothionein Expression and Concentrations of Copper and Zinc are Associated with Tumor Differentiation in Hepatocellular Carcinoma." *Liver.* 17(1997):300-306.
Tateishi-Yuyama et al. "Therapeutic Angiogenesis for Patients with Limb Ischemia by Autologous Transplantation of Bone-Marrow Cells: A Pilot Study and a Randomised Controlled Trial." *Lancet.* 360(2002):427-435.
Tateno et al. "Long-Term Cultivation of Adult Rat Hepatocytes that Undergo Multiple Cell Divisions and Express Normal Parenchymal Phenotypes." *Am. J. Pathol.* 148.2(1996):383-392. (Abstract Only).
*The Merck Index: An Encyclopedia of Chemicals, Drugs, and Biologicals.* Windholz et al., eds. Rahway, NJ: Merck & Co., Inc. (1983):549.
Tilesi et al. "Design and Validation of siRNAs and shRNAs." *Curr. Opin. Mol. Ther.* 11.2(2009):156-164.
Todisco et al. "CD38 Ligation Inhibits Normal and Leukemic Myelopoiesis." *Blood.* 95.2(2000):535-542. (Absract Only).
Tögel et al. "Administered Mesenchymal Stem Cells Protect Against Ischemic Acute Renal Failure Through Differentiation-Independent Mechanisms." *Am. J. Physiol. Renal Physiol.* 289(2005):F31-F42.
Tratschin et al. "A Human Parvovirus, Adeno-Associated Virus, as an Eucaryotic Vector: Transient Expression and Encapsidation of the Procaryotic Gene for Chloramphenicol Acetyltransferase." *Mol. Cell Biol.* 4.10(1984):2072-2081.
Tratschin et al. "Adeno-Associated Virus Vector for High-Frequency Integration, Expression, and Rescue of Genes in Mammalian Cells." *Mol. Cell. Biol.* 5.11(1985):3251-3260.
Tratschin et al. "Genetic Analysis of Adeno-Associated Virus: Properties of Deletion Mutants Constructed in Vitro and Evidence for an Adeno-Associated Virus Replication Function." *J. Virol.* 51.3(1984):611-619.
Trounson. "The Derivation and Potential Use of Human Embryonic Stem Cells." *Reprod. Fertil. Dev.* 13(2001):523-532.
Tse et al. "Angiogenesis in Ischaemic Myocardium by Intramyocardial Autologous Bone Marrow Mononuclear Cell Implantation." *Lancet.* 361(2003):47-49.
Tuba et al. "Synthesis and Structure—Activity Relationship of Neuromuscular Blocking Agents." *Curr. Med. Chem.* 9.16(2002):1507-1536.
Turnpenny et al. "Evaluating Human Embryonic Germ Cells: Concord and Conflict as Pluripotent Stem Cells." *Stem Cells.* 24(2006):212-220.
Uchida et al. "Direct Isolation of Human Central Nervous System Stem Cells." *PNAS.* 97.26(2000):14720-14725.
Ueda et al. "ADP-Ribosylation." *Ann. Rev. Biochem.* 54(1985):73-100.
Ueno et al. "A Novel Retinoic Acid Receptor (RAR)-Selective Antagonist Inhibits Differentiation and Apoptosis of HL-60 Cells: Implications of RARα-Mediated Signals in Myeloid Leukemic Cells." *Leuk. Res.* 22.6(1998):517-525.
Uludag et al. "Technology of Mammalian Cell Encapsulation." *Adv. Drug Deliv. Rev.* 42.12(2000):29-64.
Vaca et al. "Nicotinamide Induces Both Proliferation and Differentiation of Embryonic Stem Cells into Insulin-Producing Cells." *Transplant. Proc.* 35.5(2003):2021-2023.
Van Beusechem et al. "Long-Term Expression of Human Adenosine Deaminase in Rhesus Monkeys Transplanted with Retrovirus-Infected Bone-Marrow Cells." *PNAS.* 89(1992):7640-7644.
Van Epps et al. "Harvesting, Characterization, and Culture of CD34+ Cells from Human Bone Marrow, Peripheral Blood, and Cord Blood." *Blood Cells.* 20.2-3(1994):411-423.
van Poll et al. "Mesenchymal Stem Cell-Derived Molecules Directly Modulate Hepatocellular Death and Regeneration In Vitro and In Vivo." *Hepatol.* 47.5(2008):1634-1643.
Vanham et al. "Decreased Expression of the Memory Maker CD26 on Both CD4+ and CD8 T Lymphocytes fo HIV-Infected Subjects." *J. Acq. Immune Def. Synd.* 6(1993):749-757.
Verfaillie. "Can Human Hematopoietic Stem Cells be Cultured Ex Vivo?" *Stem Cells.* 12.5(1994):466-476. (Abstract Only).
Verfaillie. "Direct Contact Between Human Primitive Hematopoietic Progenitors and Bone Marrow Stroma is not Required for Long-Term in Vitro Hematopoiesis." *Blood.* 79.11(1992):2821-2826.

(56) References Cited

OTHER PUBLICATIONS

Verhoeyen et al. "Reshaping Human Antibodies: Grafting an Antilysozyme Activity." *Science.* 239(1988):1534-1536.
Verlinden et al. "Interaction of Two Novel 12-Epivitamin D3 Analogs with Vitamin D3 Receptor-Retinoid X Receptor Heterodimers on Vitamin D3 Response Elements." *J. Bone Min. Res.* 16.4(2001):625-638.
Verneris et al. "The Phenotypic and Functional Characteristics of Umbilical Cord Blood and Peripheral Blood Natural Killer Cells." *Brit. J. Haematol.* 147.2(2009):185-191.
Vilensky et al. "British Anti-Lewisite (Dimercaprol): An Amazing History." *Ann. Emerg. Med.* 41.3(2003):378-383. (Abstract Only).
Virág et al. "The Therapeutic Potential of Poly(ADP-Ribose) Polymerase Inhibitors." *Pharmacol. Rev.* 54.3(2002):375-429.
Vlahos et al. "A Specific Inhibitor of Phosphatidylinostiol 3-Kinase 2-(4-Morpholinyl)-8 Phernyl-4H-1-Benzopyran-4-Oone (LY294002)." *J. Biol. Chem.* 269.7(1994):5241-5248. (Abstract Only).
Wagers et al. "Little Evidence for Developmental Plasticity of Adult Hematopoietic Stem Cells." *Science.* 297.5590(2002):2256-2259. (Abstract Only).
Wagner et al. "Replicative Sensescence of Mesenchymal Stem Cells: A Continuous and Organized Process." *PLoS One.* 3.5(2008):e2213.
Wall et al. "Inhibition of the Intrinsic NAD+ Glycohydrolase Activity of CD38 by Carbocyclic NAD Analogues." *Biochem. J.* 335.3(1998):631-636.
Walton et al. "Prediction of Antisense Oligonucleotide Binding Affinity to a Structured RNA Target." *Biotechnol. Bioeng.* 65.1(1999):1-9.
Wang et al. "In vitro Culture of Umbilical Cord Blood MNC and CD34+ Selected Cells." *Sheng Wu Gong Cheng Xue Bao.* 18.3(2002):343-347. (English Abstract Only).
Wang et al. "pH-Sensitive Immunoliposome Mediate Target-Cell-Specific Delivery and Controlled Expression of a Foreign Gene in Mouse." *PNAS.* 84(1987):7851-7855.
Wasa et al. "Copper Deficiency with Pancytopenia During Total Parental Nutrition." *JPEN.* 18.2(1994):190-192.
Weissmann. "Translating Stem and Progenitor Cell Biology to the Clinic: Barriers and Opportunities." *Science.* 287.5457(2000):1442-1446. (Abstract Only).
Wendling et al. "Retinoid X Receptor are Essential for Early Mouse Development and Placentogenesis." *PNAS.* 96.2(1999):547-551. (Abstract Only).
Whitlow et al. "Single-Chain Fv Proteins and Their Fusion Proteins." *Methods.* 2.2(1991):97-105.
Wick et al. "New Ways in Hepatocyte Cultures: Cell Immobilisation Technique." *ALTEX.* 14.2(1997):51-56. (Abstract Only).
Williams et al. "In Vitro Chondrogenesis of Bone Marrow-Derived Mesenchymal Stem Cells in a Photopolymerizing Hydrogel." *Tissue Eng.* 9.4(2003):679-688.
Williams et al. "Selection and Expansion of Peripheral Blood CD34+ Cells in Autologous Stem Cell Transplantation for Breast Cancer." *Blood.* 87.5(1996):1687-1691.
Williams. "Small is Beautiful: Microparticle and Nanoparticle Technology in Medical Devices." *Med. Device Technol.* 10.3(1999):6-9.
Wilson et al. "Hepatocyte-Directed Gene Transfer In Vivo Leads to Transient Improvement fo Hypercholesterolemia in Low Density Lipoprotein Receptor-Deficient Rabbits." *J. Biol. Chem.* 267.2(1992):963-967.
Wilson et al. "Retrovirus-Mediated Transduction of Adult Hepatocytes." *PNAS.* 85(1988):3014-3018.
Wolff et al. "Direct Gene Transfer into Mouse Muscles In Vivo." *Science.* 247(1990):1465-1468.
Wondisford et al. "Cloning of the Human Thyrotropin β-Subunit Gene and Transient Expression of Biologically Active Human Thyrotropin after Gene Transfection." *Mol. Endocrinol.* 2(1988):32-39.
Wu et al. "Receptor-Mediated Gene Delivery and Expression in Vivo." *J. Biol. Chem.* 263.29(1988):14621-14624.
Wulf et al. "Somatic Stem Cell Plasticity: Current Evidence and Emerging Concepts." *Exp. Hematol.* 29(2001):1361-1370.
Xia et al. "Surface Fucosylation of Human Cord Blood Cells Augments Binding to P-Selectin and E-Selectin and Enhances Engraftment in Bone Marrow." *Blood.* 104.10(2004):3091-3096.
Yang et al. "In vitro Trans-Differentiation of Adult Hepatic Stem Cells Into Pancreatic Endocrine Hormone-Producing Cells." *PNAS.* 99.12(2002):8078-8083.
Yang et al. "Mesenchymal Stem/Progenitor Cells Developed in Cultures from UC Blood." *Cytotherapy.* 6.5(2004):476-486.
Yau et al. "Endogenous Mono-ADP-Ribosylation Mediates Smooth Muscle Cell Proliferation and Migration via Protein-Kinase Induction of C-*fos* Expression." *Eur. J. Biochem.* 270(2003):101-110.
Yin et al. "AC133, A Novel Marker for Human Hematopoietic Stem and Progenitor Cells." *Blood.* 90.12(1997):5002-5012.
Yla-Herttuala et al. "Gene Transfer as a Tool to Induce Therapeutic Vascular Growth." *Nat. Med.* 9.6(2003):694-701.
Yoon et al. "Clonally Expanded Novel Multipotent Stem Cells from Human Bone Marrow Regenerate Myocardium after Myocardial Infarction." *J. Clin. Invest.* 115.2(2005):326-338.
Zatloukalová et al. "β-Naphthoflavone and 3'-methoxy-4'-nitroflavone Exert Ambiguous Effect on Ah Receptor-Dependent Cell Proliferation and Gene Expression in Rat Liver 'Stem-Like' Cells." *Biochem. Pharmacol.* 73.10(2007):1622-1634.
Zhang et al. "Comparison of Mesenchymal Stem Cells from Human Placenta and Bone Marrow." *Chin. Med. J.* 117.6(2004):882-887.
Zhang et al. "Flavonoids as Aryl Hydrocarbon Receptor Agonists/Antagonists: Effect of Structure and Cell Context." *Environ. Health Persp.* 111.16(2003):1877-1882.
Zhang et al. "Human Placenta-Derived Mesenchymal Progenitor Cells Support Culture Expansion of Long-Term Culture-Initiating Cells from Cord Blood CD34+ Cells." *Exp. Hematol.* 32(2004):657-664.
Zidar et al. "Observations on the Anemia and Neutropenia of Human Copper Deficiency." *Am. J. Hematol.* 3(1977):177-185.
Zimmerman et al. "Large-Scale Selection of CD34+ Peripheral Blood Progenitors and Expansion of Neutrophil Precursors for Clinical Applications." *J. Hematother.* 5(1996):247-253.
Zocchi et al. "Ligand-Induced Internalization of CD38 Results in Intracellular Ca2+ Mobilization: Role of NAD+ Transport Across Cell Membranes." *FASEB J.* 13.2(1999):273-283. (Abstract Only).
Zon et al. "Developmental Biology of Hematopoiesis." *Blood.* 86.8(1995):2876-2891.
Zulewski et al. "Multipotent Nestin-Positive Stem Cells Isolated from Adult Pancreatic Islets Differentiate Ex Vivo into Pancreatic Endocrine, Exocrine, and Hepatic Phenotypes." *Diabetes.* 50(2001):521-533.
"13th Annual Meeting on Surgical Research." *Langenbeck's Archives of Surgery.* 394.5(2009):915-970.
Boland et al. "Wnt 3a Promotes Proliferation and Suppresses Osteogenic Differentiation of Adult Human Mesenchymal Stem Cells", Journal of Cellular Biochemistry, 93: 1210-1230, 2004.
Bonewald et al. "Role of Active and Latent Transforming Growth Factor Beta in Bone Formation", Journal of Cellular Biochemistry, 55: 350-357, 1994.
Cargnoni et al. "Conditioned Medium From Amniotic Mesenchymal Tisstie Cells Reduces Progression of Bleomycin-Induced Lung Fibrosis", Cytotherapy, 14: 153-161, 2012.
Colleoni et al. "Isolation, Growth and Differentiation of Equine Mesenchymal Stem Cells: Effect of Donor, Source, Amount of Tissue and Supplementation With Basi Fibroblast Growth Factor", Veterinary Research Communications, 33(8): 811-821, Dec. 2009.
Furge et al. "Met Receptor Tyrosine Kinase: Enhanced Signaling Through Adapter Proteins", Oncogene, 19: 5582-5589, 2000.
Gnecchi et al. "Bone Marrow-Derived Mesenchymal Stem Cells: Isolation, Expansion, Characterization, Viral Transduction, and Production of Conditioned Medium", Stem Cells in Regenerative Medicine: Methods and Protocols, 482(Chap.18): 281-294, 2009.
Kassis et al. "Isolation of Mesenchymal Stem Cells From G-CSF-Mobilized Human Peripheral Blood Using Fibrin Microbeads", Bone Marrow Transplantation, 37(10): 967-976, May 2006.

(56) References Cited

OTHER PUBLICATIONS

Krampera et al. "HB-EGF/HER-1 Signaling in Bone Marrow Mesenchymal Stem Cells: Inducing Cell Expansion and Reversibly Preventing Multilineage Differentiation", Blood, 106(1): 59-66, Jul. 1, 2005.

Lin et al. "The Isolation of Novel Mesenchymal Stromal Cell Chemotactic Factors From the Conditioned Medium of Tumor Cells", Experimental Cell Research, 314: 3107-3117, Available Online Aug. 8, 2008.

Longobardi et al. "Effect of IGF-I in the Chondrogenesis of Bone Marrow Mesenchymal Stem Cells in the Presence of Absence of TGF-Beta Signaling", Journal of Bone and Mineral Research, 21(4): 626-636, Published Online Dec. 26, 2005.

Pons et al. "VEGF Improves Survival of Mesenchymal Stem Cells in Infarcted Hearts", Biochemical and Biophysical Research Communications, 376: 419-422, Available Online Sep. 18, 2008.

Stewart et al. "BMP-3 Promotes Mesenchymal Stem Cell Proliferation Through the TGF-Beta/Activin Signaling Pathway", Journal of Cellular Physiology, 223: 658-666, Feb. 8, 2010.

Tamama et al. "Epidermal Growth Factor (EGF) Treatment on Multipotential Stromal Cells (MSCs). Possible Enhancement of Therapeutic Potential of MSC", Journal of Biomedicine and Biotechnology, 2010(795385): 1-10, 2010.

Tamama et al. "Epidermal Growth Factor as a Candidate for Ex Vivo Expansion of Bone Marrow-Derived Mesenchymal Stem Cells", Stem Cells, 24: 686-695, First Published Sep. 8, 2005.

Van Koppen et al. "Human Embryonic Mesenchymal Stem Cell-Derived Conditioned Medium Rescues Kidney Function in Rats With Established Chronic Kidney Disease", PLoS One, 7(6): e38746-1-e38746-12, Jun. 19, 2012.

Wagner et al. "Replicative Senescence of Mesenchymal Stem Cells: A Continuous and Organized Process", PLoS One, 3(5): e2213-1-e2213-12, May 21, 2008.

Wang et al. "Clinical Applications of Mesenchymal Stem Cells", Journal of Hematology & Oncology, 5(19): 1-9, 2012.

Wang et al. "Mesenchymal Stem Cell-Conditioned Medium Facilitates Angiogenesis and Fracture Healing in Diabetic Rats", Journal of Tissue Engineering and Regenerative Medicine, 6: 559-569, Published Online Sep. 13, 2011.

Yew et al. "Enhancement of Wound Healing by Human Multipotent Stromal Cell Conditioned Medium: The Paracrine Factors and P38 MAPK Activation", Cell Transplantation, 20: 693-706, Published Online Dec. 22, 2010.

Zhang et al. "Comparison of Mesenchymal Stem Cells From Human Placenta and Bone Marrow", Chinese Medical Journal, 117(6): 882-887, 2004.

Search Report and Written Opinion Dated Apr. 8, 2015 From the Intellectual Property Office of Singapore Re. Application No. 11201404608W.

Da Silva Meirelles et al. "Mechanisms Involved in the Therapeutic Properties of Mesenchymal Stem Cells", Cytokine & Growth Factor Reviews, 20: 419-427, 2009.

Daan Van Poll et al. "Mesenchymal Stem Cell-Derived Molecules Directly Modulate Hepatocellular Death and Regeneration In Vitro and In Vivo", Hepatology, vol. 47, No. 5, 2008.

* cited by examiner

SEQUENCE LISTING

<160> NUMBER OF SEQ ID NOS: 4

<210> SEQ ID NO 1
<211> LENGTH: 61
<212> TYPE: DNA
<213> ORGANISM: Artificial sequence
<220> FEATURE:
<223> OTHER INFORMATION: Example of an shRNA molecule which is capable
      of down-regulating the expression of AHR

<400> SEQUENCE: 1
gcggcataga gaccgactta atttcaagag aattaagtcg gtctctatgc cgcttttttg    60
g                                                                    61

<210> SEQ ID NO 2
<211> LENGTH: 65
<212> TYPE: DNA
<213> ORGANISM: Artificial sequence
<220> FEATURE:
<223> OTHER INFORMATION: Example of an shRNA molecule which is capable
      of down-regulating the expression of AHR

<400> SEQUENCE: 2
cgcgccaaaa aagcggcata gagaccgact taattctctt gaaattaagt cggtctctat    60
gccgc                                                                65

<210> SEQ ID NO 3
<211> LENGTH: 61
<212> TYPE: DNA
<213> ORGANISM: Artificial sequence
<220> FEATURE:
<223> OTHER INFORMATION: Example of an shRNA molecule which is capable
      of down-regulating the expression of AHR

<400> SEQUENCE: 3
ggcttctttg atgttgcatt aattcaagag attaatgcaa catcaaagaa gccttttttg    60
g                                                                    61

<210> SEQ ID NO 4
<211> LENGTH: 65
<212> TYPE: DNA
<213> ORGANISM: Artificial sequence
<220> FEATURE:
<223> OTHER INFORMATION: Example of an shRNA molecule which is capable
      of down-regulating the expression of AHR

<400> SEQUENCE: 4
cgcgccaaaa aaggcttctt tgatgttgca ttaatctctt gaattaatgc aacatcaaag    60
aagcc                                                                65

ENHANCEMENT OF NATURAL KILLER (NK) CELL PROLIFERATION AND ACTIVITY

RELATED APPLICATION

This application claims the benefit of priority under 35 USC 119(e) of U.S. Provisional Patent Application No. 61/674,426 filed Jul. 23, 2012, the contents of which are incorporated herein by reference in their entirety.

SEQUENCE LISTING STATEMENT

The contents of the text file, entitled "55111SequenceListing.txt", created on Jul. 18, 2013, comprising 1,642 bytes, and submitted concurrently with the filing of this application are incorporated herein by reference in their entirety.

FIELD AND BACKGROUND OF THE INVENTION

The present invention, in some embodiments thereof, relates to ex-vivo culture of natural killer (NK) cells and, more particularly, but not exclusively, to compositions and methods for enhancing propagation and/or functionality of NK cells by treating the cells with an agent which down-regulates the activity and/or expression of aryl hydrocarbon receptor (AHR).

Natural killer (hereinafter also abbreviated as "NK") cells are lymphoid cells that participate in immune reactions. These cells have variety of functions, especially the killing of tumor cells, cells undergoing oncogenic transformation and other abnormal cells in a living body, and are important components of innate immunological surveillance mechanisms. Clinical experience with adoptive immunotherapy with NK cells has emphasized the need for better methods for effectively and efficiently expanding NK cell populations while maintaining, and even enhancing their functionality in-vivo (killing ability trafficking, localization, persistence and proliferation).

NK cells represent a distinct population of lymphocytes in terms of both phenotype and function. NK cells have a large granular lymphocyte morphology and express characteristic NK cell surface receptors, and lack both TCR rearrangement and T cell, B cell, monocyte and/or macrophage cell surface markers. The cells kill by releasing small cytoplasmic granules of proteins (perforin and granzyme) that cause the target cell to die by apoptosis. NK cells possess mechanisms distinguishing between potential "target" cells and healthy cells via a multitude of inhibitory and activating receptors that engage MHC class 1 molecules, MHC class I-like molecules, and molecules unrelated to MHC (Caliguiri Blood 2008 112:461-69). Inhibitory NK cell receptors include HLA-E (CD94/NKG2A); HLA-C (group 1 or 2), KIR2DL; KIR3DL (HLA-B Bw4) and HLA-A3 or A4+ peptide. Activating NK cell receptors include HLA-E (CD94/NKG2C); KIR2DS (HLA-C) and KIR3DS (HLA-Bw4). Other receptors include the NK cell receptor protein-1 (termed NK1.1 in mice) and the low affinity receptor for the Fc portion of IgG (FcγRIII; CD16). Specific NK cell activators, the UL binding proteins (ULBPs), and their potential therapeutic use are described in detail in US patent application US20090234699 to Cosman et al. (which is incorporated herein by reference) "Activating" and "inhibitory" surface receptors control the NK cell's cytotoxic activity. Importantly for therapeutic considerations, NK cell inhibition is required to prevent destruction of normal host tissues by "activated" NK cells, but inhibitory signaling in NK cells appears to be stronger than the activating signals.

The intact bone marrow is necessary for NK cell generation. Human bone marrow-derived NK cells are large granular lymphocytes (LGL) of the CD2+CD16+CD56+ phenotype, lacking CD3 yet containing the T-cell receptor zeta-chain [zeta(ζ)-TCR]. NK cells can be found within a variety of lymphoid and nonlymphoid tissues, including blood, spleen, liver, lungs, intestines, and decidua. NK cells have been found in significant numbers in tumors, where they may exert antitumor activity.

NK cells exhibit spontaneous non-MHC-restricted cytotoxic activity against virally infected and tumor cells, and mediate resistance to viral infections and cancer development in vivo. Thus, NK cells represent major effector cells of innate immunity. In addition, NK cells possess a variety of other functions, including the ability to secrete cytokines and to regulate adaptive immune response and hemopoiesis. NK cells provide requisite interferon-gamma (IFN-gamma) during the early stages of infection in several experimental animal models.

Most cancers lack identifiable, tumor-specific antigens in the HLA context, and thus cannot succumb to antigen specific cytotoxic T lymphocytes. Since a wide range of cancer cells are sensitive to NK cytotoxicity, transplantation of natural killer (NK) cell can be employed against cancer cells in an allogeneic setting, without risk of graft-versus-host disease.

Recent studies have emphasized this potential of NK-cell therapy. In animal models of transplantation, donor NK cells lyse leukemic cells and host lympho-hematopoietic cells without affecting nonhematopoietic tissues. Because NK cells are inhibited by self-HLA molecules which bind to killer immunoglobulin-like receptors (KIR), these findings have led to the clinical practice of selecting hematopoietic stem cell transplant donors with an HLA and KIR type that favors NK-cell activation (HLA- and KIR mismatch) and thus could be expected to promote an antileukemic effect. However, selection of the "best" donor is limited to patients who have more than one potential donor and the capacity of NK cells to lyse lymphoid cells is generally low and difficult to predict. A survey of NK distribution and function in autoimmune conditions has indicated reduced numbers and functionality of the NK cell population in many autoimmune diseases (e.g., SLE, Sjogren's syndrome, sclerosis, psoriasis, RA, ulcerative colitis, etc). Thus, treatment with NK cells may actively suppress potentially pathogenic autoimmune T cells that can mediate the inflammatory responses following bone marrow transplant, regulating the activation of autoimmune memory T cells in an antigen non-specific fashion to maintain the clinical remission and prevent GVH effect.

For clinical use NK cells are usually collected from the patient or donor by leukapheresis. However, maximal NK-cell dose is limited and high NK-cell doses may only be obtained for patients with a low body weight, making children the best candidates for NK-cell therapy. Significantly, the total number and activity of NK cells may substantially decrease in viral infection and/or cancer, making immunotherapy based on the activation of endogenous NK cells ineffective. Further, refractory relapses are a major complication in cell transfusions, and many clinical protocols require repeated infusions of lymphocyte populations.

In this regard, Verneris et al. (Brit J Hematol 2009; 147:185-91), reviewing the prospects for clinical use of cord blood NK cells, has recently indicated that fresh cord blood NK cell populations may require further manipulation in order to express their full functional (cytotoxic, motility) potential. Upon systemic treatment with various biologic response modifiers, particularly IL-2, the number of activated NK cells and their antiviral and antimetastatic activities have been found to increase dramatically in various tissues. Based on this evidence, therapeutic strategies involving activation and expansion of NK cells along with IL-2 (and IL-15) have been attempted, as well as co-administration of IL-2 to the transfusion recipient. However, to date the results have been disappointing, indicating only limited homing and transient engraftment of the infused NK cells. Further, IL-2 is toxic, and must be used with extreme caution in the clinical setting.

In an attempt to develop a clinical feasible protocol for enrichment and proliferation of NK cells ex-vivo, magnetic cell-selection technology, using paramagnetic CD56 microbeads and cell selection columns, has been used to isolate a $CD56^+$ population containing both $CD3^-/56^+$ NK (60.6±10.8%) and $CD3^+/56^+$ NK T cells (30.4±8.6%) to initiate the proliferation studies. With the addition of recombinant human IL-2 or IL-2 plus recombinant human IL-15 substantial cell-expansion variability was observed, depending on the donor, and even when the same donor was tested on different occasions. The cytotoxicity of selected and propagated $CD56^+$ cells at a low E:T ratio was significantly higher than the starting population, but was comparable to non-separated PBMC cultured for 2 weeks under the same conditions. In fresh, unselected PBMC cultures, IL-15 (in combination with IL-2) induced higher killing at the 1:1 E:T ratio than IL-2 alone. Notably, since CD3+ cells were not depleted prior to culture, the proliferation of $CD3^+CD56^+$ NKT cells was 2-3 times that of $CD3^-CD56^+$ NK cells. Only moderate proliferation of $CD56^+/CD3^-$ cells occurred, with the majority of the resultant cells being $CD56^+/CD3^+$ NKT cells.

In a different approach, human CD3-CD56+ NK cells are cultured from BM-derived CD34+ hematopoietic progenitor cells (HPCs) cultured in the presence of various cytokines produced by bone marrow stromal cells and/or immune cells (such as c-kit ligand, IL-2, and IL-15). The addition of the stem cell factor to these cultures has no effect on the differentiation of the CD3-CD56+ cytotoxic effector cells, but greatly enhances their proliferation in culture. The majority of these cells lack CD2 and CD16, but do express zeta-TCR. Similar to NK cells found in peripheral blood, bone marrow derived CD2-CD16-CD56+ NK cells grown in the presence of IL-15 were found to be potent producers of IFN-gamma in response to monocyte-derived cytokines. IL-15 can induce CD34+ HPCs to differentiate into CD3-CD56+ NK cells, and KL can amplify their numbers. However, yields of NK cells are limited by the low numbers of potential NK progenitors among the CD34+ cell population.

Other methods for the propagation of NK cells have been described. Frias et al. (Exp Hematol 2008; 36: 61-68) grew NK progenitors ($CD7^+CD34^-Lin^-CD56^-$) selected from cord blood on stromal cell layers with a serum-free medium, inducing NK differentiation with SCF, IL-7, IL-15, FL and IL-2, producing increased numbers of cytotoxic cultured NK cells. Harada et al. (Exp Hematol. 2004; 32:614-21) grew NK cells on cells from a Wilm's tumor cells line. Waldmann et al. (US20070160578) describes enhanced proliferation of NK and CD8-T cells from whole blood, bone marrow or spleen cells in culture using complexes of IL-15/R-ligand activator, in order to reduce undesirable cytokine production. Campana et al. (US20090011498) describes ex-vivo culture and activation of NK cells, for transplantation, in the presence of leukemia cells expressing IL-15 and 4-1BB, and having weak or absent MHC-I or II expression. Childs et al. (US20090104170) describes ex-vivo proliferation, and activation of NK cells by co-culture with irradiated EBV-transformed lymphoblastoid cells, in the presence of IL-2. Using another approach, Tsai (US20070048290) produced continuous NK cell lines from hematopoietic stem cells by ex-vivo culture of immortalized NK-progenitors with irradiated 3T3-derived OP-9S cells, for research and potential therapeutic applications. (All the above mentioned references are incorporated herein by reference).

However, established methods for NK cell culture also support T cell proliferation and even after T cells are depleted, residual T cells typically increase in number after stimulation, precluding clinical use of the expanded cell populations due to potential graft versus host disease. This further necessitates another round of T cell depletion before infusion, making the preparatory procedure time consuming, expensive and invariably causing substantial NK cell loss.

To reduce T cell contamination following expansion, NK expansion protocols are using purified CD56+CD3− cells as the initial population to be seeded in expansion cultures. To obtain a highly purified fraction of CD56+CD3− cells, a two step purification procedure is needed: positive selection of CD56 cells followed by depletion of CD3+ cells or first the depletion of the CD3 cells followed by positive selection of CD56 cells. However, this procedure is expensive and involves a substantial cell lost during the two cycle of purification. Even in cultures initiated with purified CD56+CD3− cells there are still expanded NK products contaminated with T cells.

Protocols using cytokines only for the expansion of NK cells indicate a rather modest effect and the requirement for additional stimuli in addition to cytokines in order to obtain substantial expansion (Korean J Lab Med 2009; 29:89-96, Koehl U et al. Klin Pädiatr 2005; 217: 345-350). Irradiated feeder cells (e.g., peripheral blood mononuclear cells, Epstein-Barr virus-transformed lymphoblastoid lines (ABV-LCL), K562 myeloid leukemia cell line, genetically modified to express a membrane-bound form of interleukin-15 and the ligand for the co-stimulatory molecule 4-1BB) and others are commonly used for the expansion of NK cells as additional stimuli. While most NK expansion protocols use purified CD56+CD3− cells as the initial population, some protocols use mononuclear cells as the initial seeding population in combination with irradiated stroma or anti-CD3 antibody (Blood, 15 Mar. 2008, Vol. 111, No. 6, pp. 3155-3162). Following expansion these cultures are heavily contaminated with CD3+ and CD3+CD56+ cells and therefore CD56+CD3− cells need to be purified before infusion. Miller et al. (Blood, 1992 80: 2221-2229) obtained a 30-fold expansion of NK cells at 18 days culture using a fraction enriched for NK progenitors and monocytes comprising CD56+CD3− cells in combination with purified CD14+ cells or MNC depleted of CD5 and CD8 by panning on antibody-coated plastic flasks. Ve'ronique Decot et al. (Experimental Hematology 2010; 38:351-362) reported about 20 fold expansion of NK cells on irradiated T and B cells by depleting mononuclear cells of T and B, and found that the contaminating population after depletion was mainly monocytes. However, in this culture model, feeder cells and cytokines were necessary to obtain NK cell amplification because no expansion was observed in the presence of cytokines alone or feeder cells alone. Therefore, in contrast to Miller, even thought monocytes were enriched in the seeding population, no expansion of NK cells was observed in the absence of irradiated T and B stroma cells (Decot et al., Exper Hematology 2010; 38:351-362).

Yet further, while ex-vivo cultured NK cells often demonstrate considerable activity (e.g., cytotoxicity) against unrelated target cells, activity against more clinically relevant tumor and cancer cells, both in-vitro and in-vivo has often been disappointing, and methods for enhancing activation have been proposed. Zitvogel et al. (U.S. Pat. No. 6,849,452) (which is incorporated herein by reference) teaches ex-vivo or in-vivo activation of NK cells by contacting with triggered dendritic cells. Others have suggested enhancing activation by culturing NK cells with cells lacking MHC-I molecules and genetically modified to express IL-15 (Campana et al., US Patent Application No. 2009011498) or pre-treatment of NK cell recipients with proteasome inhibitors (Berg et al. Cytotherapy 2009; 11:341-55) (which reference is incorporated herein by reference). However, none of the protocols have yielded significantly expanded NK cell populations capable of survival and expansion in appropriate host target organs following transplantation (homeostatic proliferation) and immunotherapy with ex vivo proliferated NK cells is still limited by the inability to obtain sufficient numbers of highly purified, functionally competent NK cells suitable for use in clinical protocols (see Bachanova et al., Canc Immunol. Immunother. 2010; 59:739-44; Guven, Karolinska Institute, 2005; Schuster et al., E. J. Immunology 2009; 34:2981-90; Bernardini et al. Blood 2008; 111:3626-34). Thus there is a need for simplified, cost-effective methods to preferentially propagate NK ex-vivo, as isolated NK cells, or from a mixed population of mononuclear cells either depleted or not from CD3+ cells.

WO 2011/080740 discloses compositions and methods for enhancing propagation and/or functionality of NK cells by treating the cells with nicotinamide.

U.S. Patent Application having Publication No. 2010/0183564 discloses compositions and methods for expanding a population of hematopoietic stem cells, which utilize compounds which are antagonists of the aryl hydrocarbon receptor.

SUMMARY OF THE INVENTION

In view of the growing need for greater numbers of therapeutically competent NK cells for clinical applications such as cell therapy for leukemia and other cancers, there is a need for improved, simplified and cost-effective methods for enhanced ex-vivo proliferation and activation of natural killer cells suitable for use in the clinical setting.

Thus, expansion of NK cells in ex vivo cultures, and enhancing their functionality following infusion is critical to their clinical applicability in adoptive immunotherapy.

According to an aspect of some embodiments of the present invention there is provided a method of ex-vivo culturing natural killer (NK) cells, the method comprising culturing a population of cells comprising NK cells with an aryl hydrocarbon receptor (AHR) antagonist.

According to some embodiments of the present invention, culturing the population of cells is with the AHR antagonist and at least one growth factor.

According to some embodiments of the present invention, a concentration of the AHR antagonist ranges from 1 to 100000 nM.

According to some embodiments of the present invention, the culturing is effected for a time period that ranges from 3 days to 6 weeks.

According to some embodiments of the present invention, culturing the NK cells with the AHR antagonist results in at least one of the following:

(a) elevated expression of CD62L as compared to NK cells cultured under otherwise identical culturing conditions without added AHR antagonist;

(b) Reduced expression of CD200R or PD-1 or both as compared to NK cells cultured under otherwise identical culturing conditions without added AHR antagonist;

(c) elevated homing and in-vivo retention as compared to NK cells cultured under otherwise identical culturing conditions without added AHR antagonist; and (d) greater proliferation as compared to NK cells cultured under otherwise identical culturing conditions without added AHR antagonist.

According to some embodiments of the present invention, the at least one growth factor is IL-2, the exposure time is from seeding of the population of cells comprising NK cells, the exposure duration is from about 2 to about 3 weeks and the concentration of the AHR antagonist is about 250 to about 1000 nM.

According to some embodiments of the present invention, the concentration of the AHR antagonist is about 50 nM, about 100 nM, about 250 nM, about 500 nM or about 1000 nM.

According to some embodiments of the present invention, the exposure duration is about 1 week, about 2 weeks or about 3 weeks.

According to some embodiments of the present invention, the population of cells comprising the NK cells is obtained from a source selected from the group consisting of cord blood, bone marrow and peripheral blood.

According to some embodiments of the present invention, the population of cells comprising the NK cells is a heterogenous cell population which comprises an NK cell fraction and a CD3+ cell fraction.

According to some embodiments of the present invention, the CD3+ cell fraction is greater than the NK cell fraction.

According to some embodiments of the present invention, the NK cell fraction is greater than the CD3+ cell fraction.

According to some embodiments of the present invention, the population of cells comprising the NK cells is a mononuclear or total nuclear cell population depleted of CD3+ cells.

According to some embodiments of the present invention, the population of cells comprising the NK cells is a mononuclear or total nuclear cell population depleted of CD3+ and CD19+ cells.

According to some embodiments of the present invention, the population of cells comprising the NK cells is an unselected NK cell population.

According to some embodiments of the present invention, the NK cells comprise CD56+CD3− cells or CD56+CD16+CD3− cells.

According to some embodiments of the present invention, culturing the population of cells comprising the NK cells is effected without a feeder layer or feeder cells.

According to some embodiments of the present invention, the at least one growth factor comprises a growth factor selected from the group consisting of SCF, FLT3, IL-2, IL-7, IL-15, IL-12 and IL-21.

According to some embodiments of the present invention, the at least one growth factor is IL-2 or IL-2 and IL-15.

According to some embodiments of the present invention, the at least one growth factor is solely IL-2.

According to some embodiments of the present invention, the expression of CD62L is determined by a method selected from the group consisting of flow cytometry, immunodetection, quantitative cDNA amplification and hybridization.

According to some embodiments of the present invention, the expression of CD62L is determined by fluorescent activated cell sorting (FACS).

According to some embodiments of the present invention, the expression of CD62L is determined is using fluorescent anti-human CD62L monoclonal antibodies.

According to some embodiments of the present invention, the expression of CD200R or PD-1 or both is determined by a method selected from the group consisting of flow cytometry, immunodetection, quantitative cDNA amplification and hybridization.

According to some embodiments of the present invention, the elevated homing and in-vivo retention is determined by FACS, expressed as percent engrafted NK cells in target organs following infusion, and the target organ is selected from the group consisting of spleen, bone marrow and lymph nodes.

According to some embodiments of the present invention, the homing and in-vivo retention is determined about 1 day to about 2 weeks following infusion of NK cells.

According to some embodiments of the present invention, the proliferation rate is determined by clonogenic assays, mechanical assays, metabolic assays, and direct proliferation assays.

According to some embodiments of the present invention, the proliferation rate is determined by FACS analysis of percentage CD56+CD3− cells and expressed as fold increase over time.

According to another aspect of some embodiments of the present invention there is provided a population of NK cells cultured with added aryl hydrocarbon receptor antagonists according to the methods of the present invention.

According to another aspect of some embodiments of the present invention there is provided a population of NK cells characterized by at least one of the following:

(a) elevated expression of CD62L as compared to NK cells cultured under otherwise identical culturing conditions without added AHR antagonist;

(b) reduced expression of CD200R or PD-1 or both as compared to NK cells cultured under otherwise identical culturing conditions without added AHR antagonist;

(c) elevated homing and in-vivo retention as compared to NK cells cultured under otherwise identical culturing conditions without added AHR antagonist;

(d) greater proliferation as compared to NK cells cultured under otherwise identical culturing conditions without added AHR antagonist; and (e) a reduced ratio of CD3+ to CD56+/CD3− cells as compared to a population of NK cells cultured under otherwise identical culturing conditions without added AHR antagonist.

According to another aspect of some embodiments of the present invention there is provided a population of NK cells characterized by enhanced homing, engraftment and retention when transplanted, wherein infusion of at least 15×10$^6$ of said NK cell population into an irradiated NSG mouse host, results in at least 12% donor-derived NK cells in a host spleen tissue, as detected by immunodetection and flow cytometry, at 4 days post infusion.

According to some embodiments of the present invention the population is further characterized by expression of CD62L in at least 30% of the cell population at the time of infusion, as detected by immunodetection and flow cytometry.

According to some embodiments of the present invention the population is further characterized by a ratio of CD3+ to CD56+/CD3− cells of equal to or less than 1:100 at the time of infusion.

According to another aspect of some embodiments of the present invention there is provided a method of inhibiting tumor growth in a subject in need thereof, comprising administering a therapeutically effective amount of the population of NK cells cultured with added aryl hydrocarbon receptor antagonist according to the methods of the present invention to the subject.

According to another aspect of some embodiments of the present invention there is provided a method of treating or preventing a viral infection in a subject in need thereof, comprising administering a therapeutically effective amount of the ex-vivo cultured population of NK cells cultured with added aryl hydrocarbon receptor antagonist according to the methods of the present invention to the subject.

According to another aspect of some embodiments of the present invention there is provided a method of treating or preventing graft versus host disease in a subject in need thereof, comprising administering a therapeutically effective amount of the ex-vivo cultured population of NK cells cultured with added aryl hydrocarbon receptor antagonist according to the methods of the present invention to the subject.

According to another aspect of some embodiments of the present invention there is provided a method of treating or preventing a leukemic disease or condition in a subject in need thereof, comprising administering a therapeutically effective amount of the ex-vivo cultured population of NK cells cultured with added aryl hydrocarbon receptor antagonist according to the methods of the present invention to the subject.

According to some embodiments of the present invention the subject is receiving a hematopoietic cell transplant concomitantly with the administering of the NK cell population.

According to another aspect of some embodiments of the present invention there is provided a method of treating or preventing an autoimmune disease or condition in a subject in need thereof, comprising administering a therapeutically effective amount of the ex-vivo cultured population of NK cells cultured with an added aryl hydrocarbon receptor antagonist according to the methods of the present invention to the subject.

According to some embodiments of the present invention the population of NK cells is autologous to the subject.

According to some embodiments of the present invention the population of NK cells is allogeneic to the subject.

According to some embodiments of the present invention the administering is by a single infusion of the NK cell population.

According to some embodiments of the present invention the administering is by repeated infusions of the NK cell population.

According to some embodiments of the present invention the subject is being treated with at one growth factor concomitantly with the administering of the NK cell population.

According to some embodiments of the present invention the at least one growth factor is IL-2 or IL-2 and IL-15.

According to another aspect of some embodiments of the present invention there is provided a method of transducing ex-vivo cultured NK cells with an exogene, the method comprising:

(a) ex-vivo culturing a population of NK cells with an added aryl hydrocarbon receptor antagonist according to the methods of the present invention; and (b) transducing the cultured population of NK cells with the exogene.

According to some embodiments of the present invention the AHR antagonist is represented by Formula I:

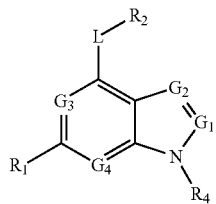

Formula I wherein:

G$_1$ is selected from N and CR$_3$;

R$_3$ is selected from hydrogen, C$_{1-4}$alkyl and biphenyl;

G$_2$, G$_3$ and G$_4$ are each independently selected from —CH— and N; with the proviso that at least one of G$_3$ and G$_4$ is N; and with the proviso that G$_1$ and G$_2$ are not both N;

L is selected from a substituted or unsubstituted alkylamino, a substituted or unsubstituted amino or a substituted or unsubstituted alkyl;

R$_1$ is selected from hydrogen, a substituted or unsubstituted aryl and a substituted or unsubstituted heteroaryl; with the proviso that R$_1$ and R$_3$ are not both hydrogen;

R$_2$ is selected from —S(O)$_2$NR$_{6a}$R$_{6b}$, —NR$_{9a}$C(O)R$_{9b}$, —NR$_{6a}$C(O)NR$_{6b}$R$_{6c}$, a substituted or unsubstituted aryl and a substituted or unsubstituted heteroaryl; and R$_4$ is selected from a substituted or unsubstituted C$_{1-10}$alkyl, a substituted or unsubstituted C$_{1-10}$alkenyl, a substituted or unsubstituted cycloalkyl, a substituted or unsubstituted aryl, a substituted or unsubstituted alkaryl, a substituted or unsubstituted heteroalicyclic and a substituted or unsubstituted heteroaryl.

According to some embodiments of the present invention L is selected from —NR$_{5a}$(CH$_2$)$_{0-3}$—, —NR$_{5a}$CH(C(O)OCH$_3$)CH$_2$—, —NR$_{5a}$(CH$_2$)$_2$NR$_{5b}$—, —NR$_{5a}$(CH$_2$)$_2$S—, —NR$_{5a}$CH$_2$CH(CH$_3$)CH$_2$—, —NR$_{5a}$CH$_2$CH(OH)— and —NR$_{5a}$CH(CH$_3$)CH$_2$—, wherein R$_{5a}$ and R$_{5b}$ are independently selected from hydrogen and C$_{1-4}$alkyl;

According to some embodiments of the present invention R$_1$ is selected from phenyl, thiophenyl, furanyl, 1H-benzoimidazolyl, isoquinolinyl, 1H-imidazopyridinyl, benzothiophenyl, pyrimidinyl, 1H-pyrazolyl, pyridinyl, 1H-imidazolyl, pyrrolidinyl, pyrazinyl, pyridazinyl, 1H-pyrrolyl and thiazolyl), each being optionally substituted by 1 to 3 substituents selected from cyano, hydroxy, C$_{1-4}$alkyl, C$_{1-4}$alkoxy, halo, halo-substituted-C$_{1-4}$alkyl, halo-substituted-C$_{1-4}$alkoxy, amino, —C(O)R$_{8a}$, —S(O)$_{0-2}$R$_{8a}$, —C(O)OR$_{8a}$ and —C(O)NR$_{8a}$R$_{8b}$, wherein each of R$_{8a}$ and R$_{8b}$ can independently be hydrogen or C$_{1-4}$alkyl. According to some embodiments of the present invention R$_4$ is selected from C$_{1-10}$alkyl, prop-1-en-2-yl, cyclohexyl, cyclopropyl, phenyl, benzyl, benzhydryl, 2-(2-oxopyrrolidin-1-yl)ethyl, oxetan-3-yl, tetrahydro-2H-pyran-3-yl, tetrahydro-2H-pyran-4-yl, tetrahydrofuran-3-yl, (4-pentylphenyl)(phenyl)methyl and 1-(1-(2-oxo-6,9,12-trioxa-3-azatetradecan-14-yl)-1H-1,2,3-triazol-4-yl)ethyl, each being optionally substituted with 1 to 3 substituents independently selected from hydroxy, C$_{1-4}$alkyl and halo-substituted-C$_{1-4}$alkyl.

According to some embodiments of the present invention R$_2$ is selected from phenyl, 1H-pyrrolopyridin-3-yl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl and 1H-indazolyl, each being optionally substituted with 1 to 3 substituents selected from hydroxy, halo, methyl, methoxy, amino, —O(CH$_2$)nNR$_{7a}$R$_{7b}$, —S(O)$_2$NR$_{7a}$R$_{7b}$, —OS(O)$_2$NR$_{7a}$R$_{7b}$ and —NR$_{7a}$S(O)$_2$R$_{7b}$, wherein each of R$_{7a}$ and R$_{7b}$ is independently hydrogen or C$_{1-4}$alkyl.

According to some embodiments of the present invention G$_1$ is CR$_3$, and G$_2$, G$_3$ and G$_4$ are each N, the anatagonist of said AHR being represented by Formula Ia:

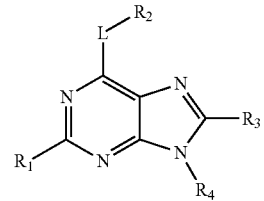

Formula Ia wherein R$_1$-R$_4$ and L are as defined above.

According to further embodiments of the present invention G$_2$ is CH, and G$_1$, G$_3$ and G$_4$ are each N, the antagonist of AHR is represented by Formula Ib:

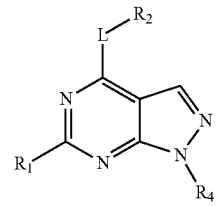

Formula Ib wherein R$_1$, R$_2$, R$_4$ and L are as defined above.

According to some embodiments of the present invention G$_1$ is CR$_3$, G$_2$ and G$_4$ are each N, and G$_3$ is CH, the AHR antagonist being represented by Formula Ic:

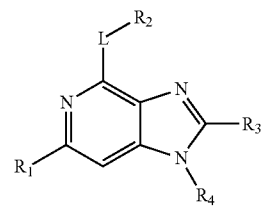

Formula Ic wherein R$_1$-R$_4$ and L are as defined above.

According to some embodiments of the present invention G$_1$ is CR$_3$, G$_2$ and G$_3$ are each N, and G$_4$ is CH, the AHR antagonist being represented by Formula Id:

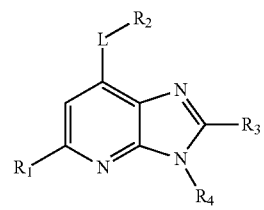

Formula Id wherein R$_1$-R$_4$ and L are as defined above.

According to some embodiments of the present invention $G_1$ is $CR_3$, $G_3$ and $G_4$ are each N, and $G_2$ is CH, the AHR antagonist being represented by Formula Ie:

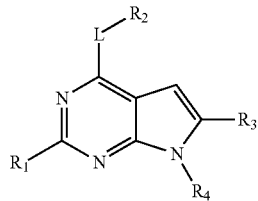

Formula Ie wherein $R_1$-$R_4$ and L are as defined above.

According to some embodiments of the present invention L is selected from —$NR_{5a}(CH_2)_{0-3}$—, —$NR_{5a}CH(C(O)OCH_3)CH_2$—, —$NR_{5a}(CH_2)_2NR_{5b}$—, —$NR_{5a}(CH_2)_2S$—, —$NR_{5a}CH_2CH(CH_3)CH_2$—, —$NR_{5a}CH_2CH(OH)$— and —$NR_{5a}CH(CH_3)CH_2$—, wherein $R_{5a}$ and $R_{5b}$ are each independently selected from hydrogen and $C_{1-4}$alkyl.

According to some embodiments of the present invention $R_1$ is selected from hydrogen and an aryl or heteroaryl selected from phenyl, thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, 1H-pyrazol-4-yl, pyridin-2-yl, pyridin-4-yl, 1H-imidazol-1-yl, pyrrolidin-1-yl, pyrazin-2-yl, pyridin-3-yl, pyridazin-4-yl, 1H-pyrrol-2-yl and thiazol-5-yl), wherein said aryl or heteroaryl of $R_1$ is optionally substituted by 1 to 3 substituents independently selected from cyano, hydroxy, $C_{1-4}$alkyl, $C_{1-4}$alkoxy, halo, halo-substituted-$C_{1-4}$alkyl, —$S(O)_{0-2}R_{8a}$ and —$C(O)OR_{8a}$, wherein $R_{8a}$ and $R_{8b}$ are independently selected from hydrogen and $C_{1-4}$alkyl; with the proviso that $R_1$ and $R_3$, if both present, are not both hydrogen.

According to some embodiments of the present invention $R_2$ is selected from —$NR_{6a}C(O)NR_{6b}R_{6c}$, and an aryl, heteroaryl or heteroalicyclic selected from 1H-pyrrolo[2,3-b]pyridin-3-yl, 1H-pyrrolo[2,3-b]pyridin-5-yl, 1H-indol-3-yl, thiophen-3-yl, pyridin-2-yl, pyridin-3-yl, pyridin-4-yl, 2-oxoimidazolidin-1-yl, 1H-pyrazol-3-yl, 1H-pyrazol-4-yl, 2-oxo-2,3-dihydro-1H-benzo[d]imidazol-5-yl and 1H-indazol-3-yl, wherein $R_{6a}$, $R_{6b}$ and $R_{6c}$ are independently selected from hydrogen and $C_{1-4}$alkyl, and wherein each of said aryl, heteroaryl and heteroalicyclic of $R_2$ is independently optionally substituted with 1 to 3 substituents independently selected from hydroxy, halo, methoxy, amino, —$OS(O)_2NR_{7a}R_{7b}$ and —$NR_{7a}S(O)_2R_{7b}$, wherein $R_{7a}$ and $R_{7b}$ are independently selected from hydrogen and $C_{1-4}$alkyl.

According to some embodiments of the present invention $R_3$, when present, is selected from hydrogen, $C_{1-4}$alkyl and biphenyl; and $R_4$ is selected from a substituted or unsubstituted alkyl or alkenyl.

According to some embodiments of the present invention the alkyl or alkenyl is selected from isopropyl, methyl, ethyl, prop-1-en-2-yl, isobutyl, sec-butyl, (S)-sec-butyl, (R)-sec-butyl, 1-hydroxypropan-2-yl, (S)-1-hydroxypropan-2-yl, (R)-1-hydroxypropan-2-yl, nonan-2-yl), cycloalkyl (e.g., cyclohexyl), aryl (e.g., phenyl), alkaryl (e.g., benzyl and benhydryl), and a heteroalicyclic or heteroaryl (e.g., 2-(2-oxopyrrolidin-1-yl)ethyl, oxetan-3-yl, oxetan-2-yl, tetrahydro-2H-pyran-2-yl, tetrahydrofuran-3-yl); each of the alkyl or alkenyl being optionally substituted with 1 to 3 substituents independently selected from $C_{1-4}$alkyl and halo-substituted-$C_{1-4}$alkyl.

According to some embodiments of the present invention L is —$NR_{5a}(CH_2)_{1-3}$.

According to some embodiments of the present invention the AHR antagonist is selected from:

4-(2-(2-(benzo[b]thiophen-3-yl)-9-isopropyl-9H-purin-6-ylamino)ethyl)phenol;

4-(2-(2-(benzo[b]thiophen-3-yl)-9-sec-butyl-9H-purin-6-ylamino)ethyl)phenol;

4-(2-(9-benzhydryl-2-(benzo[b]thiophen-3-yl)-9H-purin-6-ylamino)ethyl)phenol;

4-(2-(2-(benzo[b]thiophen-3-yl)-9-(tetrahydro-2H-pyran-3-yl)-9H-purin-6-yl amino)ethyl)phenol;

4-(2-(9-isopropyl-2-(thiophen-2-yl)-9H-purin-6-ylamino)ethyl)phenol;

4-(2-(2-(benzo[b]thiophen-3-yl)-9-(4-(trifluoromethyl)benzyl)-9H-purin-6-yl amino)ethyl)phenol;

4-(2-(2-(benzo[b]thiophen-3-yl)-9-isobutyl-9H-purin-6-ylamino)ethyl)phenol;

4-(2-(2-(benzo[b]thiophen-3-yl)-9-methyl-9H-purin-6-ylamino)ethyl)phenol;

4-(2-(2-(benzo[b]thiophen-3-yl)-9-(4-methylbenzyl)-9H-purin-6-ylamino)ethyl)phenol;

N-(2-(1H-indol-3-yl)ethyl)-2-(benzo[b]thiophen-3-yl)-9-isopropyl-9H-purin-6-amine;

2-(benzo[b]thiophen-3-yl)-9-isopropyl-N-(2-(thiophen-3-yl)ethyl)-9H-purin-6-amine;

3-(2-(2-(benzo[b]thiophen-3-yl)-9-isopropyl-9H-purin-6-ylamino)ethyl)phenol;

2-(benzo[b]thiophen-3-yl)-N-(4-fluorophenethyl)-9-isopropyl-9H-purin-6-amine;

N-(4-aminophenethyl)-2-(benzo[b]thiophen-3-yl)-9-isopropyl-9H-purin-6-amine;

4-(2-(9-isopropyl-2-(pyrimidin-5-yl)-9H-purin-6-ylamino)ethyl)phenol;

4-(2-(9-isopropyl-2-(pyridin-3-yl)-9H-purin-6-ylamino)ethyl)phenol;

4-(2-(9-isopropyl-2-phenyl-9H-purin-6-ylamino)ethyl)phenol;

4-(2-(9-isopropyl-2-(thiophen-3-yl)-9H-purin-6-ylamino)ethyl)phenol;

4-(2-(2-(furan-3-yl)-9-isopropyl-9H-purin-6-ylamino)ethyl)phenol;

2-(benzo[b]thiophen-3-yl)-N-(4-fluorophenethyl)-9-phenyl-9H-purin-6-amine;

N-benzyl-8-(biphenyl-4-yl)-9-isopropyl-9H-purin-6-amine;

4-(2-(2-(benzo[b]thiophen-3-yl)-9-(nonan-2-yl)-9H-purin-6-ylamino)ethyl)phenol;

N-(2-(1H-indol-3-yl)ethyl)-2-(benzo[b]thiophen-3-yl)-9-sec-butyl-9H-purin-6-amine;

3-(2-(2-(benzo[b]thiophen-3-yl)-9-isopropyl-9H-purin-6-ylamino)ethyl)-1H-indol-5-yl, 5-((3aS,4S,6aR)-2-oxohexahydro-1H-thieno[3,4-d]imidazol-4-yl)pentanoate;

N-(2-(2-(2-(2-(4-(1-(2-(benzo[b]thiophen-3-yl)-6-(4-hydroxyphenethylamino)-9H-purin-9-yl)ethyl)-1H-1,2,3-triazol-1-yl)ethoxy)ethoxy)ethoxy)ethyl)acetamide;

4-(2-(9-isopropyl-2-(pyridin-4-yl)-9H-purin-6-ylamino)ethyl)phenol;

ethyl 5-(6-(4-hydroxyphenethylamino)-9-isopropyl-9H-purin-2-yl)nicotinate;

ethyl 5-(6-(4-hydroxyphenethylamino)-9-isopropyl-9H-purin-2-yl)nicotinate;

4-(2-(2-(6-fluoropyridin-3-yl)-9-isopropyl-9H-purin-6-ylamino)ethyl)phenol;

4-(2-(9-isopropyl-2-(4-methylpyridin-3-yl)-9H-purin-6-ylamino)ethyl)phenol;
5-(6-(4-hydroxyphenethylamino)-9-isopropyl-9H-purin-2-yl)nicotinonitrile;
4-(2-(9-isopropyl-2-(pyrrolidin-1-yl)-9H-purin-6-ylamino)ethyl)phenol;
4-(2-(2-(1H-imidazol-1-yl)-9-isopropyl-9H-purin-6-ylamino)ethyl)phenol;
4-(2-(9-isopropyl-2-(pyridazin-4-yl)-9H-purin-6-ylamino)ethyl)phenol;
4-(2-(9-isopropyl-2-(pyrazin-2-yl)-9H-purin-6-ylamino)ethyl)phenol;
4-(2-(9-isopropyl-2-(pyridin-2-yl)-9H-purin-6-ylamino)ethyl)phenol;
4-(2-(9-isopropyl-2-(5-(methylsulfonyl)pyridin-3-yl)-9H-purin-6-ylamino)ethyl)phenol;
4-(2-(9-isopropyl-2-(5-methylpyridin-3-yl)-9H-purin-6-ylamino)ethyl)phenol;
4-(2-(2-(4-chloropyridin-3-yl)-9-isopropyl-9H-purin-6-ylamino)ethyl)phenol;
4-(2-(2-(5-fluoropyridin-3-yl)-9-isopropyl-9H-purin-6-ylamino)ethyl)phenol;
4-(2-(9-isopropyl-2-(1-methyl-1H-pyrazol-4-yl)-9H-purin-6-ylamino)ethyl)phenol;
4-(2-(9-isopropyl-2-(pyridin-3-yl)-9H-purin-6-ylamino)ethyl)-2-methoxy phenol;
4-(2-(9-isopropyl-2-(pyridin-3-yl)-9H-purin-6-ylamino)ethyl)-2-methoxy phenol;
N-[2-(6-methoxy-1H-indol-3-yl)ethyl]-9-(propan-2-yl)-2-(pyridin-3-yl)-9H-purin-6-amine;
N-[2-(5-methyl-1H-indol-3-yl)ethyl]-9-(propan-2-yl)-2-(pyridin-3-yl)-9H-purin-6-amine;
1-(2-{[9-(propan-2-yl)-2-(pyridin-3-yl)-9H-purin-6-yl]amino}ethyl)imidazolidin-2-one;
N-(2-{[9-(propan-2-yl)-2-(pyridin-3-yl)-9H-purin-6-yl]amino}ethyl)pyridin-2-amine;
9-(propan-2-yl)-N-[3-(1H-pyrazol-4-yl)propyl]-2-(pyridin-3-yl)-9-H-purin-6-amine;
N-{2-[(3-methyl-1H-1,2,4-triazol-5-yl)sulfanyl]ethyl}-9-(propan-2-yl)-2-(pyridin-3-yl)-9H-purin-6-amine;
1-(2-{[2-(1-benzothiophen-3-yl)-9-(propan-2-yl)-9H-purin-6-yl]amino}ethyl)imidazolidin-2-one;
N-[2-(5-amino-1H-1,2,4-triazol-3-yl)ethyl]-2-(1-benzothiophen-3-yl)-9-(propan-2-yl)-9H-purin-6-amine;
N-(2-{[2-(1-benzothiophen-3-yl)-9-(propan-2-yl)-9H-purin-6-yl]amino}ethyl)pyridin-2-amine;
2-(1-benzothiophen-3-yl)-9-(propan-2-yl)-N-[3-(1H-pyrazol-4-yl)propyl]-9H-purin-6-amine;
2-(1-benzothiophen-3-yl)-N-[3-(3,5-dimethyl-1H-pyrazol-4-yl)propyl]-9-(propan-2-yl)-9H-purin-6-amine;
(2-{[2-(1-benzothiophen-3-yl)-9-(propan-2-yl)-9H-purin-6-yl]amino}ethyl)urea;
5-({[2-(1-benzothiophen-3-yl)-9-(propan-2-yl)-9H-purin-6-yl]amino}methyl)-2,3-dihydro-1H-1,3-benzodiazol-2-one;
N-[2-(1H-indol-3-yl)ethyl]-9-(propan-2-yl)-2-(pyridin-3-yl)-9H-purin-6-amine;
N-(4-(2-(9-isopropyl-2-(pyridin-3-yl)-9H-purin-6-ylamino)ethyl)phenyl)methane-sulfonamide;
4-(2-(2-(pyridin-3-yl)-9-(tetrahydrofuran-3-yl)-9H-purin-6-ylamino)ethyl)-phenol;
4-(2-(9-isopropyl-2-(pyridin-3-yl)-9H-purin-6-ylamino)propyl)phenol;
4-(2-(9-(oxetan-3-yl)-2-(pyridin-3-yl)-9H-purin-6-ylamino)ethyl)phenol;
5-(6-(4-hydroxyphenethylamino)-9-isopropyl-9H-purin-2-yl)-N-methylnicotin-amide;
4-(2-(9-(1-hydroxypropan-2-yl)-2-(pyridin-3-yl)-9H-purin-6-ylamino)-ethyl)phenol;
4-(2-(9-isopropyl-2-(pyridin-3-yl)-9H-purin-6-ylamino)ethyl)phenyl sulfamate;
4-(2-(2-(2-fluoropyridin-3-yl)-9-isopropyl-9H-purin-6-ylamino)ethyl)phenol;
4-(2-(9-isopropyl-2-(1-methyl-1H-pyrrol-2-yl)-9H-purin-6-ylamino)ethyl)-phenol;
4-(2-(9-isopropyl-2-(thiazol-5-yl)-9H-purin-6-ylamino)ethyl)phenol;
4-(2-(2-(1H-benzo[d]imidazol-1-yl)-9-isopropyl-9H-purin-6-ylamino)ethyl)-phenol;
4-(2-(2-(2,4-dimethyl-1H-imidazol-1-yl)-9-isopropyl-9H-purin-6-ylamino)ethyl)phenol;
4-(2-(9-isopropyl-2-(2-methyl-1H-imidazol-1-yl)-9H-purin-6-ylamino)ethyl)-phenol;
5-(9-sec-butyl-6-(4-hydroxy-3-methylphenethylamino)-9H-purin-2-yl)-nicotinonitrile;
N-(2-(1H-pyrrolo[2,3-b]pyridin-5-yl)ethyl)-9-isopropyl-2-(pyridin-3-yl)-9-H-purin-6-amine;
9-isopropyl-N-(2-(5-methyl-1H-pyrazol-3-yl)ethyl)-2-(pyridin-3-yl)-9H-purin-6-amine;
4-(2-(2-(5-fluoropyridin-3-yl)-9-(oxetan-3-yl)-9H-purin-6-ylamino)ethyl)phenol;
4-(2-(2-(5-chloropyridin-3-yl)-9-isopropyl-9H-purin-6-ylamino)ethyl)phenol;
4-(2-(9-isopropyl-2-(5-(trifluoromethyl)pyridin-3-yl)-9H-purin-6-ylamino)ethyl)phenol;
5-(6-(2-(1H-indol-3-yl)ethylamino)-9-sec-butyl-9H-purin-2-yl)nicotinonitrile;
N-(2-(1H-indol-3-yl)ethyl)-9-sec-butyl-2-(5-methylpyridin-3-yl)-9H-purin-6-amine;
(R)—N-(2-(1H-indol-3-yl)ethyl)-9-sec-butyl-2-(5-fluoropyridin-3-yl)-9H-purin-6-amine;
(S)—N-(2-(1H-indol-3-yl)ethyl)-9-sec-butyl-2-(5-fluoropyridin-3-yl)-9H-purin-6-amine;
N-(2-(1H-indol-3-yl)ethyl)-9-sec-butyl-2-(5-fluoropyridin-3-yl)-9H-purin-6-amine;
(R)—N-(2-(1H-indol-3-yl)ethyl)-9-sec-butyl-2-(5-methylpyridin-3-yl)-9H-purin-6-amine;
(S)—N-(2-(1H-indol-3-yl)ethyl)-9-sec-butyl-2-(5-methylpyridin-3-yl)-9H-purin-6-amine;
5-(6-(4-hydroxyphenethylamino)-9-(oxetan-3-yl)-9H-purin-2-yl)nicotinonitrile;
4-(2-(6-(5-fluoropyridin-3-yl)-1-isopropyl-1H-pyrazolo[3,4-d]pyrimidin-4-yl amino)ethyl)phenol;
4-(2-(6-(benzo[b]thiophen-3-yl)-1-isopropyl-1H-pyrazolo[3,4-d]pyrimidin-4-yl amino)ethyl)phenol;
(R)-4-(2-(2-(5-fluoropyridin-3-yl)-9-(tetrahydrofuran-3-yl)-9H-purin-6-yl-amino)ethyl)phenol;
4-(2-(9-isopropyl-2-(pyridin-3-yl)-9H-purin-6-ylamino)ethyl)-3-methylphenol;
5-(6-(4-hydroxyphenethylamino)-9-isopropyl-9H-purin-2-yl)picolinonitrile;
3-(6-(4-hydroxyphenethylamino)-9-isopropyl-9H-purin-2-yl)isonicotinonitrile;
4-(2-(2-(5-fluoropyridin-3-yl)-7-isopropyl-7H-pyrrolo[2,3-d]pyrimidin-4-yl amino)ethyl)phenol;
3-(6-(4-hydroxyphenethylamino)-9-isopropyl-9H-purin-2-yl)picolinonitrile;
4-(2-(9-isopropyl-2-(6-methylpyridin-3-yl)-9H-purin-6-ylamino)ethyl)phenol;
4-(2-(9-isopropyl-2-(isoquinolin-4-yl)-9H-purin-6-ylamino)ethyl)phenol;
2-chloro-4-(2-(9-isopropyl-2-(pyridin-3-yl)-9H-purin-6-ylamino)ethyl)phenol;

3-fluoro-4-(2-(9-isopropyl-2-(pyridin-3-yl)-9H-purin-6-ylamino)ethyl)phenol;
N-(2-(5-chloro-1H-indol-3-yl)ethyl)-9-isopropyl-2-(pyridin-3-yl)-9H-purin-6-amine;
N-(2-(5-fluoro-1H-indol-3-yl)ethyl)-9-isopropyl-2-(pyridin-3-yl)-9H-purin-6-amine;
4-(2-(9-isopropyl-2-(pyridin-3-yl)-9H-purin-6-ylamino)ethyl)-2-methylphenol;
4-(2-(2-(benzo[b]thiophen-3-yl)-9-(oxetan-3-yl)-9H-purin-6-ylamino)ethyl)-phenol;
(S)-4-(2-(2-(benzo[b]thiophen-3-yl)-9-(tetrahydrofuran-3-yl)-9H-purin-6-yl amino)ethyl)phenol;
(R)-4-(2-(2-(benzo[b]thiophen-3-yl)-9-(tetrahydrofuran-3-yl)-9H-purin-6-yl amino)ethyl)phenol;
2-(6-(2-(1H-indol-3-yl)ethylamino)-2-(5-fluoropyridin-3-yl)-9H-purin-9-yl)propan-1-ol;
(R)-2-(6-(2-(1H-indol-3-yl)ethylamino)-2-(5-fluoropyridin-3-yl)-9H-purin-9-yl)propan-1-ol;
(S)-2-(6-(2-(1H-indol-3-yl)ethylamino)-2-(5-fluoropyridin-3-yl)-9H-purin-9-yl)propan-1-ol;
(R)—N-(2-(1H-indol-3-yl)ethyl)-2-(5-fluoropyridin-3-yl)-9-(tetrahydrofuran-3-yl)-9H-purin-6-amine;
4-(2-(2-(3H-imidazo[4,5-b]pyridin-3-yl)-9-isopropyl-9H-purin-6-ylamino)ethyl)phenol;
4-(2-(2-(1H-imidazo[4,5-b]pyridin-1-yl)-9-isopropyl-9H-purin-6-ylamino)ethyl)phenol;
4-(2-(6-(5-fluoropyridin-3-yl)-1-isopropyl-1H-imidazo[4,5-c]pyridin-4-yl amino)ethyl)phenol;
4-(2-(2-(4,5-dimethyl-1H-imidazol-1-yl)-9-isopropyl-9H-purin-6-ylamino)ethyl)phenol;
2-(5-fluoropyridin-3-yl)-9-isopropyl-N-(2-(pyridin-3-yl)ethyl)-9H-purin-6-amine;
4-(2-(2-(5-fluoropyridin-3-yl)-9-isopropyl-9H-purin-6-ylamino)-1-hydroxy ethyl)phenol;
2-(5-fluoropyridin-3-yl)-9-isopropyl-N-(2-(6-methoxy-1H-indol-3-yl)ethyl)-9H-purin-6-amine;
N-(2-(1H-indol-3-yl)ethyl)-2-(5-fluoropyridin-3-yl)-9-isopropyl-9H-purin-6-amine;
2-(5-fluoropyridin-3-yl)-9-isopropyl-N-(2-(5-methoxy-1H-indol-3-yl)ethyl)-9H-purin-6-amine;
N-(2-(1H-indol-3-yl)ethyl)-2-(5-fluoropyridin-3-yl)-9-(prop-1-en-2-yl)-9H-purin-6-amine;
5-(2-(2-(5-fluoropyridin-3-yl)-9-isopropyl-9H-purin-6-ylamino)ethyl)pyridin-2-ol;
N-(2-(1H-pyrrolo[2,3-b]pyridin-3-yl)ethyl)-2-(5-fluoropyridin-3-yl)-9-isopropyl-9H-purin-6-amine;
N-(2-(6-(2-(diethylamino)ethoxy)-1H-indol-3-yl)ethyl)-2-(5-fluoropyridin-3-yl)-9-isopropyl-9H-purin-6-amine;
4-(2-(5-(5-fluoropyridin-3-yl)-3-isopropyl-3H-imidazo[4,5-b]pyridin-7-yl amino)ethyl)phenol;
N-(2-(1H-indol-3-yl)ethyl)-9-sec-butyl-2-(2-methyl-1H-imidazol-1-yl)-9H-purin-6-amine;
4-(2-(2-(2-ethyl-1H-imidazol-1-yl)-9-isopropyl-9H-purin-6-ylamino)ethyl)phenol;
4-(2-(9-isopropyl-2-(2-propyl-1H-imidazol-1-yl)-9H-purin-6-ylamino)-ethyl)phenol;
3-(2-(2-(5-fluoropyridin-3-yl)-9-isopropyl-9H-purin-6-ylamino)ethyl)-1H-indol-6-ol;
N-(2-(1H-indol-3-yl)ethyl)-9-isopropyl-2-(5-methylpyridin-3-yl)-9H-purin-6-amine;
N-(2-(1H-indol-3-yl)ethyl)-9-isopropyl-2-(2-methyl-1H-imidazol-1-yl)-9H-purin-6-amine;
2-(5-fluoropyridin-3-yl)-9-isopropyl-N-(2-(7-methyl-1H-indol-3-yl)ethyl)-9H-purin-6-amine;
N-(2-(1H-indol-3-yl)ethyl)-2-(5-fluoropyridin-3-yl)-9-(oxetan-3-yl)-9H-purin-6-amine;
N-(2-(1H-indol-3-yl)ethyl)-2-(5-methylpyridin-3-yl)-9-(oxetan-3-yl)-9H-purin-6-amine;
N-(2-(6-fluoro-1H-indol-3-yl)ethyl)-2-(5-fluoropyridin-3-yl)-9-isopropyl-9H-purin-6-amine;
2-(5-fluoropyridin-3-yl)-9-isopropyl-N-(2-(6-methyl-1H-indol-3-yl)ethyl)-9H-purin-6-amine;
2-(5-fluoropyridin-3-yl)-9-isopropyl-N-(2-(2-methyl-1H-indol-3-yl)ethyl)-9H-purin-6-amine;
N-(2-(4-fluoro-1H-indol-3-yl)ethyl)-2-(5-fluoropyridin-3-yl)-9-isopropyl-9H-purin-6-amine;
N-(2-(7-fluoro-1H-indol-3-yl)ethyl)-2-(5-fluoropyridin-3-yl)-9-isopropyl-9H-purin-6-amine;
2-(5-fluoropyridin-3-yl)-9-isopropyl-N-(2-(4-methyl-1H-indol-3-yl)ethyl)-9H-purin-6-amine;
4-(2-(2-(benzo[b]thiophen-3-yl)-7-isopropyl-7H-pyrrolo[2,3-d]pyrimidin-4-yl amino)ethyl)phenol;
9-isopropyl-2-(pyridin-3-yl)-N-(2-(pyridin-4-yl)ethyl)-9H-purin-6-amine;
N-(2-(1H-pyrrolo[2,3-b]pyridin-5-yl)ethyl)-9-isopropyl-2-(pyridin-3-yl)-9H-purin-6-amine;
4-(2-(2-(5-fluoropyridin-3-yl)-9-(1-hydroxypropan-2-yl)-9H-purin-6-ylamino)ethyl)-2-methylphenol;
4-(2-(2-(benzo[b]thiophen-3-yl)-9-cyclohexyl-9H-purin-6-ylamino)ethyl)phenol;
4-(2-(9-isopropyl-2-(thiophen-3-yl)-9H-purin-6-ylamino)ethyl)phenol; and
1-(2-(2-(benzo[b]thiophen-3-yl)-6-(4-hydroxyphenethylamino)-9H-purin-9-yl)ethyl)pyrrolidin-2-one.

According to some embodiments of the present invention the AHR antagonist is represented by the Formula Ia.

According to some embodiments of the present invention L is selected from —NR$_{5a}$(CH$_2$)$_{0-3}$—, —NR$_{5a}$CH(C(O)OCH$_3$)CH$_2$—, —NR$_{5a}$(CH$_2$)$_2$NR$_{5b}$—, —NR$_{5a}$(CH$_2$)$_2$S—, —NR$_{5a}$CH$_2$CH(CH$_3$)CH$_2$—, —NR$_{5a}$CH(CH$_3$)CH$_2$—, —(CH$_2$)$_3$—, —CH$_2$OCH$_2$—, —CH$_2$NR$_{5a}$CH$_2$—, —NR$_{5a}$C(O)CH$_2$— and —NR$_{5a}$Y—, wherein R$_{5a}$ and R$_{5b}$ are independently selected from hydrogen and methyl; and Y is selected from isoxazole and 1,3,4-oxadiazole.

According to some embodiments of the present invention R$_3$ is hydrogen, R$_1$ is benzothiphoene, and L is ethylamino, such that the AHR antagonist is represented by Formula If:

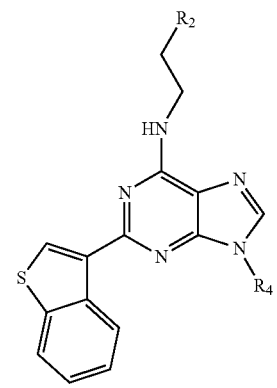

Formula If wherein:
R$_2$ is selected from a substituted or unsubstituted heteroaryl and a substituted or unsubstituted aryl; and
R$_4$ is selected from branched alkyl, alkaryl, a heteroalicyclic.

According to some embodiments of the present invention R$_2$ is selected from 1H-indol-3-yl and phenyl, each being optionally substituted by hydroxyl.

According to some embodiments of the present invention R$_4$ is selected from isopropyl, sec-butyl, benzhydryl, and nonan-2-yl, oxetan-3-yl and tetrahydrofuran-3-yl.

According to some embodiments of the present invention the AHR antagonist is 4-(2-(2-(benzo[b]thiophen-3-yl)-9-isopropyl-9H-purin-6-ylamino)ethyl)phenol (Stem Reginin 1).

According to some embodiments of the present invention R$_3$ is hydrogen, R$_1$ is a substituted or unsubstituted pyridine-3-yl, and L is ethylamino, such that the AHR antagonist is represented by Formula Ig:

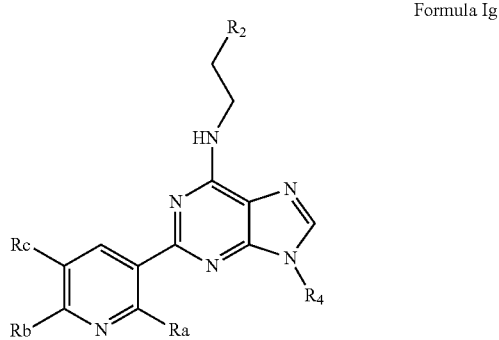

Formula Ig wherein:

R$_2$ is selected from a substituted or unsubstituted aryl and a substituted or unsubstituted heteroaryl;

R$_4$ is selected from branched alkyl, alkaryl, a heteroalicyclic; and

Ra, Rb and Rc are independently selected from hydrogen, cyano, methyl, halo, —SO$_2$CH$_3$ and trifluoromethyl.

According to some embodiments of the present invention R$_2$ is selected from 1H-pyrrolo[2,3-b]pyridin-3-yl, 1H-indol-3-yl and phenyl, each being optionally substituted with 1 to 2 substituents independently selected from halo, methyl, hydroxy and methoxy.

According to some embodiments of the present invention R$_4$ is selected from isopropyl, sec-butyl, benzhydryl, and nonan-2-yl, oxetan-3-yl and tetrahydrofuran-3-yl.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

Figure 1:
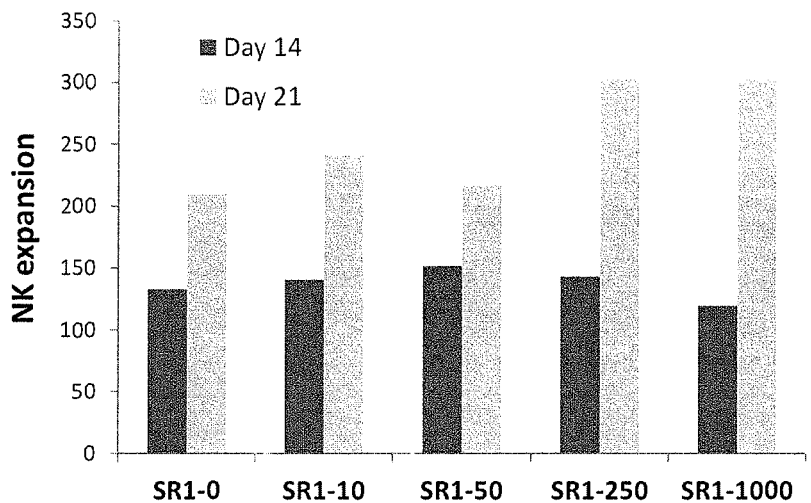
FIG. 1 is a histogram illustrating the expansion of human peripheral blood NK cells over three weeks culture with StemRegenin 1 (SR1), an exemplary ARH antagonist according to some embodiments of the present invention. Peripheral blood NK cells prepared by T-cell (CD3+ or CD3+CD19+) depletion of the mononuclear cells fraction of fresh units [MidiMACS isolation (MACS separation column, Cat. No. 130-042-901) or RosetteSep Human CD3+ Cell Depletion Cocktail (Stem Cell Technologies, RosestteSep, Cat. No. 15661)] were characterized by FACS analysis, and cultured in VueLife Bags in the presence of the indicated concentrations of SR1. Control=cytokines only (SR1 0). Culture medium contained MEMα, Human Serum (10% v/v) and cytokines (20 ng/ml IL-15 and 50 ng/ml IL-2 or only 20 ng/ml IL-15). Culture volume was doubled after 1 and 2 weeks and the cells were counted and stained for FACS analysis after 14 and 21 days. Note the greatly increased expansion (fold increase relative to day 0) on day 21 in the presence of SR1, while cytokines-only (SR1 0) controls show tendency to lose self-renewal capacity over time.

The present invention, in some embodiments thereof, relates to ex-vivo culture of natural killer (NK) cells and, more particularly, but not exclusively, to compositions and methods for enhancing propagation and/or functionality of NK cells by treating the cells with an agent which down-regulates the activity and/or expression of aryl hydrocarbon receptor (AHR).

Some embodiments of the present invention are of methods of propagating a population of natural killer (NK) cells, while at the same time, maintaining or enhancing function of the cells ex-vivo and/or in-vivo. In one embodiment, ex-vivo culture of NK cells with an agent which down-regulates the activity and/or expression of aryl hydrocarbon receptor, and optionally also NK cell growth factors, facilitates the production of NK cell populations for use as a therapeutic ex-vivo cultured cell preparation, which includes a propagated population of functional NK cells, in which proliferation of CD3+ cells is inhibited while NK cell proliferation is preferentially enhanced. Specifically in this respect, the present invention can be used to provide robust populations of functional NK cells, which can be used for applications in cell transplants for treatment of cancer and other disease, and in generation of NK cells suitable for genetic manipulations, which may be used for cellular gene therapy. Additional, non-limiting applications may include treatment of graft versus host disease (e.g., in bone marrow reconstitution), allogeneic and autologous adoptive immunotherapy, treatment of autoimmune disease, combination therapy with sensitizing agents and gene transfer in NK cells. The present invention further relates to NK cell preparations useful for transfusion and to articles-of-manufacture for preparing same.

The principles and operation of the present invention may be better understood with reference to the Examples and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Natural killer (hereinafter also abbreviated as "NK") cells are lymphoid cells that participate in immune reactions. These cells have variety of functions, especially the killing of tumor cells, cells undergoing oncogenic transformation and other abnormal cells in a living body, and are important components of innate immunological surveillance mechanisms. NK cells exhibit spontaneous non-MHC-restricted cytotoxic activity against virally infected and tumor cells, and mediate resistance to viral infections and cancer development in vivo. Thus, methods for effectively increasing the number of NK cells can be useful for treatment of tumors and elimination of virus-infected cells considered potential sources of tumor generation.

Thus, developing clinical-grade protocols (e.g., no stromal layer, minimal cytokines) for effectively expanding the number of viable NK cells and effectively enhancing their function and likelihood of homing to lymph nodes and their homeostatic proliferation in-vivo following infusion, could improve the success of adoptive immunotherapy with NK cells for the treatment of solid tumors, hematopoietic malignancies, viral and autoimmune disorders and the like.

Figure 2:
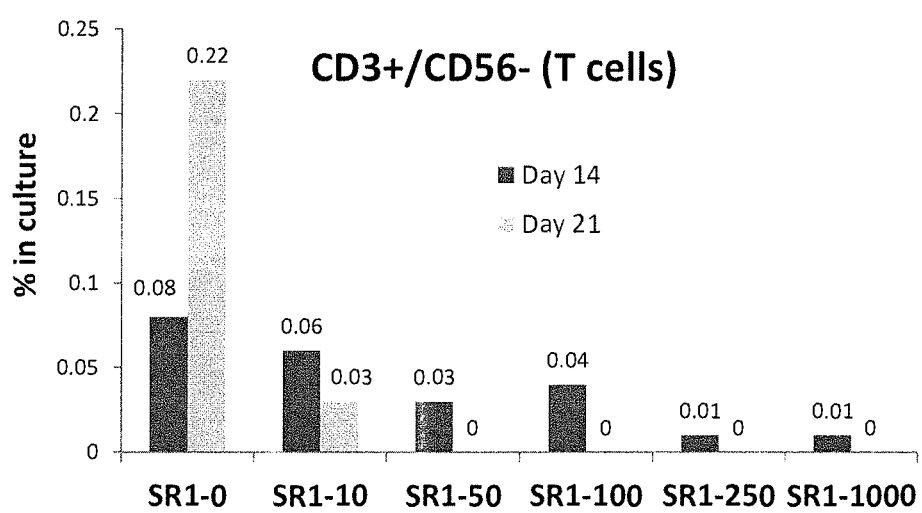
FIG. 2 is a histogram showing the percentages of CD3+ CD56− cells in 21 day cultures of human peripheral blood NK cells. Peripheral blood NK cells were prepared by T-cell (CD3+ or CD3+CD19+) depletion of the mononuclear cells as detailed in FIG. 1, and seeded at 5×10$^5$ cells per/ml, with 10 ml in each culture bag. Cells were then cultured in the presence of indicated concentrations (10 to 1000 nM) of SR1, or cytokines only (SR1 0). Note that although T-cell contamination was relatively moderate in all groups, in cultures exposed to SR1 the T-cell component was less prominent than in control (SR1=0) cultures.

The present invention is based on the surprising discovery that ex-vivo exposure of NK cells to an agent which down-regulates the activity and/or expression of aryl hydrocarbon receptor (also referred to herein as an AHR antagonist), for example, during short or long-term culture, effectively enhances proliferation and/or functionality of functionally competent NK cells (see Examples I-III), and results in significant reduction in the T cell fraction of the culture (see Example I, FIG. 2). As such, in an embodiment thereof, the present invention provides clinically appropriate culture conditions capable of efficiently inducing the proliferation and/or function of functionally mature NK cells ex-vivo and in-vitro, without concomitant induction of non-NK cell (e.g. CD3+) proliferation.

The AHR Antagonist:

Aryl hydrocarbon receptor (AHR) is a transcriptional factor regulating the transcription of various genes in human.

Herein, an AHR antagonist encompasses any agent which down-regulates (or inhibits) the activity and/or expression of AHR or which is capable of down-regulating (or inhibiting) the activity and/or expression of aryl hydrocarbon receptor and/or any agent which is a down-stream effector of aryl hydrocarbon receptor pathway.

Herein, the expressions "an AHR antagonist", "an AHR inhibitor", "an agent/compound that inhibits AHR activity", "an agent/compound that down-regulates an activity and/or expression of AHR", "an agent/compound that is a down-stream effecter of AHR pathway", and "a down-stream effecter of AHR pathway", are used interchangeably.

Herein an agent that inhibits AHR activity describes a compound which decreases AHR activity to at least 10%, 20%, 30%, 50%, 60%, 70%, 80% or at least 90% the transcriptional activity of AHR as observed under activated conditions. An assay to measure AHR inhibitory activity is, for example, the dioxin-induced AHR dependent luciferase reporter gene assay. In some embodiments, an inhibitor of AHR activity is a compound that has an $EC_{50}$ of less than 10 µM, preferably less than 5 µM as measured in the dioxin-induced AHR dependent luciferase reporter gene assay.

Exemplary organic compounds which have been described in the art as inhibiting an AHR activity and are therefore suitable for use in embodiments of the present invention include, but are not limited to, 2-methyl-2H-pyrazole-3-carboxylic acid (2-methyl-4-o-tolylazophenyl)amide (CH223191), alpha napthoflavone, resveratrol (Nutr. Metab. Cardiovasc. Dis., 2003 April; 13(2):104-13), 3'-methoxy-4'-nitroflavone (Biochem. Pharmacol., 2007 May 15; 73(10): 1622-34, Epub 2007 Jan. 30 and 6-methyl-1,3,8-trichlorodibenzofuran (Cancer Res., 2004, Apr. 15; 64(8):2889-97). According to some embodiments of the present invention, an AHR antagonist as described herein does not encompass any of the nicotinamide derivatives and/or analogs as defined in WO 2011/080740.

Herein, a down-stream effector of AHR pathway is a gene which is directly regulated at the transcriptional level by AHR. Examples of such genes include, but are not limited to, Cyp1B1 (coding sequence GenBank Accession no. U56438.1), Cyp1A1 (GenBank Accession No. BC023019.1), and AHRR (GenBank Accession No. BC152406.1). AHR also functions in pathways outside of its well-characterized role in xenobiotic enzyme induction. Xenobiotic ligands of AHR have been shown to regulate beta-catenin, STAT5, STAT1, HES-1, c-Myc, C/EBP, PU.1, p21, P27, pRb, deoxynucleotidyl transferase, CXCR4, and its chemokine ligand CXCL12 (SDF-1).

In some embodiments, an agent capable of down-regulating the activity and/or expression of aryl hydrocarbon receptor is a compound of Formula I:

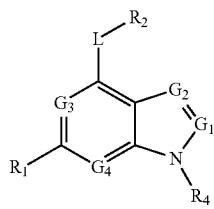

Formula I wherein:

$G_1$ is selected from N and $CR_3$;

$R_3$ is selected from hydrogen, $C_{1-4}$alkyl and biphenyl;

$G_2$, $G_3$ and $G_4$ are each independently selected from —CH— and N; with the proviso that at least one of $G_3$ and $G_4$ is N; and with the proviso that $G_1$ and $G_2$ are not both N;

L is a substituted or unsubstituted amino or alkylamino such as, for example, —$NR_{5a}(CH_2)_{0-3}$— (0-3 herein means 0, 1, 2 or 3), —$NR_{5a}CH(C(O)OCH_3)CH_2$—, —$NR_{5a}(CH_2)_2NR_{5b}$—, —$NR_{5a}(CH_2)_2S$—, —$NR_{5a}CH_2CH(CH_3)CH_2$—, —$NR_{5a}CH_2CH(OH)$— and —$NR_{5a}CH(CH_3)CH_2$—; wherein $R_{5a}$ and $R_{5b}$ are independently selected from the group consisting of hydrogen and $C_{1-4}$alkyl;

$R_1$ is selected from hydrogen, aryl (e.g., phenyl) and heteroaryl (e.g., thiophenyl, furanyl, 1H-benzoimidazolyl, isoquinolinyl, 1H-imidazopyridinyl, benzothiophenyl, pyrimidinyl, 1H-pyrazolyl, pyridinyl, 1H-imidazolyl, pyrrolidinyl, pyrazinyl, pyridazinyl, 1H-pyrrolyl and thiazolyl), wherein the aryl or heteroaryl can be optionally substituted by 1 to 3 substituents such as, but not limited to, cyano, hydroxy, $C_{1-4}$alkyl, $C_{1-4}$alkoxy, halo, halo-substituted-$C_{1-4}$alkyl, halo-substituted-$C_{1-4}$alkoxy, amino, —$C(O)R_{8a}$, —$S(O)_{0-2}R_{8a}$, —$C(O)OR_{8a}$ and —$C(O)NR_{8a}R_{8b}$; wherein each of $R_{8a}$ and $R_{8b}$ can independently be hydrogen or $C_{1-4}$alkyl (or optionally cycloalkyl and aryl); with the proviso that $R_1$ and $R_3$ are not both hydrogen;

$R_2$ is selected from —$S(O)_2NR_{6a}R_{6b}$, —$NR_{9a}C(O)R_{9b}$, —$NR_{6a}C(O)NR_{6b}R_{6c}$, aryl (e.g., phenyl), and heteroaryl (e.g., 1H-pyrrolopyridin-3-yl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl and 1H-indazolyl); wherein $R_{6a}$, $R_{6b}$ and $R_{6c}$ are independently selected from hydrogen and $C_{1-4}$alkyl; wherein said aryl and heteroaryl is optionally substituted with 1 to 3 substituents such as, but not limited to, hydroxy, halo, methyl, methoxy, amino, —$O(CH_2)nNR_{7a}R_{7b}$, —$S(O)_2NR_{7a}R_{7b}$, —$OS(O)_2NR_{7a}R_{7b}$ and —$NR_{7a}S(O)_2R_{7b}$; wherein each of $R_{7a}$ and $R_{7b}$ can independently be hydrogen or $C_{1-4}$alkyl (or optionally cycloalkyl and aryl); and $R_4$ is selected from $C_{1-10}$alkyl, $C_{1-10}$alkenyl (e.g., prop-1-en-2-yl), cycloalkyl (e.g., cyclohexyl, cyclopropyl), aryl (e.g., phenyl), alkaryl (e.g., benzyl, benzhydryl), heteroalicyclic and heteroaryl (e.g., 2-(2-oxopyrrolidin-1-yl)ethyl, oxetan-3-yl, tetrahydro-2H-pyran-3-yl, tetrahydro-2H-pyran-4-yl, tetrahydrofuran-3-yl, (4-pentylphenyl)(phenyl)methyl and 1-(1-(2-oxo-6,9,12-trioxa-3-azatetradecan-14-yl)-1H-1,2,3-triazol-4-yl)ethyl; wherein each of said alkyl, alkenyl, cycloalkyl, aryl, heteroaryl and heteroalicyclic can be optionally substituted with 1 to 3 substituents independently selected from hydroxy, $C_{1-4}$alkyl and halo-substituted-$C_{1-4}$alkyl; or the N-oxide derivatives, prodrug derivatives, protected derivatives, individual isomers and mixture of isomers thereof; or the salts (preferably the pharmaceutically acceptable salts) and solvates (e.g. hydrates) of such compounds.

In some embodiments, the AHR antagonist has Formula I as described herein, wherein $G_1$ is $CR_3$, as defined herein, and $G_2$, $G_3$ and $G_4$ are each N. Compounds encompassed by these embodiments can be collectively represented by Formula Ia as follows:

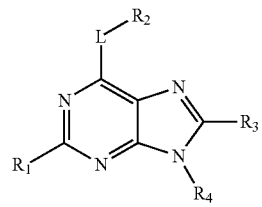

Formula Ia wherein $R_1$-$R_4$ and L are as defined herein for Formula I.

In some embodiments, the AHR antagonist has Formula I as described herein, wherein $G_2$ is CH, and $G_1$, $G_3$ and $G_4$ are each N. Compounds encompassed by these embodiments can be collectively represented by Formula Ib as follows:

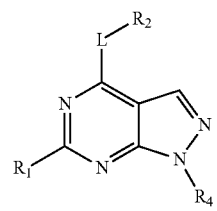

Formula Ib wherein $R_1$, $R_2$, $R_4$ and L are as defined herein for Formula I.

In some embodiments, the AHR antagonist has Formula I as described herein, wherein $G_1$ is $CR_3$, as defined herein, $G_2$ and $G_4$ are each N, and $G_3$ is CH. Compounds encompassed by these embodiments can be collectively represented by Formula Ic as follows:

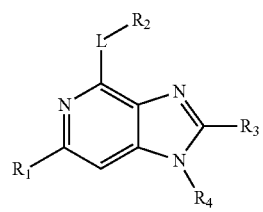

Formula Ic wherein $R_1$-$R_4$ and L are as defined herein for Formula I.

In some embodiments, the AHR antagonist has Formula I as described herein, wherein $G_1$ is $CR_3$, as defined herein, $G_2$ and $G_3$ are each N, and $G_4$ is CH. Compounds encompassed by these embodiments can be collectively represented by Formula Id as follows:

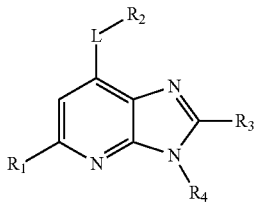

Formula Id wherein $R_1$-$R_4$ and L are as defined herein for Formula I.

In some embodiments, the AHR antagonist has Formula I as described herein, wherein $G_1$ is $CR_3$, as defined herein, $G_3$ and $G_4$ are each N, and $G_2$ is CH. Compounds encompassed by these embodiments can be collectively represented by Formula Ie as follows:

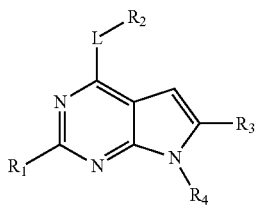

Formula Ie wherein $R_1$-$R_4$ and L are as defined herein for Formula I.

In some embodiments, for any of Formulae Ia-Ie, L is selected from —$NR_{5a}(CH_2)_{0-3}$—, —$NR_{5a}CH(C(O)OCH_3)CH_2$—, —$NR_{5a}(CH_2)_2NR_{5b}$—, —$NR_{5a}(CH_2)_2S$—, —$NR_{5a}CH_2CH(CH_3)CH_2$—, —$NR_{5a}CH_2CH(OH)$— and —$NR_{5a}CH(CH_3)CH_2$—; wherein $R_{5a}$ and $R_{5b}$ are each independently selected from hydrogen and $C_{1-4}$alkyl; wherein the right side of the L moiety as shown is attached to $R_2$, for example: —$NR_{5a}(CH_2)_{0-3}$—$R_2$, —$NR_{5a}CH(C(O)OCH_3)CH_2$—$R_2$, —$NR_{5a}(CH_2)_2NR_{5b}$—$R_2$, —$NR_{5a}(CH_2)_2S$—$R_2$, —$NR_{5a}CH_2CH(CH_3)CH_2$—$R_2$, —$NR_{5a}CH_2CH(OH)$—$R_2$ and —$NR_{5a}CH(CH_3)CH_2$—$R_2$.

In some embodiments, L is an amine or an aminoalkyl and $R_2$ is attached to the carbon atom at the distal end of the alkyl substituting the amino, if present, or to a substituent of this carbon atom, if present.

$R_1$ is selected from hydrogen, aryl (e.g., phenyl), and heteroaryl (e.g., thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, 1H-pyrazol-4-yl, pyridin-2-yl, pyridin-4-yl, 1H-imidazol-1-yl, pyrrolidin-1-yl, pyrazin-2-yl, pyridin-3-yl, pyridazin-4-yl, 1H-pyrrol-2-yl and thiazol-5-yl); wherein said aryl or heteroaryl of $R_1$ can be optionally substituted by 1 to 3 substituents independently selected from cyano, hydroxy, $C_{1-4}$alkyl, $C_{1-4}$alkoxy, halo, halo-substituted-$C_{1-4}$alkyl, —$S(O)_{0-2}R_{8a}$ and —$C(O)OR_{8a}$; wherein $R_{9a}$ and $R_{9b}$ are independently selected from hydrogen and $C_{1-4}$alkyl; with the proviso that $R_1$ and $R_3$, if both present, are not both hydrogen;

$R_2$ is selected from —$NR_{6a}C(O)NR_{6b}R_{6c}$ (a urea or urea derivative radical), aryl (e.g., phenyl), and heteroaryl or heteroalicyclic such as, but not limited to, 1H-pyrrolo[2,3-b]pyridin-3-yl, 1H-pyrrolo[2,3-b]pyridin-5-yl, 1H-indol-3-yl, thiophen-3-yl, pyridin-2-yl, pyridin-3-yl, pyridin-4-yl, 1H-1,2,4-triazol-5-yl, 2-oxoimidazolidin-1-yl, 1H-pyrazol-3-yl, 1H-pyrazol-4-yl, 2-oxo-2,3-dihydro-1H-benzo[d]imidazol-5-yl and 1H-indazol-3-yl; wherein $R_{6a}$, $R_{6b}$ and $R_{6c}$ are independently selected from hydrogen and $C_{1-4}$alkyl; wherein said aryl, heteroaryl and heteroalicyclic of $R_2$ is each independently optionally substituted with 1 to 3 substituents independently selected from hydroxy, halo, methoxy, amino, —$OS(O)_2NR_{7a}R_{7b}$ and —$NR_{7a}S(O)_2R_{7b}$; wherein $R_{7a}$ and $R_{7b}$ are independently selected from hydrogen and $C_{1-4}$alkyl;

$R_3$, when present, is selected from hydrogen, $C_{1-4}$alkyl and biphenyl; and $R_4$ is selected from substituted or unsubstituted alkyl or alkenyl (e.g., isopropyl, methyl, ethyl, prop-1-en-2-yl, isobutyl, sec-butyl, (S)-sec-butyl, (R)-sec-butyl, 1-hydroxypropan-2-yl, (S)-1-hydroxypropan-2-yl, (R)-1-hydroxypropan-2-yl, nonan-2-yl), cycloalkyl (e.g., cyclohexyl), aryl (e.g., phenyl), alkaryl (e.g., benzyl and benhydryl), and a heteroalicyclic or heteroaryl (e.g., 2-(2-oxopyrrolidin-1-yl)ethyl, oxetan-3-yl, oxetan-2-yl, tetrahydro-2H-pyran-2-yl, tetrahydrofuran-3-yl); wherein said cycloalkyl, heteroalicyclic, aryl, alkaryl and heteroaryl can each be optionally substituted with 1 to 3 substituents independently selected from $C_{1-4}$alkyl and halo-substituted-$C_{1-4}$alkyl.

In some embodiments, for each of Formulae I and Ia-Ie, L is selected from —$NR_{5a}(CH_2)_{0-3}$—, —$NR_{5a}CH(C(O)OCH_3)CH_2$—, —$NR_{5a}(CH_2)_2NR_{5b}$—, —$NR_{5a}(C_{1-2})_2S$—, —$NR_{5a}CH_2CH(CH_3)CH_2$—, —$NR_{5a}CH(CH_3)CH_2$— and —$NR_{5a}CH_2CH(OH)$—; wherein $R_{5a}$ and $R_{5b}$ are independently selected from hydrogen and methyl; and $R_1$ is selected from hydrogen, phenyl, thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, 1H-pyrazol-4-yl, pyridin-2-yl, pyridin-4-yl, 1H-imidazol-1-yl, pyrrolidin-1-yl, pyrazin-2-yl, pyridin-3-yl, pyridazin-4-yl, 1H-pyrrol-2-yl and thiazol-5-yl; wherein said phenyl, thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, pyridin-2-yl, pyridin-4-yl, 1H-imidazol-1-yl, pyrrolidin-1-yl, pyrazin-2-yl, pyridin-3-yl, pyridazin-4-yl, 1H-pyrrol-2-yl or thiazol-5-yl of $R_1$ can be optionally substituted by 1 to 3 substituents independently selected from cyano, hydroxy, $C_{1-4}$alkyl, $C_{1-4}$alkoxy, halo, halo-substituted-$C_{1-4}$alkyl, —$S(O)_{0-2}R_{8a}$ and —$C(O)OR_{8a}$; wherein $R_{8a}$ and $R_{8b}$ are independently selected from hydrogen and $C_{1-4}$alkyl; with the proviso that $R_1$ and $R_3$, if both present, are not both hydrogen.

In one embodiment, when L is —$NR_{5a}(CH_2)_{0-3}$, it is preferably —$NR_{5a}(CH_2)_{1-3}$ (where 1-3 herein is 1, 2 or 3).

In any of the above-described embodiments, $R_2$, $R_3$ and $R_4$ are as defined herein.

In any of the above-described embodiments, $R_2$ is selected from urea (or a derivative thereof, as described hereinabove), phenyl, 1H-indol-2-yl, 1H-indol-3-yl, thiophen-3-yl, piperidin-1-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, 2-oxo-2,3-dihydro-1H-benzo[d]imidazol-5-yl, 1H-benzo[d]imidazol-5-yl and 1H-imidazol-4-yl; wherein said phenyl, 1H-indol-2-yl, 1H-indol-3-yl, thiophen-3-yl, piperidin-1-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, 2-oxo-2,3-dihydro-1H-benzo[d]imidazol-5-yl or 1H-benzo[d]imidazol-5-yl of $R_2$ is optionally substituted with one or more of hydroxy, methoxy, methyl, halo, amino and amino-sulfonyl.

In any of the above-described embodiments, $R_3$, if present, is selected from hydrogen, methyl and biphenyl; and $R_4$ is selected from isopropyl, methyl, ethyl, prop-1-en-2-yl, isobutyl, cyclohexyl, sec-butyl, (S)-sec-butyl, (R)-sec-butyl, 1-hydroxypropan-2-yl, (S)-1-hydroxypropan-2-yl, (R)-1-hydroxypropan-2-yl, nonan-2-yl, 2-(2-oxopyrrolidin-1-yl)ethyl, oxetan-3-yl, oxetan-2-yl, benzhydryl, tetrahydro-2H-pyran-2-yl, phenyl, tetrahydrofuran-3-yl and benzyl; wherein said cyclohexyl, 2-(2-oxopyrrolidin-1-yl)ethyl, oxetan-3-yl, oxetan-2-yl, benzhydryl, tetrahydro-2H-pyran-4-yl, phenyl, tetrahydrofuran-3-yl or benzyl can be optionally substituted with 1 to 3 substituents independently selected from methyl and trifluoromethyl.

Exemplary compounds which are suitable for use as AHR antagonists according to some embodiments of the present invention include, but are not limited to:

4-(2-(2-(benzo[b]thiophen-3-yl)-9-isopropyl-9H-purin-6-ylamino)ethyl)phenol;
4-(2-(2-(benzo[b]thiophen-3-yl)-9-sec-butyl-9H-purin-6-ylamino)ethyl)phenol;
4-(2-(9-benzhydryl-2-(benzo[b]thiophen-3-yl)-9H-purin-6-ylamino)ethyl)phenol;
4-(2-(2-(benzo[b]thiophen-3-yl)-9-(tetrahydro-2H-pyran-3-yl)-9H-purin-6-yl amino)ethyl)phenol;
4-(2-(9-isopropyl-2-(thiophen-2-yl)-9H-purin-6-ylamino)ethyl)phenol;
4-(2-(2-(benzo[b]thiophen-3-yl)-9-(4-(trifluoromethyl)benzyl)-9H-purin-6-yl amino)ethyl)phenol;
4-(2-(2-(benzo[b]thiophen-3-yl)-9-isobutyl-9H-purin-6-ylamino)ethyl)phenol;
4-(2-(2-(benzo[b]thiophen-3-yl)-9-methyl-9H-purin-6-ylamino)ethyl)phenol;
4-(2-(2-(benzo[b]thiophen-3-yl)-9-(4-methylbenzyl)-9H-purin-6-ylamino)ethyl)phenol;
N-(2-(1H-indol-3-yl)ethyl)-2-(benzo[b]thiophen-3-yl)-9-isopropyl-9H-purin-6-amine;
2-(benzo[b]thiophen-3-yl)-9-isopropyl-N-(2-(thiophen-3-yl)ethyl)-9H-purin-6-amine;
3-(2-(2-(benzo[b]thiophen-3-yl)-9-isopropyl-9H-purin-6-ylamino)ethyl)phenol;
2-(benzo[b]thiophen-3-yl)-N-(4-fluorophenethyl)-9-isopropyl-9H-purin-6-amine;
N-(4-aminophenethyl)-2-(benzo[b]thiophen-3-yl)-9-isopropyl-9H-purin-6-amine;
4-(2-(9-isopropyl-2-(pyrimidin-5-yl)-9H-purin-6-ylamino)ethyl)phenol;
4-(2-(9-isopropyl-2-(pyridin-3-yl)-9H-purin-6-ylamino)ethyl)phenol;
4-(2-(9-isopropyl-2-phenyl-9H-purin-6-ylamino)ethyl)phenol;
4-(2-(9-isopropyl-2-(thiophen-2-yl)-9H-purin-6-ylamino)ethyl)phenol;
4-(2-(2-(furan-3-yl)-9-isopropyl-9H-purin-6-ylamino)ethyl)phenol;
2-(benzo[b]thiophen-3-yl)-N-(4-fluorophenethyl)-9-phenyl-9H-purin-6-amine;
N-benzyl-8-(biphenyl-4-yl)-9-isopropyl-9H-purin-6-amine;
4-(2-(2-(benzo[b]thiophen-3-yl)-9-(nonan-2-yl)-9H-purin-6-ylamino)ethyl)phenol;
N-(2-(1H-indol-3-yl)ethyl)-2-(benzo[b]thiophen-3-yl)-9-sec-butyl-9H-purin-6-amine;
3-(2-(2-(benzo[b]thiophen-3-yl)-9-isopropyl-9H-purin-6-ylamino)ethyl)-1H-indol-5-yl,
5-((3aS,4S,6aR)-2-oxohexahydro-1H-thieno[3,4-d]imidazol-4-yl)pentanoate;
N-(2-(2-(2-(2-(4-(1-(2-(benzo[b]thiophen-3-yl)-6-(4-hydroxyphenethylamino)-9H-purin-9-yl)ethyl)-1H-1,2,3-triazol-1-yl)ethoxy)ethoxy)ethoxy)ethyl)acetamide;
4-(2-(9-isopropyl-2-(pyridin-4-yl)-9H-purin-6-ylamino)ethyl)phenol;
ethyl 5-(6-(4-hydroxyphenethylamino)-9-isopropyl-9H-purin-2-yl)nicotinate;
ethyl 5-(6-(4-hydroxyphenethylamino)-9-isopropyl-9H-purin-2-yl)nicotinate;
4-(2-(2-(6-fluoropyridin-3-yl)-9-isopropyl-9H-purin-6-ylamino)ethyl)phenol;
4-(2-(9-isopropyl-2-(4-methylpyridin-3-yl)-9H-purin-6-ylamino)ethyl)phenol;
5-(6-(4-hydroxyphenethylamino)-9-isopropyl-9H-purin-2-yl)nicotinonitrile;
4-(2-(9-isopropyl-2-(pyrrolidin-1-yl)-9H-purin-6-ylamino)ethyl)phenol;
4-(2-(2-(1H-imidazol-1-yl)-9-isopropyl-9H-purin-6-ylamino)ethyl)phenol;
4-(2-(9-isopropyl-2-(pyridazin-4-yl)-9H-purin-6-ylamino)ethyl)phenol;
4-(2-(9-isopropyl-2-(pyrazin-2-yl)-9H-purin-6-ylamino)ethyl)phenol;
4-(2-(9-isopropyl-2-(pyridin-2-yl)-9H-purin-6-ylamino)ethyl)phenol;
4-(2-(9-isopropyl-2-(5-(methylsulfonyl)pyridin-3-yl)-9H-purin-6-ylamino)ethyl)phenol;
4-(2-(9-isopropyl-2-(5-methylpyridin-3-yl)-9H-purin-6-ylamino)ethyl)phenol;
4-(2-(2-(4-chloropyridin-3-yl)-9-isopropyl-9H-purin-6-ylamino)ethyl)phenol;
4-(2-(2-(5-fluoropyridin-3-yl)-9-isopropyl-9H-purin-6-ylamino)ethyl)phenol;
4-(2-(9-isopropyl-2-(1-methyl-1H-pyrazol-4-yl)-9H-purin-6-ylamino)ethyl)phenol;
4-(2-(9-isopropyl-2-(pyridin-3-yl)-9H-purin-6-ylamino)ethyl)-2-methoxy phenol;
4-(2-(9-isopropyl-2-(pyridin-3-yl)-9H-purin-6-ylamino)ethyl)-2-methoxy phenol;
N-[2-(6-methoxy-1H-indol-3-yl)ethyl]-9-(propan-2-yl)-2-(pyridin-3-yl)-9H-purin-6-amine;
N-[2-(5-methyl-1H-indol-3-yl)ethyl]-9-(propan-2-yl)-2-(pyridin-3-yl)-9H-purin-6-amine;
1-(2-{[9-(propan-2-yl)-2-(pyridin-3-yl)-9H-purin-6-yl]amino}ethyl)imidazolidin-2-one;
N-(2-{[9-(propan-2-yl)-2-(pyridin-3-yl)-9H-purin-6-yl]amino}ethyl)pyridin-2-amine;
9-(propan-2-yl)-N-[3-(1H-pyrazol-4-yl)propyl]-2-(pyridin-3-yl)-9-H-purin-6-amine;
N-{2-[(3-methyl-1H-1,2,4-triazol-5-yl)sulfanyl]ethyl}-9-(propan-2-yl)-2-(pyridin-3-yl)-9H-purin-6-amine;
1-(2-{[2-(1-benzothiophen-3-yl)-9-(propan-2-yl)-9H-purin-6-yl]amino}ethyl)imidazolidin-2-one;
N-[2-(5-amino-1H-1,2,4-triazol-3-yl)ethyl]-2-(1-benzothiophen-3-yl)-9-(propan-2-yl)-9H-purin-6-amine;
N-(2-{[2-(1-benzothiophen-3-yl)-9-(propan-2-yl)-9H-purin-6-yl]amino}ethyl)pyridin-2-amine;
2-(1-benzothiophen-3-yl)-9-(propan-2-yl)-N-[3-(1H-pyrazol-4-yl)propyl]-9H-purin-6-amine;
2-(1-benzothiophen-3-yl)-N-[3-(3,5-dimethyl-1H-pyrazol-4-yl)propyl]-9-(propan-2-yl)-9H-purin-6-amine;
(2-{[2-(1-benzothiophen-3-yl)-9-(propan-2-yl)-9H-purin-6-yl]amino}ethyl)urea;
5-({[2-(1-benzothiophen-3-yl)-9-(propan-2-yl)-9H-purin-6-yl]amino}methyl)-2,3-dihydro-1H-1,3-benzodiazol-2-one;
N-[2-(1H-indol-3-yl)ethyl]-9-(propan-2-yl)-2-(pyridin-3-yl)-9H-purin-6-amine;
N-(4-(2-(9-isopropyl-2-(pyridin-3-yl)-9H-purin-6-ylamino)ethyl)phenyl)methane-sulfonamide;
4-(2-(2-(pyridin-3-yl)-9-(tetrahydrofuran-3-yl)-9H-purin-6-ylamino)ethyl)-phenol;

4-(2-(9-isopropyl-2-(pyridin-3-yl)-9H-purin-6-ylamino) propyl)phenol;
4-(2-(9-(oxetan-3-yl)-2-(pyridin-3-yl)-9H-purin-6-ylamino) ethyl)phenol;
5-(6-(4-hydroxyphenethylamino)-9-isopropyl-9H-purin-2-yl)-N-methylnicotin-amide;
4-(2-(9-(1-hydroxypropan-2-yl)-2-(pyridin-3-yl)-9H-purin-6-ylamino)-ethyl)phenol;
4-(2-(9-isopropyl-2-(pyridin-3-yl)-9H-purin-6-ylamino) ethyl)phenyl sulfamate;
4-(2-(2-(2-fluoropyridin-3-yl)-9-isopropyl-9H-purin-6-ylamino)ethyl)phenol;
4-(2-(9-isopropyl-2-(1-methyl-1H-pyrrol-2-yl)-9H-purin-6-ylamino)ethyl)-phenol;
4-(2-(9-isopropyl-2-(thiazol-5-yl)-9H-purin-6-ylamino) ethyl)phenol;
4-(2-(2-(1H-benzo[d]imidazol-1-yl)-9-isopropyl-9H-purin-6-ylamino)ethyl)-phenol;
4-(2-(2-(2,4-dimethyl-1H-imidazol-1-yl)-9-isopropyl-9H-purin-6-ylamino)ethyl)phenol;
4-(2-(9-isopropyl-2-(2-methyl-1H-imidazol-1-yl)-9H-purin-6-ylamino)ethyl)-phenol;
5-(9-sec-butyl-6-(4-hydroxy-3-methylphenethylamino)-9H-purin-2-yl)-nicotinonitrile;
N-(2-(1H-pyrrolo[2,3-b]pyridin-5-yl)ethyl)-9-isopropyl-2-(pyridin-3-yl)-9-H-purin-6-amine;
9-isopropyl-N-(2-(5-methyl-1H-pyrazol-3-yl)ethyl)-2-(pyridin-3-yl)-9H-purin-6-amine;
4-(2-(2-(5-fluoropyridin-3-yl)-9-(oxetan-3-yl)-9H-purin-6-ylamino)ethyl)phenol;
4-(2-(2-(5-chloropyridin-3-yl)-9-isopropyl-9H-purin-6-ylamino)ethyl)phenol;
4-(2-(9-isopropyl-2-(5-(trifluoromethyl)pyridin-3-yl)-9H-purin-6-ylamino)ethyl)phenol;
5-(6-(2-(1H-indol-3-yl)ethylamino)-9-sec-butyl-9H-purin-2-yl)nicotinonitrile;
N-(2-(1H-indol-3-yl)ethyl)-9-sec-butyl-2-(5-methylpyridin-3-yl)-9H-purin-6-amine;
(R)—N-(2-(1H-indol-3-yl)ethyl)-9-sec-butyl-2-(5-fluoropyridin-3-yl)-9H-purin-6-amine;
(S)—N-(2-(1H-indol-3-yl)ethyl)-9-sec-butyl-2-(5-fluoropyridin-3-yl)-9H-purin-6-amine;
N-(2-(1H-indol-3-yl)ethyl)-9-sec-butyl-2-(5-fluoropyridin-3-yl)-9H-purin-6-amine;
(R)—N-(2-(1H-indol-3-yl)ethyl)-9-sec-butyl-2-(5-methylpyridin-3-yl)-9H-purin-6-amine;
(S)—N-(2-(1H-indol-3-yl)ethyl)-9-sec-butyl-2-(5-methylpyridin-3-yl)-9H-purin-6-amine;
5-(6-(4-hydroxyphenethylamino)-9-(oxetan-3-yl)-9H-purin-2-yl)nicotinonitrile;
4-(2-(6-(5-fluoropyridin-3-yl)-1-isopropyl-1H-pyrazolo[3,4-d]pyrimidin-4-yl amino)ethyl)phenol;
4-(2-(6-(benzo[b]thiophen-3-yl)-1-isopropyl-1H-pyrazolo[3,4-d]pyrimidin-4-yl amino)ethyl)phenol;
(R)-4-(2-(2-(5-fluoropyridin-3-yl)-9-(tetrahydrofuran-3-yl)-9H-purin-6-yl-amino)ethyl)phenol;
4-(2-(9-isopropyl-2-(pyridin-3-yl)-9H-purin-6-ylamino) ethyl)-3-methylphenol;
5-(6-(4-hydroxyphenethylamino)-9-isopropyl-9H-purin-2-yl)picolinonitrile;
3-(6-(4-hydroxyphenethylamino)-9-isopropyl-9H-purin-2-yl)isonicotinonitrile;
4-(2-(2-(5-fluoropyridin-3-yl)-7-isopropyl-7H-pyrrolo[2,3-d]pyrimidin-4-yl amino)ethyl)phenol;
3-(6-(4-hydroxyphenethylamino)-9-isopropyl-9H-purin-2-yl)picolinonitrile;
4-(2-(9-isopropyl-2-(6-methylpyridin-3-yl)-9H-purin-6-ylamino)ethyl)phenol;
4-(2-(9-isopropyl-2-(isoquinolin-4-yl)-9H-purin-6-ylamino) ethyl)phenol;
2-chloro-4-(2-(9-isopropyl-2-(pyridin-3-yl)-9H-purin-6-ylamino)ethyl)phenol;
3-fluoro-4-(2-(9-isopropyl-2-(pyridin-3-yl)-9H-purin-6-ylamino)ethyl)phenol;
N-(2-(5-chloro-1H-indol-3-yl)ethyl)-9-isopropyl-2-(pyridin-3-yl)-9H-purin-6-amine;
N-(2-(5-fluoro-1H-indol-3-yl)ethyl)-9-isopropyl-2-(pyridin-3-yl)-9H-purin-6-amine;
4-(2-(9-isopropyl-2-(pyridin-3-yl)-9H-purin-6-ylamino) ethyl)-2-methylphenol;
4-(2-(2-(benzo[b]thiophen-3-yl)-9-(oxetan-3-yl)-9H-purin-6-ylamino)ethyl)-phenol;
(S)-4-(2-(2-(benzo[b]thiophen-3-yl)-9-(tetrahydrofuran-3-yl)-9H-purin-6-yl amino)ethyl)phenol;
(R)-4-(2-(2-(benzo[b]thiophen-3-yl)-9-(tetrahydrofuran-3-yl)-9H-purin-6-yl amino)ethyl)phenol;
2-(6-(2-(1H-indol-3-yl)ethylamino)-2-(5-fluoropyridin-3-yl)-9H-purin-9-yl)propan-1-ol;
(R)-2-(6-(2-(1H-indol-3-yl)ethylamino)-2-(5-fluoropyridin-3-yl)-9H-purin-9-yl)propan-1-ol;
(S)-2-(6-(2-(1H-indol-3-yl)ethylamino)-2-(5-fluoropyridin-3-yl)-9H-purin-9-yl)propan-1-ol;
(R)—N-(2-(1H-indol-3-yl)ethyl)-2-(5-fluoropyridin-3-yl)-9-(tetrahydrofuran-3-yl)-9H-purin-6-amine;
4-(2-(2-(3H-imidazo[4,5-b]pyridin-3-yl)-9-isopropyl-9H-purin-6-ylamino)ethyl)phenol;
4-(2-(2-(1H-imidazo[4,5-b]pyridin-1-yl)-9-isopropyl-9H-purin-6-ylamino)ethyl)phenol;
4-(2-(6-(5-fluoropyridin-3-yl)-1-isopropyl-1H-imidazo[4,5-c]pyridin-4-yl amino)ethyl)phenol;
4-(2-(2-(4,5-dimethyl-1H-imidazol-1-yl)-9-isopropyl-9H-purin-6-ylamino)ethyl)phenol;
2-(5-fluoropyridin-3-yl)-9-isopropyl-N-(2-(pyridin-3-yl) ethyl)-9H-purin-6-amine;
4-(2-(2-(5-fluoropyridin-3-yl)-9-isopropyl-9H-purin-6-ylamino)-1-hydroxy ethyl)phenol;
2-(5-fluoropyridin-3-yl)-9-isopropyl-N-(2-(6-methoxy-1H-indol-3-yl)ethyl)-9H-purin-6-amine;
N-(2-(1H-indol-3-yl)ethyl)-2-(5-fluoropyridin-3-yl)-9-isopropyl-9H-purin-6-amine;
2-(5-fluoropyridin-3-yl)-9-isopropyl-N-(2-(5-methoxy-1H-indol-3-yl)ethyl)-9H-purin-6-amine;
N-(2-(1H-indol-3-yl)ethyl)-2-(5-fluoropyridin-3-yl)-9-(prop-1-en-2-yl)-9H-purin-6-amine;
5-(2-(2-(5-fluoropyridin-3-yl)-9-isopropyl-9H-purin-6-ylamino)ethyl)pyridin-2-ol;
N-(2-(1H-pyrrolo[2,3-b]pyridin-3-yl)ethyl)-2-(5-fluoropyridin-3-yl)-9-isopropyl-9H-purin-6-amine;
N-(2-(6-(2-(diethylamino)ethoxy)-1H-indol-3-yl)ethyl)-2-(5-fluoropyridin-3-yl)-9-isopropyl-9H-purin-6-amine;
4-(2-(5-(5-fluoropyridin-3-yl)-3-isopropyl-3H-imidazo[4,5-b]pyridin-7-yl amino)ethyl)phenol;
N-(2-(1H-indol-3-yl)ethyl)-9-sec-butyl-2-(2-methyl-1H-imidazol-1-yl)-9H-purin-6-amine;
4-(2-(2-(2-ethyl-1H-imidazol-1-yl)-9-isopropyl-9H-purin-6-ylamino)ethyl)phenol;
4-(2-(9-isopropyl-2-(2-propyl-1H-imidazol-1-yl)-9H-purin-6-ylamino)-ethyl)phenol;
3-(2-(2-(5-fluoropyridin-3-yl)-9-isopropyl-9H-purin-6-ylamino)ethyl)-1H-indol-6-ol;
N-(2-(1H-indol-3-yl)ethyl)-9-isopropyl-2-(5-methylpyridin-3-yl)-9H-purin-6-amine;

N-(2-(1H-indol-3-yl)ethyl)-9-isopropyl-2-(2-methyl-1H-imidazol-1-yl)-9H-purin-6-amine;
2-(5-fluoropyridin-3-yl)-9-isopropyl-N-(2-(7-methyl-1H-indol-3-yl)ethyl)-9H-purin-6-amine;
N-(2-(1H-indol-3-yl)ethyl)-2-(5-fluoropyridin-3-yl)-9-(oxetan-3-yl)-9H-purin-6-amine;
N-(2-(1H-indol-3-yl)ethyl)-2-(5-methylpyridin-3-yl)-9-(oxetan-3-yl)-9H-purin-6-amine;
N-(2-(6-fluoro-1H-indol-3-yl)ethyl)-2-(5-fluoropyridin-3-yl)-9-isopropyl-9H-purin-6-amine;
2-(5-fluoropyridin-3-yl)-9-isopropyl-N-(2-(6-methyl-1H-indol-3-yl)ethyl)-9H-purin-6-amine;
2-(5-fluoropyridin-3-yl)-9-isopropyl-N-(2-(2-methyl-1H-indol-3-yl)ethyl)-9H-purin-6-amine;
N-(2-(4-fluoro-1H-indol-3-yl)ethyl)-2-(5-fluoropyridin-3-yl)-9-isopropyl-9H-purin-6-amine;
N-(2-(7-fluoro-1H-indol-3-yl)ethyl)-2-(5-fluoropyridin-3-yl)-9-isopropyl-9H-purin-6-amine;
2-(5-fluoropyridin-3-yl)-9-isopropyl-N-(2-(4-methyl-1H-indol-3-yl)ethyl)-9H-purin-6-amine;
4-(2-(2-(benzo[b]thiophen-3-yl)-7-isopropyl-7H-pyrrolo[2,3-d]pyrimidin-4-yl amino)ethyl)phenol;
9-isopropyl-2-(pyridin-3-yl)-N-(2-(pyridin-4-yl)ethyl)-9H-purin-6-amine;
N-(2-(1H-pyrrolo[2,3-b]pyridin-5-yl)ethyl)-9-isopropyl-2-(pyridin-3-yl)-9H-purin-6-amine;
4-(2-(2-(5-fluoropyridin-3-yl)-9-(1-hydroxypropan-2-yl)-9H-purin-6-ylamino)ethyl)-2-methylphenol;
4-(2-(2-(benzo[b]thiophen-3-yl)-9-cyclohexyl-9H-purin-6-ylamino)ethyl)phenol;
4-(2-(9-isopropyl-2-(thiophen-3-yl)-9H-purin-6-ylamino)ethyl)phenol; and
1-(2-(2-(benzo[b]thiophen-3-yl)-6-(4-hydroxyphenethylamino)-9H-purin-9-yl)ethyl)pyrrolidin-2-one.

In some embodiments, the AHR antagonist is a compound of Formula Ia, as depicted herein, wherein:

L is selected from an alkylamino (wherein the alkyl can be substituted or unsubstituted, linear or branched), alkyl (optionally substituted, for example, by alkoxy or by an aminoalkyl), N-amide, and an amine substituted by a heteroaryl or a heteroalicyclic.

In some embodiments, L is selected from —$NR_{5a}(CH_2)_{0-3}$— (as an exemplary amino or alkylamino), —$NR_{5a}CH(C(O)OCH_3)CH_2$— (as an exemplary carboxy-substituted alkylamino), —$NR_{5a}(CH_2)_2NR_{5b}$— (as an exemplary aminoalkyl in which the distal carbon atom is substituted by an amine, as defined herein), —$NR_{5a}(CH_2)_2S$-(as an exemplary aminoalkyl, in which the distal carbon atom is substituted by thio, as defined herein), —$NR_{5a}CH_2CH(CH_3)CH_2$— and —$NR_{5a}CH(CH_3)CH_2$— (as exemplary amino alkyls wherein the alkyl is a branched alkyl), —$(CH_2)_3$-(as an exemplary alkyl), —$CH_2OCH_2$— as an exemplary alkyl substituted by alkoxy, or as an exemplary ether), —$CH_2NR_{5a}CH_2$— (an exemplary alkyl substituted by an amino, as defined herein), —$NR_{5a}C(O)CH_2$— (as an exemplary N-amide) and —$NR_{5a}Y$— (as an exemplary amine substituted by a heterocylic moiety); wherein $R_{5a}$ and $R_{5b}$ are independently selected from hydrogen and $C_{1-4}$alkyl; and Y is a 5-membered heteroaryl ring containing up to 3 heteroatoms selected from O, N and S;

In some embodiments, for any of the above-described embodiments for Formula Ia, $R_1$ is selected from hydrogen, and substituted or unsubstituted aryl, heteroaryl and heteroalicyclic.

In some of these embodiments, $R_1$ is selected from phenyl, thiophen-2-yl, thiophen-3-yl, furan-2-yl, furan-3-yl, benzo[b]thiophen-2-yl, benzo[b]thiophen-3-yl, benzofuran-2-yl, benzofuran-3-yl, pyrimidin-4-yl, pyrimidin-5-yl, 1H-pyrazol-4-yl, 1H-pyrazol-3-yl, pyridin-2-yl, pyridazin-3-yl, pyridin-4-yl, 1H-imidazol-1-yl, pyrrolidin-1-yl, pyrazin-2-yl, pyridin-3-yl, 1H-pyrazol-1-yl, pyridazin-4-yl, 1H-indol-2-yl, thiazol-4-yl, 1H-indol-3-yl, 1H-pyrrol-2-yl and thiazol-5-yl. When said phenyl, thiophen-2-yl, thiophen-3-yl, furan-2-yl, furan-3-yl, benzo[b]thiophen-2-yl, benzo[b]thiophen-3-yl, benzofuran-2-yl, benzofuran-3-yl, pyrimidin-4-yl, pyrimidin-5-yl, 1H-pyrazol-4-yl, 1H-pyrazol-3-yl, pyridin-2-yl, pyridazin-3-yl, pyridin-4-yl, 1H-imidazol-1-yl, pyrrolidin-1-yl, pyrazin-2-yl, pyridin-3-yl, 1H-pyrazol-1-yl, pyridazin-4-yl, 1H-indol-2-yl, thiazol-4-yl, 1H-indol-3-yl, 1H-pyrrol-2-yl or thiazol-5-yl, or any other aryl, heteroaryl or heteroalicyclic of $R_1$, is substituted, it may comprise one or more, e.g., 1 to 3, substituents, such as, but not limited to, cyano, hydroxy, $C_{1-4}$alkyl, $C_{1-4}$alkoxy, halo, halo-substituted-$C_{1-4}$alkyl, halo-substituted-$C_{1-4}$ alkoxy, hydroxy, amino, —$C(O)R_{8a}$, —$S(O)_{0-2}R_{8a}$, —$C(O)OR_{8a}$ and —$C(O)NR_{8a}R_{8b}$; wherein $R_{8a}$ and $R_{8b}$ are independently selected from hydrogen and $C_{1-4}$alkyl.

In some embodiments, $R_1$ and $R_3$ are not both hydrogen.

In some embodiments, for any of the above-described embodiments for Formula Ia, $R_2$ is selected from S-sulfonamide, N-amide, urea or a derivative thereof, and substituted or unsubstituted aryl, heteroaryl and heteroalicyclic.

In some of these embodiments, $R_2$ is selected from —$S(O)_2NR_{6a}R_{6b}$, —$NR_{9a}C(O)R_{9b}$, —$NR_{6a}C(O)NR_{6b}R_{6c}$, phenyl, 1H-indol-2-yl, 1H-indol-3-yl, benzo[b]thiophen-2-yl, benzo[b]thiophen-3-yl, benzofuran-2-yl, benzofuran-3-yl, thiophen-2-yl, thiophen-3-yl, furan-2-yl, furan-3-yl, piperidin-4-yl, piperidin-3-yl, piperidin-2-yl, piperidin-1-yl, pyridin-2-yl, pyridin-3-yl, pyridin-4-yl, 1H-1,2,4-triazol-3-yl, 2-oxoimidazolidin-1-yl, 1H-pyrazol-3-yl, 1H-pyrazol-4-yl, 3-oxopiperazin-1-yl, 2-oxo-2,3-dihydro-1H-benzo[d]imidazol-5-1,2,3,4-tetrahydronaphthalen-2-yl, indolin-5-yl, 2-oxoindolin-5-yl, 1H-benzo[d]imidazol-5-yl, 1H-indazol-5-yl and 1H-imidazol-4-yl; wherein $R_{6a}$, $R_{6b}$ and $R_{6c}$ are independently selected from hydrogen and $C_{1-4}$alkyl.

Whenever any of the aryl, heteroaryl or heteroalicyclic of $R_2$ is substituted, it comprises one or more (e.g., 1 to 3) substituents such as, but not limited to, hydroxy, halo, alkyl (e.g., methyl), alkoxy (e.g., methoxy), amino, —$S(O)_2NR_{7a}R_{7b}$, —$OS(O)_2NR_{7a}R_{7b}$ and —$NR_{7a}S(O)_2R_{7b}$; wherein $R_{7a}$ and $R_{7b}$ are each independently selected from hydrogen and $C_{1-4}$alkyl, or, alternatively it comprises a single substituent selected from 5-((3aS,4S,6aR)-2-oxohexahydro-[3,4-d]imidazol-4-yl)pentanoyloxy-, 2-(2-(5-((3aS,4S,6aR)-2-oxohexahydro-1H-thieno[3,4-d]imidazol-4-yl)pentanamido)ethoxy)ethoxy and 2-(4-(4-hex-5-ynamidobenzoyl)phenylamino)-2-oxoethoxy.

In some embodiments of any of the above-described embodiments of Formula Ia, $R_3$ is selected from hydrogen, $C_{1-4}$alkyl and aryl (e.g., biphenyl).

In some embodiments of any of the above-described embodiments of Formula Ia, $R_4$ is selected from a substituted or unsubstituted, linear or branched alkyl, and a substituted or unsubstituted cycloalkyl, alkaryl, aryl, heteroaryl or heteroalicyclic.

In some of these embodiments, $R_4$ is selected from isopropyl, isobutyl, sec-butyl, 1-hydroxypropan-2-yl, cyclopropyl, oxetan-3-yl, oxetan-2-yl, benzhydryl, piperidin-4-yl, piperidin-3-yl, piperidin-2-yl, tetrahydro-2H-pyran-2-yl, tetrahydro-2H-pyran-3-yl, tetrahydro-2H-pyran-4-yl, phenyl, tetrahydrofuran-3-yl, tetrahydrofuran-2-yl, benzyl, (4-pentylphenyl)(phenyl)methyl and 1-(1-(2-oxo-6,9,12-trioxa-3-azatetradecan-14-yl)-1H-1,2,3-triazol-4-yl)ethyl.

Whenever the cycloalkyl, alkaryl, aryl, heteroaryl or heteroalicyclic is substituted, it comprises one or more (e.g., 1 to 3) substituents, each independently selected from $C_{1-4}$alkyl and halo-substituted-$C_{1-4}$alkyl.

For any of the embodiments described herein for Formula Ia, encompassed are also the N-oxide derivatives, prodrug derivatives, protected derivatives, individual isomers and mixture of isomers thereof; or the pharmaceutically acceptable salts and solvates (e.g. hydrates) of any of the described compounds.

In some embodiments, with reference to compounds of Formula Ia, L is selected from —$NR_{5a}(CH_2)_{0-3}$—, —$NR_{5a}CH(C(O)OCH_3)CH_2$—, —$NR_{5a}(CH_2)_2NR_{5b}$—, —$NR_{5a}(CH_2)_2S$—, $NR_{5a}CH_2CH(CH_3)CH_2$—, —$NR_{5a}CH(CH_3)CH_2$—, —$(CH_2)_3$—, —$CH_2OCH_2$—, —$CH_2NR_{5a}CH_2$—, —$NR_{5a}C(O)CH_2$— and —$NR_{5a}Y$—; wherein $R_{5a}$ and $R_{5b}$ are independently selected from hydrogen and methyl; and Y is selected from isoxazole and 1,3,4-oxadiazole.

In some of these embodiments, when L is —$NR_{5a}(CH_2)_{0-3}$, it is preferably —$NR_{5a}(CH_2)_{1-3}$ (where 1-3 herein means 1, 2 or 3).

In some embodiments, for any of the above-described embodiments for Formula Ia, $R_1$ is selected from hydrogen, phenyl, thiophen-3-yl, thiophen-2-yl, furan-3-yl, furan-2-yl, benzo[b]thiophen-3-yl, pyrimidin-5-yl, pyridin-4-yl, pyridin-2-yl, pyrrolidin-1-yl, 1H-pyrazol-4-yl, pyrazin-2-yl, pyridazin-3-yl, pyridazin-4-yl, 1H-pyrazol-1-yl, 1H-pyrazol-3-yl, 1H-imidazol-1-yl, thiazol-4-yl, 1H-pyrrol-2-yl, thiazol-5-yl, and pyridin-3-yl; wherein said phenyl, thiophen-3-yl, thiophen-2-yl, furan-3-yl, furan-2-yl, benzo[b]thiophen-3-yl, pyrimidin-5-yl, pyridin-4-yl, pyridin-2-yl, pyrrolidin-1-yl, 1H-pyrazol-4-yl, pyrazin-2-yl, pyridazin-3-yl, pyridazin-4-yl, 1H-pyrazol-1-yl, 1H-pyrazol-3-yl, 1H-imidazol-1-yl, thiazol-4-yl, 1H-pyrrol-2-yl, thiazol-5-yl or pyridin-3-yl of $R_1$ is optionally substituted with 1 to 3 substituents, each independently selected from cyano, methyl, methyl-sulfonyl, methoxy, halo, hydroxy, carboxyl, ethoxy-carbonyl, methyl-amino-carbonyl and amino; with the proviso that $R_1$ and $R_3$ are not both hydrogen.

In some embodiments, for any of the above-described embodiments for Formula Ia, $R_2$ is selected from amino-sulfonyl, methyl-carbonyl-amino, methyl-sulfonyl-amino, amino-sulfonyl-oxy, urea, phenyl, 1H-indol-2-yl, 1H-indol-3-yl, benzo[b]thiophen-2-yl, benzo[b]thiophen-3-yl, benzofuran-2-yl, benzofuran-3-yl, thiophen-2-yl, thiophen-3-yl, furan-2-yl, furan-3-yl, piperidin-4-yl, piperidin-3-yl, piperidin-2-yl, piperidin-1-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, 3-oxopiperazin-1-yl, 2-oxo-2,3-dihydro-1H-benzo[d]imidazol-5-yl, 1,2,3,4-tetrahydronaphthalen-2-yl, indolin-5-yl, 2-oxoindolin-5-yl, 1H-benzo[d]imidazol-5-yl, 1H-indazol-5-yl and 1H-imidazol-4-yl;

wherein said phenyl, 1H-indol-2-yl, 1H-indol-3-yl, benzo[b]thiophen-2-yl, benzo[b]thiophen-3-yl, benzofuran-2-yl, benzofuran-3-yl, thiophen-2-yl, thiophen-3-yl, furan-2-yl, furan-3-yl, piperidin-4-yl, piperidin-3-yl, piperidin-2-yl, piperidin-1-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, 3-oxopiperazin-1-yl, 2-oxo-2,3-dihydro-1H-benzo[d]imidazol-5-yl, 1,2,3,4-tetrahydronaphthalen-2-yl, indolin-5-yl, 2-oxoindolin-5-yl, 1H-benzo[d]imidazol-5-yl, 1H-indazol-5-yl and 1H-imidazol-4-yl of $R_2$ is optionally substituted with hydroxy, methoxy, methyl, halo, amino, amino-sulfonyl, 5-(((3 aS,4S,6aR)-2-oxohexahydro-1H-thieno[3,4-d]imidazol-4-yl)pentanoyloxy-, 2-(2-(5-((3 aS,4S,6aR)-2-oxohexahydro-1H-thieno[3,4-d]imidazol-4-yl)pentanamido)ethoxy)ethoxy and 2-(4-(4-hex-5-ynamidobenzoyl)phenylamino)-2-oxoethoxy.

In some embodiments, for any of the above-described embodiments for Formula Ia, $R_3$ is selected from hydrogen, methyl, and biphenyl; and $R_4$ is selected from isopropyl, isobutyl, sec-butyl, 1-hydroxypropan-2-yl, cyclopropyl, oxetan-3-yl, oxetan-2-yl, benzhydryl, piperidin-4-yl, piperidin-3-yl, piperidin-2-yl, tetrahydro-2H-pyran-2-yl, tetrahydro-2H-pyran-3-yl, tetrahydro-2H-pyran-4-yl, phenyl, tetrahydrofuran-3-yl, tetrahydrofuran-2-yl, benzyl, (4-pentylphenyl)(phenyl)methyl and 1-(1-(2-oxo-6,9,12-trioxa-3-azatetradecan-14-yl)-1H-1,2,3-triazol-4-yl)ethyl;

wherein said cyclopropyl, oxetan-3-yl, oxetan-2-yl, benzhydryl, piperidin-4-yl, piperidin-3-yl, piperidin-2-yl, tetrahydro-2H-pyran-2-yl, tetrahydro-2H-pyran-3-yl, tetrahydro-2H-pyran-4-yl, phenyl, tetrahydrofuran-3-yl, tetrahydrofuran-2-yl, benzyl, (4-pentylphenyl)(phenyl)methyl or 1-(1-(2-oxo-6,9,12-trioxa-3-azatetradecan-14-yl)-1H-1,2,3-triazol-4-yl)ethyl can be optionally substituted with 1 to 3 substituents, each independently selected from methyl and trifluoromethyl.

Exemplary AHR antagonists encompassed by some embodiments of the present invention include, but are not limited to:
4-(2-(2-(benzo[b]thiophen-3-yl)-9-isopropyl-9H-purin-6-ylamino)ethyl)phenol;
4-(2-(2-(benzo[b]thiophen-3-yl)-9-sec-butyl-9H-purin-6-ylamino)ethyl)phenol;
4-(2-(9-benzhydryl-2-(benzo[b]thiophen-3-yl)-9H-purin-6-ylamino)ethyl)phenol;
4-(2-(2-(benzo[b]thiophen-3-yl)-9-(tetrahydro-2H-pyran-3-yl)-9H-purin-6-yl amino)ethyl)phenol;
4-(2-(2-(benzo[b]thiophen-3-yl)-9-(4-(trifluoromethyl)benzyl)-9H-purin-6-yl amino)ethyl)phenol;
4-(2-(2-(benzo[b]thiophen-3-yl)-9-isobutyl-9H-purin-6-ylamino)ethyl)phenol;
4-(2-(2-(benzo[b]thiophen-3-yl)-9-methyl-9H-purin-6-ylamino)ethyl)phenol;
4-(2-(2-(benzo[b]thiophen-3-yl)-9-(4-methylbenzyl)-9H-purin-6-ylamino)ethyl)phenol;
N-(2-(1H-indol-3-yl)ethyl)-2-(benzo[b]thiophen-3-yl)-9-isopropyl-9H-purin-6-amine;
2-(benzo[b]thiophen-3-yl)-9-isopropyl-N-(2-(thiophen-3-yl)ethyl)-9H-purin-6-amine;
3-(2-(2-(benzo[b]thiophen-3-yl)-9-isopropyl-9H-purin-6-ylamino)ethyl)phenol;
2-(benzo[b]thiophen-3-yl)-N-(4-fluorophenethyl)-9-isopropyl-9H-purin-6-amine;
N-(4-aminophenethyl)-2-(benzo[b]thiophen-3-yl)-9-isopropyl-9H-purin-6-amine;
4-(2-(9-isopropyl-2-(pyrimidin-5-yl)-9H-purin-6-ylamino)ethyl)phenol;
4-(2-(9-isopropyl-2-(pyridin-3-yl)-9H-purin-6-ylamino)ethyl)phenol;
4-(2-(9-isopropyl-2-phenyl-9H-purin-6-ylamino)ethyl)phenol;
4-(2-(9-isopropyl-2-(thiophen-3-yl)-9H-purin-6-ylamino)ethyl)phenol;
4-(2-(2-(furan-3-yl)-9-isopropyl-9H-purin-6-ylamino)ethyl)phenol;
2-(benzo[b]thiophen-3-yl)-N-(4-fluorophenethyl)-9-phenyl-9H-purin-6-amine;
N-benzyl-8-(biphenyl-4-yl)-9-isopropyl-9H-purin-6-amine;
4-(2-(2-(benzo[b]thiophen-3-yl)-9-(nonan-2-yl)-9H-purin-6-ylamino)ethyl)phenol;
4-(2-(2-(benzo[b]thiophen-3-yl)-9-((4-pentylphenyl)(phenyl)methyl)-9H-purin-6-ylamino)ethyl)phenol;

N-(2-(1H-indol-3-yl)ethyl)-2-(benzo[b]thiophen-3-yl)-9-sec-butyl-9H-purin-6-amine;
4-(2-(2-(benzo[b]thiophen-3-yl)-9-sec-butyl-9H-purin-6-ylamino)ethyl)phenol;
3-(2-(2-(benzo[b]thiophen-3-yl)-9-isopropyl-9H-purin-6-ylamino)ethyl)-1H-indol-5-ol;
3-(2-(2-(benzo[b]thiophen-3-yl)-9-isopropyl-9H-purin-6-ylamino)ethyl)-1H-indol-5-yl,
5-((3aS,4S,6aR)-2-oxohexahydro-1H-thieno[3,4-d]imidazol-4-yl)pentanoate;
N-(2-(2-(3-(2-(2-(benzo[b]thiophen-3-yl)-9-isopropyl-9H-purin-6-ylamino)ethyl)-1H-indol-5-yloxy)ethoxy)ethyl)-5-((3aS,4S,6aR)-2-oxohexahydro-1H-thieno[3,4-d]imidazol-4-yl)pentanamide;
N-(4-(4-(2-(3-(2-(2-(benzo[b]thiophen-3-yl)-9-isopropyl-9H-purin-6-ylamino)ethyl)-1H-indol-5-yloxy)acetamido)benzoyl)phenyl)hex-5-ynamide;
N-(2-(2-(2-(2-(4-(1-(2-(benzo[b]thiophen-3-yl)-6-(4-hydroxyphenethylamino)-9H-purin-9-yl)ethyl)-1H-1,2,3-triazol-1-yl)ethoxy)ethoxy)ethoxy)ethyl)acetamide;
4-(2-(9-isopropyl-2-(pyridin-4-yl)-9H-purin-6-ylamino)ethyl)phenol;
ethyl 5-(6-(4-hydroxyphenethylamino)-9-isopropyl-9H-purin-2-yl)nicotinate;
ethyl 5-(6-(4-hydroxyphenethylamino)-9-isopropyl-9H-purin-2-yl)nicotinate;
4-(2-(2-(6-fluoropyridin-3-yl)-9-isopropyl-9H-purin-6-ylamino)ethyl)phenol;
4-(2-(9-isopropyl-2-(4-methylpyridin-3-yl)-9H-purin-6-ylamino)ethyl)phenol;
4-(2-(9-isopropyl-2-(2-methoxypyridin-3-yl)-9H-purin-6-ylamino)ethyl)phenol;
5-(6-(4-hydroxyphenethylamino)-9-isopropyl-9H-purin-2-yl)nicotinonitrile;
4-(2-(9-isopropyl-2-(pyrrolidin-1-yl)-9H-purin-6-ylamino)ethyl)phenol;
4-(2-(9-isopropyl-2-(1H-pyrazol-1-yl)-9H-purin-6-ylamino)ethyl)phenol;
4-(2-(2-(1H-imidazol-1-yl)-9-isopropyl-9H-purin-6-ylamino)ethyl)phenol;
4-(2-(9-isopropyl-2-(pyridazin-3-yl)-9H-purin-6-ylamino)ethyl)phenol;
4-(2-(9-isopropyl-2-(pyridazin-4-yl)-9H-purin-6-ylamino)ethyl)phenol;
4-(2-(9-isopropyl-2-(pyrazin-2-yl)-9H-purin-6-ylamino)ethyl)phenol;
4-(2-(9-isopropyl-2-(pyridin-2-yl)-9H-purin-6-ylamino)ethyl)phenol;
4-(2-(9-isopropyl-2-(5-(methylsulfonyl)pyridin-3-yl)-9H-purin-6-ylamino)ethyl)phenol;
4-(2-(9-isopropyl-2-(5-methylpyridin-3-yl)-9H-purin-6-ylamino)ethyl)phenol;
4-(2-(2-(2-chloropyridin-3-yl)-6-isopropyl-2,6-dihydroimidazo[4,5-c]pyrazol-3-ylamino)ethyl)phenol;
4-(2-(2-(4-chloropyridin-3-yl)-9-isopropyl-9H-purin-6-ylamino)ethyl)phenol;
4-(2-(9-isopropyl-2-(4-methoxypyridin-3-yl)-9H-purin-6-ylamino)ethyl)phenol;
4-(2-(2-(5-fluoropyridin-3-yl)-9-isopropyl-9H-purin-6-ylamino)ethyl)phenol;
4-(2-(9-isopropyl-2-(thiazol-4-yl)-9H-purin-6-ylamino)ethyl)phenol;
4-(2-(9-isopropyl-2-(1-methyl-1H-pyrazol-4-yl)-9H-purin-6-ylamino)ethyl)-phenol;
4-(2-(9-isopropyl-2-(1H-pyrazol-3-yl)-9H-purin-6-ylamino)ethyl)phenol;
4-(2-(9-isopropyl-2-(1H-pyrazol-4-yl)-9H-purin-6-ylamino)ethyl)phenol;
4-(2-(9-isopropyl-2-(thiophen-2-yl)-9H-purin-6-ylamino)ethyl)phenol;
4-(6-(4-hydroxyphenethylamino)-9-isopropyl-9H-purin-2-yl)thiophene-2-carboxylic acid;
4-(2-(2-(furan-2-yl)-9-isopropyl-9H-purin-6-ylamino)ethyl)phenol;
4-(2-(9-isopropyl-2-(4-methylthiophen-3-yl)-9H-purin-6-ylamino)ethyl)phenol;
4-(2-(9-isopropyl-2-(pyridin-3-yl)-9H-purin-6-ylamino)ethyl)-2-methoxy-phenol;
4-(2-(9-isopropyl-2-(pyridin-3-yl)-9H-purin-6-ylamino)ethyl)-2-methoxy phenol;
N-[2-(6-methoxy-1H-indol-3-yl)ethyl]-9-(propan-2-yl)-2-(pyridin-3-yl)-9H-purin-6-amine;
N-[2-(5-methyl-1H-indol-3-yl)ethyl]-9-(propan-2-yl)-2-(pyridin-3-yl)-9H-purin-6-amine;
N-[2-(piperidin-4-yl)ethyl]-9-(propan-2-yl)-2-(pyridin-3-yl)-9H-purin-6-amine;
1-(2-{[9-(propan-2-yl)-2-(pyridin-3-yl)-9H-purin-6-yl]amino}ethyl)piperidin-4-ol;
methyl (2S)-3-(4-hydroxyphenyl)-2-{[9-(propan-2-yl)-2-(pyridin-3-yl)-9H-purin-6-yl]amino}propanoate;
4-(2-{[9-(propan-2-yl)-2-(pyridin-3-yl)-9H-purin-6-yl]amino}ethyl)benzene-1-sulfonamide;
2-{[2-(1-benzothiophen-3-yl)-9-(propan-2-yl)-9H-purin-6-yl]amino}ethane-1-sulfonamide;
4-(2-{[9-(propan-2-yl)-2-(pyridin-3-yl)-9H-purin-6-yl]amino}ethyl)benzene-1,2-diol;
N-[2-(1H-imidazol-4-yl)ethyl]-9-(propan-2-yl)-2-(pyridin-3-yl)-9H-purin-6-amine;
1-(2-{[9-(propan-2-yl)-2-(pyridin-3-yl)-9H-purin-6-yl]amino}ethyl)imidazolidin-2-one;
N-[2-(5-amino-1H-1,2,4-triazol-3-yl)ethyl]-9-(propan-2-yl)-2-(pyridin-3-yl)-9H-purin-6-amine;
N-(2-{[9-(propan-2-yl)-2-(pyridin-3-yl)-9H-purin-6-yl]amino}ethyl)pyridin-2-amine;
9-(propan-2-yl)-N-[3-(1H-pyrazol-4-yl)propyl]-2-(pyridin-3-yl)-9-H-purin-6-amine;
N-[2-({[9-(propan-2-yl)-2-(pyridin-3-yl)-9H-purin-6-yl]amino}methyl)propyl]acetamide;
4-(2-{[9-(propan-2-yl)-2-(pyridin-3-yl)-9H-purin-6-yl]amino}ethyl)piperazin-2-one;
N-{2-[(3-methyl-1H-1,2,4-triazol-5-yl)sulfanyl]ethyl}-9-(propan-2-yl)-2-(pyridin-3-yl)-9H-purin-6-amine;
N-[3-(3,5-dimethyl-1H-pyrazol-4-yl)propyl]-9-(propan-2-yl)-2-(pyridin-3-yl)-9H-purin-6-amine;
(2-{[9-(propan-2-yl)-2-(pyridin-3-yl)-9H-purin-6-yl]amino}ethyl)urea;
5-({[9-(propan-2-yl)-2-(pyridin-3-yl)-9H-purin-6-yl]amino}methyl)-2,3-dihydro-1H-1,3-benzodiazol-2-one;
2-(1-benzothiophen-3-yl)-N-[2-(1H-imidazol-4-yl)ethyl]-9-(propan-2-yl)-9H-purin-6-amine;
1-(2-{[2-(1-benzothiophen-3-yl)-9-(propan-2-yl)-9H-purin-6-yl]amino}ethyl)imidazolidin-2-one;
N-[2-(5-amino-1H-1,2,4-triazol-3-yl)ethyl]-2-(1-benzothiophen-3-yl)-9-(propan-2-yl)-9H-purin-6-amine;
N-(2-{[2-(1-benzothiophen-3-yl)-9-(propan-2-yl)-9H-purin-6-yl]amino}ethyl)pyridin-2-amine;
2-(1-benzothiophen-3-yl)-9-(propan-2-yl)-N-[3-(1H-pyrazol-4-yl)propyl]-9H-purin-6-amine;
N-[2-({[2-(1-benzothiophen-3-yl)-9-(propan-2-yl)-9H-purin-6-yl]amino}methyl)propyl]acetamide;
4-(2-{[2-(1-benzothiophen-3-yl)-9-(propan-2-yl)-9H-purin-6-yl]amino}ethyl)piperazin-2-one;

2-(1-benzothiophen-3-yl)-N-{2-[(3-methyl-1H-1,2,4-triazol-5-yl)sulfanyl]ethyl}-9-(propan-2-yl)-9H-purin-6-amine;
2-(1-benzothiophen-3-yl)-N-[3-(3,5-dimethyl-1H-pyrazol-4-yl)propyl]-9-(propan-2-yl)-9H-purin-6-amine;
(2-{[2-(1-benzothiophen-3-yl)-9-(propan-2-yl)-9H-purin-6-yl]amino}ethyl)urea;
5-({[2-(1-benzothiophen-3-yl)-9-(propan-2-yl)-9H-purin-6-yl]amino}methyl)-2,3-dihydro-1H-1,3-benzodiazol-2-one;
N-[2-(1H-indol-3-yl)ethyl]-9-(propan-2-yl)-2-(pyridin-3-yl)-9H-purin-6-amine;
N-(4-(2-(9-isopropyl-2-(pyridin-3-yl)-9H-purin-6-ylamino)ethyl)phenyl)methanesulfonamide;
4-(2-(2-(pyridin-3-yl)-9-(tetrahydrofuran-3-yl)-9H-purin-6-ylamino)ethyl)phenol;
4-(2-(9-isopropyl-2-(pyridin-3-yl)-9H-purin-6-ylamino)propyl)phenol;
4-(2-(9-(oxetan-3-yl)-2-(pyridin-3-yl)-9H-purin-6-ylamino)ethyl)phenol;
5-(6-(4-hydroxyphenethylamino)-9-isopropyl-9H-purin-2-yl)-N-methyl nicotinamide;
6-(9-isopropyl-2-(pyridin-3-yl)-9H-purin-6-ylamino)-5,6,7,8-tetrahydronaphthalen-2-ol;
N-(2-(1H-indazol-3-yl)ethyl)-9-isopropyl-2-(pyridin-3-yl)-9H-purin-6-amine;
4-(2-((9-isopropyl-2-(pyridin-3-yl)-9H-purin-6-yl)(methyl)amino)ethyl)phenol;
4-(2-(9-isopropyl-8-methyl-2-(pyridin-3-yl)-9H-purin-6-ylamino)ethyl)phenol;
1-(2-(9-isopropyl-2-(pyridin-3-yl)-9H-purin-6-ylamino)ethyl)-1H-benzo[d]imidazol-2(3H)-one;
4-(3-(9-isopropyl-2-(pyridin-3-yl)-9H-purin-6-yl)propyl)phenol;
4-((((9-isopropyl-2-(pyridin-3-yl)-9H-purin-6-yl)methyl)(methyl)amino)methyl)phenol;
4-(((9-isopropyl-2-(pyridin-3-yl)-9H-purin-6-yl)methylamino)methyl)phenol;
4-(((9-isopropyl-2-(pyridin-3-yl)-9H-purin-6-yl)methoxy)methyl)phenol;
N-(2-(indolin-5-yl)ethyl)-9-isopropyl-2-(pyridin-3-yl)-9H-purin-6-amine;
4-(2-(9-(1-methylpiperidin-4-yl)-2-(pyridin-3-yl)-9H-purin-6-ylamino)ethyl)phenol;
4-(2-(9-(piperidin-4-yl)-2-(pyridin-3-yl)-9H-purin-6-ylamino)ethyl)phenol;
N-(2-(1H-indazol-5-yl)ethyl)-9-isopropyl-2-(pyridin-3-yl)-9H-purin-6-amine;
N-(2-(1H-benzo[d]imidazol-5-yl)ethyl)-9-isopropyl-2-(pyridin-3-yl)-9H-purin-6-amine;
5-(2-(9-isopropyl-2-(pyridin-3-yl)-9H-purin-6-ylamino)ethyl)indolin-2-one;
4-(2-(9-cyclopropyl-2-(pyridin-3-yl)-9H-purin-6-ylamino)ethyl)phenol;
4-(2-(9-(1-hydroxypropan-2-yl)-2-(pyridin-3-yl)-9H-purin-6-ylamino)ethyl)phenol;
4-(2-(9-isopropyl-2-(pyridin-3-yl)-9H-purin-6-ylamino)ethyl)phenyl sulfamate;
2-(4-hydroxyphenyl)-N-(9-isopropyl-2-(pyridin-3-yl)-9H-purin-6-yl)acetamide;
4-(5-(9-isopropyl-2-(pyridin-3-yl)-9H-purin-6-ylamino)isoxazol-3-yl)phenol;
4-(5-(9-isopropyl-2-(pyridin-3-yl)-9H-purin-6-ylamino)-1,3,4-oxadiazol-2-yl)phenol;
4-(2-(2-(2-fluoropyridin-3-yl)-9-isopropyl-9H-purin-6-ylamino)ethyl)phenol;
4-(2-(9-isopropyl-2-(1-methyl-1H-pyrrol-2-yl)-9H-purin-6-ylamino)ethyl)-phenol; and
4-(2-(9-isopropyl-2-(thiazol-5-yl)-9H-purin-6-ylamino)ethyl)phenol.

In some embodiments, for any of the above-described embodiments of Formula Ia, $R_3$ is hydrogen, $R_1$ is benzothipohene, and L is an alkylamino such as ethylamino. Compounds encompassed by these embodiments can be collectively represented by Formula If:

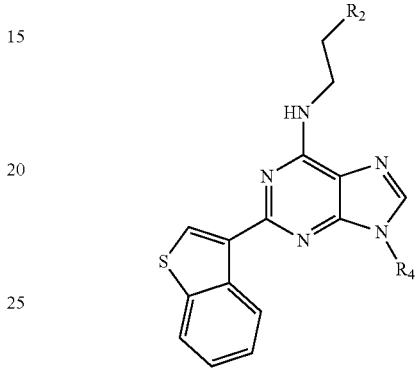

Formula If wherein:

$R_2$ is selected from a heteroaryl, preferably, 1H-indol-3-yl and aryl, preferably phenyl, each may optionally by substituted with hydroxy; and $R_4$ is selected from branched alkyl or alkaryl, preferably selected from isopropyl, sec-butyl, benzhydryl, and nonan-2-yl, and heteroalicyclic, preferably selected from oxetan-3-yl and tetrahydrofuran-3-yl.

Exemplary compounds encompassed by these embodiments include, but are not limited to:

4-(2-(2-(benzo[b]thiophen-3-yl)-9-isopropyl-9H-purin-6-ylamino)ethyl)phenol;
4-(2-(2-(benzo[b]thiophen-3-yl)-9-sec-butyl-9H-purin-6-ylamino)ethyl)phenol;
4-(2-(9-benzhydryl-2-(benzo[b]thiophen-3-yl)-9H-purin-6-ylamino)ethyl)phenol;
N-(2-(1H-indol-3-yl)ethyl)-2-(benzo[b]thiophen-3-yl)-9-isopropyl-9H-purin-6-amine;
4-(2-(2-(benzo[b]thiophen-3-yl)-9-(nonan-2-yl)-9H-purin-6-ylamino)ethyl)phenol;
N-(2-(1H-indol-3-yl)ethyl)-2-(benzo[b]thiophen-3-yl)-9-sec-butyl-9H-purin-6-amine;
4-(2-(2-(benzo[b]thiophen-3-yl)-9-(oxetan-3-yl)-9H-purin-6-ylamino)ethyl)phenol;
(S)-4-(2-(2-(benzo[b]thiophen-3-yl)-9-(tetrahydrofuran-3-yl)-9H-purin-6-yl amino)ethyl)phenol; and
(R)-4-(2-(2-(benzo[b]thiophen-3-yl)-9-(tetrahydrofuran-3-yl)-9H-purin-6-yl amino)ethyl)phenol.

In some embodiments, for any of the above-described embodiments of Formula Ia, $R_3$ is hydrogen, $R_1$ is a substituted or unsubstituted pyridine-3-yl, and L is an alkylamino such as ethylamino. Compounds encompassed by these embodiments can be collectively represented by Formula Ig:

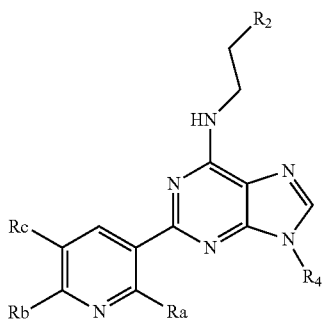

Formula Ig wherein:

R₂ is selected from a heteroaryl, preferably 1H-pyrrolo[2,3-b]pyridin-3-yl or 1H-indol-3-yl, which may optionally be substituted with 1 to 2 substituents independently selected from halo, methyl and methoxy; and aryl, preferably phenyl, which may optionally be substituted with 1 to 2 substituents independently selected from methyl, halo and hydroxy;

R₄ is selected from branched alkyl or alkaryl, preferably selected from isopropyl, sec-butyl, benzhydryl, and nonan-2-yl, and heteroalicyclic, preferably selected from oxetan-3-yl and tetrahydrofuran-3-yl; and Ra, Rb and Rc are independently selected from hydrogen, cyano, methyl, halo, —SO₂CH₃ and trifluoromethyl.

Exemplary compounds encompassed by these embodiments include, but are not limited to:

4-(2-(9-isopropyl-2-(pyridin-3-yl)-9H-purin-6-ylamino)ethyl)phenol;
4-(2-(2-(6-fluoropyridin-3-yl)-9-isopropyl-9H-purin-6-ylamino)ethyl)phenol;
4-(2-(9-isopropyl-2-(4-methylpyridin-3-yl)-9H-purin-6-ylamino)ethyl)phenol;
5-(6-(4-hydroxyphenethylamino)-9-isopropyl-9H-purin-2-yl)nicotinonitrile;
4-(2-(9-isopropyl-2-(5-methylpyridin-3-yl)-9H-purin-6-ylamino)ethyl)phenol;
4-(2-(9-isopropyl-2-(5-(methylsulfonyl)pyridin-3-yl)-9H-purin-6-ylamino)ethyl)phenol;
4-(2-(2-(4-chloropyridin-3-yl)-9-isopropyl-9H-purin-6-ylamino)ethyl)phenol;
4-(2-(2-(5-fluoropyridin-3-yl)-9-isopropyl-9H-purin-6-ylamino)ethyl)phenol;
9-isopropyl-N-(2-(6-methoxy-1H-indol-3-yl)ethyl)-2-(pyridin-3-yl)-9H-purin-6-amine;
9-isopropyl-N-(2-(5-methyl-1H-indol-3-yl)ethyl)-2-(pyridin-3-yl)-9H-purin-6-amine;
N-(2-(1H-indol-3-yl)ethyl)-9-isopropyl-2-(pyridin-3-yl)-9H-purin-6-amine;
4-(2-(9-(oxetan-3-yl)-2-(pyridin-3-yl)-9H-purin-6-ylamino)ethyl)phenol;
4-(2-(9-(1-hydroxypropan-2-yl)-2-(pyridin-3-yl)-9H-purin-6-ylamino)ethyl)phenol;
4-(2-(2-(2-fluoropyridin-3-yl)-9-isopropyl-9H-purin-6-ylamino)ethyl)phenol;
5-(9-sec-butyl-6-(4-hydroxy-3-methylphenethylamino)-9H-purin-2-yl)nicotinonitrile;
4-(2-(2-(5-fluoropyridin-3-yl)-9-(oxetan-3-yl)-9H-purin-6-ylamino)ethyl)phenol;
4-(2-(2-(5-chloropyridin-3-yl)-9-isopropyl-9H-purin-6-ylamino)ethyl)phenol;
4-(2-(9-isopropyl-2-(5-(trifluoromethyl)pyridin-3-yl)-9H-purin-6-ylamino)ethyl)phenol;
5-(6-(2-(1H-indol-3-yl)ethylamino)-9-sec-butyl-9H-purin-2-yl)nicotinonitrile;
N-(2-(1H-indol-3-yl)ethyl)-9-sec-butyl-2-(5-methylpyridin-3-yl)-9H-pu-rin-6-amine;
(R)—N-(2-(1H-indol-3-yl)ethyl)-9-sec-butyl-2-(5-fluoropyridin-3-yl)-9H-purin-6-amine;
(S)—N-(2-(1H-indol-3-yl)ethyl)-9-sec-butyl-2-(5-fluoropyridin-3-yl)-9H-purin-6-amine;
N-(2-(1H-indol-3-yl)ethyl)-9-sec-butyl-2-(5-fluoropyridin-3-yl)-9H-purin-6-amine;
(R)—N-(2-(1H-indol-3-yl)ethyl)-9-sec-butyl-2-(5-methylpyridin-3-yl)-9H-purin-6-amine;
(S)—N-(2-(1H-indol-3-yl)ethyl)-9-sec-butyl-2-(5-methylpyridin-3-yl)-9H-purin-6-amine;
5-(6-(4-hydroxyphenethylamino)-9-(oxetan-3-yl)-9H-purin-2-yl)nicotinonitrile;
4-(2-(6-(5-fluoropyridin-3-yl)-1-isopropyl-1H-pyrazolo[3,4-d]pyrimidin-4-yl amino)ethyl)phenol;
3-(6-(4-hydroxyphenethylamino)-9-isopropyl-9H-purin-2-yl)isonicotinonitrile; 4-(2-(2-(5-fluoropyridin-3-yl)-7-isopropyl-7H-pyrrolo[2,3-d]pyrimidin-4-ylamino)ethyl)phenol;
4-(2-(9-isopropyl-2-(6-methylpyridin-3-yl)-9H-purin-6-ylamino)ethyl)phenol;
2-chloro-4-(2-(9-isopropyl-2-(pyridin-3-yl)-9H-purin-6-ylamino)ethyl)phenol;
3-fluoro-4-(2-(9-isopropyl-2-(pyridin-3-yl)-9H-purin-6-ylamino)ethyl)phenol;
N-(2-(5-fluoro-1H-indol-3-yl)ethyl)-9-isopropyl-2-(pyridin-3-yl)-9H-purin-6-amine;
N-(2-(5-chloro-1H-indol-3-yl)ethyl)-9-isopropyl-2-(pyridin-3-yl)-9H-purin-6-amine;
4-(2-(9-isopropyl-2-(pyridin-3-yl)-9H-purin-6-ylamino)ethyl)-2-methylphenol;
2-(6-(2-(1H-indol-3-yl)ethylamino)-2-(5-fluoropyridin-3-yl)-9H-purin-9-yl)propan-1-ol;
(R)-2-(6-(2-(1H-indol-3-yl)ethylamino)-2-(5-fluoropyridin-3-yl)-9H-purin-9-yl)propan-1-ol;
(S)-2-(6-(2-(1H-indol-3-yl)ethylamino)-2-(5-fluoropyridin-3-yl)-9H-purin-9-yl)propan-1-ol;
(R)—N-(2-(1H-indol-3-yl)ethyl)-2-(5-fluoropyridin-3-yl)-9-(tetrahydrofuran-3-yl)-9H-purin-6-amine;
4-(2-(6-(5-fluoropyridin-3-yl)-1-isopropyl-1H-imidazo[4,5-c]pyridin-4-yl amino)ethyl)phenol;
N-(2-(1H-indol-3-yl)ethyl)-2-(5-fluoropyridin-3-yl)-9-isopropyl-9H-purin-6-amine;
2-(5-fluoropyridin-3-yl)-9-isopropyl-N-(2-(6-methoxy-1H-indol-3-yl)ethyl)-9H-purin-6-amine;
2-(5-fluoropyridin-3-yl)-9-isopropyl-N-(2-(5-methoxy-1H-indol-3-yl)ethyl)-9H-purin-6-amine;
N-(2-(1H-indol-3-yl)ethyl)-2-(5-fluoropyridin-3-yl)-9-(prop-1-en-2-yl)-9H-purin-6-amine;
N-(2-(1H-pyrrolo[2,3-b]pyridin-3-yl)ethyl)-2-(5-fluoropyridin-3-yl)-9-isopropyl-9H-purin-6-amine;

4-(2-(5-(5-fluoropyridin-3-yl)-3-isopropyl-3H-imidazo[4,5-b]pyridin-7-yl amino)ethyl)phenol;
N-(2-(1H-indol-3-yl)ethyl)-9-isopropyl-2-(5-methylpyridin-3-yl)-9H-purin-6-amine;
2-(5-fluoropyridin-3-yl)-9-isopropyl-N-(2-(7-methyl-1H-indol-3-yl)ethyl)-9H-purin-6-amine;
N-(2-(1H-indol-3-yl)ethyl)-2-(5-fluoropyridin-3-yl)-9-(oxetan-3-yl)-9H-purin-6-amine;
N-(2-(1H-indol-3-yl)ethyl)-2-(5-methylpyridin-3-yl)-9-(oxetan-3-yl)-9H-purin-6-amine;
N-(2-(6-fluoro-1H-indol-3-yl)ethyl)-2-(5-fluoropyridin-3-yl)-9-isopropyl-9H-purin-6-amine;
2-(5-fluoropyridin-3-yl)-9-isopropyl-N-(2-(2-methyl-1H-indol-3-yl)ethyl)-9H-purin-6-amine;
2-(5-fluoropyridin-3-yl)-9-isopropyl-N-(2-(6-methyl-1H-indol-3-yl)ethyl)-9H-purin-6-amine;
N-(2-(4-fluoro-1H-indol-3-yl)ethyl)-2-(5-fluoropyridin-3-yl)-9-isopropyl-9H-purin-6-amine;
2-(5-fluoropyridin-3-yl)-9-isopropyl-N-(2-(4-methyl-1H-indol-3-yl)ethyl)-9H-purin-6-amine;
N-(2-(7-fluoro-1H-indol-3-yl)ethyl)-2-(5-fluoropyridin-3-yl)-9-isopropyl-9H-purin-6-amine; and
4-(2-(2-(5-fluoropyridin-3-yl)-9-(1-hydroxypropan-2-yl)-9H-purin-6-ylamino)ethyl)-2-methylphenol.

In some embodiments, the AHR antagonist has Formula Ia as depicted herein, wherein:
$R_3$ is hydrogen;
$R_1$ is selected from linear and branched alkyl, alkaryl, heteroalicyclic and aryl;
L is selected from substituted or unsubstituted alkylamino such as ethylamino and 1,ω-diaminoalkyl such as 1,2-diaminoethyl;
$R_2$ is selected from substituted or unsubstituted phenol, substituted or unsubstituted phenyl, substituted or unsubstituted heteroaryl such as, but not limited to, indole; and
$R_4$ is selected from substituted or unsubstituted aryl and heteroaryl.

In some of these embodiments, $R_1$ is isopropyl and L, $R_2$ and $R_4$ are as defined herein.

In some of these embodiments, $R_1$ is sec-butyl and L, $R_2$ and $R_4$ are as defined herein.

$R_1$ is 2-nonyl and L, $R_2$ and $R_4$ are as defined herein.

In some of these embodiments, $R_2$ is phenol and L, $R_1$ and $R_4$ are as defined herein.

In some of these embodiments, $R_2$ is indole and L, $R_1$ and $R_4$ are as defined herein.

In some of these embodiments, $R_4$ is benzothiophene and L, $R_1$ and $R_2$ are as defined herein.

In some of these embodiments, $R_4$ is substituted or unsubstituted pyridine and L, $R_1$ and $R_2$ are as defined herein.

In some of these embodiments, L is a substituted or unsubstituted alkylamino such as ethylamino and $R_1$, $R_2$ and $R_4$ are as defined herein.

In some embodiments of any of the embodiments described herein for Formula If, $R_1$ is isopropyl, L is ethylamino, $R_2$ is phenol (substituting the second carbon atom in the ethyl moiety, $R_3$ is hydrogen and $R_4$ is benzothiophene.

A compound according to these embodiments is (4-(2-(2-(benzo[b]thiophen-3-yl)-9-isopropyl-9H-purin-6-ylamino)ethyl)phenol), and is also referred to herein and in the art as StemRegenin 1 or SR1.

StemReginin 1 has the following structure:

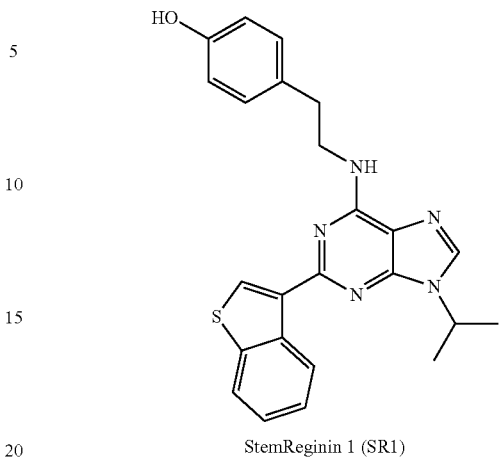

StemReginin 1 (SR1)

For any of the herein described AHR antagonists, encompassed also are pharmaceutically acceptable salts, prodrugs, solvates, hydrates, and polymorphs thereof.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound.

In the context of some of the present embodiments, a pharmaceutically acceptable salt of the compounds described herein may optionally be an acid addition salt comprising at least one basic (e.g., amine) group of the compound which is in a positively charged form (e.g., an ammonium ion), in combination with at least one counter-ion, derived from the selected acid, that forms a pharmaceutically acceptable salt.

The acid addition salts of the compounds described herein may therefore be complexes formed between one or more —NR—, —NH—, and —N= groups of the compound and one or more equivalents of an acid.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Additional optional salts are described hereinbelow. Each of these acid addition salts can be either a mono-addition salt or a poly-addition salt, as these terms are defined herein.

In the context of some of the present embodiments, a pharmaceutically acceptable salt of the compounds described herein may optionally be a base addition salt comprising at least one group of the compound which is in a form of an anion, in combination with at least one counter ion (i.e., cation) that forms a pharmaceutically acceptable salt. Examples of suitable cations include metal cations of metals such as, but not limited to, sodium, potassium, magnesium, and calcium or ammonium.

Each of these base addition salts can be either a mono-addition salt or a poly-addition salt, as these terms are defined herein.

Depending on the stoichiometric proportions between the basic or acidic charged group(s) in the compound (e.g., amine group(s)) and the counter-ion in the salt, the acid or base additions salts can be either mono-addition salts or poly-addition salts.

The phrase "mono-addition salt", as used herein, refers to a salt in which the stoichiometric ratio between the counter-ion and charged form of the compound is 1:1, such that the addition salt includes one molar equivalent of the counter-ion per one molar equivalent of the compound.

The phrase "poly-addition salt", as used herein, refers to a salt in which the stoichiometric ratio between the counter-ion and the charged form of the compound is greater than 1:1 and is, for example, 2:1, 3:1, 4:1 and so on, such that the addition salt includes two or more molar equivalents of the counter-ion per one molar equivalent of the compound.

As used herein, the term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. The prodrug may also have improved solubility as compared with the parent drug in pharmaceutical compositions. Prodrugs are also often used to achieve a sustained release of the active compound in vivo. An example, without limitation, of a prodrug would be the AHR antagonist, having one or more carboxylic acid moieties, which is administered as an ester (the "prodrug"). Such a prodrug is hydrolysed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the heterocyclic compounds described herein) and a solvent, whereby the solvent does not interfere with the biological activity of the solute.

The term "hydrate" refers to a solvate, as defined hereinabove, where the solvent is water.

The present embodiments further encompass any stereoisomers (enantiomers and diastereomers) of the compounds described herein, as well as polymorphs thereof, and further encompasses any pharmaceutically acceptable salts, prodrugs, solvates or hydrates of the stereoisomers and polymorphs.

As used herein, the term "amine" or "amino" describes both a —NR'R" group and a NR'— group, wherein R' and R" can each independently be hydrogen, or substituted or unsubstituted alkyl, cycloalkyl, heteroalicyclic (bonded through a ring carbon), aryl or heteroaryl (bonded through a ring carbon). R' and R" are bound via a carbon atom thereof. Optionally, R' and R" are selected from hydrogen and alkyl comprising 1 to 4 carbon atoms. Optionally, R' and R" are hydrogen.

When one of R' and R" is an alkyl, the amino group is described herein as an aminoalkyl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "amine-oxide" or "N-oxide" describes a —N(OR')(R") or a —N(OR')— group, where R' and R" are as defined herein.

The term "alkyl", as used herein, describes a saturated aliphatic hydrocarbon including straight chain and branched chain groups. In some embodiments, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. In some embodiments, the alkyl is a lower alkyl having 1 to 4 carbon atoms. The alkyl group may be substituted or unsubstituted, as indicated herein.

Herein, the term "alkyl" is also used to describe a group or a structural element of other groups, for example halo-substituted-alkyl and alkoxy, can be either straight-chained (linear) or branched. For example, alkyl includes methyl, ethyl, propyl, isopropyl, butyl, isobutyl, sec-butyl, t-butyl, etc.

$C_{1-4}$-alkoxy includes methoxy, ethoxy, and the like. Halo-substituted alkyl includes trifluoromethyl, pentafluoroethyl, and the like.

The term alkenyl, as used herein, describes an alkyl, as defined herein, which contains a carbon-to-carbon double bond.

The term alkynyl, as used herein, describes an alkyl, as defined herein, which contains carbon-to-carbon triple bond.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted, as indicated herein.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted, as indicated herein.

The term "alkoxy" describes both an —O-alkyl and an —O-cycloalkyl group, as defined herein.

The term "aryloxy" describes an —O-aryl, as defined herein.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

The term "heteroalicyclic" or "heterocyclyl" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofurane, tetrahydropyrane, morpholino and the like.

Herein, the term "aryl" also means a monocyclic or fused bicyclic or tricyclic aromatic ring assembly containing six to 14 ring carbon atoms. For example, aryl may be phenyl or naphthyl, preferably phenyl. The term "arylene" means a divalent radical derived from an aryl group as defined herein.

As used herein, the term "heteroaryl" is also as defined for aryl where one or more of the ring members are a heteroatom or moiety selected from —O—, —N=, —NR—, —C(=O)—, —S—, —S(=O)— or —S(=O)$_2$—, wherein R is hydrogen, $C_{1-4}$alkyl or a nitrogen protecting group. For example heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

Herein, the term "cycloalkyl" also means a saturated or partially unsaturated, monocyclic, fused bicyclic or bridged polycyclic ring assembly containing 3 to 20, or 3 to 16, or 3 to 12, or 3 to 10 ring atoms (optionally indicated). For example, $C_{3-10}$cycloalkyl includes cyclopropyl, cyclobutyl, cyclopentyl, cyclohexyl, etc.

Herein, the term "heterocycloalkyl" or "heteroalicyclic" also means cycloalkyl, as defined herein, provided that one or more of the ring carbons are replaced by a moiety selected from —O—, —N=, —NR—, —C(=O)—, —S—, —S(=O)— or —S(=O)$_2$—, wherein R is hydrogen, $C_{1-4}$alkyl or a nitrogen protecting group. For example, $C_{3-8}$heterocycloalkyl as used herein includes morpholino, pyrrolidinyl, piperazinyl, piperidinyl, piperidinylone, 2-Oxopyrrolidin-1-yl, 1,4-dioxa-8-aza-spiro[4.5]dec-8-yl, etc.

The term "piperazine" refers to a

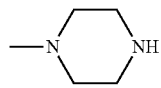

group or a

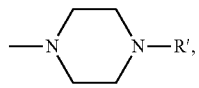

where R' as defined hereinabove.

The term "piperidine" refers to a

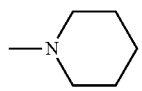

group.

The term "pyrrolidine" refers to a

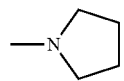

group.

The term "pyridine" refers to a

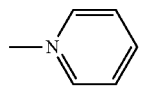

group.

The term "morpholine" refers to a

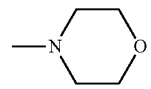

group, and encompasses also thiomorpholine.

The term "thiomorpholine" refers to a

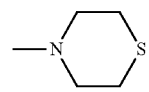

group.

The term "hexahydroazepine" refers to a

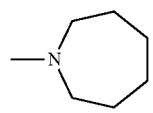

group.

Each of the alkyl, cycloalkyl, aryl, heteroaryl and heteroalicyclic groups described herein may be substituted by one or more substituents, whereby each substituent group can independently be, for example, halogen, alkyl, alkoxy, cycloalkyl, alkoxy, nitro, amine, hydroxyl, thiol, thioalkoxy, thiohydroxy, carboxy, amide, aryl and aryloxy, depending on the substituted group and its position in the molecule. Additional substituents are also contemplated.

Each of the cycloalkyl, aryl, heteroaryl and heteroalicyclic groups described herein can be connected to another group (for example, as indicated for $R_1$-$R_4$ in any of Formulae I and Ia-Ig herein) through any of its ring atoms.

For example, phenol can be connected to another group (for example to groups representing the variable L) via a carbon atom at the ortho, metal or para with respect to its OH group. Pyridine can be connected to another group (for example, as $R_4$) via a carbon atom at the ortho, para or meta position with respect to the nitrogen atom in its ring. A substituted pyridine can be connected to another group (for example, as $R_4$) via a carbon atom at the meta, ortho or para position with respect to the substituent. A benzothiophene can be connected to another group (for example, as $R_4$) via any carbon atom in its rings. Etc.

The term "phenol" describes a phenyl substituted by hydroxy.

The term "alkaryl" describes an alkyl substituted by one or more aryl, as defined herein. Examples include benzyl and benhydryl.

The term "haloalkyl" describes an alkyl group as defined herein, further substituted by one or more halide(s).

The term "hydroxyl" or "hydroxy" describes a —OH group.

The term "thiohydroxy" or "thiol" describes a —SH group.

The term "thio" describes a —S— group.

The term "thioalkoxy" describes both an —S-alkyl group, and a —S-cycloalkyl group, as defined herein.

The term "thioaryloxy" describes both an —S-aryl and a —S-heteroaryl group, as defined herein.

A "sulfonyl" group describes an —S(=O)—R' group, where R' is as defined herein.

A "sulfonyl" group describes an —S(=O)$_2$—R' group, where Rx is as defined herein.

A "carbamyl" group describes an —OC(=O)—NR'R" group, where R' is as defined herein and R" is as defined for R'.

A "nitro" group refers to a —NO$_2$ group.

A "cyano" or "nitrile" group refers to a —C≡N group.

As used herein, the term "azide" refers to a —N$_3$ group.

The term "sulfonamide" refers to a —S(=O)$_2$—NR'R" group, with R' and R" as defined herein.

The term "C-carboxylate" describes a —C(=O)—OR' or a —C(=O)—O—, where R' is as defined herein.

The term "O-carboxylate" describes a —OC(=O)R' or a —OC(=O)—, where R' is as defined herein.

The term "C-thiocarboxylate" describes a —C(=S)—OR' or a —C(=S)—O—, where R' is as defined herein.

The term "O-thiocarboxylate" describes a —OC(=S)R' or a —OC(=S)—, where R' is as defined herein.

The term "N-carbamate" describes an R"OC(=O)—NR'— or a —OC(=O)—NR'—, with R' and R" as defined herein.

The term "O-carbamate" describes an —OC(=O)—NR'R" or an —OC(=O)—NR'—, with R' and R" as defined herein.

The term "O-thiocarbamate" describes a —OC(=S)—NR'R" or a —OC(=S)—NR'—, with R' and R" as defined herein.

The term "N-thiocarbamate" describes an R"OC(=S)NR'— or a —OC(=S)NR'—, with R' and R" as defined herein.

The term "S-dithiocarbamate" describes a —SC(=S)—NR'R" or a —SC(=S)NR'—, with R' and R" as defined herein.

The term "N-dithiocarbamate" describes an R"SC(=S)NR'— or a —SC(=S)NR'—, with R' and R" as defined herein.

The term "urea", which is also referred to herein as "ureido", describes a —NR'C(=O)—NR"R''' or a —NR'C(=O)—NR"— group, where R' and R" are as defined herein and R''' is as defined herein for R' and R". The term "urea" is also referred to herein wherein each of R' and R" is hydrogen, whereby derivatives of urea are also defined as an urea in which one or more of R and R" is not hydrogen.

The term "thiourea", which is also referred to herein as "thioureido", describes a —NR'—C(=S)—NR"R''' or a —NR'—C(=S)—NR"—, with R', R" and R''' as defined herein.

The term "C-amide" describes a —C(=O)—NR'R" or a —C(=O)—NR'—, where R' and R" are as defined herein.

The term "N-amide" describes a R'C(=O)—NR"— or a R'C(=O)—N—, where R' and R" are as defined herein.

The term "guanyl" describes a R'R"NC(=N)— or a —R'NC(=N)-1, where R' and R" are as defined herein.

The term "guanidine" describes a —R'NC(=N)—NR"R''' or a —R'NC(=N)—NR"—, where R', R" and R''' are as defined herein.

The term "hydrazine" describes a —NR'—NR"R''' or a —NR'—NR"—, with R', R", and R''' as defined herein.

A "cyclic ring" encompasses an all-carbon ring structure, such as aryl or cycloalkyl, as defined herein, and further encompasses structures containing more than one ring (e.g., bicyclic structures).

A "heterocyclic ring" encompasses a ring structure that contains one or more heteroatoms such as nitrogen, oxygen, sulfur, and the like, such as heteroalicyclic and heteroaryl, as defined herein, and further encompasses structures containing more than one ring (e.g., bicyclic structures).

In any of the embodiments described herein, the AHR antagonist can be a commercially available compound (e.g., SR1) and can thus be obtained from commercial vendors, or, it can be prepared by methods known in the art.

Exemplary processes for preparing an AHR antagonist as described herein are provided in the following.

In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

The following reaction schemes 1-5 describe exemplary processes of preparing the AHR antagonists as described herein. It will be appreciated by one skilled in the art that, following introduction by the methods detailed below, any of the groups $R_1$, $R_2$, $R_3$, $R_4$, and $L_1$ may optionally be further elaborated by known transformations to arrive at the desired final compounds of Formula I.

Compounds of Formula I can be prepared according the following Reaction Scheme 1:

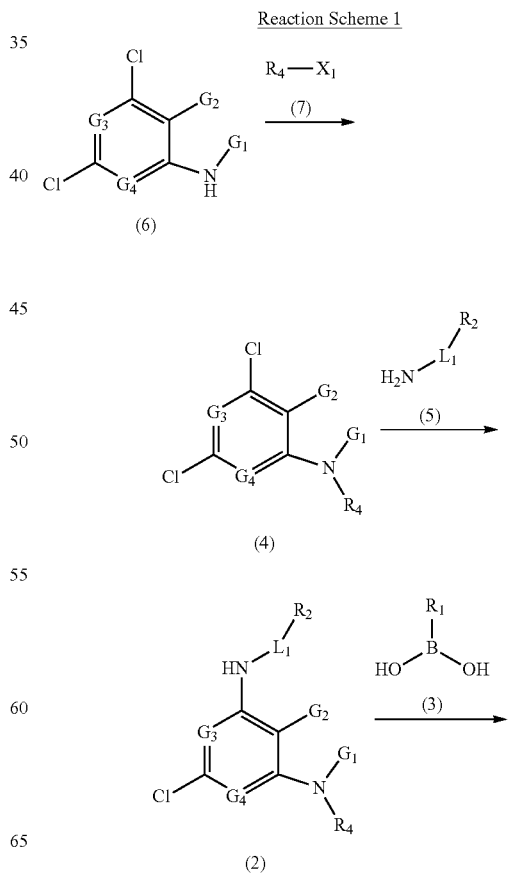

-continued

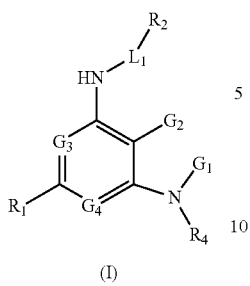

(I)

in which $G_1$, $G_2$, $G_3$, $G_4$, $R_1$, $R_2$ and $R_4$ are as defined for Formula I herein and L of Formula I is defined in the reaction scheme as —NH-$L_1$- which is equivalent to, for example, —$NR_{5a}(CH_2)_{0-3}$— where $R_{5a}$ is hydrogen and —$(CH_2)_{0-3}$— is $L_1$.

Compounds of Formula I can be prepared by reacting a compound of Formula 2 with a compound of Formula 3 in the presence of a suitable catalyst (e.g., $Pd_2(dba)_3$, or the like) in the presence of an appropriate ligand (e.g., 1,3-bis(2,4,6-trimethylphenyl)imidazolium chloride), a suitable base (e.g., $Cs_2CO_3$, or the like) and an appropriate solvent (e.g., 1,4-dioxane) at a temperature of about 80 to 100° C. for 2 to about 48 hours. Compounds of Formula 2 in turn can be prepared by reacting a compound of Formula 4 with a slight excess of an amine compound of Formula 5 in an appropriate solvent (e.g. isopropanol) at a temperature of about room temperature to about 80° C. Compounds of Formula 4 can be prepared by alkylation of a compound of Formula 6 with a suitable alkylating agent 7, in which $X_1$ is chlorine, bromine, iodine, or a sulfonate ester, in the presence of a suitable base (e.g. sodium hydride or potassium carbonate), in a suitable solvent (e.g. DMF), at a temperature of about 0° C. to about 80° C. Alternatively, the reaction can be performed under Mitsunobu conditions using a suitable alcohol $R_4$—OH in the presence of a suitable phosphine (e.g. triphenylphosphine) and azodicarboxylate (e.g. diethylazodicarboxylate), in an inert solvent such as THF or toluene, at a temperature from about 0° C. to about room temperature.

Compounds of Formula Ia, in which $G_1$ is $CR_3$ and in which all other G groups are N, can also be prepared by proceeding as in the following Reaction Scheme 2:

Reaction Scheme 2

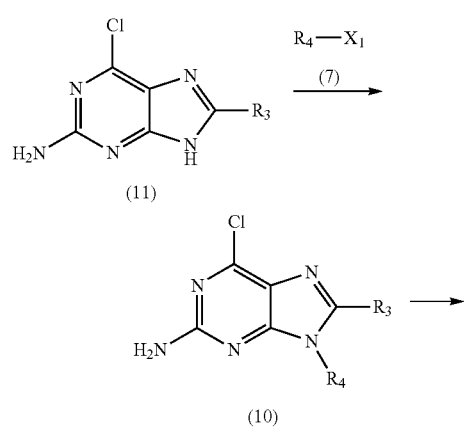

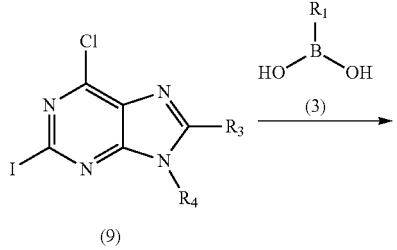

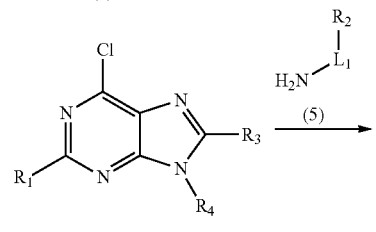

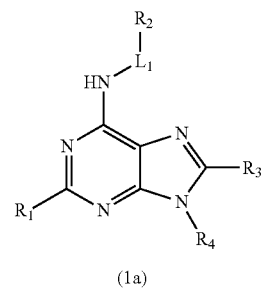

(1a)

in which $R_1$, $R_2$, $R_3$ and $R_4$ are as defined for Formula I herein and L of Formula I is defined in the reaction scheme as —NH-$L_1$- which is equivalent to, for example, —$NR_{5a}(CH_2)_{0-3}$— where $R_{5a}$ is hydrogen and —$(CH_2)_{0-3}$— is $L_1$.

Compounds of Formula I can be prepared by reacting a compound of Formula 8 with an amine compound of Formula 5 in an appropriate solvent (e.g. isopropanol) at a temperature of about room temperature to about 100° C. Compounds of Formula 8 can in turn be prepared by reacting a compound of Formula 9 with a compound of Formula 3 in the presence of a suitable catalyst (e.g., $Pd(Ph_3P)_4$, $Pd_2(dba)_3$, or the like), optionally in the presence of an appropriate ligand (e.g., 1,3-bis(2,4,6-trimethylphenyl)imidazolium chloride), a suitable base (e.g., $Cs_2CO_3$, or the like) and an appropriate solvent (e.g., 1,4-dioxane) at a temperature of about 80 to 100° C. for 2 to about 48 hours. Compounds of Formula 9 in turn can be prepared by reacting a compound of Formula 10 with a mixture of di-iodomethane, copper(I) iodide, and an alkyl nitrite (e.g. isoamylnitrite), optionally in the presence of an inert solvent, at a temperature of about 50 to 100° C. Compounds of Formula 10 can be prepared by alkylation of a compound of Formula 11 with a suitable alkylating agent 7, in which $X_1$ is chlorine, bromine, iodine, or a sulfonate ester, in the presence of a suitable base (e.g. sodium hydride or potassium carbonate), in a suitable solvent (e.g. DMF), at a temperature of about 0° C. to about 80° C. Alternatively, the reaction can be performed under Mitsunobu conditions using a suitable alcohol $R_4$—OH in the presence of a suitable phosphine (e.g. triphenylphosphine) and azodicarboxylate (e.g. diethylazodicarboxylate), in an inert solvent such as THF or toluene, at a temperature from about 0° C. to about room temperature.

Compounds of Formula II, which are a subset of compounds of Formula I in which $R_1$ is N-linked heterocyclyl or N-linked heteroaryl, can be prepared as detailed in the following Reaction Scheme 3:

Reaction Scheme 3

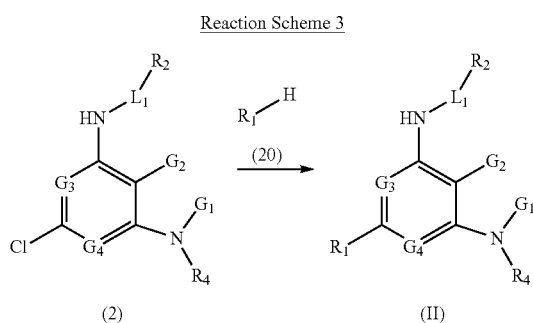

With $G_1$, $G_2$, $G_3$, $G_4$, $R_1$, $R_2$ and $R_4$ are as defined for Formula I herein and L of Formula I is defined in the reaction scheme as —NH-$L_1$- which is equivalent to, for example, —$NR_{5a}(CH_2)_{0-3}$— where $R_{5a}$ is hydrogen and —$(CH_2)_{0-3}$— is $L_1$. Compounds of Formula II can be prepared by reacting a compound of Formula 2 with a compound of Formula 20 in the presence of an excess of cyclic amine or NH-bearing heterocycle (for example, substituted pyrazole, substituted imidazole, and the like), at a temperature of about 50° C. to about 250° C., for about 1 to about 24 hours, optionally in the presence of a base such as sodium hydride or DBU.

Compounds of Formula 10 in which $G_1$ is $CR_3$, and in which all other G groups are N, can also be prepared by proceeding as in the following Reaction Scheme 4:

Reaction Scheme 4

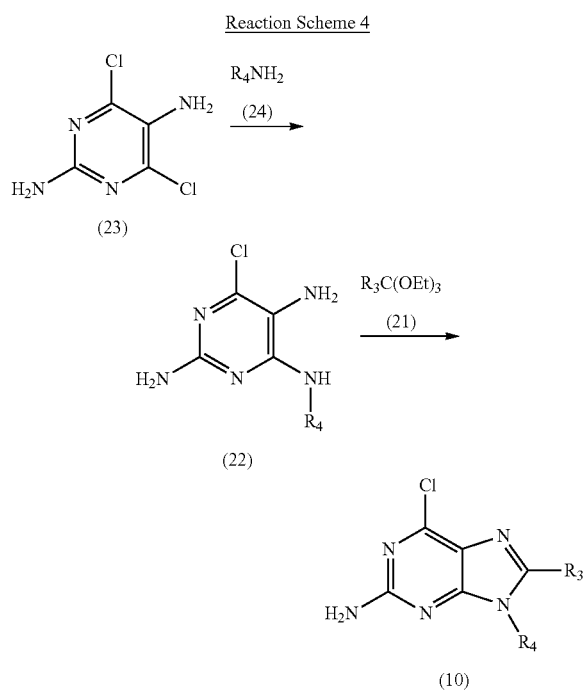

in which $R_3$ and $R_4$ are as defined for Formula I herein. Compounds of Formula 10 can be prepared according to procedures described in J. Med. Chem., 1972, 456, and J. Med. Chem., 1992, 4180. An orthoester compound of Formula 21 is reacted with a compound of Formula 22, optionally in the presence of an acid such as acetic acid, at a temperature of about room temperature to about 150° C., for about 1 to about 24 hours. A compound of Formula 22 can in turn be prepared by reacting a compound of Formula 23 with a primary amine compound of Formula 24, optionally in the presence of an acid such as pTSA, or a base such as triethylamine or DBU, at a temperature of about 50 to about 200° C.

Compounds of Formula IV can be prepared as detailed in the following Reaction Scheme 5:

Reaction Scheme 5

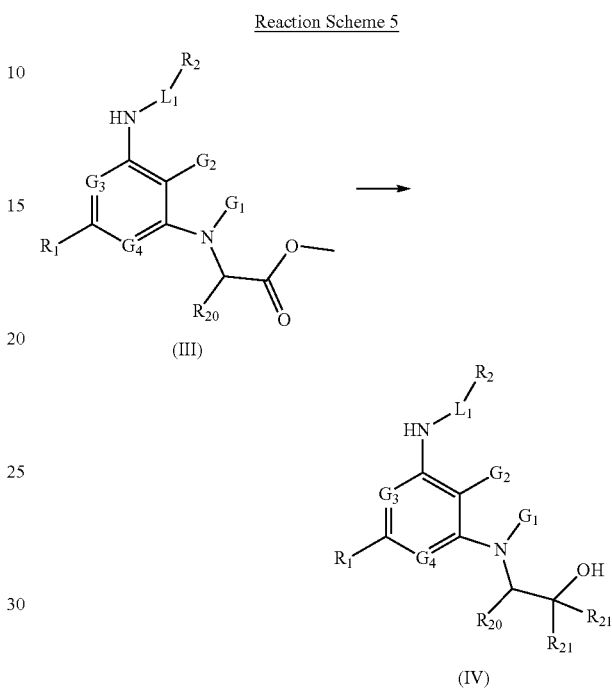

in which $G_1$, $G_2$, $G_3$, $G_4$, $R_1$ and $R_2$ are as defined for Formula I herein and L of Formula I is defined in the reaction scheme as —NH-$L_1$- which is equivalent to, for example, —$NR_{5a}(CH_2)_{0-3}$— where $R_{5a}$ is hydrogen and —$(CH_2)_{0-3}$— is $L_1$. $R_{20}$ and $R_{21}$ are independently selected from hydrogen and $C_{1-4}$alkyl. A compound of Formula IV, in which $R_{21}$ is hydrogen, can be prepared from a compound of Formula III by treatment with a suitable reducing agent such as lithium aluminum hydride or di-isobutyl aluminum hydride, in a suitable solvent such as THF or toluene, at a temperature of about −78° C. to about 50° C. The reaction takes about 0.5 to about 16 hours to complete. A compound of Formula IV, in which $R_{21}$ is lower alkyl, can be prepared by treatment of a compound of Formula III with an alkyl lithium or Grignard reagent, in a suitable solvent such as ether or tetrahydrofuran, at a temperature of about −78° C. to about 50° C. The reaction takes about 0.5 to about 16 hours to complete.

Any of the AHR antagonists as described herein can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds as described herein can be prepared using salts of the starting materials or intermediates.

For example, salt forms of 4-(2-(2-(benzo[b]thiophen-3-yl)-9-isopropyl-9H-purin-6-ylamino)ethyl)phenol (SR1) can be synthesized as follows:

Mesylate salt: 4-(2-(2-(benzo[b]thiophen-3-yl)-9-isopropyl-9H-purin-6-ylamino)ethyl)phenol free base (0.60 gram;

1.40 mmoles) are dissolved in 12 ml acetone at 50° C. Methanesulfonic acid (0.137 gram; 1.40 mmoles) is added drop wise. The crystallization takes place rapidly. The white suspension is allowed to cool over about 30 minutes with cooling to room temperature. The slurry is stirred for 18 hours at room temperature and filtered. The solid is washed with acetone (6 ml) in three portions and dried first for about 3 hours at 50° C./about 10 mbar and then for about 16 hours at 80° C./about 10 mbar. The material has a melting point at about 233° C. with a melting enthalpy of 98 g/J.

In another embodiment, a mesylate salt of SR1 is prepared. In a further embodiment, the mesylate salt of SR1 comprises the following powder X-ray diffraction peaks $(Angle)_2\text{-}\theta°$: 6.4, 6.7, 18.3, 18.6, 26.9; and which in an additional embodiment comprises the following powder X-ray diffraction peaks (Angle 2-$\theta°$): 6.4, 6.7, 10.3, 12.9, 16.4, 18.3, 25.8, 26.5, 26.9.

The tosylate salt of SR1 can be prepared as follows: 4-(2-(2-(benzo[b]thiophen-3-yl)-9-isopropyl-9H-purin-6-ylamino)ethyl)phenol free base (0.60 gram; 1.40 mmoles) are dissolved in 12 ml at 50° C. A solution of para-toluenesulfonic acid mono-hydrate (0.271 gram; 1.40 mmoles) in acetone (1.2 ml) is added drop wise. The solution is seeded at 50° C. and crystallization takes place quickly. The suspension is allowed to cool over about 30 minutes to room temperature and stirred for about 18 hours. After filtration the solid is washed with acetone (6 ml) in three portions and dried first for about 3 hours at 50° C./about 10 mbar and then for about 16 hours at 80° C./about 10 mbar. The material has a melting point at about 233° C. with a melting enthalpy of 88 g/J.

In another embodiment, a tosylate salt of R1 is prepared. In a further embodiment, the tosylate salt of SR1 comprisES the following powder X-ray diffraction peaks (Angle 2-$\theta°$): 6.2, 13.3, 16.7, 19.5, 25.4; and which in an additional embodiment comprises the following powder X-ray diffraction peaks: 6.2, 7.6, 12.4, 13.3, 15.1, 16.7, 17.7, 19.5, 20.2, 24.6, 24.9, 25.4, 25.6.

The sulfate salt of SR1 can be prepared as follows: 4-(2-(2-(benzo[b]thiophen-3-yl)-9-isopropyl-9H-purin-6-ylamino)ethyl)phenol free base (0.60 gram; 1.40 mmoles) are dissolved in 10 ml acetone and 1 ml water at about 55° C. A solution of sulfuric acid (0.280 gram; 2.79 mmoles) in 1 ml water is added drop wise. The crystallization takes place rapidly. The suspension is allowed to cool over about 30 minutes with cooling to room temperature, stirred for about 18 hours and filtered. The filter cake is washed with 6 ml acetone in three portions and dried first for about 3 hours at 50° C./about 10 mbar and then for about 16 hours at 80° C./about 10 mbar. The material has a melting point at about 224° C. with a melting enthalpy of 91 g/J.

In another embodiment, the sulfate salt of SR1 comprises the following powder X-ray diffraction peaks (Angle 2-$\theta°$): 6.5, 6.8, 10.7, 13.5, 26.4, 27.6; and which in an additional embodiment comprises the following powder X-ray diffraction peaks (Angle 2-$\theta°$.): 6.5, 6.8, 10.7, 13.1, 13.5, 18.6, 18.8, 20.8, 26.4, 27.1, 27.6.

The esylate salt of SR1 can be prepared as follows: 4-(2-(2-(benzo[b]thiophen-3-yl)-9-isopropyl-9H-purin-6-ylamino)ethyl)phenol free base (0.60 gram; 1.40 mmoles) are dissolved in 12 ml acetone at 50° C. Ethanesulfonic acid (0.155 gram; 1.40 mmoles) is added drop wise. The crystallization takes place quickly. The resulting white suspension is allowed to cool over about 30 minutes to room temperature. The suspension is stirred for about 18 hours at room temperature and filtered. The solid is washed with 6 ml acetone in three portions and dried first for about 3 hours at 50° C./about 10 mbar and then for about 16 hours at 80° C./about 10 mbar. The material has a melting point at about 231° C. with a melting enthalpy of 76 g/J.

In another embodiment, the i esylate salt of SR1 comprises the following powder X-ray diffraction peaks (Angle 2-$\theta°$): 6.3, 9.9, 18.4, 25.3, 26.1; and which in an additional embodiment comprises the following powder X-ray diffraction peaks (Angle 2-$\theta°$): 6.3, 9.9, 17.1, 17.9, 18.4, 19.0, 22.0, 25.3, 26.1, 27.1.

The hydrobromide salt of SR1 can be prepared as follows: 4-(2-(2-(benzo[b]thiophen-3-yl)-9-isopropyl-9H-purin-6-ylamino)ethyl)phenol free base (0.60 gram; 1.40 mmoles) are dissolved in 6 ml DMF at 65° C. Hydrobromic acid 48% (0.235 gram; 1.40 mmoles) is added drop wise. The solution is allowed to cool over about 30 minutes to room temperature. Seeds are added at 55° C. and crystallization takes place slowly. The suspension is stirred for about 18 hours at room temperature and filtered. The solid is washed with 4 ml DMF/water 1:1 and 6 ml water. The salt is dried as described herein for the other salts. The material has a melting point at about 285° C. with a melting enthalpy of 119 g/J.

In another embodiment, the i hydrobromide salt of SR1 comprises the following powder X-ray diffraction peaks (Angle 2-$\theta°$): 7.0, 25.9, 26.8, 27.9; and which in an additional embodiment comprises the following powder X-ray diffraction peaks (Angle 2-$\theta°$): 7.0, 11.4, 13.3, 21.4, 23.4, 25.9, 26.4, 26.8, 27.9.

The orotate salt of SR1 is prepared as follows: 4-(2-(2-(benzo[b]thiophen-3-yl)-9-isopropyl-9H-purin-6-ylamino) ethyl)phenol free base (0.60 gram; 1.40 mmoles) and orotic acid (0.222 gram; 1.40 mmoles) are dissolved in 7.8 ml NMP (1-Methyl-2-pyrrolidone) at 85° C. The solution is cooled to 60° C. and 6 ml water is added drop wise over about 5 minutes. The resulting white suspension is allowed to cool over about 30 minutes to room temperature and stirred for 18 hours. After filtration the filter cake is washed with 4 ml NMP/water 1:1 in two portions and 6 ml water in three portions. The solid is dried as described herein for other salts. The material has a melting point at about 240° C. with a melting enthalpy of 130 g/J.

In another embodiment, the i orotate salt of SR1 comprisES the following powder X-ray diffraction peaks (Angle 2-$\theta°$): 7.1, 16.3, 19.2, 23.5, 25.6, 26.9; and which in an additional embodiment comprises the following powder X-ray diffraction peaks (Angle 2-$\theta°$): 7.1, 14.4, 16.3, 18.6, 19.2, 21.7, 23.0, 23.5, 25.6, 26.9, 28.7.

The hemi-fumarate salt of SR1 can be prepared as follows: 4-(2-(2-(benzo[b]thiophen-3-yl)-9-isopropyl-9H-purin-6-ylamino)ethyl)phenol free base (0.60 gram; 1.40 mmoles) are dissolved in 18 ml methanol at 65° C. Fumaric acid (0.164 gram; 1.40 mmoles) and 6 ml methanol are added. The solution is allowed to cool over about 30 minutes to room temperature. Some seed crystals are added at 60° C. and crystallization takes place slowly. The suspension is stirred for 18 hours at room temperature and filtered. The solid is washed with 6 ml methanol in three portions and dried as described herein for the other salts. The material has a melting point at about 223° C. with a melting enthalpy of 83 g/J.

In another embodiment, the hemi-fumarate salt of SR1 comprises the following powder X-ray diffraction peaks (Angle 2-$\theta°$): 7.2, 8.7, 14.4, 15.8, 17.4, 19.0, 23.7; and which in an additional embodiment comprises the following powder X-ray diffraction peaks (Angle 2-$\theta°$): 7.2, 8.7, 10.8, 14.4, 15.8, 17.4, 17.8, 19.0, 20.1, 23.7, 27.5.

The besylate salt of SR1 can be prepared as follows: 4-(2-(2-(benzo[b]thiophen-3-yl)-9-isopropyl-9H-purin-6-ylamino)ethyl)phenol free base (0.60 gram; 1.40 mmoles) are dissolved in 12 ml acetone at 50° C. A solution of benzenesulfonic acid (0.225 gram; 2.79 mmoles) in 1.2 ml acetone is added drop wise. Seed crystals are added at 48° C. and the crystallization takes place slowly. The suspension is allowed to cool over about 30 minutes to room temperature. The slurry is stirred for about 18 hours at room temperature and filtered. The salt is washed with 6 ml acetone in three portions and dried as described herein for other salts. The material has a melting point at about 219° C. with a melting enthalpy of 92 g/J.

In another embodiment, the besylate salt of SR1 comprises the following powder X-ray diffraction peaks (Angle 2-θ°.): 6.2, 7.7, 17.7, 25.5; and which in an additional embodiment comprises the following powder X-ray diffraction peaks (Angle 2-θ°): 6.2, 7.7, 15.2, 16.7, 17.1, 17.7, 19.8, 20.2, 24.9, 25.2, 25.5.

The napadisylate salt of SR1 can be prepared as follows: 4-(2-(2-(benzo[b]thiophen-3-yl)-9-isopropyl-9H-purin-6-ylamino)ethyl)phenol free base (0.60 gram; 1.40 mmoles) and 0.259 gram 1,5-naphthalenedisulfonic acid (0.70 mmoles) are dissolved in 9 ml DMF at 87° C. The clear solution is allowed to cool over about 30 minutes to room temperature. Seeds are added at 65° C. and crystallization takes place slowly. The suspension is stirred for about 18 hours at room temperature and filtered. The solid is washed with 4 ml DMF/water 1:1 in two portions and 6 ml water in three portions. The salt is dried as described herein for other salts. The material has a melting point at about 304° C. with a melting enthalpy of 83 g/J. A broad endothermic phenomenon is observed at 107° C. that might be attributed to the loss of water.

In another embodiment, the napadysilate salt of SR1 comprises the following powder X-ray diffraction peaks (Angle 2-θ°): 6.4, 9.6, 13.1, 15.7, 16.1, 26.0; and which in an additional embodiment comprises the following powder X-ray diffraction peaks (Angle 2-θ°): 9.6, 13.1, 15.7, 16.1, 16.4, 20.4, 20.9, 23.7, 26.0, 26.9.

The hydrochloride salt of SR1 is prepared as follows: 4-(2-(2-(benzo[b]thiophen-3-yl)-9-isopropyl-9H-purin-6-ylamino)ethyl)phenol free base (0.60 gram; 1.40 mmoles) are dissolved in 12 ml acetone at 55° C. Hydrochloric acid 37% (0.138 gram; 1.40 mmoles) is added drop wise. The crystallization takes place quickly. The white suspension is allowed to cool over about 30 minutes to room temperature and stirred for 18 hours. After filtration the solid is washed with 6 ml acetone in three portions and dried as described herein for the other salts. The material is exhibiting an exothermic event at about 162° C. with an enthalpy of −13.8 J/g. This phenomenon might be attributed to a solid transformation into a more stable modification. An endothermic event is then seen at about 259° C. with an enthalpy of 99.7 J/g.

In another embodiment, the hydrochloride salt of SR1 comprises the following powder X-ray diffraction peaks (Angle 2-θ°): 6.1, 7.0, 19.8, 26.1; and which in an additional embodiment comprises the following powder X-ray diffraction peaks (Angle 2-θ°): 6.1, 7.0, 18.1, 19.8, 24.7, 26.1, 27.0, 27.7.

free acid or free base forms of the AHR antagonists as described herein can be prepared from the corresponding base addition salt or acid addition salt form, respectively. For example, an AHR antagonist in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc.). The nitrate salt of SR1 can be made using methods known to the skilled person.

AHR antagonists in unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the AHR antagonists as described herein can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the AHR antagonists as described herein can be made by means known to those of ordinary skill in the art. A detailed description of techniques applicable to the creation of protecting groups and their removal can be found in T. W. Greene, "Protecting Groups in Organic Chemistry", 3.sup.rd edition, John Wiley and Sons, Inc., 1999.

The AHR antagonists as described herein can be conveniently prepared as solvates (e.g., hydrates). Hydrates of the AHR antagonists as described herein can be conveniently prepared by recrystallization from an aqueous/organic solvent mixture, using organic solvents such as dioxin, tetrahydrofuran or methanol.

The AHR antagonists as described herein can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981. Compounds of the invention can also be prepared as their individual stereoisomers by using chiral chromatography techniques, in particular, by use of HPLC or SFC chromatography using a chiral stationary phase.

In summary, the AHR antagonists as described herein can be made by a process, which involves:
(a) those of reaction schemes 1-5; and
(b) optionally converting a AHR antagonist as described herein into a pharmaceutically acceptable salt;
(c) optionally converting a salt form of an AHR antagonist as described herein to a non-salt form;
(d) optionally converting an unoxidized form of an AHR antagonist as described herein into a pharmaceutically acceptable N-oxide;
(e) optionally converting an N-oxide form of the AHR antagonist to its unoxidized form;

(f) optionally resolving an individual isomer of an AHR antagonist as described herein from a mixture of isomers;

(g) optionally converting a non-derivatized AHR antagonist as described herein into a pharmaceutically acceptable prodrug derivative; and (h) optionally converting a prodrug derivative of an AHR antagonist as described herein to its non-derivatized form.

Insofar as the production of the starting materials is not particularly described, the compounds are known or can be prepared analogously to methods known in the art.

In another embodiment, an agent capable of down-regulating the activity and/or expression of aryl hydrocarbon receptor is an antisense oligonucleotide or a small interfering RNA molecule (siRNA), capable of down-regulating AHR protein expression or the protein expression of one more downstream effectors of AHR.

Design of antisense oligonucleotides which can be used to efficiently inhibit the AHR protein expression must be effected in a way that such oligonucleotides specifically bind the designated mRNA within cells in a way which inhibits translation thereof. Sequence suitable for use in design and synthesis of antisense oligonucleotides which specifically bind to AHR mRNA, genomic DNA and/or its promoter or other control sequences are available in published sequence of AHR, in particular human AHR. In addition, algorithms for identifying sequences with the highest predicted binding affinity for their target mRNA based on thermodynamic cycle that accounts for the energetics of structural alterations in both the target mRNA and the oligonucleotides are also available.

Synthesis of RNAi molecules suitable for in the context of the present embodiments can be affected as follows: First, the AHR mRNA sequence (or one or more of its down-stream effectors) is scanned downstream of the AUG start codon for AA-dinucleotide sequences. Occurrence of each AA and the 19 3'-adjacent is recorded as a potential siRNA target site. Then, potential target sites are compared to an appropriate genomic database (e.g, human, mouse, rat, etc.) using any sequence alignment software. Putative target site that exhibit significant homology to other coding sequences are filtered out. Preferred sequences are then those including low G/C content, in particular sequences with G/C content lower than 55%. Several target sites are then selected along the length of the target gene. Methods or algorithms to identify putative target site of siRNA are described for example in (Tilesi, et al., Curr. Opin. Mol. Ther. 11:156, 2009).

Examples of siRNA molecules which are capable of down-regulating the expression of AHR include, but are not limited to, AHR 111S, 5' GCG GCA TAG AGA CCG ACT TAA TTT CAA GAG AAT TAA GTC GGT CTC TAT GCC GCT TTT TTG G 3' (SEQ ID NO: 1); AHR 111AS, 5' CGC GCC AAA AAA GCG GCA TAG AGA CCG ACT TAA TTC TCT TGA AAT TAA GTC GGT CTC TAT GCC GC 3'(SEQ ID NO: 2); AHR 242S, 5' GGC TTC TTT GAT GTT GCA TTA ATT CAA GAG ATT AAT GCA ACA TCA AAG AAG CCT TTT TTG G 3'(SEQ ID NO: 3); AHR 242AS, 5' CGC GCC AAA AAA GGC TTC TTT GAT GTT GCA TTA ATC TCT TGA ATT AAT GCA ACA TCA AAG AAG CC 3'(SEQ ID NO: 4).

Thus, according to one aspect of an embodiment of the present invention there is provided a method of ex-vivo culturing natural killer (NK) cells, the method comprising culturing a population of cells comprising NK cells with an antagonist of the aryl hydrocarbon receptor (AHR).

In some embodiments, culturing the NK cells with an antagonist of an AHR comprises culturing the NK cells with an effective concentration, effective exposure time and/or effective duration of antagonist of the aryl hydrocarbon receptor.

In some embodiments the culturing of the NK cells is with the AHR antagonist and with one or more growth factors.

In some embodiments, the culturing of the NK cells with the AHR antagonist and optionally also with one or more growth factors, results in at least one of the following:

(a) elevated expression of CD62L as compared to NK cells cultured under otherwise identical culturing conditions without added antagonists of the aryl hydrocarbon receptor;

(b) reduced expression of CD200R and PD-1 or both as compared to NK cells cultured under otherwise identical culturing conditions without added antagonists of the aryl hydrocarbon receptor;

(c) elevated homing and in-vivo retention as compared to NK cells cultured under otherwise identical culturing conditions without added antagonists of the aryl hydrocarbon receptor; and (d) greater proliferation as compared to NK cells cultured under otherwise identical culturing conditions without added antagonists of the aryl hydrocarbon receptor.

As used herein, the term "natural killer cells" or "NK cells" describes large granular lymphocytes involved in the innate immune response. Functionally, NK cells exhibit cytolytic activity against a variety of targets via exocytosis of cytoplasmic granules containing a variety of proteins, including perforin, and granzyme proteases. Killing is triggered in a contact-dependent, non-phagocytotic process which does not require prior sensitization to an antigen. Human NK cells are characterized by the presence of the cell-surface markers CD16 and CD56, and the absence of the T cell receptor (CD3). Human bone marrow-derived NK cells are further characterized by the CD2+CD16+CD56+CD3− phenotype, further containing the T-cell receptor zeta-chain [zeta($\zeta$)-TCR], and often characterized by NKp46, NKp30 or NKp44. Non-NK cells such as NKT cells or CD8NKT possess characteristics and cell-surface markers of both T cells and NK cells. In one embodiment, the method of the present invention is employed for ex-vivo propagation of mature NK cells from a population of cells. As used herein, the term "mature NK cell" is defined as a committed NK cell, having characteristic surface markers and NK cell function, and lacking the potential for further differentiation. As use herein, mature NK cells include, but are not limited to $CD56^{bright}$ cells, which can proliferate and produce abundant cytokines, $CD56^{dim}$ cells, exhibiting robust cytotoxicity, $CD56^{bright}CD94^{high}$ and $CD56^{dim}CD94^{high}$ cells. In another embodiment, NK progenitor cells, or mixed populations of NK progenitor cells and mature NK cells are propagated. Cell surface expression of the CD56, CD3, CD16, CD94 and other markers can be determined, for example, via FACS analysis or immunohistological staining techniques.

As used herein, the term "progenitor" refers to an immature cell capable of dividing and/or undergoing differentiation into one or more mature effector cells. Lymphocyte progenitors include, for example, pluripotent hematopoietic stem cells capable of giving rise to mature cells of the B cell, T cell and NK lineages. In the B cell lineage (that is, in the developmental pathway that gives rise to mature B cells), progenitor cells also include pro-B cells and pre-B cells characterized by immunoglobulin gene rearrangement and expression. In the T and NK cell lineages, progenitor cells also include bone-marrow derived bipotential T/NK cell progenitors [e.g., CD34(+)CD45RA(hi)CD7(+) and CD34(+)CD45RA(hi)Lin (−)CD10(+) cells], as well as intrathymic progenitor cells, including double negative (with respect to CD4 and CD8) and double positive thymocytes (T cell lineage) and committed NK cell progenitors. Hematopoietic progenitors include CD34+ and early progenitors such as CD133+, CD34+CD38- and CD34+Lin– cells.

As used herein the term "ex-vivo" refers to a process in which cells are removed from a living organism and are propagated outside the organism (e.g., in a test tube). As used herein, the term "in-vitro" refers to a process by which cells known to propagate only in-vitro, such as various cell lines are cultured.

Ex-vivo expansion of NK cells can be effected, according to this aspect of the present invention, by providing NK cells ex vivo with conditions for cell proliferation and ex vivo culturing the NK cells with antagonists of the aryl hydrocarbon receptor, thereby ex-vivo propagating the population of NK cells.

As used herein "culturing" includes providing the chemical and physical conditions (e.g., temperature, gas) which are required for NK cell maintenance, and growth factors. In one embodiment, culturing the NK cells includes providing the NK cells with conditions for proliferation. Examples of chemical conditions which may support NK cell proliferation include but are not limited to buffers, nutrients, serum, vitamins and antibiotics as well as cytokines and other growth factors which are typically provided in the growth (i.e., culture) medium. In one embodiment, the NK culture medium includes MEMα comprising 10% FCS or CellGro SCGM (Cell Genix) comprising 5% Human Serum/LiforCell® FBS Replacement (Lifeblood Products). Other media suitable for use with the invention include, but are not limited to Glascow's medium (Gibco Carlsbad Calif.), RPMI medium (Sigma-Aldrich, St Louis Mo.) or DMEM (Sigma-Aldrich, St Louis Mo.). According to some embodiments of the present invention, culturing the NK cells with growth factors comprises providing the cells with nutrients and with at least one growth factor. In some embodiments the at least one growth factor includes cytokines and/or chemokines, such as, but not limited to, stem cell factor (SCF), FLT3 ligand, interleukin-2 (IL-2), interleukin-7 (IL-7), interleukin-15 (IL-15), interleukin-12 (IL-12) and interleukin-21 (IL-21). The use of other cytokines and growth factors is contemplated, for example, addition of IL-1, TNF-α, etc. Cytokines and other growth factors are typically provided in concentrations ranging from 0.5-100 ng/ml, or 1.0-80 ng/ml, more typically 5-750 ng/ml, yet more typically 5.0-50 ng/ml (up to 10× such concentrations may be contemplated), and are available commercially, for example, from Perpo Tech, Inc., Rocky Hill, N.J., USA. In one embodiment, the at least one growth factor is IL-2. In another embodiment, the growth factor is IL-15. In yet another embodiment, NK cells are cultured with IL-2 and IL-15.

Further, it will be appreciated in this respect that novel cytokines are continuously discovered, some of which may find uses in the methods of NK cell proliferation of the present invention. For applications, in which cells are introduced (or reintroduced) into a human subject, it is often preferable to use serum-free formulations, such as AIM V.® serum free medium for lymphocyte culture or MARROWMAX.® bone marrow medium. Such medium formulations and supplements are available from commercial sources such as Invitrogen (GIBCO) (Carlsbad, Calif.). The cultures can be supplemented with amino acids, antibiotics, and/or with cytokines to promote optimal viability, proliferation, functionality and/or and survival.

According to one embodiment, the cells are cultured with growth factors and antagonists of the aryl hydrocarbon receptor.

As used herein, the phrase "effective concentration" of antagonists of the aryl hydrocarbon receptor is defined as that concentration which, when provided to the population of NK cells in culture, for an effective duration of exposure to the antagonist of the aryl hydrocarbon receptor and at an effective time of exposure to antagonist of the aryl hydrocarbon receptor in culture, results in one or more of elevated expression of CD62L, reduced expression of CD200R and/or PD-1, elevated homing and in-vivo retention, greater proliferation and increased cytotoxic activity of the NK cells, as compared to NK cells cultured under identical conditions but without added antagonists of the aryl hydrocarbon receptor. Antagonist of the aryl hydrocarbon receptor concentrations suitable for use in some embodiments of the present invention are typically in the range of about 0.1 nM to about 100000 nM, about 1.0 nM to about 25 nM, about 1.0 nM to about 25 nM, about 2.5 nM to about 10 nM, about 5.0 nM to about 10 nM, 10 nM to about 100000 nM, about 50 nM to about 1000 nM, about 50 nM to about 500 nM, about 100 nM to about 2500 nM, about 100 nM to about 5000 nM, about 500 nM to about 10000 nM, about 1000 nM to about 20000 nM, about 1000 nM to about 20000 nM, about 5000 nM to about 50000 nM, about 1000 nM to about 100000 nM. Examples I-III below demonstrate exemplary effective concentrations of the aryl hydrocarbon receptor antagonist of about 10 to about 1000 nM, typically 50, 100 or 250 nM, based on the effect of these concentrations of AHR antagonist on proliferation and NK cell function. According to some embodiments of the invention, AHR antagonist concentrations in the range (mM) of about 0.5, about 0.75, about 1.0, about 1.25, about 1.5, about 1.75, about 2.0, about 2.25, about 2.5, about 2.75, about 3.0, about 3.25, about 3.5, about 3.75, about 4.0, about 4.25, about 4.5, about 4.75, about 5.0, about 5.25, about 5.5, about 5.75, about 6.0, about 6.25, about 6.5, about 6.75, about 7.0, about 7.25, about 7.5, about 7.75, about 8.0, about 8.25, about 8.5, about 8.75, about 9.0, about 9.25, about 9.5, about 9.75, about 10.0, about 11.0, about 12.0, about 13.0, about 14.0, about 15.0, about 16.0, about 17.0, about 18.0 and about 20.0, about 50, about 75, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1600, about 1700, about 1800 and about 2000 nM, about 3000, about 4000, about 5000, about 10000, about 20000, about 50000, about 75000, about 100000 nM, and all effective intermediate concentrations are contemplated.

Effective concentrations of the antagonists of the aryl hydrocarbon receptor can be determined according to any assay of NK proliferation and/or activity, for example, cell culture or function protocols as detailed in Examples I-III below. According to one embodiment, an effective concentration of antagonists of the aryl hydrocarbon receptor is a concentration which use thereof in culture "enhances", or results in a net increase of proliferation and/or function of NK cells in culture, compared to "control" cultures lacking added antagonists of the aryl hydrocarbon receptor and tested from the same cord blood, bone marrow or peripheral blood preparation, in the same assay and under similar culture conditions (duration of exposure to antagonists of the aryl hydrocarbon receptor, time of exposure to antagonists of the aryl hydrocarbon receptor).

As used herein, the phrase "effective duration of time" of exposure of the NK cells to antagonist(s) of the aryl hydrocarbon receptor is defined as that duration of exposure to antagonist(s) of the aryl hydrocarbon receptor during which, when the antagonist(s) of the aryl hydrocarbon receptor is provided to the population of NK cells in culture in an effective concentration and at an effective time of exposure, results in one or more of elevated expression of CD62L, reduced expression of CD200R and/or PD-1, elevated homing and in-vivo retention, greater proliferation and increased cytotoxic activity of the NK cells, as compared to NK cells cultured under identical conditions without added antagonist(s) of the aryl hydrocarbon receptor. Duration of exposure of the NK cell populations to antagonist(s) of the aryl hydrocarbon receptor suitable for use in some embodiments of the present invention are typically in the range of about 2 hours to about 5 weeks, about 30 hours to about 4 weeks, about 2 days to about 3 weeks, about 1 week, about 2 weeks, about 3 weeks. Examples I below demonstrate exemplary effective durations of exposure to antagonist(s) of the aryl hydrocarbon receptor of about 1 week to about 3 weeks, based on the effect of the exposure to antagonist(s) of the aryl hydrocarbon receptor on proliferation and NK cell function. According to some embodiments of the invention, duration of exposure to antagonist(s) of the aryl hydrocarbon receptor is about 1.0, about, about 2.0, about 2.5, about 3.0, about 3.5, about 4.0, about 4.5, about 5.0, about 6.0, about 7.0, about 8.0, about 9.0, about 10.0, about 11.0, about 12.0, about 13.0, about 14.0, about 15.0, about 16.0, about 17.0, about 18.0, about 19.0, about 20.0, about 21.0 days, about 25 days, about 30 days, about 35 days and all effective intermediate durations are contemplated. Effective durations of time of exposure to antagonist(s) of the aryl hydrocarbon receptor can be determined according to any assay of NK proliferation and/or activity, for example, cell culture or function protocols as detailed in Examples I-III below.

It will be appreciated that exposure of the NK cell populations to antagonist(s) of the aryl hydrocarbon receptor can be initiated with establishment of the cell culture, or at any time during cell culture, even for a short duration just prior to use (e.g., infusion) of NK cells. As used herein, the phrase "effective exposure time" of the NK cell population to antagonist(s) of the aryl hydrocarbon receptor is defined as the time at which, during the culture of the NK population, the antagonist(s) of the aryl hydrocarbon receptor is provided to the population of NK cells, in an effective concentration and for an effective duration of time, resulting in one or more of elevated expression of CD62L, reduced CD200R and/or PD-1 expression migration response, elevated homing and in-vivo retention, greater proliferation and increased cytotoxic activity of the NK cells, as compared to NK cells cultured under identical conditions without added the antagonists of the aryl hydrocarbon receptor. Time of exposure of the NK cell populations to the antagonists of the aryl hydrocarbon receptor suitable for some embodiments of the present invention is typically from seeding of the NK cells to about 5 weeks after culturing, from about 1 hour after seeding to about 3 weeks after culturing, from about 24 hours to about 3 weeks after culturing, and from the time of seeding of the NK cell population in culture. According to some embodiments of the invention, time of exposure of the NK cells to antagonists of the aryl hydrocarbon receptor is at seeding, about 2 hours after seeding of the cells, about 12 hours after seeding of the cells, about 24 hours after seeding of the cells, about 2 days after seeding of the cells, about 4 days after seeding of the cells, about 7 days after seeding of the cells, about 8.0, about 9.0, about 10.0, about 11.0, about 12.0, about 13.0, about 14.0, about 15.0, about 16.0, about 17.0, about 18.0, about 19.0, about 20.0, about 21.0 days, about 25 days, about 30 days, about 35 days after seeding of the cells and all effective intermediate times are contemplated. Effective times of exposure to antagonists of the aryl hydrocarbon receptor can be determined according to any assay of NK proliferation and/or activity, for example, cell culture or function protocols as detailed herein, for example, in Examples I-III hereinbelow.

As detailed in the Examples section that follows, culturing NK cell populations with at least one growth factor and effective concentrations of the antagonists of the aryl hydrocarbon receptor, provided at an effective exposure time for an effective duration of culture, results in at least one of enhanced proliferation and/or enhanced NK cell function of the cultured cells, as compared to NK cells cultured under identical conditions without added the antagonists of the aryl hydrocarbon receptor.

As used herein, the term "propagation" or "proliferation" refers to growth, for example, cell growth, and multiplication of cell numbers. Propagation and proliferation, as used herein relate to increased numbers of NK cells accruing during the incubation period. Propagation in vitro or in vivo of cells displaying the phenotype of NK cells is a known phenomenon following their stimulation, for example with IL-2, Epstein-Barr virus-transformed lymphoblastoid lines and others.

Assays for cell proliferation well known in the art, including, but not limited to clonogenic assays, in which cells are seeded and grown in low densities, and colonies counted, mechanical assays [flow cytometry (e.g., FACS™), propidium iodide], which mechanically measure the number of cells, metabolic assays (such as incorporation of tetrazolium salts e.g., XTT, MTT, etc), which measure numbers of viable cells, direct proliferation assays (such as BUdR, thymidine incorporation, and the like), which measure DNA synthesis of growing populations. In one embodiment, cell proliferation of populations of NK cells cultured with an effective concentration of the antagonists of the aryl hydrocarbon receptor according to the present invention is measured at a predetermined time after seeding NK cells in culture (for example, about 10 hours, 12 hours, about 1, 2, 3, 4, 5, 6, 7 days, about 1, 2, 3, 4, 5 weeks, 2 months or more) is determined by FACS analysis, using anti-CD56 and anti-CD3 markers to identify and quantitate the CD56+CD3− NK cell fraction of the population. Proliferation of NK cells can be expressed as the fold increase, (e.g., expansion or fold expansion) of NK cells, as compared to the original NK cell fraction before culture. In some embodiments, populations of NK cells exposed to effective concentrations of the antagonists of the aryl hydrocarbon receptor according to the present invention have a fold increase of the NK cell population of at least 2×, at least 10×, at least 20×, at least 40×, at least 50×, at least 75×, at least 100×, at least 150×, at least 250× and at least 500× or more, after about 5, about 7, about 12, about 14, about 18, about 21, about 25, about 30 or more days culture. In another embodiment, the fold expansion of populations of NK cells, as determined by FACS™, exposed to effective concentrations of the antagonists of the aryl hydrocarbon receptor is at least about 1.2×, about 1.3×, about 1.5×, about 1.75×, about 2×, about 2.25×, about 2.5×, about 2.75×, about 3.0, about 3.5×, about 4×, about 4.5×, about 5×, about 6×, about 7×, about 8×, about 9×, about 10×, more than that of NK cells cultured in identical conditions without added antagonists of the aryl hydrocarbon receptor.

As used herein, the term "function" or "NK cell function" refers to any biological function ascribed to NK cells. A non-limiting list of NK cell functions includes, for example, cytotoxicity, induction of apoptosis, cell motility, directed migration, cytokine and other cell signal response, cytokine/ chemokine production and secretion, expression of activating and inhibitory cell surface molecules in-vitro, cell homing and engraftment (in-vivo retention) in a transplanted host, and alteration of disease or disease processes in vivo. In some embodiments, NK cell functions enhanced by exposure to antagonists of the aryl hydrocarbon receptor include at least one of elevated expression of CD62L surface marker, reduced expression of CD200R and/or PD-1 surface marker, and greater cytotoxic activity of the NK cells, as well as elevated homing and in-vivo retention of infused NK cells.

Assays for adhesion and migration molecules such as CD62L, CXCR-4, CD49e and the like, important for homing/engraftment and retention of cells in transplantation, and supressory surface receptors CD200R and PD-1, which function in tumor immunoevasion, are well known in the art. CD62L, CD200R and/or PD-1 expression in a cell can be assayed, for example, by flow cytometry, immunodetection, quantitative cDNA amplification, hybridization and the like. In one embodiment, CD62L expression is detected in different populations of NK cells by exposure of the cells to a fluorescent-tagged specific anti-human CD62L monoclonal antibody [e.g., CD62L PE, Cat. No. 304806 from BioLegend (San Diego, Calif., USA)], and sorting of the cells by fluorescent activated cell sorting (FACS). In one embodiment, CD200R or PD-1 expression is detected in different populations of NK cells by exposure of the cells to a fluorescent-tagged specific anti-human CD200R or PD-1 monoclonal antibody, and sorting of the cells by fluorescent activated cell sorting (FACS). In some embodiments, populations of NK cells exposed to effective concentrations of antagonists of the aryl hydrocarbon receptor have at least 25%, at least 30%, at least 40% or more of the cells detected expressing CD62L, as determined by FACS™. In another embodiment, populations of NK cells exposed to antagonists of the aryl hydrocarbon receptor according to the present invention have at least about 1.2×, about 1.3×, about 1.5×, about 1.75×, about 2×, about 2.25×, about 2.5×, about 2.75×, about 3.0, about 3.5×, about 4×, about 4.5×, about 5×, about 6×, about 7×, about 8×, about 9×, about 10× or more expression of CD62L, as determined by FACS™, when compared to NK cells cultured in identical conditions without added antagonists of the aryl hydrocarbon receptor. In some embodiments, populations of NK cells exposed to effective concentrations of antagonists of the aryl hydrocarbon receptor have at least 25%, at least 30%, at least 40% or less of the cells detected expressing CD200R or PD-1, as determined by FACS™. In another embodiment, populations of NK cells exposed to antagonists of the aryl hydrocarbon receptor according to the present invention have at least about 1.2×, about 1.3×, about 1.5×, about 1.75×, about 2×, about 2.25×, about 2.5×, about 2.75×, about 3.0, about 3.5×, about 4×, about 4.5×, about 5×, about 6×, about 7×, about 8×, about 9×, about 10× or more reduction in expression of CD200R or PD-1, or both, as determined by FACS™, when compared to NK cells cultured in identical conditions with less than 0.1 nM added antagonists of the aryl hydrocarbon receptor.

Assays for cells migration are well known in the art. Migration of cells can be assayed, for example, by transmigration assays or gap closure assays. In transmigration assays, such as the two-chamber technique, cells are separated from a stimulus by a barrier (e.g., filter), and migration of the cells is detected by counting loss of cells from the origin, accumulation of cells across the barrier, or both, at specific intervals. In the gap closure assay, cells are placed on the periphery of a visible gap (scored agar plate, around a circle, etc) and incubated with a stimulus. Closure of the space between the cells applied by cell motility, in response to a stimulus, is visualized using cytometry, immunodetection, microscopy/morphometrics, etc. In one embodiment, migration potential of different populations of NK cells is determined by the "Transwell"™ transmigration assay, in response to SDF (250 ng/ml). In some embodiments, populations of NK cells exposed to effective concentrations of antagonists of the aryl hydrocarbon receptor according to the present invention have least 40%, at least 50%, at least 60%, at least 70% and at least 80% or more migration measure by the Transwell assay described herein. In another embodiment, populations of NK cells exposed to effective concentrations of antagonists of the aryl hydrocarbon receptor have at least about 1.2×, about 1.3×, about 1.5×, about 1.75×, about 2×, about 2.25×, about 2.5×, about 2.75×, about 3.0, about 3.5×, about 4×, about 4.5×, about 5×, about 6×, about 7×, about 8×, about 9×, about 10× or more migration, as determined by the transwell assay, when compared to NK cells cultured in identical conditions without added antagonists of the aryl hydrocarbon receptor.

Assays for homing and in-vivo retention of transfused or transplanted cells are well known in the art. As used herein, the term "homing" refers to the ability of a transfused or transplanted cell to reach, and survive, in a host target organ. For example, NK cells target organs can be the lymphoid tissue, hepatocytes target organs can be liver parenchyma, alveolar cells target organs can be lung parenchyma, etc. As used herein, the term "in-vivo retention" (also known as "engraftment") refers to the ability of the transfused or transplanted cells to proliferate and remain viable in the target organs. Animal models for assaying homing and in-vivo retention of transplanted NK cells include, but are not limited to immunodeficient small mammals (such as SCID, NSG and IL2R$\gamma^{null}$ mice and the like). The SCID-Hu mouse model employs C.B-17 scid/scid (SCID) mice transplanted with human fetal thymus and liver tissue or fetal BM tissue and provides an appropriate model for the evaluation of transplanted human NK cells retention and therapeutic potential. Homing and in-vivo retention of transplanted cells can be assessed in human host subjects as well. In one embodiment, homing and in-vivo retention is assayed in irradiated NOD.Cg-Prkdcscid Il2rgtm1Wjl/SzJ (NSG) mice (see Example III herein), transfused with, for example, about $15 \times 10^4$, about $15 \times 10^5$, about $15 \times 10^6$, about $15 \times 10^7$ or more human NK cells cultured with an effective concentrations of antagonists of the aryl hydrocarbon receptor according to the present invention, and sacrificed at a predetermined time post transfusion (for example, about 5 hours, 10 hours, 12 hours, 1, 2, 3, 4, 5, 6, 7 days, 1, 2, 3, 4, 5 weeks, 2, 3, 4 months or more post transfusion). Upon sacrifice of the mice, samples of spleen, bone marrow, peripheral blood, and other organs are evaluated by FACS for the presence of human NK cells (CD56+CD45+) using human specific Abs. Percent in vivo retention is expressed as the percent of cells of the organ displaying the donor phenotype (e.g., CD45 for human cells). In other embodiments, infused cells are stained with CFSE and upon sacrifice of the mice, samples of spleen, bone marrow, peripheral blood, and other organs are evaluated for the presence of the cells bearing the CFSE stain. In some embodiments, target organs (e.g., lymphoid tissue such as bone marrow, spleen, thymus, lymph nodes, GALT) of host mice transfused with populations of NK cells exposed to effective concentrations of antagonists of the aryl hydrocarbon receptor according to the present invention have at least 5%, at least 10%, at least 20%, at least 25%, at least 30%, at least 40%, at least 50%, at least 60%, at least 70% and at least 80% or more homing and in vivo retention. In one specific embodiment, $15 \times 10^6$ NK cells cultured with an effective concentration of antagonists of the aryl hydrocarbon receptor according to the present invention are transfused to irradiated NSG mice, and at least 25% NK cells having donor-specific lineage are detected in the host spleen, 4 days after the transfusion. In another embodiment, populations of NK cells exposed to effective concentrations of antagonists of the aryl hydrocarbon receptor have at least about 1.2×, about 1.3×, about 1.5×, about 1.75×, about 2×, about 2.25×, about 2.5×, about 2.75×, about 3.0, about 3.5×, about 4×, about 4.5×, about 5×, about 6×, about 7×, about 8×, about 9×, about 10× or more homing and in-vivo retention, as determined by FACS™, when compared to homing and in-vivo retention of NK cells cultured in identical conditions without added antagonists of the aryl hydrocarbon receptor.

As used herein, the term "homeostatic proliferation" refers to proliferation within the target organ or tissue capable of maintaining stable numbers of the infused NK cells over time, preferably months or years.

Currently many clinical trials involving transplantation of NK cells into patients are being conducted, for conditions including, for example, but not exclusively, leukemia (NCT 00799799 and NCT 00303667), hematological malignancies (NCT 00697671, NCT 00354172 and 00640796), post-ASCT (NCT 00586703), neuroblastoma (NCT 00698009), malignant melanoma (NCT 00846833), combination therapy with chemotherapy (NCT 00625729), solid tumors (NCT 00640796) and nasopharyngeal carcinoma (NCT 00717184) and for diverse malignancies (NCT01105650). A complete, current and detailed list of current clinical trials and detailed protocols for NK cell therapy is available at the U.S. National Institutes of Health Clinical Trial website.

Assays for cytotoxicity ("cell killing") are well known in the art. Examples of suitable target cells for use in redirected killing assays are cancer cell line, primary cancer cells solid tumor cells, leukaemic cells, or virally infected cells. Particularly, K562, BL-2, colo250 and primary leukaemic cells can be used, but any of a number of other cell types can be used and are well known in the art (see, e.g., Sivori et al. (1997) J. Exp. Med. 186: 1129-1136; Vitale et al. (1998) J. Exp. Med. 187: 2065-2072; Pessino et al. (1998) J. Exp. Med. 188: 953-960; Neri et al. (2001) Clin. Diag. Lab. Immun. 8:1131-1135). Cell killing is assessed by cell viability assays (e.g., dye exclusion, chromium release, CFSE), metabolic assays (e.g., tetrazolium salts), and direct observation. In one embodiment, cytotoxicity potential of different populations of NK cells is determined by CFSE retention and PI uptake in cells exposed to NK cells at E:T of 1:1, 2.5:1, 5:1, or 10:1, and populations of NK cells exposed to effective concentrations of antagonists of the aryl hydrocarbon receptor according to the present invention kill at least 20%, at least 25%, at least 30%, at least 40%, at least 50%, at least 60%, at least 70% and at least 80% or more of the target cells, as measured by the dye exclusion assay described herein. In another embodiment, populations of NK cells exposed to effective concentrations of antagonists of the aryl hydrocarbon receptor have at least about 1.2×, about 1.3×, about 1.5×, about 1.75×, about 2×, about 2.25×, about 2.5×, about 2.75×, about 3.0, about 3.5×, about 4×, about 4.5×, about 5×, about 6×, about 7×, about 8×, about 9×, about 10× or more killing potential, as determined by the dye exclusion assay, when compared to NK cells cultured in identical conditions without added antagonists of the aryl hydrocarbon receptor.

Culturing the NK cells can be effected with or without feeder cells or a feeder cell layer. Feeder layer-free ex-vivo culture is highly advantageous for clinical applications of cultured cells, including NK cells. As detailed in the Examples section below, effective enhancement of NK cell ex-vivo proliferation and cell function was observed in feeder layer and feeder cell-free long and short term NK cell cultures derived from selected and unselected cord blood and bone marrow cells. Thus, according to one embodiment, culturing the population of NK cells is effected without feeder layer or feeder cells.

According to some embodiments of the present invention, and as detailed in the Examples section which follows, the NK cell population is cultured with IL-2 and 10-1000 nM or greater antagonists of the aryl hydrocarbon receptor the exposure time to antagonists of the aryl hydrocarbon receptor is from seeding of the population of cells comprising NK cells, and the exposure duration is from about 2 weeks to about 3 weeks, optionally 2 weeks, and optionally 3 weeks.

In some embodiments of the present invention, populations of NK cells exposed to effective concentrations of antagonists of the aryl hydrocarbon receptor according to the present invention can have at least any two, optionally any three, optionally any four and optionally all five of elevated expression of CD62L surface marker, reduced expression of CD200R and PD-1 surface markers, and greater cytotoxic activity of the NK cells, as well as elevated homing and in-vivo retention of infused NK cells, as compared to NK cells cultured in identical conditions without added antagonists of the aryl hydrocarbon receptor. In one particular embodiment, populations of NK cells exposed to effective concentrations of antagonists of the aryl hydrocarbon receptor according to the present invention have greater proliferation, elevated CD62L expression, reduced expression of CD200R and PD-1 surface markers and elevated homing and in-vivo retention of infused NK cells, as compared to NK cells cultured in identical conditions without added antagonists of the aryl hydrocarbon receptor.

As detailed herein, enhancement of NK cell proliferation and cellular function by exposure to antagonists of the aryl hydrocarbon receptor is observed as well in the presence of feeder cells. Thus, in another embodiment, the NK cells are cultured in the presence of feeder cells or a feeder layer. Typically, feeder layers comprise irradiated stromal cells, cells of immortalized cell lines, and the like. Methods for culturing NK cells on feeder layers or with feeder cells are described in detail in, for example, Frias et al. (Exp Hematol 2008; 36: 61-68), Harada et al. (Exp Hematol 2004; 32:614-21), Campana et al. (US20090011498) Childs et al. (US20090104170) and Tsai (US20070048290) (which are incorporated herein by reference).

NK cells of the present invention may be derived from any source which comprises such cells. NK cells are found in many tissues, and can be obtained, for example, from lymph nodes, spleen, liver, lungs, intestines, deciduas and can also be obtained from iPS cells or embryonic stem cells (ESC). Typically, cord blood, peripheral blood, mobilized peripheral blood and bone marrow, which contain heterogeneous lymphocyte cell populations, are used to provide large numbers of NK cells for research and clinical use. Thus, according to one aspect of one embodiment of the present invention, the method comprises culturing a population of NK cells derived from one of cord blood, peripheral blood or bone marrow. As detailed herein, it was uncovered that significant differences in the proportions of lymphocyte cell types are found between NK cell preparations from different sources. For example, CD56+ cells isolated (by immunomagnetic isolation) from cord blood typically include a greater proportion of CD56+ CD3− NK cells and fewer NKT cells co-expressing CD56 NK marker and CD3 T cell marker (CD56+CD3+) than the CD56+ fraction of bone marrow or peripheral blood. Thus, in certain embodiments, NK cells are cultured from a heterogeneous cell population comprising NK cells, CD3− cells and CD3+ cells. In one embodiment the CD3+ fraction is greater than the CD3− NK cell fraction, as is typical of bone marrow, cord blood or peripheral blood. In yet another embodiment, the NK cell population is selected or enriched for NK cells. In some embodiments NK cells can be propagated from fresh cell populations, while other embodiments propagate NK cells from stored cell populations (such as cyropreserved and thawed cells) or previously cultured cell populations.

NK cells are associated with mononuclear cell fraction of cord blood or peripheral blood or bone marrow. In one embodiment, the population of cells comprising said NK cells is a mononuclear or total nuclear cell population depleted of CD3+ cells, or CD3+ and CD19+ cells. In another embodiment, the population of cells comprising the NK cells is an unselected NK cell population. In yet another embodiment, the cells are further selected and the NK cells comprise CD56+CD16+CD3− cells and or CD56+CD16−CD3−. Methods for selection of NK cells according to phenotype (e.g., immunodetection and FACS analysis) are detailed herein, for example, in the Methods section that follows.

Most commonly, whole blood or bone marrow samples are further processed to obtain populations of cells prior to placing the lymphocytes into culture medium (or buffer). For example, the blood or bone marrow sample can be processed to enrich or purify or isolate specific defined populations of cells. The terms "purify" and "isolate" do not require absolute purity; rather, these are intended as relative terms. Thus, for example, a purified lymphocyte population is one in which the specified cells are more enriched than such cells are in its source tissue. A preparation of substantially pure lymphocytes can be enriched such that the desired cells represent at least 50% of the total cells present in the preparation. In certain embodiments, a substantially pure population of cells represents at least 60%, at least 70%, at least 80%, at least 85%, at least 90%, or at least 95% or more of the total cells in the preparation.

Methods for enriching and isolating lymphocytes are well known in the art, and appropriate methods can be selected based on the desired population. For example, in one approach, the source material is enriched for lymphocytes by removing red blood cells. In its simplest form, removal of red blood cells can involve centrifugation of unclotted whole blood or bone marrow. Based on density red blood cells are separated from lymphocytes and other cells. The lymphocyte rich fractions can then be selectively recovered. Lymphocytes and their progenitors can also be enriched by centrifugation using separation mediums such as standard Lymphocyte Separation Medium (LSM) available from a variety of commercial sources. Alternatively, lymphocytes/progenitors can be enriched using various affinity based procedures. Numerous antibody mediated affinity preparation methods are known in the art such as antibody conjugated magnetic beads. Lymphocyte enrichment can also be performed using commercially available preparations for negatively selecting unwanted cells, such as FICOLL-HYPAQUE™ and other density gradient mediums formulated for the enrichment of whole lymphocytes, T cells or NK cells.

Methods of selection of NK cells from blood, bone marrow or tissue samples are well known in the art (see, for example, U.S. Pat. No. 5,770,387 to Litwin et al) (which is incorporated herein in its entirety by reference). Most commonly used are protocols based on isolation and purification of CD56+ cells, usually following mononuclear cell fractionation, and depletion of non-NK cells such as CD3+, CD34+, CD133+ and the like. Combinations of two or more protocols can be employed to provide NK cell populations having greater purity from non-NK contaminants. The purity of the NK cell preparation is of great significance for clinical applications, as non-NK cells, such as T-cells and NKT cells, contribute to antigen-specific reactions such as GVHD, compromising the potential benefits of NK cell transplantation. Commercially available kits for isolation of NK cells include one-step procedures (for example, CD56 microbeads and CD56+, CD56+CD16+ isolation kits from Miltenyi Biotec, Auburn Calif.), and multistep procedures, including depletion, or partial depletion, of CD3+ or depletion with non-NK cell antibodies recognizing and removing T cells (for example, OKT-3), B cells, stem cells, dendritic cells, monocytes, granulocytes and erythroid cells. Thus, in some embodiments, the NK cells are selected CD56+CD3−, CD56+CD16+CD3−, CD56+CD16−CD3− or other purified NK cell populations. It will be noted, however, that clinical applications typically favor fewer manipulations of the candidate cell population.

In one embodiment, the NK cells are propagated ex-vivo by short or long term culture. As detailed in Example I, culture of NK cells with growth factors and antagonists of the aryl hydrocarbon receptor, according to the methods of the present invention resulted in enhanced, preferential proliferation and/or functionality of the cultured NK cells, as compared to cells cultured with cytokines but without added antagonists of the aryl hydrocarbon receptor. Thus, in some embodiments of the present invention, culturing the NK cell population is for at least 3, least 5, at least 7, optionally 10, optionally 12, optionally 14, optionally 16, optionally 18, optionally 20 and optionally 21 days, or 1, 2 or three weeks, four weeks, five weeks, six weeks, or more. Exemplary, non-limiting culture durations, as detailed in Examples I-III, are 14 days (2 weeks) and 21 days (3 weeks).

NK cell populations can be cultured using a variety of methods and devices. Selection of culture apparatus is usually based on the scale and purpose of the culture. Scaling up of cell culture preferably involves the use of dedicated devices. Apparatus for large scale, clinical grade NK cell production is detailed, for example, in Spanholtz et al. (PLoS ONE 2010; 5:e9221) and Sutlu et al. (Cytotherapy 2010, Early Online 1-12).

While enhancing proliferation of NK cells in ex-vivo culture is an important goal of the present invention, short term ex-vivo exposure of NK cells to antagonists of the aryl hydrocarbon receptor, for periods of minutes, hours, 1 day, and the like is envisaged. Such short term exposure of NK cells to antagonists of the aryl hydrocarbon receptor, for periods of time not sufficient for proliferation, can potentially enhance, for example, NK cell functionality (cytotoxicity, migration potential, cell surface molecule expression, engraftment potential and the like). Short term treatment with antagonists of the aryl hydrocarbon receptor can be provided to fresh cells, cryopreserved and thawed cells, cells in culture, purified cells, mixed cell populations, and the like. In one embodiment, such short term antagonists of the aryl hydrocarbon receptor treatment is provided immediately before use (transplantation, infusion, etc) of the NK cells.

The inventors have surprisingly observed that culture of a mixed cell population comprising NK (CD56+) cells and non-NK cells (e.g., T (CD3+) cells, NKT (CD56+CD3+) cells and the like) in the presence of an effective concentration of antagonists of the aryl hydrocarbon receptor in the culture medium not only enhances NK cell proliferation, growth and functionality, but also inhibits the proliferation and growth of the non-NK (e.g., T and NKT cells) in the same culture (see Example I-III herein). Thus, in one embodiment of the invention culturing a heterogeneous population of NK and CD3+ cells with an effective concentration of antagonists of the aryl hydrocarbon receptor results in a population of NK cells having a reduced ratio of CD3+ to CD56+CD3− cells, as compared to a population of NK cells cultured under otherwise identical cultural conditions without added antagonists of the aryl hydrocarbon receptor. In yet another embodiment, culturing a heterogeneous population of NK and CD3+ cells with an effective concentration of antagonists of the aryl hydrocarbon receptor, according to the method of the invention results in a population of NK cells having reduced numbers of CD14+ and CD15+ cells, as compared to a population of NK cells cultured under otherwise identical cultural conditions without added antagonists of the aryl hydrocarbon receptor.

The methods described hereinabove for ex-vivo culturing NK cells populations can result, inter alia, in a cultured population of NK cells.

Thus, further according to an aspect of the present invention there is provided a population of NK cells characterized by at least one of elevated expression of CD62L, reduced expression of CD200R and/or PD-1, elevated homing and in-vivo retention, greater proliferation, increased cytotoxic activity, and a reduced ratio of CD3+ to CD56+/CD3− cells, as compared to a population of NK cells cultured under otherwise identical culturing conditions without added antagonists of the aryl hydrocarbon receptor. In some embodiments, the population of NK cells is characterized by at least any two, at least any three, at least any four, at least any five or all six of elevated expression of CD62L, reduced expression of CD200R and/or PD-1, elevated homing and in-vivo retention, greater proliferation, increased cytotoxic activity, and a reduced ratio of CD3+ to CD56+/CD3− cells, as compared to a population of NK cells cultured under otherwise identical culturing conditions without added antagonists of the aryl hydrocarbon receptor.

In Example III the inventors have shown that NK populations prepared according to the methods of the invention have increased in-vivo functional potential, as demonstrated by localization and in-vivo retention in the target organ (e.g., spleen, bone marrow and peripheral blood, in this example spleen). Thus, in a particular aspect of some embodiments of the present invention there is provided a population of NK cells characterized by enhanced homing, engraftment and in-vivo retention when transplanted, wherein infusion of at least $15 \times 10^6$ cells of the NK cell population into an irradiated host (e.g., a NSG mouse) results in at least 5%, at least 10%, at least 15%, at least 20%, at least 25%, at least 30%, at least 35%, at least 40%, at least 45%, at least 50%, at least 55%, at least 60%, at least 70%, at least 80% and at least 90% or more donor-derived NK cells in the host lymphoid tissue, as detected by immunodetection and flow cytometry, at 4 days post-infusion. In one embodiment, infusion at least $15 \times 10^6$ cells of the NK population results in at least 12% donor-derived NK cells in the host spleen tissue, as detected by immunodetection and flow cytometry, at 4 days post-infusion.

Additional, relevant criteria may be applied for characterizing the NK population. Thus, in yet another embodiment, the NK population of the invention is further characterized by expression of CD62L in at least 30% of the cell population at the time of infusion into the host, as detected by flow cytometry and immunodetection. In still another embodiment, the NK cell population can be further characterized according to the degree of purity from contamination by CD3+ cells, e.g., an NK cell population having a ratio of CD3+ to CD56+/CD3− cells of equal to or less than 1:100 at the time of infusion.

It will be appreciated, in the context of the present invention, that a therapeutic NK cell population can be provided along with the culture medium containing antagonists of the aryl hydrocarbon receptor, isolated from the culture medium, and combined with a pharmaceutically acceptable carrier. Hence, cell populations of the invention can be administered in a pharmaceutically acceptable carrier or diluent, such as sterile saline and aqueous buffer solutions. The use of such carriers and diluents is well known in the art.

In one particular embodiment of this aspect of the present invention, the NK cell population comprises a population of NK cells cultured ex-vivo in the presence of an effective amount of antagonists of the aryl hydrocarbon receptor; and a pharmaceutically acceptable carrier. In still another embodiment, the ex-vivo cultured population comprises NK cells which are activated and have increased cytotoxic capacity to a target cell, when compared to populations of NK cells cultured with growth factors without added antagonists of the aryl hydrocarbon receptor.

The ability of antagonists of the aryl hydrocarbon receptor to maintain NK cell proliferation and functionality can be further used in various technical applications.

According to a further aspect of the present invention there is provided a method of preserving NK cells. In one embodiment, the method is effected by handling the NK cells in at least one of the following steps: harvest, isolation and/or storage, in a presence of an effective amount of an antagonist(s) of the aryl hydrocarbon receptor.

According to still a further aspect of the present invention there is provided a NK cells collection/culturing bag. The cells collection/culturing bag of the present invention is supplemented with an effective amount of an antagonist(s) of the aryl hydrocarbon receptor.

According to the present invention there is also provided a NK cell separation and/or washing buffer. The separation and/or washing buffer is supplemented with an effective amount of an antagonist(s) of the aryl hydrocarbon receptor.

As is further detailed below, NK cells may be genetically modified.

In ex-vivo gene therapy cells are removed from a patient, and while being cultured are treated in-vitro. Generally, a functional replacement gene is introduced into the cells via an appropriate gene delivery vehicle/method (transfection, transduction, homologous recombination, etc.) and an expression system as needed and then the modified cells are cultured and returned to the host/patient. These genetically re-implanted cells have been shown to express the transfected genetic material in situ.

Hence, further according to an aspect of the present invention, there is provided a method of transducing ex-vivo cultured NK cells with an exogene. The method, according to this aspect of the present invention, is effected by: (a) ex-vivo culturing a population of NK cells by culturing the population of NK cells according to the methods of NK cell culture of the present invention, and (b) transducing cells of the cultured population of NK cells with the exogene. It will be appreciated that the order of steps (a) and (b) can be reversed. Methods for transduction of cultured NK cells are known in the art, for example, the use of ex-vivo modified NK cells has been disclosed by Campana et al. (US20090011498).

Accordingly, the cultured cells of the present invention can be modified to express a gene product. As used herein, the phrase "gene product" refers to proteins, peptides and functional RNA molecules. Generally, the gene product encoded by the nucleic acid molecule is the desired gene product to be supplied to a subject. Examples of such gene products include proteins, peptides, glycoproteins and lipoproteins normally produced by a cell of the recipient subject. Alternatively, the encoded gene product is one, which induces the expression of the desired gene product by the cell (e.g., the introduced genetic material encodes a transcription factor, which induces the transcription of the gene product to be supplied to the subject). For example, the NK cells can be modified to express cell surface molecules, or intracellular gene products which can enhance or modulate NK cell function, such as cytokines, adhesion molecules, activating and/or inhibitory receptors, and the like.

Description of suitable vectors, constructs and protocols for transfection of eukaryotic cells can be found in Current Protocols in Molecular Biology, Ausubel, F. M. et al. (eds.) Greene Publishing Associates (1989), Section 9.2 and in Molecular Cloning: A Laboratory Manual, 2nd Edition, Sambrook et al. Cold Spring Harbor Laboratory Press, (1989) (which is incorporated herein by reference), for example, Sections 16.41-16.55, 9 or other standard laboratory manuals.

As is discussed in detail hereinabove, ex-vivo propagation of NK cells can be advantageously utilized in NK cells transplantation or implantation. Hence, according to another aspect of the present invention there is provided a method of NK cells transplantation or implantation into a recipient. The method according to this aspect of the present invention is effected by (a) ex-vivo culturing a population of NK cells with growth factors and an effective concentration of an antagonist(s) of the aryl hydrocarbon receptor according to the methods of the invention and administering a therapeutic amount of said cultured NK cells to said subject.

The donor and the recipient can be the same individual or different individuals, for example, allogeneic individuals. Thus, the population of NK cells can be autologous or allogeneic to the subject. When allogeneic transplantation is practiced, regimes for reducing implant rejection and/or graft vs. host disease, as well known in the art, can be undertaken. Such regimes are currently practiced in human therapy. Most advanced regimes are disclosed in publications by Slavin S. et al., e.g., J Clin Immunol (2002) 22: 64, and J Hematother Stem Cell Res (2002) 11: 265), Gur H. et al. (Blood (2002) 99: 4174), and Martelli M F et al., (Semin Hematol (2002) 39: 48), which are incorporated herein by reference.

According to one embodiment, transplantation of the NK cell population is for treatment or prevention of a disease in the subject.

According to yet another aspect of one embodiment of the present invention there is provided a method of inhibiting tumor growth in a subject in need thereof. The method according to this aspect of the present invention is effected by administering a therapeutically effective amount of a population of NK cells of the invention to said subject.

"Treating" or "treatment" includes, but is not limited to the administration of an enriched, activated or cultured NK cell composition or population of the present invention to prevent or delay the onset of the symptoms, complications, or biochemical indicia of a disease, alleviating the symptoms or arresting or inhibiting further development of the disease, condition, or disorder (e.g., cancer, metastatic cancer, or metastatic solid tumors). Treatment can be prophylactic, i.e., adjuvant (to prevent or delay the onset of the disease, or to prevent the manifestation of clinical or subclinical symptoms thereof) or therapeutic suppression or alleviation of symptoms after the manifestation of the disease.

In one embodiment, the NK cell population is administered in an amount effective to reduce or eliminate a cancer, such as a solid tumor or a malignancy, or prevent its occurrence or recurrence. "An amount effective to reduce or eliminate the solid tumor or to prevent its occurrence or recurrence" or "an amount effective to reduce or eliminate the hyperproliferative disorder or to prevent its occurrence or recurrence" refers to an amount of a therapeutic composition that improves a patient outcome or survival following treatment for the tumor disease state or hyperproliferative disorder as measured by patient test data, survival data, elevation or suppression of tumor marker levels, reduced susceptibility based upon genetic profile or exposure to environmental factors. "Inhibiting tumor growth" refers to reducing the size or viability or number of cells of a tumor. "Cancer", "malignancy", "solid tumor" or "hyperproliferative disorder" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancerous" or "malignant cell" or "solid tumor cell" is understood as a cell having specific structural properties, lacking differentiation and being capable of invasion and metastasis. "Cancer" refers to all types of cancer or neoplasm or malignant tumors found in mammals, including carcinomas and sarcomas. Examples are cancers of the breast, lung, non-small cell lung, stomach, brain, head and neck, medulloblastoma, bone, liver, colon, genitourinary, bladder, urinary, kidney, testes, uterus, ovary, cervix, prostate, melanoma, mesothelioma, sarcoma, (see DeVita, et al., (eds.), 2001, Cancer Principles and Practice of Oncology, 6th. Ed., Lippincott Williams & Wilkins, Philadelphia, Pa.; this reference is herein incorporated by reference in its entirety for all purposes).

"Cancer-associated" refers to the relationship of a nucleic acid and its expression, or lack thereof, or a protein and its level or activity, or lack thereof, to the onset of malignancy in a subject cell. For example, cancer can be associated with expression of a particular gene that is not expressed, or is expressed at a lower level, in a normal healthy cell. Conversely, a cancer-associated gene can be one that is not expressed in a malignant cell (or in a cell undergoing transformation), or is expressed at a lower level in the malignant cell than it is expressed in a normal healthy cell.

"Hyperproliferative disease" refers to any disease or disorder in which the cells proliferate more rapidly than normal tissue growth. Thus, a hyperproliferating cell is a cell that is proliferating more rapidly than normal cells.

"Advanced cancer" means cancer that is no longer localized to the primary tumor site, or a cancer that is Stage III or IV according to the American Joint Committee on Cancer (AJCC).

"Well tolerated" refers to the absence of adverse changes in health status that occur as a result of the treatment and would affect treatment decisions.

"Metastatic" refers to tumor cells, e.g., human solid tumor or genitourinary malignancy, that are able to establish secondary tumor lesions in the lungs, liver, bone or brain of immune deficient mice upon injection into the mammary fat pad and/or the circulation of the immune deficient mouse.

A "solid tumor" includes, but is not limited to, sarcoma, melanoma, carcinoma, or other solid tumor cancer. "Sarcoma" refers to a tumor which is made up of a substance like the embryonic connective tissue and is generally composed of closely packed cells embedded in a fibrillar or homogeneous substance. Sarcomas include, but are not limited to, chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

"Melanoma" refers to a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

"Carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidernoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma viflosum.

"Leukemia" refers to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number of abnormal cells in the blood-leukemic or aleukemic (subleukemic). Leukemia includes, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia. Additional cancers include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macro globulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

In another particular embodiment of this aspect of the present invention the method is affected concomitantly with, following or prior to hematopoietic, hematopoietic progenitor or hematopoietic stem cell transplantation into said subject. In yet further embodiments, the subject is being concomitantly treated with a sensitizing or potentiating agent (e.g., proteasome inhibitor, IL-2, IL-15, etc) further enhancing the in-vivo function of the transfused NK cells (for details see, for example, U.S. Patent Application Publication No. 20090104170 to Childs et al).

Decreased numbers and functionality of NK cells in autoimmune patients has been observed, indicating the possibility of NK cell therapy in a variety of autoimmune diseases and conditions (see Schleinitz, et al., Immunology 2010; 131:451-58, and French and Yokohama, Arthrit Res Ther 2004; 6:8-14). Thus, in still another embodiment of the present invention there is provided a method of treating an autoimmune disease or condition in a subject in need thereof. The method according to this aspect of the present invention is effected by administering a therapeutic amount of a population of NK cells of the invention to said subject.

Autoimmune diseases which can be treated by the method of the invention include, but are not limited to cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis, myocardial infarction, thrombosis, Wegener's granulomatosis, Takayasu's arteritis, Kawasaki syndrome, anti-factor VIII autoimmune disease, necrotizing small vessel vasculitis, microscopic polyangiitis, Churg and Strauss syndrome, pauci-immune focal necrotizing and crescentic glomerulonephritis, antiphospholipid syndrome, antibody-induced heart failure, thrombocytopenic purpura, autoimmune hemolytic anemia, cardiac autoimmunity in Chagas' disease and anti-helper T lymphocyte autoimmunity.

Examples of autoimmune rheumatoid diseases include, but are not limited to rheumatoid arthritis and ankylosing spondylitis.

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes, autoimmune thyroid diseases, Graves' disease, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome.

Examples of autoimmune gastrointestinal diseases include, but are not limited to, chronic inflammatory intestinal diseases, celiac disease, colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis, primary biliary cirrhosis and autoimmune hepatitis.

Examples of autoimmune neurological diseases include, but are not limited to, multiple sclerosis, Alzheimer's disease, myasthenia gravis, neuropathies, motor neuropathies; Guillain-Barre syndrome and autoimmune neuropathies, myasthenia, Lambert-Eaton myasthenic syndrome; paraneoplastic neurological diseases, cerebellar atrophy, paraneoplastic cerebellar atrophy and stiff-man syndrome; non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies; dysimmune neuropathies; acquired neuromyotonia, arthrogryposis multiplex congenita, neuritis, optic neuritis and neurodegenerative diseases.

Examples of autoimmune muscular diseases include, but are not limited to, myositis, autoimmune myositis and primary Sjogren's syndrome and smooth muscle autoimmune disease.

Examples of autoimmune nephric diseases include, but are not limited to, nephritis and autoimmune interstitial nephritis.

Examples of autoimmune diseases related to reproduction include, but are not limited to, repeated fetal loss.

Examples of autoimmune connective tissue diseases include, but are not limited to, ear diseases, autoimmune ear diseases and autoimmune diseases of the inner ear.

Examples of autoimmune systemic diseases include, but are not limited to, systemic lupus erythematosus and systemic sclerosis.

In yet another embodiment of the present invention there is provided a method of inhibiting a viral infection in a subject in need thereof. The method according to this aspect of the present invention is effected by (a) ex-vivo culturing a population of NK cells with NK cell growth factors and an effective concentration of antagonists of the aryl hydrocarbon receptor, wherein said effective concentration of antagonists of the aryl hydrocarbon receptor enhances proliferation of said NK cells, as compared to said population of cells cultured with growth factors without said concentration of antagonists of the aryl hydrocarbon receptor; and (b) administering a therapeutic amount of said cultured NK cells to said subject. Viral infections suitable for treatment with NK cells or NK cell compositions of the invention include, but are not limited to HIV, lymphatic choriomenengitis virus (LCMV), cytomegalovirus (CMV), vaccinia virus, influenza and para-influenza virus, hepatitis (including hepatitis A, hepatitis B, hepatitis C, non-A-non-B, etc), herpes simplex virus, herpes zoster virus, Theiler's virus and HSV-1. Other infectious diseases suitable for treatment with NK cells or NK cell preparations of the present invention include, but are not limited to parasitic infections such as Plasmodium, Leishmania and Toxiplasma infections, and bacterial infections such as mycobacteria and Listeria (for a review of NK cells in treatment of viral, bacterial and protozoan diseases see Zucchini et al., Exp Rev Anti-Infect Ther 2008; 6:867-85, which reference is incorporated by reference herewith).

Transplantation of hematopoietic cells has become the treatment of choice for a variety of inherited or malignant diseases. However, hematopoietic cell compositions are often rich in T lymphocytes, which contribute to graft-versus-host disease. Since patients suffering from hematological malignancies are often deficient in NK cell numbers and function, exogenous administration NK cells along with hematopoietic cell transplantation is currently being investigated for enhanced long term engraftment and prevention of graft versus host disease. Thus, in yet another embodiment of the present invention there is provided a method of treating or preventing graft versus host disease in a subject in need thereof. Thus, in still another embodiment of the present invention there is provided a method of treating an autoimmune disease or condition in a subject in need thereof. The method according to this aspect of the present invention is effected by administering a therapeutic amount of a population of NK cells of the invention to said subject.

Clinical protocols for treatment with NK cells, and combinations treatments with NK and HSC cells populations are well known in the art. For example, recent reports have established that NK cells infusions are safe, and do not cause GVHD in the recipient. One such protocol involves myeloablation, infusion of IL-2 activated, NK enriched (non-NK depleted) HLA-mismatched cord blood, followed by a double cord blood infusion for HSC repopulation [see Miller et al., Blood 2006; 108:3111 (Abstract)]. The authors reported that transplantation of NK cells, along with cord blood HSC, resulted in improved long-term engraftment of the HSC.

Treatment Regimen

According to some aspects of some embodiments of the present invention, there are provided pharmaceutical compositions comprising an NK cell population for the treatment of disease, e.g., metastic cancer, solid tumors, autoimmune disease, hyperproliferative disorder or a viral infection, formulated together with a pharmaceutically acceptable carrier. Some compositions include a combination of multiple (e.g., two or more) NK cell populations of the invention.

In prophylactic applications, pharmaceutical compositions or medicaments are administered to a patient susceptible to, or otherwise at risk of a disease or condition (i.e., a hyperproliferative disease or solid tumor) in an amount sufficient to eliminate or reduce the risk of recurrence of the hyperproliferative disease or solid tumor, lessen the severity, or delay the outset of the disease, including biochemical, histologic and/or behavioral symptoms of the disease, its complications and intermediate pathological phenotypes presenting during development of the disease. In therapeutic applications, compositions or medicants are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient anti-proliferative response has been achieved. Typically, the anti-proliferative response is monitored and repeated dosages are given if the anti-proliferative response starts to wane.

Effective Dosages

Effective doses of a composition of an NK cell population for the treatment of disease, e.g., metastic cancer, solid tumors, or a hyperproliferative disorder, described herein vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy.

For administration with a therapeutic NK cell population, the dosage ranges from about $1\times10^6$ to about $1\times10^9$ NK cells per patient. For administration with an NK cell population, the dosage ranges from about $1\times10^5$ to about $1\times10^9$ NK cells per kilogram recipient weight, or the dosage ranges from about $5\times10^5$ to about $1\times10^8$ NK cells per kilogram recipient weight. An exemplary treatment regime entails administration once per every two weeks or once a month or once every 3 to 6 months. In some methods, two or more NK cell populations are administered simultaneously, in which case the dosage of each NK cell populations administered falls within the ranges indicated. Multiple administrations of NK cell populations can occur. Intervals between single dosages can be weekly, monthly or yearly. Intervals can also be irregular as indicated by measuring blood levels of the NK cell population in the patient. Alternatively, the NK cell populations can be administered as a sustained release formulation, in which case less frequent administration is required. Dosage and frequency vary depending on the half-life of the NK cell populations in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Routes of Administration

Compositions of a therapeutic NK cell population for the treatment of disease, e.g., metastic cancer, solid tumors, or a hyperproliferative disorder, can be administered by intravenous, intravesicular, intrathecal, parenteral, topical, subcutaneous, oral, intranasal, intraarterial, intracranial, intraperitoneal, or intramuscular means. As a prophylactic/adjuvant or for treatment of disease, therapeutic NK cell populations target a hyperproliferative disorder or solid tumor, e.g., a genitourinary malignancy, and/or therapeutic treatment. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where deposits have accumulated, for example intracranial injection. Intramuscular injection on intravenous infusion are preferred for administration of an NK cell population. In some methods, a particular therapeutic NK cell population is injected directly into the bladder.

Formulation

Compositions of an NK cell population for the treatment of disease, e.g., metastic cancer, solid tumors, viral infection, or a hyperproliferative disorder.

Compositions of a therapeutic NK cell population for the treatment of disease, e.g., metastic cancer, solid tumors, or a hyperproliferative disorder, are often administered as pharmaceutical compositions comprising an active therapeutic agent, i.e., and a variety of other pharmaceutically acceptable components. See, e.g., Alfonso R Gennaro (ed), Remington: The Science and Practice of Pharmacy, (Formerly Remington's Pharmaceutical Sciences) 20th ed., Lippincott, Williams & Wilkins, 2003, incorporated herein by reference in its entirety. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. An example of such diluent is X-vivo 20 media (Cambrex Bio Science, Walkersville, Md.) containing 10% heat inactivated human AB serum or 10% autologous serum. Further examples of such diluents are distilled water, physiological phosphate-buffered saline, Ringer's solutions, dextrose solution, and Hank's solution. In addition, the pharmaceutical composition or formulation can also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, compositions of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Therapeutic NK cell populations can be administered in the form of a depot injection or implant preparation which can be formulated in such a manner as to permit a sustained release of the active ingredient. An exemplary composition comprises a therapeutic NK cell population at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science, 249: 1527, 1990; Hanes, Advanced Drug Delivery Reviews, 28: 97-119, 1997, incorporated herein by reference in their entirety. The agents of this invention can be administered in the form of a depot injection or implant preparation which can be formulated in such a manner as to permit a sustained or pulsatile release of the active ingredient. Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

The pharmaceutical compositions generally comprise a composition of the therapeutic NK cell population in a form suitable for administration to a patient. The pharmaceutical compositions are generally formulated as sterile, substantially isotonic and in fall compliance with all Good Manufacturing Practice (GMP) regulations of the U.S. Food and Drug Administration.

Toxicity

Preferably, a therapeutically effective dose of a composition of the NK cell population described herein will provide therapeutic benefit without causing substantial toxicity.

Toxicity of the therapeutic NK cell population described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the therapeutic NK cell population described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition. (See, e.g., Fingl, et al., The Pharmacological Basis Of Therapeutics, Ch. 1, 1975), incorporated herein by reference in its entirety.

Kits

Also within the scope of the invention are kits comprising the compositions (e.g., a therapeutic NK cell population) of the invention and instructions for use. The kit can further contain a least one additional reagent, or one or more additional human antibodies of the invention (e.g., a human antibody having a complementary activity which binds to an epitope in the antigen distinct from the first human antibody). Kits typically include a label indicating the intended use of the contents of the kit. The term label includes any writing, or recorded material supplied on or with the kit, or which otherwise accompanies the kit.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1, 2, 317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Procedures

Stemreginin I (SR1)
SR1, as a mono-HCl acid addition salt [(4-(2-((2-Benzo[b]thiphen-3-yl)-9-isopropyl-9H-purin-6-yl)amino)ethyl)phenol hydrochloride] was purchased from BioVision Inc., and was used without any further modification.

Cord Blood Samples:
Cells are obtained from umbilical cord blood after normal full-term delivery (informed consent was given). Samples are collected and frozen within 24 hours postpartum. Briefly, cord blood is collected by gravity from delivered placentas, the leukocyte-rich fraction separated by density gradient centrifugation, cells mixed with DMSO (10%) and then frozen at −80° C. Prior to use, the cells are thawed in Dextran buffer (Sigma, St. Louis, Mo., USA) containing 2.5% human serum albumin (HSA)(Bayer Corp. Elkhart, 1N, USA), and the cryoprotectant removed. Peripheral blood samples.

Peripheral blood (PB) cells were layered on a Ficoll-Hypaque gradient (1.077 g/mL; Sigma), and centrifuged at 800×g for 30 min. The mononuclear cells in the interface layer were collected and washed three times in phosphate-buffered saline (PBS) (Biological Industries, Israel) containing 0.5 HSA.

Enrichment of CD56+ Cells
Cord blood (CB), bone marrow (BM) or peripheral blood (PB) cells were layered on a Ficoll-Hypaque gradient (1.077 g/mL; Sigma), and centrifuged at 800×g for 30 minutes for separation of the mononuclear cells. The cells in the interface layer were collected and washed three times in phosphate-buffered saline (PBS) (Biological Industries, Israel) containing 0.5% HSA. To purify the CD56+ cells, the mononuclear cell fraction was subjected to two cycles of immunomagnetic bead separation, using a "MiniMACS or CliniMACS CD56 progenitor cell isolation kit" (Miltenyi Biotec Bergisch, Gladbach, Germany), according to the manufacturer's recommendations. Briefly, CD56+ cells are reacted with CD56+ specific magnetic immunobeads, separated and with a magnetic separator, and purified from unbound cells by washing. The purity of the CD56+ population thus obtained is approximately 92%, as evaluated by flow cytometry.

Optionally, cells are not separated on the Ficoll-Hypaque gradient but washed three times in phosphate-buffered saline (PBS) (Biological Industries) containing 0.5% HSA ("total mononuclear fraction"). In the last wash cells were incubated with 50 µg/ml rHu-DNAse for 10 minutes. To purify the CD56+ cells, the cells are subjected to two cycles of immunomagnetic bead separation, using a "MidiMACS CD56 progenitor cell isolation kit" (Miltenyi Biotec Bergisch, Gladbach, Germany), according to the manufacturer's recommendations. The purity of the CD56+ population thus obtained is approximately 92%, as evaluated by flow cytometry.

Optionally, bone marrow cells are depleted of CD133+ or CD34+ cells by immunomagnetic bead separation, using a "MidiMACS or CliniMACS CD133 cell isolation kit" (Miltenyi Biotec Bergisch, Gladbach, Germany), and then the CD133− or CD34 negative fraction is further enriched for NK cells by subjecting the cells to two cycles of immunomagnetic bead separation, using a "MidiMACS or CliniMACS CD56 progenitor cell isolation kit" (Miltenyi Biotec Bergisch, Gladbach, Germany), according to the manufacturer's recommendations.

Enrichment of CD56+CD3− Cells
Cord blood (CB), bone marrow (BM) or peripheral blood (PB) cells were layered on a Ficoll-Hypaque gradient (1.077 g/mL; Sigma), and centrifuged at 800×g for 30 minutes for separation of the mononuclear cells. The cells in the interface layer were collected and washed three times in phosphate-buffered saline (PBS) (Biological Industries, Israel) containing 0.5% HSA. To purify the CD56+CD3− cells, the mononuclear cell fraction was subjected to immunomagnetic bead separation, using a "MiniMACS or CliniMACS CD56 progenitor cell isolation kit" (Miltenyi Biotec Bergisch, Gladbach, Germany), according to the manufacturer's recommendations. Briefly, CD56+ cells are reacted with CD56+ specific magnetic immunobeads, separated and with a magnetic separator, and purified from unbound cells by washing. The purified CD56+ cell fraction was subjected to an additional immunomagnetic bead separation, using a "MiniMACS or CliniMACS CD3 progenitor cell isolation kit" (Miltenyi Biotec Bergisch, Gladbach, Germany), according to the manufacturer's recommendations. Briefly, CD56+ cells are reacted with CD3+ specific magnetic immunobeads, separated and with a magnetic separator, and CD56+CD3− cells recovered in the unbound cells fraction. The purity of the CD56+CD3− population thus obtained is approximately 85-97%, as evaluated by flow cytometry.

Optionally, cells are not separated on the Ficoll-Hypaque gradient but washed three times in phosphate-buffered saline (PBS) (Biological Industries) containing 0.5% HSA ("total mononuclear fraction"). In the last wash cells were incubated with 50 µg/ml rHu-DNAse for 10 minutes. To purify the CD56+ cells, the cells are subjected to two cycles of immunomagnetic bead separation, using a "MidiMACS CD56 progenitor cell isolation kit" (Miltenyi Biotec Bergisch, Gladbach, Germany), according to the manufacturer's recommendations. The purity of the CD56+ population thus obtained is approximately 92%, as evaluated by flow cytometry. To purify the CD56+CD3− cells, the cells are subjected to immunomagnetic bead separation, using a "MiniMACS or CliniMACS CD56 progenitor cell isolation kit" (Miltenyi Biotec Bergisch, Gladbach, Germany), according to the manufacturer's recommendations. Briefly, CD56+ cells are reacted with CD56+ specific magnetic immunobeads, separated and with a magnetic separator, and purified from unbound cells by washing. The purified CD56+ cell fraction was subjected to an additional immunomagnetic bead separation, using a "MiniMACS or CliniMACS CD3 progenitor cell isolation kit" (Miltenyi Biotec Bergisch, Gladbach, Germany), according to the manufacturer's recommendations. Briefly, CD56+ cells are reacted with CD3+ specific magnetic immunobeads, separated and with a magnetic separator, and CD56+CD3− cells recovered in the unbound cells fraction. The purity of the CD56+CD3− population thus obtained is approximately 85-97%, as evaluated by flow cytometry.

Optionally, bone marrow cells are depleted of CD133+ or CD34+ cells by immunomagnetic bead separation, using a "MidiMACS or CliniMACS CD133 cell isolation kit" (Miltenyi Biotec Bergisch, Gladbach, Germany), and then the CD133− or CD34 negative fraction is further enriched for NK cells by subjecting the cells to two cycles of immunomagnetic bead separation, using a "MidiMACS or CliniMACS CD56 progenitor cell isolation kit" (Miltenyi Biotec Bergisch, Gladbach, Germany), according to the manufacturer's recommendations. To purify the CD56+CD3− cells, CD133− or CD34 negative fraction was subjected to immunomagnetic bead separation, using a "MiniMACS or CliniMACS CD56 progenitor cell isolation kit" (Miltenyi Biotec Bergisch, Gladbach, Germany), according to the manufacturer's recommendations. Briefly, CD56+ cells are reacted with CD56+ specific magnetic immunobeads, separated and with a magnetic separator, and purified from unbound cells by washing. The purified CD56+ cell fraction was subjected to an additional immunomagnetic bead separation, using a "MiniMACS or CliniMACS CD3 progenitor cell isolation kit" (Miltenyi Biotec Bergisch, Gladbach, Germany), according to the manufacturer's recommendations. Briefly, CD56+ cells are reacted with CD3+ specific magnetic immunobeads, separated and with a magnetic separator, and CD56+CD3− cells recovered in the unbound cells fraction. The purity of the CD56+CD3− population thus obtained is approximately 85-97%, as evaluated by flow cytometry.

Depletion of CD3+ or CD3+CD19+ Cells Before Culture

For depletion procedure, total nuclear cells from umbilical cord blood (CB), bone marrow (BM) or peripheral blood (PB) cells were layered on a Ficoll-Hypaque gradient (1.077 g/mL; Sigma), and centrifuged at 800×g for 30 minutes for separation of the mononuclear cells. The cells in the interface layer were collected and washed three times in phosphate-buffered saline (PBS) (Biological Industries, Israel) containing 0.5% HSA. Optionally, cells are not separated on the Ficoll-Hypaque gradient but washed three times in phosphate-buffered saline (PBS) (Biological Industries) containing 0.5% HSA ("total mononuclear fraction"). CD3 cells were depleted using the CD3 cell isolation kit (Miltenyi Biotec Bergisch, Gladbach, Germany) and the entire CD3 negative cell fraction was cultured. Optionally, CD19 cells were also depleted using the CD19 cell isolation kit (Miltenyi Biotec Bergisch, Gladbach, Germany) and the CD3/CD19 negative (CD3/CD19 depleted) cell fraction was cultured. Optionally, RosetteSep Human CD3+ Cell Depletion Cocktail (Stem Cell Technologies, RosestteSep, Cat. No. 15661)] was used for CD3 depletion and the entire CD3 negative cell fraction was cultured. After negative depletion the cells were counted and characterized by FACS analysis.

Ex Vivo Cultures:

1. Total mononuclear cell fraction was cultured in culture bags (American Fluoroseal Co. Gaithersburg, Md., USA), at 0.5-2×10$^6$ cells/ml in MEMα comprising 10% Human Serum containing the human recombinant cytokines: interleukin-2 (IL-2) (5-50 ng/ml) and interleukin-15 (IL-15), with or without SR1 (10-1000 nM), and incubated at 37° C. in a humidified atmosphere of 5% $CO_2$ in air. All cultures are topped weekly with the same volume of fresh medium containing the growth factors with or without SR1. For counting, the cells were stained with trypan blue. At various time points, samples were taken to assay the relative fractions of NK cells, CD56+CD3−, CD56+CD3+, cells.

2. Purified CD56+ or CD56+CD3− cells from total nuclear or mononuclear cells or from the fraction depleted from CD34+ or CD133+ cells were cultured in culture bags, T-Flasks or 24 well plates at a concentration of 1-100×10$^4$ cells/ml in MEMα/10% FCS or CellGro SCGM (Cell Genix)/5% Human Serum/LiforCell® FBS Replacement (Lifeblood Products) containing the following human recombinant cytokines, interleukin-2 (IL-2) (5-50 ng/ml), interleukin-15 (IL-15), FLT-3 or SCF or FLT3 and SCF or IL-2 and IL-15 or IL-2 only (Perpo Tech, Inc., Rocky Hill, N.J., USA), with or without SR1 (10-1000 nM), and incubated at 37° C. in a humidified atmosphere of 5% $CO_2$ in air. The cultures were topped up once or twice a week with the same volume of fresh medium containing growth factors with or without antagonists of the aryl hydrocarbon receptor. Eventually cultures can be supplemented once or several times a week with IL-2 and or IL-2 and IL-15. To estimate the number of cells in culture, cell samples were stained with trypan blue for counting. At various time points, samples were taken for FACS analysis to assay the relative fractions of NK cells, CD56+CD3−, CD56+CD3+, CD34+CD56+, CD56+CD16+ and/or CD56+ NKG2A cells.

3. CD3+ depleted, or CD3+/CD19+ depleted mononuclear cell fraction from PB were cultured in culture bags, at a concentration of 1-7×10$^5$ cells/ml in MEMα/10% Human Serum containing the human recombinant cytokines interleukin-2 (IL-2) and interleukin-15 (IL-15) (Perpo Tech, Inc., Rocky Hill, N.J., USA), with or without SR1 (10-1000 nM) and incubated at 37° C. in a humidified atmosphere of 5%

$CO_2$ in air. The cultures were topped weekly with the same volume of fresh medium containing growth factors with or without SR1. To estimate number of cells in culture, cell samples were counted following staining with trypan blue. At various time points, samples are taken to FACS analysis to assay the relative fractions of NK cells, CD56+CD3−, CD56+CD3+.

4. Total mononuclear cell fraction, purified CD56+ or CD56+CD3− cells from total nuclear or mononuclear cells or from the fraction depleted from CD34+ or CD133+, and CD3+ depleted, or CD3+/CD19+ depleted mononuclear cell fraction from PB, BM and CB cells can be also cultured in a bioreactor such as GE Wave Bioreactor bag or Gas Permeable Cultureware flasks (Wilson Wolf) at $1-10000\times10^4$ cells/ml) Culture medium contained MEMα, Human Serum (10% v/v), 20 ng/ml IL-2, and optionally 50 ng/ml IL-2 and optionally IL-15, with SR1. The cultures were topped up weekly or twice a week with the same volume of fresh medium containing growth factors with or without added SR1. Cultures were later supplemented once or several times a week with IL-2 and or IL-2 and IL-15 and the cells were counted and stained for FACS analysis after 1, 2 and 3 weeks.

NK Cell Culture with Irradiated Stroma

NK cells from total mononuclear cell fraction, purified CD56+ or CD56+CD3− cells from total nuclear or mononuclear cells or from the fraction depleted from CD34+ or CD133+ cells, or CD3+ depleted, or CD3+/CD19+ depleted mononuclear cell fraction from PB, BM and CB can be cultured with irradiated stroma. For the preparation of irradiated stroma (feeder cells), mononuclear cells are irradiated with 3000 rad. After CD56 or CD56+CD3− selection or CD3 depletion the cells are counted and characterized by FACS analysis as described hereinabove. Cells are cultured as described hereinabove, with and without SR1, with and without irradiated stroma at a concentration of irradiated cells of $20\times10^5$ cells/ml.

FACS Analysis

For FACS analysis cells were stained with the following fluorescent antibodies: CD15 FITC, Cat. No. 332778, CD14 FITC, Cat. No. 345784, CD3 APC, Cat. No. 345767, all from Becton Dickinson (San Jose, Calif., USA), CD62L PE, Cat. No. 304806 from BioLegend (San Diego, Calif., USA), CD56 FITC, Cat. No. 11-0569-42 from eBioscience (San Diego, Calif., USA) and CD45 PE, Cat. No. R7807 from Dako (Glostrup, Denmark) and anti-CD200R and anti-PD-1 fluorescent antibodies.

NK cells are also characterized by CXCR4, KIR3, DL1/2, DL2/2, DL1, NKG2A, NKG2C, NKG2D, TRAIL, Fc-gamma receptor Mb, NKp44, NKp30, NKp46, Fas-L, L-Selectin, phycoerythrin, IL-2 receptor γ chain (CD16), VLA-5α chain and CD8.

Calculation of Number of NK Cells Seeded at Day 0

In order to calculate the number of NK cells on day 0, the total number of cells seeded on day 0 was multiplied by the percent of CD56+/CD3− cells measured by the FACS on day 0.

Calculation of NK Cell Number in Culture and Fold Increase 14 and 21 Days Post Seeding To determine total number of cells on day 14 and 21, the cell count/ml was multiplied by the volume of the culture medium. In order to determine the number of NK cells in culture, the total number of cells in culture was multiplied by the percent of CD56+/CD3− cells measured with the FACS on days 14 or 21. To measure fold expansion, total number of NK cells on days 14 and 21 was divided by total number of NK cells seeded in culture on day-0.

Surface Antigen Analysis

The cells were washed with a PBS solution containing 1% BSA, and stained (at 4° C. for 30 min) with fluorescein isothiocyanate (FITC)- or phycoerythrin (PE)-conjugated antibodies or allophycocyanin (APC). The cells were then washed in the above buffer and analyzed using a FACScalibur® flow cytometer (Becton Dickinson, San Jose, Calif., USA). The cells were passed at a rate of up to 1000 cells/second, using a 488 nm or 661 nm argon laser beam as the light source for excitation. Emission of $10^4$ cells was measured using logarithmic amplification, and analyzed using the CellQuest software (Becton Dickinson). Cells stained with FITC, PE and APC-conjugated isotype control antibodies were used to determine background fluorescence.

Determination of the Functionality of NK Cells

"Killing" Assay:

NK cells (effectors cells=E) are combined with K562 or BL2 (target cells=T), or bi-phenotypic leukemia cells at different E to T ratio (E:T). BL2 or K562, or bi-phenotypic leukemia target cells in PBS are labeled with 1 ng/ml CFSE (Invitrogen) for 15 min at 37° C. Calf Serum is added to the cells for 15 minutes, the cells are then washed and resuspended in RPMI medium. 100 μL of bi-phenotypic leukemia, BL2 or K562 cells are placed in a 96 round bottom plate at a concentration of $5\times10^3$ cells per well. 100 μL of non-stained NK cells are added to the bi-phenotypic leukemia, BL2 or K562 cells at a E:T ratio of 1:1, 2.5:1, 5:1, 10:1 or 20:1 ($5\times10^3$, $1.25\times10^4$, $2.5\times10^4$, $5\times10^4$ and $1\times10^5$ cells/well, respectively, as indicated). Between 2-48 hours later. Killing of target cells in cell lines such as K562 and BL-2 is determined by FACS as a percentage propidium-iodine (PI)-positive (dead) CFSE-labeled cells. Killing of the primary leukemia cells is determined by counting with the FACS the number of CFSE stained cells that remained in the culture after their culture with the NK cells. A lower number of CFSE+ cells is indicative of higher level of killing.

Chemotaxis ("Migration") Assay:

Migration response (chemotaxis) of human NK cells is assayed by Transwell migration assay (Costar, Cambridge, Mass.; 6.5-mm diameter, 5-μm pore size). Briefly, 100 μl chemotaxis buffer (RPMI 1640, 1% FCS) containing $2\times10^5$ NK cells is added to the upper chamber, and 0.5 mL chemotaxis buffer with or without 250 ng/ml stromal-derived factor CXCL12 ("SDF-1") (R&D Systems) is added to the bottom chamber. Cells migrating within 4 hours to the bottom chamber of the "transwell" is counted for 60 seconds using FACScalibur (Becton Dickinson Immunocytometry Systems).

"In-Vivo" Homing and Engraftment:

NK cells were expanded with or without 1000 nM SR1, as described above. After 2 weeks in culture, cells were stained with CFSE and similar numbers ($15\times10^6$) of cells were infused into irradiated (350 Rad) NSG mice. Mice were sacrificed 4-days post infusion. Spleens were analyzed for the homing and engraftment of human NK cells based on the CFSE fluorescence, in order to distinguish them from endogenous cells. Engraftment is expressed as the % of cells staining with CFSE.

Assay of CD62L, CD200R, PD-1 Expression on NK Cell Surface

Cultures were initiated with CD3 depleted peripheral-blood and activated with cytokines (including IL-2 and IL-15) with or without SR1 (10-1000 nM). NK cells were stained with specific antibodies for the specified surface markers (CD62L, CD200R, PD-1) after 3 weeks incubation with SR1, and then monitored by FACS.

Results

Example I

SR1 and the Self Renewal Capacity of Cultured Peripheral Blood NK Cells

When peripheral blood mononuclear cells are depleted of the CD3+ or CD3+/CD19+ populations, a population enriched in NK cells is obtained, comprising 2-10% NK cells, with the majority of seeded cells belonging to the myeloid cell lineages. Following 2-3 weeks in culture with SR1, however, more than 90% of the cells in culture were NK (CD56+CD3-) cells.

FIG. 1 illustrates the expansion of peripheral blood NK (T-cell depleted) cells during a three week culture period, in the presence of cytokines (IL-2 or IL-2+IL-15), in scaled-up (10 ml volumes in culture bags) cultures. After 21 days, NK expansion was significantly higher in cultures treated with both SR1 relative to control cultures grown without SR1 (SR1 0). As can be seen in FIG. 1, a greatly increased expansion (fold increase relative to day 0) was observed on day 21 in the presence of SR1, while cytokines-only (SR1 0) controls exhibit a tendency to lose self-renewal capacity over time.

FIG. 2 illustrates the percentages of CD3+CD56− cells, representing the T-cell fraction, in 21 day cultures of T-cell-depleted human peripheral blood NK cells, with cytokines, with and without various concentrations of SR1. As can be seen in FIG. 2, while the contamination of the T cells was low in all groups after 14 and 21 days in culture, in cultures exposed to SR1 the T-cell percentages is lower than in control cultures, without SR1. The unexpected reduction in T-cell contamination in T-cell depleted cultures exposed to the AHR antagonist, provides significant advantage for SR1 and AHR antagonists in enhancing proliferation of NK cells in culture.

Example II

Ex-Vivo Exposure to SR1 Enhances NK Cell Function

Figure 3:
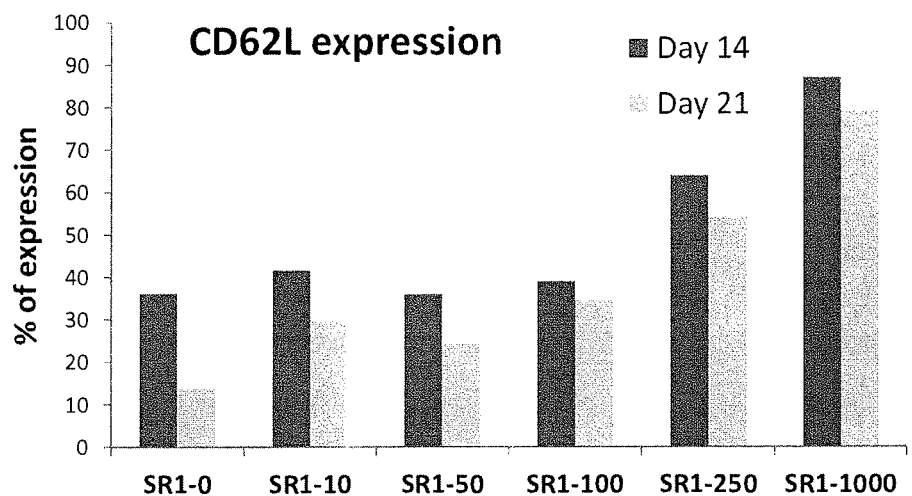
FIG. 3 is a histogram showing the increased expression of the migratory receptor CD62L in cultures of human peripheral blood NK cells exposed to SR1. Peripheral blood NK cells were prepared by T-cell (CD3+ or CD3+CD19+) depletion of the mononuclear cells as detailed in FIG. 1, and expanded in the presence of indicated concentrations (10-1000 nM) of SR1, or cytokines only (cytokines). After 14 and 21 days, cultured cells were reacted with specific antibodies for the specified surface markers, and then monitored by FACS. Note the dramatically enhanced expression of CD62L, increasing with duration of exposure and SR1 concentration, in cells cultured in the presence of SR1 compared to controls (cytokines only)
Figure 4A:
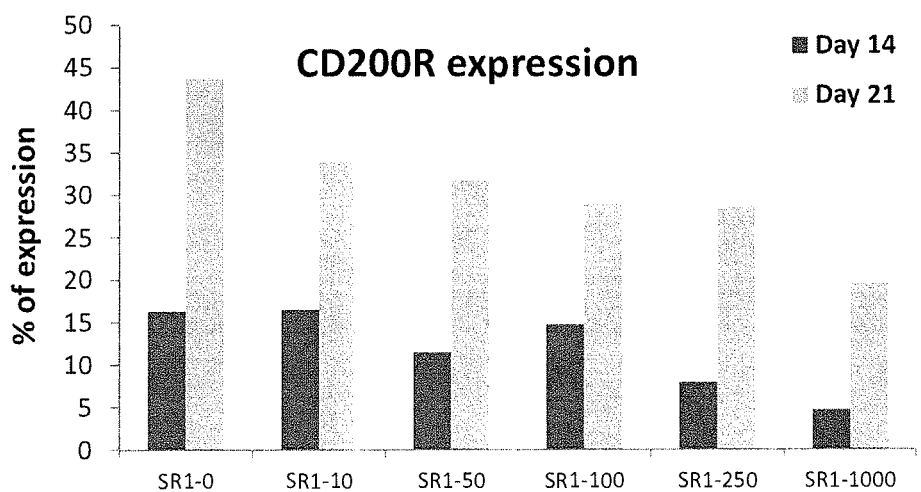
FIGS. 4A and 4B are histograms showing the reduced expression of NK-supressory CD200R and programmed death receptor-1 (PD-1) on NK cells in cultures of human peripheral blood NK cells exposed to SR1. Peripheral blood NK cells were prepared by T-cell (CD3+ or CD3+CD19+) depletion of the mononuclear cells as detailed in FIG. 1, and expanded in the presence of indicated concentrations (10-1000 nM) of SR1, or cytokines only (SR1 0). After 14 and 21 days, cultured cells were reacted with specific antibodies for CD200R (FIG. 14A) or PD-1 (FIG. 14B), and then monitored by FACS.
Figure 4B:
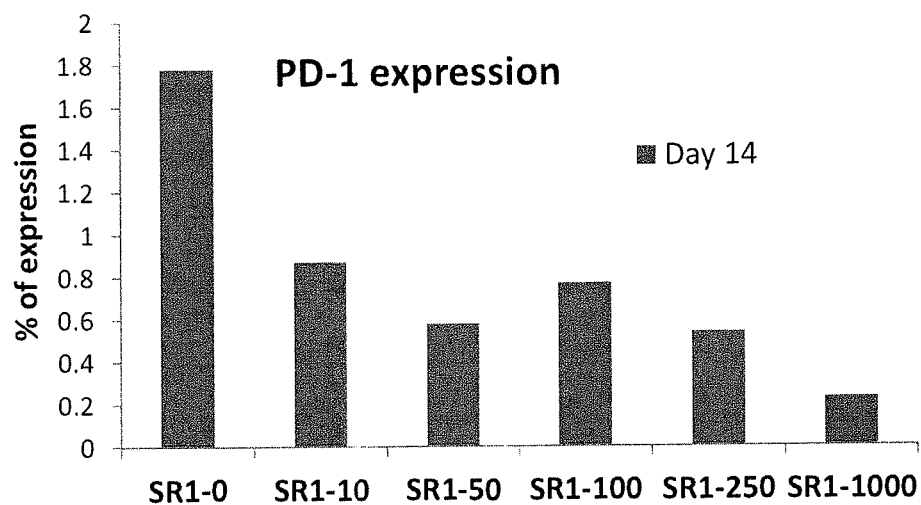

The effect of SR1 on functionally related cell surface receptors was investigated. When expression of cell receptors involved in immunoevasion (CD200R and PD-1) and trafficking (CD62L) in the cultured PB derived NK cells were analyzed using specific antibodies and FACS analysis, strongly enhanced expression of CD62L (FIG. 3), and reduced expression of CD200R and PD1 (FIGS. 4A and 4B) in cells cultured in the presence of SR1 compared to controls (cytokines only) was observed. This strongly suggests an increased ability of the SR1-treated cells to migrate and home to the bone marrow, lymphoid organs and other target organs, and a decrease in cell surface receptors associated with suppression of NK cell anti-tumor activity and tumor immunoevasion.

Example III

Engraftment and Therapeutic Potential of SR1-Cultured NK Cells

NK cells expanded in the presence of SR1 were tested for localization to target organs and engraftment into the organs in-vivo following transplantation of the NK cells into living hosts.

Figure 5:
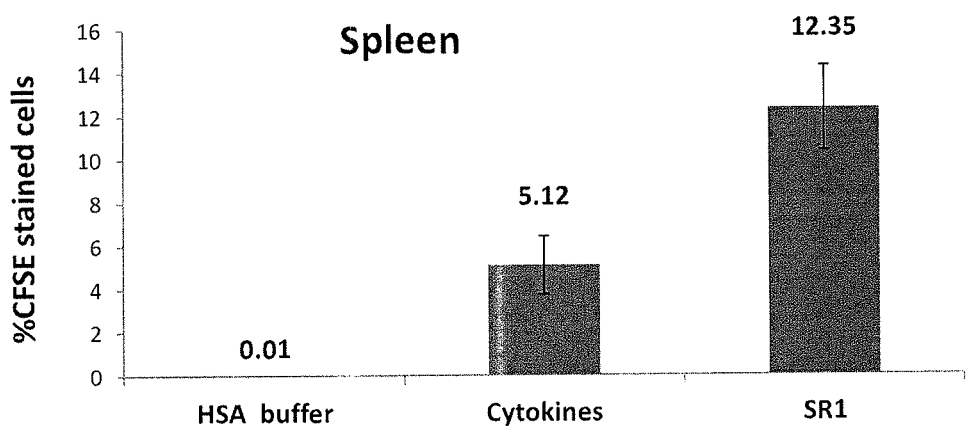
FIG. 5 is a histogram showing increased in-vivo functionality (homing and engraftment) of NK cells expanded in the presence of SR1. Peripheral blood NK cells were prepared by CD3+ or CD3+CD19+ depletion of the mononuclear cells as detailed in FIG. 1, and expanded in the presence of indicated concentration of SR1 or cytokines only. After 2-3 weeks in culture, 15×10$^6$ NK cells from each experimental group were stained with CFSE and then infused into irradiated (350 Rad) NOD.Cg-Prkdcscid Il2rgtm1Wjl/SzJ (NSG) mice. Mice were sacrificed 4-days post infusion, and spleens were analyzed for the homing and engraftment of human NK cells based on the CFSE fluorescence. Engraftment is expressed as the % of cells staining with CFSE. Note the significantly higher in vivo homing/retention/engraftment of NK cells cultured with SR1 as compared with that of NK cells cultured without SR1.

Irradiated (350 Rad) NOD.Cg-Prkdcscid Il2rgtm1Wjl/SzJ (NSG) mice received 15×10$^6$ cells from human peripheral blood NK (T-cell depleted) cultures maintained for up to 3 weeks with SR1 or without (SR1 0) SR1. Prior to infusion NK cells were stained with CFSE. Upon sacrifice of the mice 4 days post infusion, samples of spleen were evaluated by FACS for the percent of cells that are stained with CFSE. FIG. 5 shows the increased localization and engraftment into the spleen target tissues of the NK cells expanded with SR1, expressed as percentage of the total NK cells from the spleen, with the higher concentration of SR1 demonstrating a stronger effect. Thus, culture of the NK cells with SR1 not only increases the numbers of the NK cells, but serves to increase their in-vivo functional potential, as demonstrated by localization and engraftment into the target organs (e.g., spleen).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

LIST OF REFERENCES

Bachanova et al. Canc Immunol Immunother 2010; 59:739-44
Beider et al. Blood 2003; 102:1951-
Berg et al. Cytotherapy 2009; 11:341-55
Bernardini et al. Blood 2008; 111:3626-34
Caliguiri Blood 2008 112:461-69
Cho and Campana, Korean J Lab Med 2009; 29:89-96
Décor, et al. Exper Hematology 2010; 38; 351-62
Frias et al. Exp Hematol 2008; 36: 61-68
Gahrton et al. Blood 2008; 111:3155-62
Guven, Karolinska Institute 2005
Harada et al. Exp Hematol. 2004; 32:614-21
H-g Klingemann; J Martinson. Cytotherapy 2004; 6(1): 15
Humeau L., et al. Blood 1997, 90:3496
Koehl et al., Klin Padiatr 2005; 217:345-50
Markel et al. PLoS ONE 2009; 4:Issue 5
Meyer-Monad et al. Transfusion 2009; 49:362-71
Miller et al., Blood 1992; 80:2221-29
Miller et al., Blood 2006; 108:3111 (Abstract)
Olson et al. J Immunology 2009; 183:3219-28
Robertson, M. J., J. Ritz. Blood 1990; 76:2421
Rosenberg, S. A. J. Natl Cancer Inst 1985. 75:595.
Rosenberg, et al. J. Natl. Canc. Inst. 1993; 85:622-32
Rosenberg, S. A. et al. J. Natl. Cancer Inst. 1994; 85:622
Schleinitz et al. Immunology 2010 131:451-58
Schuster et al. E. J. Immunol 2009; 34:2981-90
Verneris et al. Brit J Hematol 2009; 147:185-91
Von Drygalski A et al. Stem Cells Dev; 2004:13(1):101-11
Yu et al. Blood 2010; 115:274-81
Zucchini et al., Exp Rev Anti-Infect Ther 2008; 6:867-85

What is claimed is:

1. A method of ex-vivo culturing natural killer (NK) cells, the method comprising culturing a population of cells comprising NK cells with an aryl hydrocarbon receptor (AHR) antagonist, wherein said AHR antagonist is represented by Formula I:

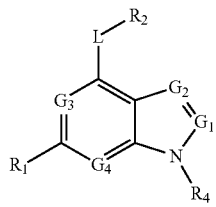

Formula I wherein:
$G_1$ is selected from N and $CR_3$;
$R_3$ is selected from hydrogen, $C_{1-4}$alkyl and biphenyl;
$G_2$, $G_3$ and $G_4$ are each independently selected from —CH— and N; with the proviso that at least one of $G_3$ and $G_4$ is N; and with the proviso that $G_1$ and $G_2$ are not both N;
L is selected from a substituted or unsubstituted alkylamino, a substituted or unsubstituted amino or a substituted or unsubstituted alkyl;
$R_1$ is selected from hydrogen, a substituted or unsubstituted aryl and a substituted or unsubstituted heteroaryl; with the proviso that $R_1$ and $R_3$ are not both hydrogen;
$R_2$ is selected from —S(O)$_2$NR$_{6a}$R$_{6b}$, —NR$_{9a}$C(O)R$_{9b}$, —NR$_{6a}$C(O)NR$_{6b}$R$_{6c}$, a substituted or unsubstituted aryl and a substituted or unsubstituted heteroaryl; and
$R_4$ is selected from a substituted or unsubstituted $C_{1-10}$alkyl, a substituted or unsubstituted $C_{1-10}$alkenyl, a substituted or unsubstituted cycloalkyl, a substituted or unsubstituted aryl, a substituted or unsubstituted alkaryl, a substituted or unsubstituted heteroalicyclic and a substituted or unsubstituted heteroaryl.

2. The method of claim 1, wherein said culturing is of said population of cells with said AHR antagonist and at least one growth factor.

3. The method of claim 1, wherein a concentration of said AHR antagonist ranges from 1 to 100000 nM.

4. The method of claim 1, wherein said culturing is effected for a time period that ranges from 3 days to 6 weeks.

5. The method of claim 1, wherein culturing said NK cells with said AHR antagonist results in at least one of the following:
(a) elevated expression of CD62L as compared to NK cells cultured under otherwise identical culturing conditions without added AHR antagonist;
(b) reduced expression of CD200R or PD-1 or both as compared to NK cells cultured under otherwise identical culturing conditions without added AHR antagonist;
(c) elevated homing and in-vivo retention as compared to NK cells cultured under otherwise identical culturing conditions without added AHR antagonist; and
(d) greater proliferation as compared to NK cells cultured under otherwise identical culturing conditions without added AHR antagonist.

6. The method of claim 2, wherein said at least one growth factor is IL-2, said exposure time is from seeding of said population of cells comprising NK cells, said exposure duration is from 2 to 3 weeks and said concentration of said AHR antagonist is 250 to 1000 nM.

7. The method of claim 1, wherein said population of cells comprising said NK cells is obtained from a source selected from the group consisting of cord blood, bone marrow and peripheral blood.

8. The method of claim 1, wherein said population of cells comprising said NK cells is a heterogenous cell population which comprises an NK cell fraction and a CD3+ cell fraction.

9. The method of claim 8, wherein said population of cells comprising said NK cells is a mononuclear or total nuclear cell population depleted of CD3+ cells.

10. The method of claim 1, wherein said population of cells comprising said NK cells is an unselected NK cell population.

11. The method of claim 1, wherein said culturing said population of cells comprising said NK cells is effected without a feeder layer or feeder cells.

12. The method of claim 2, wherein said at least one growth factor comprises a growth factor selected from the group consisting of SCF, FLT3, IL-2, IL-7, IL-15, IL-12 and IL-21.

13. The method of claim 1, wherein said AHR antagonist is 4-(2-(2-(benzo[b]thiophen-3-yl)-9-isopropyl-9H-purin-6-ylamino)ethyl) phenol (Stem Reginin 1).

14. The method of claim 1, wherein said AHR antagonist is selected from:
4-(2-(2-(benzo[b]thiophen-3-yl)-9-isopropyl-9H-purin-6-ylamino)ethyl)phenol;
4-(2-(2-(benzo[b]thiophen-3-yl)-9-sec-butyl-9H-purin-6-ylamino)ethyl)phenol;
4-(2-(9-benzhydryl-2-(benzo[b]thiophen-3-yl)-9H-purin-6-ylamino)ethyl)phenol;
4-(2-(2-(benzo[b]thiophen-3-yl)-9-(tetrahydro-2H-pyran-3-yl)-9H-purin-6-ylamino)ethyl)phenol;
4-(2-(9-isopropyl-2-(thiophen-2-yl)-9H-purin-6-ylamino)ethyl)phenol;
4-(2-(2-(benzo[b]thiophen-3-yl)-9-(4-(trifluoromethyl)benzyl)-9H-purin-6-ylamino)ethyl)phenol;
4-(2-(2-(benzo[b]thiophen-3-yl)-9-isobutyl-9H-purin-6-ylamino)ethyl)phenol;
4-(2-(2-(benzo[b]thiophen-3-yl)-9-methyl-9H-purin-6-ylamino)ethyl)phenol;
4-(2-(2-(benzo[b]thiophen-3-yl)-9-(4-methylbenzyl)-9H-purin-6-ylamino)ethyl)phenol;
N-(2-(1H-indol-3-yl)ethyl)-2-(benzo[b]thiophen-3-yl)-9-isopropyl-9H-purin-6-amine;
2-(benzo[b]thiophen-3-yl)-9-isopropyl-N-(2-(thiophen-3-yl)ethyl)-9H-purin-6-amine;
3-(2-(2-(benzo[1]thiophen-3-yl)-9-isopropyl-9H-purin-6-ylamino)ethyl)phenol;
2-(benzo[b]thiophen-3-yl)-N-(4-fluorophenethyl)-9-isopropyl-9H-purin-6-amine;
N-(4-aminophenethyl)-2-(benzo[b]thiophen-3-yl)-9-isopropyl-9H-purin-6-amine;
4-(2-(9-isopropyl-2-(pyrimidin-5-yl)-9H-purin-6-ylamino)ethyl)phenol;
4-(2-(9-isopropyl-2-(pyridin-3-yl)-9H-purin-6-ylamino)ethyl)phenol;
4-(2-(9-isopropyl-2-phenyl-9H-purin-6-ylamino)ethyl)phenol;
4-(2-(9-isopropyl-2-(thiophen-3-yl)-9H-purin-6-ylamino)ethyl)phenol;
4-(2-(2-(furan-3-yl)-9-isopropyl-9H-purin-6-ylamino)ethyl)phenol;
2-(benzo[b]thiophen-3-yl)-N-(4-fluorophenethyl)-9-phenyl-9H-purin-6-amine;
N-benzyl-8-(biphenyl-4-yl)-9-isopropyl-9H-purin-6-amine;

4-(2-(2-(benzo[b]thiophen-3-yl)-9-(nonan-2-yl)-9H-purin-6-ylamino)ethyl)phenol;
N-(2-(1H-indol-3-yl)ethyl)-2-(benzo[b]thiophen-3-yl)-9-sec-butyl-9H-purin-6-amine;
3-(2-(2-(benzo[b]thiophen-3-yl)-9-isopropyl-9H-purin-6-ylamino)ethyl)-1H-indol-5-yl, 5-((3aS,4S,6aR)-2-oxohexahydro-1H-thieno[3,4-d]imidazol-4-yl)pentanoate;
N-(2-(2-(2-(2-(4-(1-(2-(benzo[b]thiophen-3-yl)-6-(4-hydroxyphenethylamino)-9H-purin-9-yl)ethyl)-1H-1,2,3-triazol-1-yl)ethoxy)ethoxy)ethoxy)ethyl)acetamide;
4-(2-(9-isopropyl-2-(pyridin-4-yl)-9H-purin-6-ylamino)ethyl)phenol;
ethyl 5-(6-(4-hydroxyphenethylamino)-9-isopropyl-9H-purin-2-yl)nicotinate;
ethyl 5-(6-(4-hydroxyphenethylamino)-9-isopropyl-9H-purin-2-yl)nicotinate;
4-(2-(2-(6-fluoropyridin-3-yl)-9-isopropyl-9H-purin-6-ylamino)ethyl)phenol;
4-(2-(9-isopropyl-2-(4-methylpyridin-3-yl)-9H-purin-6-ylamino)ethyl)phenol;
5-(6-(4-hydroxyphenethylamino)-9-isopropyl-9H-purin-2-yl)nicotinonitrile;
4-(2-(9-isopropyl-2-(pyrrolidin-1-yl)-9H-purin-6-ylamino)ethyl)phenol;
4-(2-(2-(1H-imidazol-1-yl)-9-isopropyl-9H-purin-6-ylamino)ethyl)phenol;
4-(2-(9-isopropyl-2-(pyridazin-4-yl)-9H-purin-6-ylamino)ethyl)phenol;
4-(2-(9-isopropyl-2-(pyrazin-2-yl)-9H-purin-6-ylamino)ethyl)phenol;
4-(2-(9-isopropyl-2-(pyridin-2-yl)-9H-purin-6-ylamino)ethyl)phenol;
4-(2-(9-isopropyl-2-(5-(methylsulfonyl)pyridin-3-yl)-9H-purin-6-ylamino)ethyl)phenol;
4-(2-(9-isopropyl-2-(5-methylpyridin-3-yl)-9H-purin-6-ylamino)ethyl)phenol;
4-(2-(2-(4-chloropyridin-3-yl)-9-isopropyl-9H-purin-6-ylamino)ethyl)phenol;
4-(2-(2-(5-fluoropyridin-3-yl)-9-isopropyl-9H-purin-6-ylamino)ethyl)phenol;
4-(2-(9-isopropyl-2-(1-methyl-1H-pyrazol-4-yl)-9H-purin-6-ylamino)ethyl)phenol;
4-(2-(9-isopropyl-2-(pyridin-3-yl)-9H-purin-6-ylamino)ethyl)-2-methoxy phenol;
4-(2-(9-isopropyl-2-(pyridin-3-yl)-9H-purin-6-ylamino)ethyl)-2-methoxy phenol;
N-[2-(6-methoxy-1H-indol-3-yl)ethyl]-9-(propan-2-yl)-2-(pyridin-3-yl)-9H-purin-6-amine;
N-[2-(5-methyl-1H-indol-3-yl)ethyl]-9-(propan-2-yl)-2-(pyridin-3-yl)-9H-purin-6-amine;
1-(2-{[9-(propan-2-yl)-2-(pyridin-3-yl)-9H-purin-6-yl]amino}ethyl)imidazolidin-2-one;
N-(2-{[9-(propan-2-yl)-2-(pyridin-3-yl)-9H-purin-6-yl]amino}ethyl)pyridin-2-amine;
9-(propan-2-yl)-N-[3-(1H-pyrazol-4-yl)propyl]-2-(pyridin-3-yl)-9-H-purin-6-amine;
N-{2-[(3-methyl-1H-1,2,4-triazol-5-yl)sulfanyl]ethyl}-9-(propan-2-yl)-2-(pyridin-3-yl)-9H-purin-6-amine;
1-(2-{[2-(1-benzothiophen-3-yl)-9-(propan-2-yl)-9H-purin-6-yl]amino}ethyl)imidazolidin-2-one;
N-[2-(5-amino-1H-1,2,4-triazol-3-yl)ethyl]-2-(1-benzothiophen-3-yl)-9-(propan-2-yl)-9H-purin-6-amine;
N-(2-{[2-(1-benzothiophen-3-yl)-9-(propan-2-yl)-9H-purin-6-yl]amino}ethyl)pyridin-2-amine;
2-(1-benzothiophen-3-yl)-9-(propan-2-yl)-N-[3-(1H-pyrazol-4-yl)propyl]-9H-purin-6-amine;
2-(1-benzothiophen-3-yl)-N-[3-(3,5-dimethyl-1H-pyrazol-4-yl)propyl]-9-(propan-2-yl)-9H-purin-6-amine;
(2-{[2-(1-benzothiophen-3-yl)-9-(propan-2-yl)-9H-purin-6-yl]amino}ethyl)urea;
5-({[2-(1-benzothiophen-3-yl)-9-(propan-2-yl)-9H-purin-6-yl]amino}methyl)-2,3-dihydro-1H-1,3-benzodiazol-2-one;
N-[2-(1H-indol-3-yl)ethyl]-9-(propan-2-yl)-2-(pyridin-3-yl)-9H-purin-6-amine;
N-(4-(2-(9-isopropyl-2-(pyridin-3-yl)-9H-purin-6-ylamino)ethyl)phenyl)methane-sulfonamide;
4-(2-(2-(pyridin-3-yl)-9-(tetrahydrofuran-3-yl)-9H-purin-6-ylamino)ethyl)-phenol;
4-(2-(9-isopropyl-2-(pyridin-3-yl)-9H-purin-6-ylamino)propyl)phenol;
4-(2-(9-(oxetan-3-yl)-2-(pyridin-3-yl)-9H-purin-6-ylamino)ethyl)phenol;
5-(6-(4-hydroxyphenethylamino)-9-isopropyl-9H-purin-2-yl)-N-methylnicotin-amide;
4-(2-(9-(1-hydroxypropan-2-yl)-2-(pyridin-3-yl)-9H-purin-6-ylamino)-ethyl)phenol;
4-(2-(9-isopropyl-2-(pyridin-3-yl)-9H-purin-6-ylamino)ethyl)phenyl sulfamate;
4-(2-(2-(2-fluoropyridin-3-yl)-9-isopropyl-9H-purin-6-ylamino)ethyl)phenol;
4-(2-(9-isopropyl-2-(1-methyl-1H-pyrrol-2-yl)-9H-purin-6-ylamino)ethyl)-phenol;
4-(2-(9-isopropyl-2-(thiazol-5-yl)-9H-purin-6-ylamino)ethyl)phenol;
4-(2-(2-(1H-benzo[d]imidazol-1-yl)-9-isopropyl-9H-purin-6-ylamino)ethyl)-phenol;
4-(2-(2-(2,4-dimethyl-1H-imidazol-1-yl)-9-isopropyl-9H-purin-6-ylamino)ethyl)phenol;
4-(2-(9-isopropyl-2-(2-methyl-1H-imidazol-1-yl)-9H-purin-6-ylamino)ethyl)-phenol;
5-(9-sec-butyl-6-(4-hydroxy-3-methylphenethylamino)-9H-purin-2-yl)-nicotinonitrile;
N-(2-(1H-pyrrolo[2,3-b]pyridin-5-yl)ethyl)-9-isopropyl-2-(pyridin-3-yl)-9-H-purin-6-amine;
9-isopropyl-N-(2-(5-methyl-1H-pyrazol-3-yl)ethyl)-2-(pyridin-3-yl)-9H-purin-6-amine;
4-(2-(2-(5-fluoropyridin-3-yl)-9-(oxetan-3-yl)-9H-purin-6-ylamino)ethyl)phenol;
4-(2-(2-(5-chloropyridin-3-yl)-9-isopropyl-9H-purin-6-ylamino)ethyl)phenol;
4-(2-(9-isopropyl-2-(5-(trifluoromethyl)pyridin-3-yl)-9H-purin-6-ylamino)ethyl)phenol;
5-(6-(2-(1H-indol-3-yl)ethylamino)-9-sec-butyl-9H-purin-2-yl)nicotinonitrile;
N-(2-(1H-indol-3-yl)ethyl)-9-sec-butyl-2-(5-methylpyridin-3-yl)-9H-purin-6-amine;
(R)—N-(2-(1H-indol-3-yl)ethyl)-9-sec-butyl-2-(5-fluoropyridin-3-yl)-9H-purin-6-amine;
(S)—N-(2-(1H-indol-3-yl)ethyl)-9-sec-butyl-2-(5-fluoropyridin-3-yl)-9H-purin-6-amine;
N-(2-(1H-indol-3-yl)ethyl)-9-sec-butyl-2-(5-fluoropyridin-3-yl)-9H-purin-6-amine;
(R)—N-(2-(1H-indol-3-yl)ethyl)-9-sec-butyl-2-(5-methylpyridin-3-yl)-9H-purin-6-amine;
(S)—N-(2-(1H-indol-3-yl)ethyl)-9-sec-butyl-2-(5-methylpyridin-3-yl)-9H-purin-6-amine;
5-(6-(4-hydroxyphenethylamino)-9-(oxetan-3-yl)-9H-purin-2-yl)nicotinonitrile;
4-(2-(6-(5-fluoropyridin-3-yl)-1-isopropyl-1H-pyrazolo[3,4-d]pyrimidin-4-ylamino)ethyl)phenol;
4-(2-(6-(benzo[b]thiophen-3-yl)-1-isopropyl-1H-pyrazolo[3,4-d]pyrimidin-4-ylamino)ethyl)phenol;

(R)-4-(2-(2-(5-fluoropyridin-3-yl)-9-(tetrahydrofuran-3-yl)-9H-purin-6-yl-amino)ethyl)phenol;
4-(2-(9-isopropyl-2-(pyridin-3-yl)-9H-purin-6-ylamino)ethyl)-3-methylphenol;
5-(6-(4-hydroxyphenethylamino)-9-isopropyl-9H-purin-2-yl)picolinonitrile;
3-(6-(4-hydroxyphenethylamino)-9-isopropyl-9H-purin-2-yl)isonicotinonitrile;
4-(2-(2-(5-fluoropyridin-3-yl)-7-isopropyl-7H-pyrrolo[2,3-d]pyrimidin-4-ylamino)ethyl)phenol;
3-(6-(4-hydroxyphenethylamino)-9-isopropyl-9H-purin-2-yl)picolinonitrile;
4-(2-(9-isopropyl-2-(6-methylpyridin-3-yl)-9H-purin-6-ylamino)ethyl)phenol;
4-(2-(9-isopropyl-2-(isoquinolin-4-yl)-9H-purin-6-ylamino)ethyl)phenol;
2-chloro-4-(2-(9-isopropyl-2-(pyridin-3-yl)-9H-purin-6-ylamino)ethyl)phenol;
3-fluoro-4-(2-(9-isopropyl-2-(pyridin-3-yl)-9H-purin-6-ylamino)ethyl)phenol;
N-(2-(5-chloro-1H-indol-3-yl)ethyl)-9-isopropyl-2-(pyridin-3-yl)-9H-purin-6-amine;
N-(2-(5-fluoro-1H-indol-3-yl)ethyl)-9-isopropyl-2-(pyridin-3-yl)-9H-purin-6-amine;
4-(2-(9-isopropyl-2-(pyridin-3-yl)-9H-purin-6-ylamino)ethyl)-2-methylphenol;
4-(2-(2-(benzo[b]thiophen-3-yl)-9-(oxetan-3-yl)-9H-purin-6-ylamino)ethyl)-phenol;
(S)-4-(2-(2-(benzo[b]thiophen-3-yl)-9-(tetrahydrofuran-3-yl)-9H-purin-6-ylamino)ethyl)phenol;
(R)-4-(2-(2-(benzo[b]thiophen-3-yl)-9-(tetrahydrofuran-3-yl)-9H-purin-6-ylamino)ethyl)phenol;
2-(6-(2-(1H-indol-3-yl)ethylamino)-2-(5-fluoropyridin-3-yl)-9H-purin-9-yl)propan-1-ol;
(R)-2-(6-(2-(1H-indol-3-yl)ethylamino)-2-(5-fluoropyridin-3-yl)-9H-purin-9-yl)propan-1-ol;
(S)-2-(6-(2-(1H-indol-3-yl)ethylamino)-2-(5-fluoropyridin-3-yl)-9H-purin-9-yl)propan-1-ol;
(R)—N-(2-(1H-indol-3-yl)ethyl)-2-(5-fluoropyridin-3-yl)-9-(tetrahydrofuran-3-yl)-9H-purin-6-amine;
4-(2-(2-(3H-imidazo[4,5-b]pyridin-3-yl)-9-isopropyl-9H-purin-6-ylamino)ethyl)phenol;
4-(2-(2-(1H-imidazo[4,5-b]pyridin-1-yl)-9-isopropyl-9H-purin-6-ylamino)ethyl)phenol;
4-(2-(6-(5-fluoropyridin-3-yl)-1-isopropyl-1H-imidazo[4,5-c]pyridin-4-ylamino)ethyl)phenol;
4-(2-(2-(4,5-dimethyl-1H-imidazol-1-yl)-9-isopropyl-9H-purin-6-ylamino)ethyl)phenol;
2-(5-fluoropyridin-3-yl)-9-isopropyl-N-(2-(pyridin-3-yl)ethyl)-9H-purin-6-amine;
4-(2-(2-(5-fluoropyridin-3-yl)-9-isopropyl-9H-purin-6-ylamino)-1-hydroxyethyl)phenol;
2-(5-fluoropyridin-3-yl)-9-isopropyl-N-(2-(6-methoxy-1H-indol-3-yl)ethyl)-9H-purin-6-amine;
N-(2-(1H-indol-3-yl)ethyl)-2-(5-fluoropyridin-3-yl)-9-isopropyl-9H-purin-6-amine;
2-(5-fluoropyridin-3-yl)-9-isopropyl-N-(2-(5-methoxy-1H-indol-3-yl)ethyl)-9H-purin-6-amine;
N-(2-(1H-indol-3-yl)ethyl)-2-(5-fluoropyridin-3-yl)-9-(prop-1-en-2-yl)-9H-purin-6-amine;
5-(2-(2-(5-fluoropyridin-3-yl)-9-isopropyl-9H-purin-6-ylamino)ethyl)pyridin-2-ol;
N-(2-(1H-pyrrolo[2,3-b]pyridin-3-yl)ethyl)-2-(5-fluoropyridin-3-yl)-9-isopropyl-9H-purin-6-amine;
N-(2-(6-(2-(diethylamino)ethoxy)-1H-indol-3-yl)ethyl)-2-(5-fluoropyridin-3-yl)-9-isopropyl-9H-purin-6-amine;
4-(2-(5-(5-fluoropyridin-3-yl)-3-isopropyl-3H-imidazo[4,5-b]pyridin-7-ylamino)ethyl)phenol;
N-(2-(1H-indol-3-yl)ethyl)-9-sec-butyl-2-(2-methyl-1H-imidazol-1-yl)-9H-purin-6-amine;
4-(2-(2-(2-ethyl-1H-imidazol-1-yl)-9-isopropyl-9H-purin-6-ylamino)ethyl)phenol;
4-(2-(9-isopropyl-2-(2-propyl-1H-imidazol-1-yl)-9H-purin-6-ylamino)-ethyl)phenol;
3-(2-(2-(5-fluoropyridin-3-yl)-9-isopropyl-9H-purin-6-ylamino)ethyl)-1H-indol-6-ol;
N-(2-(1H-indol-3-yl)ethyl)-9-isopropyl-2-(5-methylpyridin-3-yl)-9H-purin-6-amine;
N-(2-(1H-indol-3-yl)ethyl)-9-isopropyl-2-(2-methyl-1H-imidazol-1-yl)-9H-purin-6-amine;
2-(5-fluoropyridin-3-yl)-9-isopropyl-N-(2-(7-methyl-1H-indol-3-yl)ethyl)-9H-purin-6-amine;
N-(2-(1H-indol-3-yl)ethyl)-2-(5-fluoropyridin-3-yl)-9-(oxetan-3-yl)-9H-purin-6-amine;
N-(2-(1H-indol-3-yl)ethyl)-2-(5-methylpyridin-3-yl)-9-(oxetan-3-yl)-9H-purin-6-amine;
N-(2-(6-fluoro-1H-indol-3-yl)ethyl)-2-(5-fluoropyridin-3-yl)-9-isopropyl-9H-purin-6-amine;
2-(5-fluoropyridin-3-yl)-9-isopropyl-N-(2-(6-methyl-1H-indol-3-yl)ethyl)-9H-purin-6-amine;
2-(5-fluoropyridin-3-yl)-9-isopropyl-N-(2-(2-methyl-1H-indol-3-yl)ethyl)-9H-purin-6-amine;
N-(2-(4-fluoro-1H-indol-3-yl)ethyl)-2-(5-fluoropyridin-3-yl)-9-isopropyl-9H-purin-6-amine;
N-(2-(7-fluoro-1H-indol-3-yl)ethyl)-2-(5-fluoropyridin-3-yl)-9-isopropyl-9H-purin-6-amine;
2-(5-fluoropyridin-3-yl)-9-isopropyl-N-(2-(4-methyl-1H-indol-3-yl)ethyl)-9H-purin-6-amine;
4-(2-(2-(benzo[b]thiophen-3-yl)-7-isopropyl-7H-pyrrolo[2,3-d]pyrimidin-4-ylamino)ethyl)phenol;
9-isopropyl-2-(pyridin-3-yl)-N-(2-(pyridin-4-yl)ethyl)-9H-purin-6-amine;
N-(2-(1H-pyrrolo[2,3-b]pyridin-5-yl)ethyl)-9-isopropyl-2-(pyridin-3-yl)-9H-purin-6-amine;
4-(2-(2-(5-fluoropyridin-3-yl)-9-(1-hydroxypropan-2-yl)-9H-purin-6-ylamino)ethyl)-2-methylphenol;
4-(2-(2-(benzo[b]thiophen-3-yl)-9-cyclohexyl-9H-purin-6-ylamino)ethyl)phenol;
4-(2-(9-isopropyl-2-(thiophen-3-yl)-9H-purin-6-ylamino)ethyl)phenol; and
1-(2-(2-(benzo[b]thiophen-3-yl)-6-(4-hydroxyphenethylamino)-9H-purin-9-yl)ethyl)pyrrolidin-2-one.

15. The method of claim 1, wherein said population of cells comprising said NK cells is a cell population a CD34+ depleted cell population.

* * * * *